United States Patent
Nagarajan et al.

(10) Patent No.: US 6,933,304 B2
(45) Date of Patent: Aug. 23, 2005

(54) HETEROARYLALKANOIC ACIDS AS INTEGRIN RECEPTOR ANTAGONISTS

(75) Inventors: Srinivasan Raj Nagarajan, Chesterfield, MO (US); Ish Kumar Khanna, Libertyville, IL (US); Michael B. Tollefson, Hainesville, IL (US); Scott B. Mohler, Chicago, IL (US); Barbara Chen, Northbrook, IL (US); Mark Russell, Gurnee, IL (US); Balekudru Devadas, Chesterfield, MO (US); Thomas D. Penning, Elmhurst, IL (US); Lori A. Schretzman, Gurnee, IL (US); Dale P. Spangler, Deerfield, IL (US); Mark Laurence Boys, Mount Prospect, IL (US); Nizal Samuel Chandrakumar, Vernon Hills, IL (US); Hung-Fun Lu, Manchester, MO (US)

(73) Assignee: Pharmacia Corporation, Chesterfield, MO (US)

( * ) Notice: Subject to any disclaimer, the term of this patent is extended or adjusted under 35 U.S.C. 154(b) by 213 days.

(21) Appl. No.: 09/881,913

(22) Filed: Jun. 15, 2001

(65) Prior Publication Data

US 2002/0133023 A1 Sep. 19, 2002

Related U.S. Application Data

(60) Provisional application No. 60/211,781, filed on Jun. 15, 2000, and provisional application No. 60/211,782, filed on Jun. 15, 2000.

(51) Int. Cl.[7] ............. A61K 31/4375; C07D 471/04
(52) U.S. Cl. .............. 514/300; 514/211; 514/215; 514/224.2; 514/230.5; 540/580; 544/47; 544/105; 546/122
(58) Field of Search .................. 540/580; 544/47, 544/105; 546/122; 514/211, 215, 224.2, 230.5, 300

(56) References Cited

U.S. PATENT DOCUMENTS

| | | | |
|---|---|---|---|
| 5,700,823 A | 12/1997 | Hirth et al. ............ | 514/380 |
| 5,773,646 A | 6/1998 | Chandrakumar ........ | 562/439 |
| 5,849,736 A | 12/1998 | Wityak ................ | 514/227.8 |
| 5,852,210 A | 12/1998 | Chen ................... | 562/439 |

FOREIGN PATENT DOCUMENTS

| | | | | |
|---|---|---|---|---|
| WO | WO 92/07468 | 5/1992 | | |
| WO | WO 94 08577 | 4/1994 | ......... | A61K/31/38 |
| WO | WO 97 44333 | 11/1997 | ......... | C07D/271/06 |
| WO | WO 99 26945 | 6/1999 | ......... | C07D/417/12 |
| WO | WO 99 30709 | 6/1999 | ......... | A61K/31/435 |
| WO | WO 99/30713 | 6/1999 | | |
| WO | WO 00/07544 | 2/2000 | | |
| WO | WO 00/72801 | 12/2000 | | |
| WO | WO 01/24797 | 4/2001 | | |

*Primary Examiner*—Bernard Dentz
(74) *Attorney, Agent, or Firm*—Harness, Dickey & Pierce

(57) ABSTRACT

The present invention relates to a class of compounds represented by the Formula I

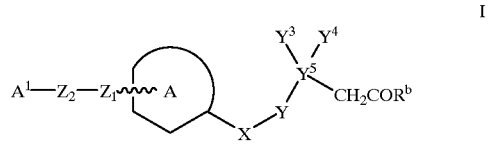

or a pharmaceutically acceptable salt thereof, pharmaceutical compositions comprising compounds of the Formula I, and methods of selectively antagonizing the $\alpha_v\beta_3$ and/or the $\alpha_v\beta_5$ integrin without significantly antagonizing the IIb/IIIa or $\alpha_v\beta_6$ integrin.

22 Claims, No Drawings

HETEROARYLALKANOIC ACIDS AS INTEGRIN RECEPTOR ANTAGONISTS

The present application claims priority under Title 35, United States Code, §119 of U.S. Provisional application Ser. No. 60/211,781 filed Jun. 15, 2000 and U.S. Provisional application Ser. No. 60/211,782 filed Jun. 15, 2000.

FIELD OF THE INVENTION

The present invention relates to pharmaceutical agents which are $\alpha_v\beta_3$ and/or $\alpha_v\beta_5$ integrin antagonists and as such are useful in pharmaceutical compositions and in methods for treating conditions mediated by $\alpha_v\beta_3$ and/or $\alpha_v\beta_5$ integrins.

BACKGROUND OF THE INVENTION

The integrin $\alpha_v\beta_3$ (also known as vitronectin receptor), is a member of the integrin family of heterodimeric transmembrane glycoprotein complexes that mediate cellular adhesion events and signal transduction processes. Integrin $\alpha_v\beta_3$ is expressed in number of cell types and has been shown to mediate several biologically relevant processes, including adhesion of osteoclasts to the bone matrix, vascular smooth muscle cell migration and angiogenesis.

The integrin avb3 has been shown to play a role in various conditions or disease states including tumor metastasis, solid tumor growth (neoplasia), osteoporosis, Paget's disease, humoral hypercalcemia of malignancy, osteopenia, angiogenesis, including tumor angiogenesis and lymphangiogenesis, retinopathy including macular degeneration, arthritis, including rheumatoid arthritis, periodontal disease, psoriasis and smooth muscle cell migration (e.g. restenosis artherosclerosis). The compounds of the present invention are $\alpha_v\beta_3$ antagonists and can be used, alone or in combination with other therapeutic agents, in the treatment or modulation of various conditions or disease states described above. Additionally, it has been found that such agents would be useful as antivirals, antifungals and antimicrobials.

The integrin $\alpha_v\beta_5$ is thought to play a role in neovascularization. M. C. Friedlander, et al., Science, 270, 1500–1502 (1995) disclose that a monoclonal antibody for $\alpha_v\beta_5$ inhibits VEFG-induced angiogenesis in the rabbit cornea and the chick chorioallantoic membrane model. Therefore compounds which act as antagonists of the $\alpha_v\beta_5$ integrin will inhibit neovascularization and will be useful for treating and preventing angiogenesis metastasis, tumor growth, macular degeneration and diabetic retionopathy.

Certain compounds may antagonize both the $\alpha_v\beta_5$ and the $\alpha_v\beta_3$ receptor and therefore are referred to as "mixed $\alpha_v\beta_5/\alpha_v\beta_3$ antagonists" or "dual $\alpha_v\beta_3/\alpha_v\beta_5$ antagonists". Such dual or mixed antagonists are useful for treating or preventing angiogenesis, tumor metastasis, tumor growth, diabetic retinopathy, macular degeneration, atherosclerosis and osteoporosis It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Further, it has not been established in the art that sparing $\alpha_v\beta_6$ integrin would be a beneficial property to be incorporated in the design of antagonists of $\alpha_v\beta_3$. Rather, $\alpha_v\beta_6$ has been identified as a target for antagonists because it is highly expressed in many carcinoma cell lines, and has been shown to enchance the proliferative capacity of a colon carcinoma cell line both in vivo and in vitro (Agrez et al., 1994, J. Cell Biol. 127, 547). Additionally, $\alpha_v\beta_6$ is expressed during the later stages of wound healing and remains expressed until the wound is closed (See Christofidou-Solomidou, et al., 1997 American J. of Pathol., 151, 975), and therefore it is believed that $\alpha_v\beta_6$ plays a role in the remodeling of the vasculature during the later stages of angiogenesis. Accordingly, antagonists of $\alpha_v\beta_6$ are seen as useful in treating or preventing cancer by inhibiting tumor growth and metastasis (see, for example, U.S. Pat. No. 6,211,191).

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Further, with the discovery that $\alpha_v\beta_3$ plays a role in the process of lymphatic dissemination via adhesion of melanoma cells to lymph node by binding the vitronectin receptor (Nip et al., J. Clin Invest 1992, 90,1406), inhibitors of $\alpha_v\beta_3$ may also be useful for making alterations in lymphatic endothelial-tumor cell adhesion, thereby further reducing the potential for tumor metastasis.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The compounds of the present invention are useful for the treatment, including prevention of angiogenic disorders. The term angiogenic disorders include conditions involving abnormal neovascularization. The growth of new blood vessels, or angiogenesis, also contributes to pathological conditions such as diabetic retinopathy including macular degeneration (Adamis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic agents for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone (for a review, see Rodan and Rodan, 1997, J. Endocrinol. 154, S47, Nakamura et al., J. Cell Science, 1999 112, 3985). Osteoclasts cause bone resorption and when such bone resorbing activity exceeds bone forming activity it leads to an increased number of bone fractures, incapacitation and increased mortality. Antagonists of $\alpha_V\beta_3$ have been shown to be potent inhibitors of osteoclastic activity both in vitro (Sato et al., *J. Cell. Biol.*, Vol. 111 (1990) 1713–1723) and in vivo (Fisher et al., *Endocrinology*, Vol. 132 (1993) 1411–1413). Antagonism of $\alpha_V\beta_3$ leads to decreased bone resorption and therefore restores a normal balance of bone forming and resorbing activity. Thus it would be beneficial to provide antagonists of osteoclast $\alpha_V\beta_3$ which are effective inhibitors of bone resorption and therefore are useful in the treatment or prevention of osteoporosis.

The role of the $\alpha_V\beta_3$ integrin in smooth muscle cell migration also makes it a therapeutic target for prevention or inhibition of neointimal hyperplasia which is a leading cause of restenosis after vascular procedures (Choi et al., *J. Vasc. Surg.* Vol. 19(1) (1994) 125–34). Prevention or inhibition of neointimal hyperplasia by pharmaceutical agents to prevent or inhibit restenosis would be beneficial.

White (*Current Biology*, Vol. 3(9)(1993) 596–599) has reported that adenovirus uses $\alpha_V\beta_3$ for entering host cells. The integrin appears to be required for endocytosis of the virus particle and may be required for penetration of the viral genome into the host cell cytoplasm. Thus compounds which inhibit $\alpha_V\beta_3$ would find usefulness as antiviral agents.

SUMMARY OF THE INVENTION

The compounds of this invention are 1) $\alpha_V\beta_3$ integrin antagonists; or 2) $\alpha_V\beta_5$ integrin antagonists; or 3) mixed or dual $\alpha_V\beta_3/\alpha_V\beta_5$ antagonists. The present invention includes compounds which inhibit the respective integrins and also includes pharmaceutical compositions comprising such compounds. The present invention further provides for methods for treating or preventing conditions mediated by the $\alpha_V\beta_3$ and/or $\alpha_V\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

Further, it has been found that the selective antagonism of the $\alpha_V\beta_3$ integrin is desirable in that the $\alpha_V\beta_6$ integrin may play a role in normal physiological processes of tissue repair and cellular turnover that routinely occur in the skin and pulmonary tissue, and $\alpha_V\beta_8$ may play a role in the regulation of growth in the human pathway. Therefore, compounds which selectively inhibit the $\alpha_V\beta_3$ integrin as opposed to the $\alpha_V\beta_6$ and/or the $\alpha_V\beta_8$ integrin have reduced side-effects associated with inhibition of the $\alpha_V\beta_6$ and/or the $\alpha_V\beta_8$ integrin. It is therefore another object of the present invention to provide compounds that are selective antagonists of $\alpha_V\beta_3$ and/or $\alpha_V\beta_5$ as opposed to $\alpha_V\beta_6$, and it is yet another object of the present invention to provide compounds that are selective antagonists of $\alpha_V\beta_3$ and/or $\alpha_V\beta_5$ as opposed to $\alpha_V\beta_8$.

It is a further object of the present invention to provide methods for treating or preventing conditions mediated by the $\alpha_V\beta_3$ and/or $\alpha_V\beta_5$ receptors in a patient in need of such treatment using compounds that have selectivity for the $\alpha_V\beta_3$ and/or $\alpha_V\beta_5$ integrin over the $\alpha_V\beta_6$ integrin.

The present invention relates to a class of compounds represented by the Formula I

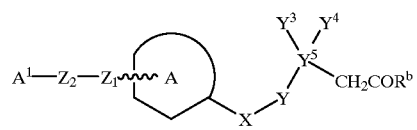

or a pharmaceutically acceptable salt thereof, wherein

is a 4–8 membered monocyclic or a 7–12 membered bicyclic ring, containing 1 to 5 heteroatoms, selected from the group consisting of O, N or S; optionally saturated or unsaturated, optionally substituted with one or more substituents selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)_m COR$ wherein m is 0–2 and R is hydroxy, alkoxy, alkyl or amino; with the proviso that when $Y^4$ in formula I is H, the ring A may not be an oxazole, with X—Y containing side-chain connected at the carbon-2 as in

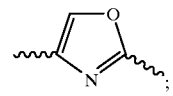

The ring A may further contain a carboxamide, sulfone, sulfonamide or an acyl group.

$A^1$ is a 5–9 membered monocyclic or 8–14 membered polycyclic heterocycle of the formula

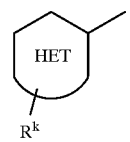

containing at least one nitrogen atom and optionally 1 to 4 heteroatoms or groups, selected from O, N, S, $SO_2$ or CO; optionally saturated or unsaturated; optionally substituted by one or more $R^k$ selected from the group consisting of hydroxy, alkyl, alkoxy, alkoxyalkyl, thioalkyl, haloalkyl, cyano, amino, alkylamino, halogen, acylamino, sulfonamide and —COR wherein R is hydroxy, alkoxy, alkyl or amino;
or $A^1$ is

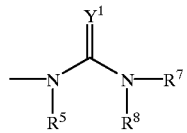

wherein $Y^1$ is selected from the group consisting of N—$R^2$, O, and S;

$R^2$ is selected from the group consisting of H; alkyl; aryl; hydroxy; alkoxy; cyano; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4–12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester;

or $R^2$ taken together with $R^7$ forms a 4–12 membered heterocycle containing one or more heteroatom selected from O, N and S optionally unsaturated;

or $R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H and alkyl;
or
$A^1$ is

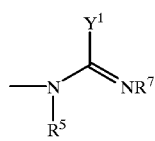

wherein $Y^2$ is selected from the group consisting of alkyl; cycloalkyl; bicycloalkyl; aryl; monocyclic heterocycles;

$Z_1$ is selected from the group consisting of $CH_2$, $CH_2O$, O, NH, CO, S, SO, CH(OH) and $SO_2$;

$Z_2$ is a 1–5 carbon linker optionally containing one or more heteroatom selected from the group consisting of O, S and N;

alternatively $Z_1$–$Z_2$ may further contain a carboxamide, sulfone, sulfonamide, alkenyl, alkynyl, or acyl group;

wherein the carbon and nitrogen atoms of $Z_1$–$Z_2$ are optionally substituted by alkyl, alkoxy, thioalkyl, alkylsulfone, aryl, alkoxyalkyl, hydroxy, alkylamino, heteroaryl, alkenyl, alkynyl, carboxyalkyl, halogen, haloalky or acylamino;

Additionally, $Z_1$–$Z_2$ may contain a 5- or 6-membered aryl or heteroaryl ring optionally substituted with $R^c$, wherein the heteroaryl ring may contain 1–3 heteroatoms selected from the group consisting of O, N and S; $R^c$ is selected from the group consisting of H, alkyl, haloalkyl, aryl, heteroaryl, halogen, alkoxyalkyl, aminoalkyl, hydroxy, alkoxy, carboxamide, or cyano.

X is selected from the group consisting of —$CHR^e$—, —$NR^f$—, —O—, —S—, —$SO_2$—, and —CO— wherein $R^e$ is H, lower alkyl, alkoxy, cycloalkyl, alkoxyalkyl, hydroxy, alkynyl, alkenyl, haloalkyl, thioalkyl or aryl; wherein when $R^e$ is hydroxy, the hydroxy group can optionally form a lactone with the carboxylic acid function of the chain; wherein $R^f$ is selected from the group consisting of H, alkyl, aryl, aralkyl, and haloalkyl;

Y is selected from the group consisting of $(CH_2)_p$, —$CHR^g$—, —$NR^g$—, CO and $SO_2$, wherein $R^g$ is selected from the group consisting of H, alkyl, haloalkyl, alkoxyalkyl, alkynyl, aryl, heteroaryl, aralkyl, hydroxy, alkoxy, and carboxyalkyl; wherein p is 0 or 1.

optionally the group X—Y can contain a moiety selected from the group consisting of acyl, alkyl, sulfonyl, amino, ether, thioether, carboxamido, sulfonamido, aminosulfonyl and olefins;

$Y^3$ and $Y^4$ are independently selected from the group consisting of H, alkyl, haloalkyl, halogen, aryl, arakyl, heteroaralkyl, heteroaryl, hydroxyalkyl, alkenes, and alkyne; wherein the alkyl chain may be straight or branched and optionally containing one or more heteroatoms selected from the group consisting of N, O, and S, and may further contain a sulfone, sulfonamide, nitrile, carboxamide, carboalkoxy or carboxyl group; wherein aryl and heteroaryl rings may be monocyclic or bicylic optionally containing 1–5 heteroatoms and wherein said ring may be saturated or unsaturated, and such rings may optionally be substituted by one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)_m COR$ wherein m is 0–2 and R is hydroxy, alkoxy, alkyl or amino;

With the proviso that when $Y^3$ or $Y^4$ is H, $Y^5$ may be C or N, otherwise $Y^5$ is C;

or $Y^3$ taken together with forms a 3–8 membered monocyclic or a 7–11 membered bicyclic ring B,

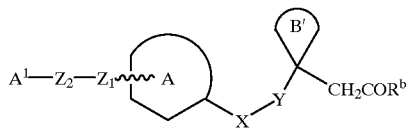

IA optionally containing one or more double bonds, optionally containing one or more heteroatom or functional group selected from O, NR$^g$, S, CO or SO$_2$, optionally substituted with one or more substituent selected from the group consisting of alkyl, hydroxy, halogen, haloalkyl, alkoxy, alkyne, cyano, alkylsulfone, sulfonamide, carboalkoxy and carboxyalkyl;

or X taken together with Y$^3$ forms a 3–7 membered monocyclic ring C,

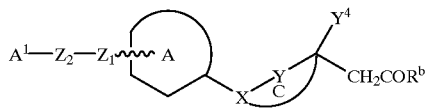

IB optionally containing one or more double bonds, optionally containing one or more heteroatom or functional group selected from O, NR$^g$, S, CO or SO$_2$, optionally substituted with one or more substituent selected from the group consisting of alkyl, halogen, alkoxy, haloalkyl, hydroxyalkyl, or alkoxyalkyl;

R$^b$ is X$_2$—R$^h$ wherein X$_2$ is selected from the group consisting of O, S and NR$^j$ wherein R$^h$ and R$^j$ are independently selected from the group consisting of H, alkyl, aryl, aralkyl, acyl and alkoxyalkyl; and It is another object of the invention to provide pharmaceutical compositions comprising compounds of the Formula 1. Such compounds and compositions are useful in selectively inhibiting or antagonizing the α$_v$β$_3$ and/or α$_v$β$_5$ integrins and therefore in another embodiment the present invention relates to a method of selectively inhibiting or antagonizing the α$_v$β$_3$ and/or α$_v$β$_5$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials. The compounds of the present invention may be used alone or in combination with other pharmaceutical agents.

DETAILED DESCRIPTION

The present invention relates to a class of compounds represented by the Formula I, described above.

In another embodiment of the present invention

is a heteroaryl substituted by one or more substituents selected from lower alkyl, alkynyl, alkenyl, halogen, alkoxy, hydroxy, cyano, amino, alkylamino, dialkylamino or methylsulfonamide. More specifically, some examples of heteroaryl include oxadiazole, pyridine, pyrimidine, imidazole, thiadiazole, triazole, tetrazole, and thiazole.

Other embodiments of

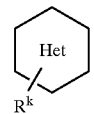

include the following heterocyclic ring systems containing at least one nitrogen atom:

B2

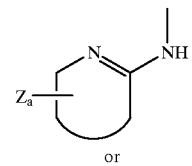

or

B3

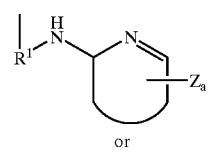

or

B4

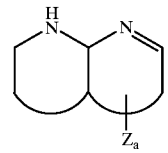

wherein Z$_a$ is H, alkyl, alkoxy, hydroxy, amine, alkylamine, dialkylamine, carboxyl, alkoxycarbonyl, hydroxyalkyl, halogen or haloalkyl and R$^1$ is H, alkyl, alkoxyalkyl, acyl, haloalkyl or alkoxycarbonyl. More specifically some examples include pyridylamino, imidazolylamino, morpholinopyridine, tetrahydronaphthyridine, oxazolylamino, thiazolylamino, pyrimidinylamino, quinoline, tetrahydroquinoline, imidazopyridine, benzimidazole, pyridone or quinolone.

The following heteroaryls include the ring systems described above.

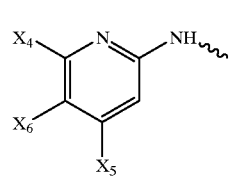 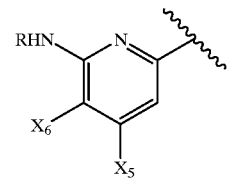

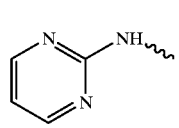 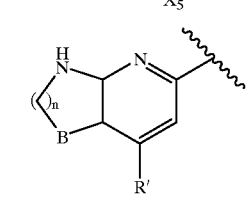

B = CH$_2$, O, CO, S, CF$_2$, SO$_2$, NR
R' = OR, OH, H, Me  n = 1 or 2

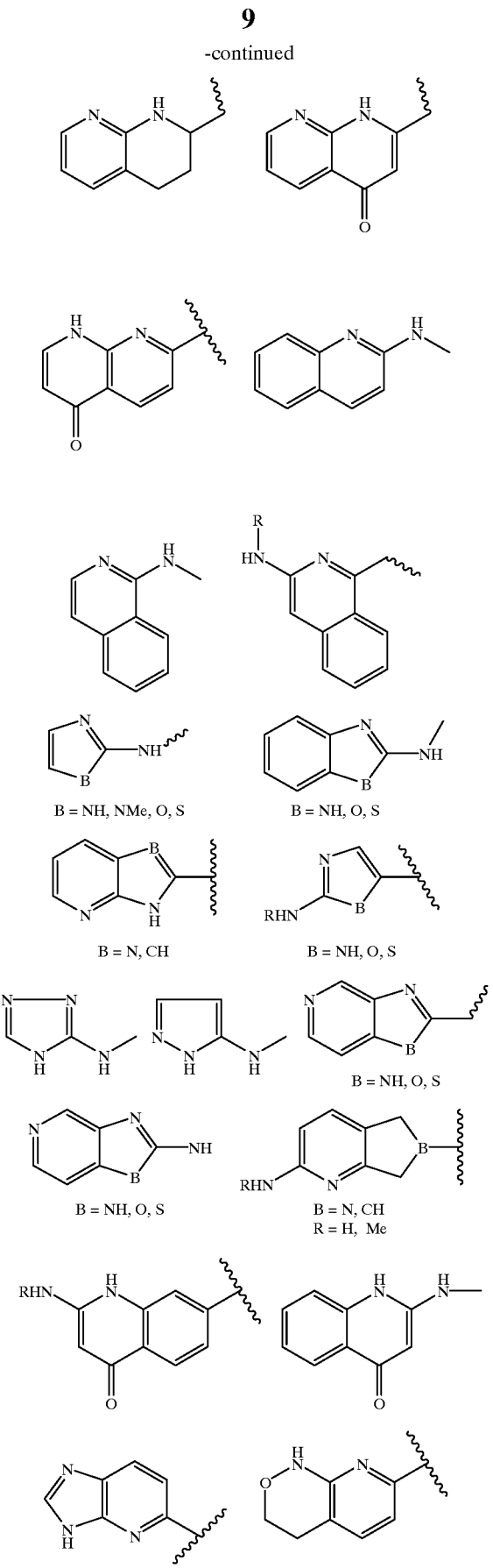
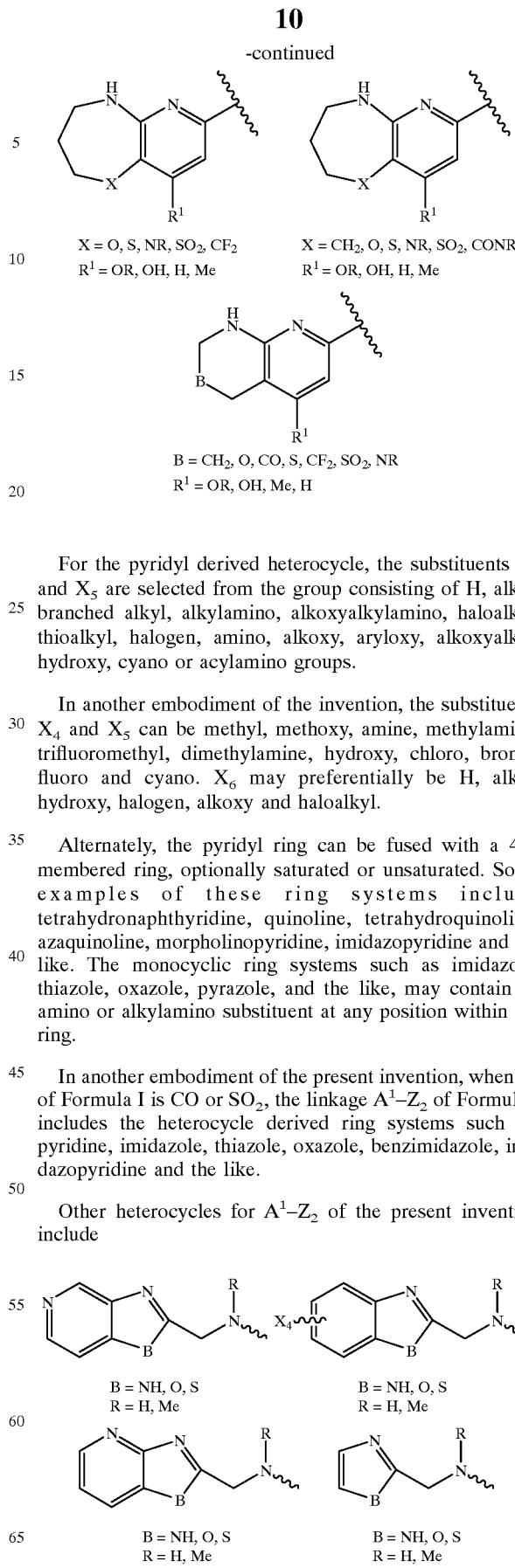

For the pyridyl derived heterocycle, the substituents $X_4$ and $X_5$ are selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano or acylamino groups.

In another embodiment of the invention, the substituents $X_4$ and $X_5$ can be methyl, methoxy, amine, methylamine, trifluoromethyl, dimethylamine, hydroxy, chloro, bromo, fluoro and cyano. $X_6$ may preferentially be H, alkyl, hydroxy, halogen, alkoxy and haloalkyl.

Alternately, the pyridyl ring can be fused with a 4–8 membered ring, optionally saturated or unsaturated. Some examples of these ring systems include tetrahydronaphthyridine, quinoline, tetrahydroquinoline, azaquinoline, morpholinopyridine, imidazopyridine and the like. The monocyclic ring systems such as imidazole, thiazole, oxazole, pyrazole, and the like, may contain an amino or alkylamino substituent at any position within the ring.

In another embodiment of the present invention, when $Z_1$ of Formula I is CO or $SO_2$, the linkage $A^1$–$Z_2$ of Formula I includes the heterocycle derived ring systems such as: pyridine, imidazole, thiazole, oxazole, benzimidazole, imidazopyridine and the like.

Other heterocycles for $A^1$–$Z_2$ of the present invention include

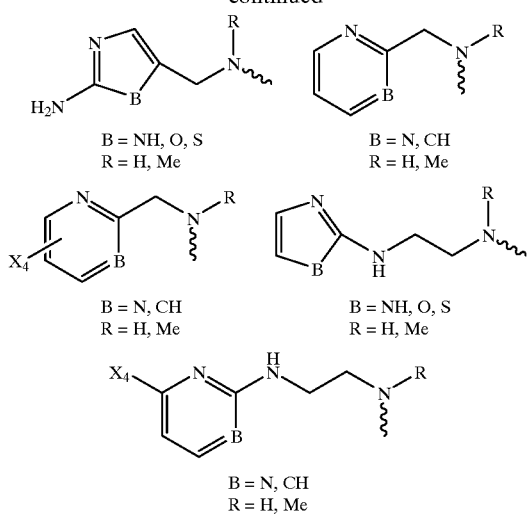

B = NH, O, S
R = H, Me

B = N, CH
R = H, Me

B = N, CH
R = H, Me

B = NH, O, S
R = H, Me

B = N, CH
R = H, Me wherein $X_4$ is as defined above.

In another embodiment, $Y^3$ or $Y^4$ is an aryl or a heteroaryl group selected from phenyl, benzofuran, benzothiophene, indole, quinoline, isoquinoline, benzimidazole, benzoxazole, 1,3-benzodioxole, 1,4-benzodioxane, benzopyran, quinolone, imidazopyridine, tetrahydroquinoline, benzotriazole, dihydroindole, dihydrobenzofuran, furan, thiophene, phenyl, oxazole, thiazole, isoxazole, pyrazole, imidazole, pyrrole, pyridine, pyrimidine, pyridone, triazole, thiadiazole and the like. The aryl system can be optionally substituted at one or more positions with alkyl, alkoxy, hydroxy, cyano, halogen or haloalkyl.

In another embodiment of the present invention, $Y^3$ or $Y^4$ may be an amine, alkylamine, acylamine, aminosulfone ($NHSO_2R$), arylamine, alkoxyalkylamine, aralkylamine, or heterocyclic amine.

In another embodiment of the present invention, $Y^3$ taken together with $Y^4$ forms a 3–8 membered monocyclic or a 7–11 membered bicyclic ring B,

IA

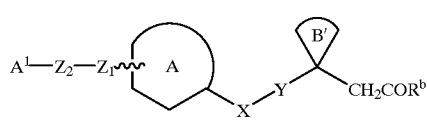

optionally containing one or more double bonds, optionally containing one or more heteroatoms or functional groups selected from O, $NR^g$, S, CO or $SO_2$, optionally substituted with one or more substituent selected from the group consisting of alkyl, haloalkyl, halogen, haloalkyl, alkoxy, alkyne, cyano, alkylsulfone, sulfonamide, carboalkoxy and carboxyalkyl; wherein $R^g$ is selected from the group consisting of H, alkyl, haloalkyl, alkoxyalkyl, aryl, heteroaryl, aralkyl, and carboxyalkyl.

In another embodiment of the present invention, X taken together with $Y^3$ forms a 3–7 membered monocyclic ring C,

IB

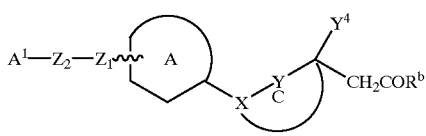

optionally containing one or more double bonds, optionally containing one or more heteroatom or functional group selected from O, $NR^g$, S, CO or $SO_2$, optionally substituted with one or more substituent selected from the group consisting of alkyl, halogen, alkoxy, haloalkyl, hydroxyalkyl, or alkoxyalkyl; wherein $R^g$ is selected from the group consisting of H, alkyl, haloalkyl, alkoxyalkyl, aryl, heteroaryl, aralkyl, and carboxyalkyl.

The invention further relates to pharmaceutical compositions containing therapeutically effective amounts of the compounds of Formula I.

The invention also relates to a method of selectively inhibiting or antagonizing the $\alpha_v\beta_3$ integrin and/or the $\alpha_v\beta_5$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, smooth muscle cell migration and restenosis by administering a therapeutically effective amount of a compound of the Formula I to achieve such inhibition together with a pharmaceutically acceptable carrier. More specifically it has been found that it is advantageous to administer compounds which are $\alpha_v\beta_3$ and/or $\alpha_v\beta_5$ selective and that such selectivity is beneficial in reducing unwanted side-effects.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula

The terms "hydroxy" and "hydroxyl" as used herein are synonymous and are represented by a radical of the formula

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula $-OR^{20}$, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

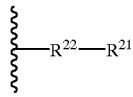

wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "nitro" is represented by a radical of the formula

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl ester" refers to a radical of the formula $-COOR^{23}$ wherein $R^{23}$ is selected from the group consisting of H, alkyl, aralkyl or aryl as defined above.

As used herein the term "carboxyl derivative" refers to a radical of the formula

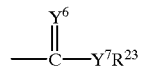

wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula $-NH_2$.

As used herein the term "alkylsulfonyl" or "alkylsulfone" refers to a radical of the formula

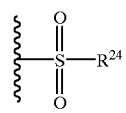

wherein $R^{24}$ is alkyl as defined above.

As used herein the term "alkylthio" refers to a radical of the formula $-SR^{24}$ wherein $R^{24}$ is alkyl as defined above.

As used herein the term "sulfonic acid" refers to a radical of the formula

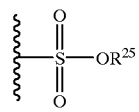

wherein $R^{25}$ is alkyl as defined above.

As used herein the term "sulfonamide" or "sulfonamido" refers to a radical of the formula

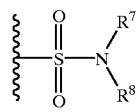

wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl and the like.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

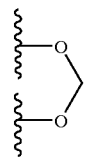

and the term "ethylenedioxy" refers to the radical

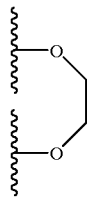

As used herein the term "4–12 membered dinitrogen containing heterocycle refers to a radical of the formula

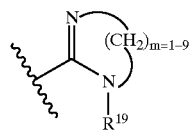

wherein m is 1 or 2 and $R^{19}$ is H, alkyl, aryl, or aralkyl and more preferably refers to 4–9 membered ring and includes rings such as imidazoline.

As used herein the term "5-membered optionally substituted heteroaromatic ring" includes for example a radical of the formula

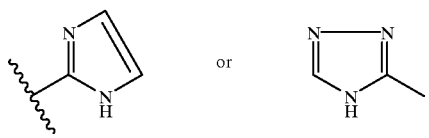

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

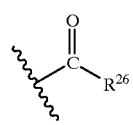

wherein $R^{26}$ is alkyl, alkenyl, alkynyl, aryl or aralkyl and optionally substituted thereon as defined above. Encompassed by such radical are the groups acetyl, benzoyl and the like.

As used herein the term "thio" refers to a radical of the formula

As used herein the term "sulfonyl" refers to a radical of the formula

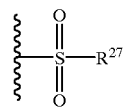

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

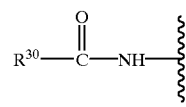

wherein $R^{30}$ is alkyl, aralkyl or aryl as defined above.

As used herein the term "amido" refers to a radical of the formula

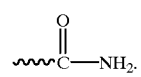

As used herein the term "alkylamino" refers to a radical of the formula —NH$R^{32}$ wherein $R^{32}$ is alkyl as defined above.

As used herein the term "dialkylamino" refers to a radical of the formula —N$R^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

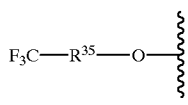

wherein $R^{35}$ is a bond or an alkylene as defined above.

As used herein the term "alkylaminosulfonyl" or "aminosulfonyl" refers to a radical of the formula

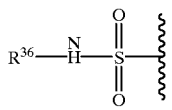

wherein $R^{36}$ is alkyl as defined above.

As used herein the term "alkylsulfonylamino" or "alkylsulfonamide" refers to a radical of the formula

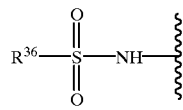

wherein $R^{36}$ is alkyl as defined above.

As used herein the term "trifluoromethylthio" refers to a radical of the formula

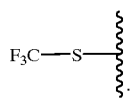

As used herein the term "trifluoromethylsulfonyl" refers to a radical of the formula

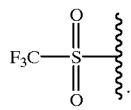

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

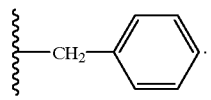

As used herein the term "phenethyl" refers to the radical

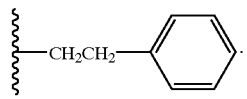

As used herein the term "4–12 membered mono-nitrogen containing monosulfur or monooxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

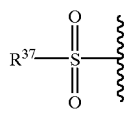

wherein $R^{37}$ is aryl as defined above.

As used herein the terms "alkylsulfoxide" or "arylsulfoxide" refer to radicals of the formula

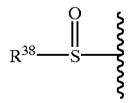

wherein $R^{38}$ is, respectively, alkyl or aryl as defined above.

As used herein the term "arylthio" refers to a radical of the formula

wherein $R^{42}$ is aryl as defined above.

As used herein the term "monocyclic heterocycle thio" refers to a radical of the formula

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

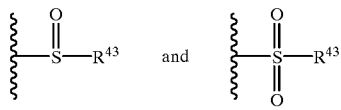

wherein $R^{43}$ is a monocyclic heterocycle radical as defined above.

As used herein the term "alkylcarbonyl" refers to a radical of the formula

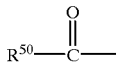

wherein $R^{50}$ is alkyl as defined above.

As used herein the term "arylcarbonyl" refers to a radical of the formula

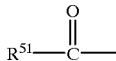

wherein $R^{51}$ is aryl as defined above.

As used herein the term "alkoxycarbonyl" refers to a radical of the formula

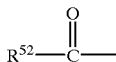

wherein $R^{52}$ is alkoxy as defined above.

As used herein the term "aryloxycarbonyl" refers to a radical of the formula

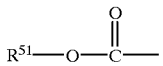

wherein $R^{51}$ is aryl as defined above.

As used herein the term "haloalkylcarbonyl" refers to a radical of the formula

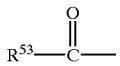

wherein $R^{53}$ is haloalkyl as defined above.

As used herein the term "haloalkoxycarbonyl" refers to a radical of the formula

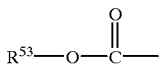

wherein $R^{53}$ is haloalkyl as defined above.

As used herein the term "alkylthiocarbonyl" refers to a radical of the formula

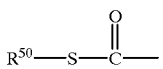

wherein $R^{50}$ is alkyl as defined above.

As used herein the term "arylthiocarbonyl" refers to a radical of the formula

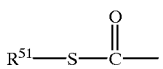

wherein $R^{51}$ is aryl as defined above.

As used herein the term "acyloxymethoxycarbonyl" refers to a radical of the formula

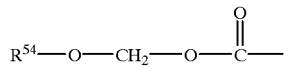

wherein $R^{54}$ is acyl as defined above.

As used herein the term "arylamino" refers to a radical of the formula $R^{51}$—NH— wherein $R^{51}$ is aryl as defined above.

As used herein the term "acyloxy" refers to a radical of the formula $R^{55}$—O— wherein $R^{55}$ is acyl as defined above.

As used herein the term "alkenylalkyl" refers to a radical of the formula $R^{50}$—$R^{57}$— wherein $R^{50}$ is an alkenyl as defined above and $R^{57}$ is alkylene as defined above.

As used herein the term "alkenylene" refers to a linear hydrocarbon radical of 1 to about 8 carbon atoms containing at least one double bond.

As used herein the term "alkoxyalkyl" refers to a radical of the formula $R^{56}$—$R^{57}$— wherein $R^{56}$ is alkoxy as defined above and $R^{57}$ is alkylene as defined above.

As used herein the term "alkynylalkyl" refers to a radical of the formula $R^{59}$—$R^{60}$— wherein $R^{59}$ is alkynyl as defined as above and $R^{60}$ is alkylene as defined as above.

As used herein the term "alkynylene" refers to divalent alkynyl radicals of 1 to about 6 carbon atoms.

As used herein the term "allyl" refers of a radical of the formula —$CH_2CH=CH_2$.

As used herein the term "aminoalkyl" refers to a radical of the formula $H_2N$—$R^{61}$ wherein $R^{61}$ is alkylene as defined above.

As used herein the term "benzoyl" refers to the aryl radical $C_6H_5$—CO—.

As used herein the term "carboxamide" or "carboxamido" refer to a radical of the formula —CO—$NH_2$.

As used herein the term "carboxyalkyl" refers to a radical HOOC—$R^{62}$— wherein $R^{62}$ is alkylene as defined as above.

As used herein the term "carboxylic acid" refers to the radical —COOH

As used herein the term "ether" refers to a radical of the formula $R^{63}$—O— wherein $R^{63}$ is selected from the group consisting of alkyl, aryl and heteroaryl.

As used herein the term "haloalkylsulfonyl" refers to a radical of the formula

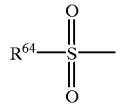

wherein the $R^{64}$ is haloalkyl as defined above.

As used herein the term "heteroaryl" refers to an aryl radical contain at least one heteroatom.

As used herein the term "hydroxyalkyl" refers to a radical of the formula HO—$R^{65}$— wherein $R^{65}$ is alkylene as defined above.

As used herein the term "keto" refers to a carbonyl group joined to 2 carbon atoms.

As used herein the term "lactone" refers to an anhydro cyclic ester produced by intramolecular condensation of a hydroxy acid with the elimination of water.

As used herein the term "olefin" refers to an unsaturated hydrocarbon radical of the type $C_nH_{2n}$.

As used herein the term "sulfone" refers to a radical of the formula $R^{66}$—$SO_2$—.

As used herein the term "thioalkyl" refers to a radical of the formula $R^{77}$—S— wherein $R^{77}$ is alkyl as defined above.

As used herein the term "thioether" refers to a radical of the formula $R^{78}$—S— wherein $R^{78}$ is alkyl, aryl or heteroaryl.

As used herein the term "trifluoroalkyl" refers to an alkyl radical as defined above substituted with three halo radicals as defined above.

The term "composition" as used herein means a product which results from the mixing or combining of more than one element or ingredient.

The term "pharmaceutically acceptable carrier", as used herein means a pharmaceutically acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
BOC=tert-butoxycarbonyl
BuLi=butyl lithium
Cat.=catalytic amount
CDI=Carbonyldiimidazole
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DEAD=diethylazodicarboxylate
DIAD=diisopropylazodicarboxylate
DI water=deionized water
DMA=N,N-dimethylacetamide
DMAC=N,N-dimethylacetamide
DMF=N,N-dimethylformamide
EDC=1-(3-dimethylaminopropyl)-3-ethylcarbodiimide hydrochloride
Et=ethyl
$Et_2O$=diethyl ether
$Et_3N$=triethylamine
EtOAc=ethyl acetate
EtOH=ethanol
FAB MS=fast atom bombardment mass spectroscopy
g=gram(s)
HOBT=1-hydroxybenzotriazole hydrate
HPLC=high performance liquid chromatography
i-Pr=iso propyl
i-Prop=iso propyl
$K_2CO_3$=potassium carbonate
$KMnO_4$=potassium permanganate
KOH=potassium hydroxide
KSCN=potassium thiocyanate
L=Liter
LiOH=lithium hydroxide
Me=methyl
MeOH=methanol
mg=milligram
$MgSO_4$=magnesium sulfate
ml=milliliter
mL=milliliter
MS=mass spectroscopy
NaH=sodium hydride
$NaHCO_3$=sodium bicarbonate
NaOH=sodium hydroxide
NaOMe=sodium methoxide
$NH_4^+HCO_2^-$=ammonium formate
NMR=nuclear magnetic resonance
Pd=palladium
Pd/C=palladium on carbon
Ph=phenyl
Pt=platinum
Pt/C=platinum on carbon
RPHPLC=reverse phase high performance liquid chromatography
RT=room temperature
t-BOC=tert-butoxycarbonyl
TFA=trifluoroacetic acid
THF=tetrahydrofuran
TLC=thin layer chromatography
TMS=trimethylsilyl
Δ=heating the reaction mixture The compounds as shown above can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I with an acid whose anion is generally considered suitable for human consumption. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid. Representative salts include the following: benzenesulfonate, hydrobromide and hydrochloride. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. All of the pharmacologically acceptable salts may be prepared by conventional means. (See Berge et al., *J Pharm. Sci.*, 66(1), 1–19 (1977) for additional examples of pharmaceutically acceptable salts.)

The compounds of the present invention can have chiral centers and occur as racemates, racemic mixtures, diastereomeric mixtures, and as individual diastereomers or enantiomers, with all isomeric forms included in the present invention. Therefore, where a compound is chiral, the separate enantiomers or diastereomers, substantially free of the other, are included within the scope of the present invention;

further included are all mixtures of the enantiomers or diastereomers. Also included within the scope of the invention are polymorphs, or hydrates or other modifiers of the compounds of invention.

The present invention includes within its scope prodrugs of the compounds of this invention. In general, such prodrugs will be functional derivatives of the compounds of this invention which are readily convertible in vivo into the required compound. For example, prodrugs of a carboxylic acid may include an ester, an amide, or an ortho-ester. Thus, in the methods of treatment of the present invention, the term "administering" shall encompass the treatment of the various conditions described with the compound specifically disclosed or with a compound which may not be specifically disclosed, but which converts to the compound of Formula I in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

For the selective inhibition or antagonism of $\alpha_v\beta_3$ and/or $\alpha_v\beta_5$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, transmuscular infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ and/or $\alpha_v\beta_5$ cell surface receptor which method comprises administering a therapeutically effective amount of a compound selected from the class of compounds depicted in the above formulas, wherein one or more compound is administered in association with one or more non-toxic, pharmaceutically acceptable carriers and/or diluents and/or adjuvants (collectively referred to herein as "carrier" materials) and if desired other active ingredients.

In another embodiment, the present invention provides a method for selective antagonism of the $\alpha_v\beta_3$ and/or $\alpha_v\beta_5$ cell surface receptors over $\alpha_{IIb}\beta_3$, and in a further embodiment, also over the $\alpha_v\beta_6$ integrin receptor.

It has not been recognized that inhibitors of $\alpha_v\beta_3$ or $\alpha_v\beta_5$ should possess selectivity based on the $\beta$-integrin. However, evidence of the toxicity of $\beta_6$ integrin antagonism indicates that it may be beneficial to spare antagonism of $\beta_6$ when designing $\alpha_v\beta_3$ antagonists.

The inhibition of the integrin $\alpha_v\beta_6$ has been found to result in the decreased activation of endogenous TGF-$\beta$1 with loss of its negative immunoregulatory properties, and thus causes inflammatory infiltrates to aggregate in many tissues, causing inflammatory lesions and fibrosis (Munger et al. 1999, *Cell* 96, 319). Targeted disruption of the TGF-$\beta$1 gene in mice results in marked infiltration of inflammatory cells in multiple tissues (including the lungs), and $\alpha_v\beta_6$ appears to be an essential regulator of TGF-$\beta$1 activation in the lungs (Shull et al. 1992, *Nature* 359, 693, Kulkarni et al., 1993 *Proc Natl Acad Sci. USA* 90, 770). This observation is further supported by the fact that mice with a targeted disruption of the $\beta_6$ gene have inflammatory infiltrates in the skin and lungs (Böttinger et al. 1997, *Kidney Int.* 51, 1355). Table 1 provides examples of compounds that exhibit selectivity of $\alpha_v\beta_3$ over $\alpha_v\beta_6$. Table 1 further provides examples of compounds that exhibit selectivity of $\alpha_v\beta_3$ over $\alpha_{IIb}\beta_3$.

Selectivite inhibition refers to a selectivity ratio of at least 10, more preferably 50, and even more preferably of at least 100. Selectivity ratio refers to the selectivity of the IC 50 of $\alpha_v\beta_6$ or $\alpha_{IIb}\beta_3$ over the selectivity of the IC$_{50}$ of $\beta_3$.

TABLE 1

Potency and Selectivity Data for selected compounds

| Example #. | 293-β3 (IC$_{50}$ <10 μM) | HT-29 β-6 Selectivity* (β6/β3) | SPRA AIIbB3 Selectivity* IIbIIIa/β3 |
|---|---|---|---|
| 62 | + | +++ | +++ |
| 36 | + | +++ | +++ |
| 38 | + | +++ | +++ |
| 39 | + | ++ | ++ |
| 42 | + | +++ | +++ |
| 57 | + | +++ | +++ |
| 40 | + | ++ | +++ |
| 4 | + | +++ | ++ |
| 37 | + | ++ | ++ |
| 41 | + | +++ | ++ |
| 69 | + | +++ | ++ |
| 35 | + | +++ | ++ |
| 21 | + | +++ | ++ |
| 19 | + | +++ | ++ |
| 17 | + | +++ | ++ |
| 23 | + | +++ | ++ |
| 25 | + | +++ | ++ |
| 27 | + | +++ | +++ |
| 29 | + | +++ | +++ |
| 12 | + | +++ | +++ |
| 43 | + | +++ | +++ |
| 44 | + | +++ | +++ |
| 46 | + | +++ | +++ |
| 47 | + | +++ | +++ |
| 51 | + | +++ | +++ |
| 45 | + | ++ | ++ |
| 50 | + | +++ | +++ |
| 70 | + | +++ | +++ |
| 34 | + | +++ | +++ |
| 20 | + | +++ | +++ |
| 18 | + | +++ | +++ |
| 16 | + | +++ | +++ |
| 22 | + | +++ | +++ |
| 32 | + | +++ | +++ |
| 24 | + | +++ | +++ |
| 26 | + | +++ | +++ |
| 28 | + | +++ | +++ |

Selectivity Ratio of 10–100 ++
Selectivity Ratio >100 +++

It is another object of the present invention to provide methods for treating or preventing conditions mediated by the $\alpha_v\beta_3$ and/or $\alpha_v\beta_5$ receptors in a mammal in need of such treatment using compounds that have selectivity for the $\alpha_v\beta_3$ and/or $\alpha_v\beta_5$ integrin over the $\alpha_v\beta_6$ integrin.

The present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating retinopathy including macular degeneration and diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Some in vivo models of angiogenesis include the CAM (chick chorioallantoic membrane) assay (Vu et al., Lab Invest 1985, 53, 4), the gelatin sponge/chorioallantoic membrane assay (Ribatti et al., J. Vasc. Res. 1997, 34, 6), the rabbit corneal micropocket assay (Gimbrone et al., J Natl Cancer Inst 52, 413) and the insertion of tumor cells in mice (Robertson et al., Cancer Res. 1999, 51, 1339). For a review of angiogenesis assays, see Auerbach et al., Pharmacol Ther 1991, 51, 1.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ and/or $\alpha_v\beta_5$ integrin plays a role.

The compounds of the invention may also be used in combination therapies. For instance, an $\alpha_v\beta_3$ inhibitor may be administered with a cytotoxic agent such as a toxin, radionuclide, or a chemotherapeutic to promote tumor regression.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 1.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regiment.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes 1–12. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention.

SCHEME 1

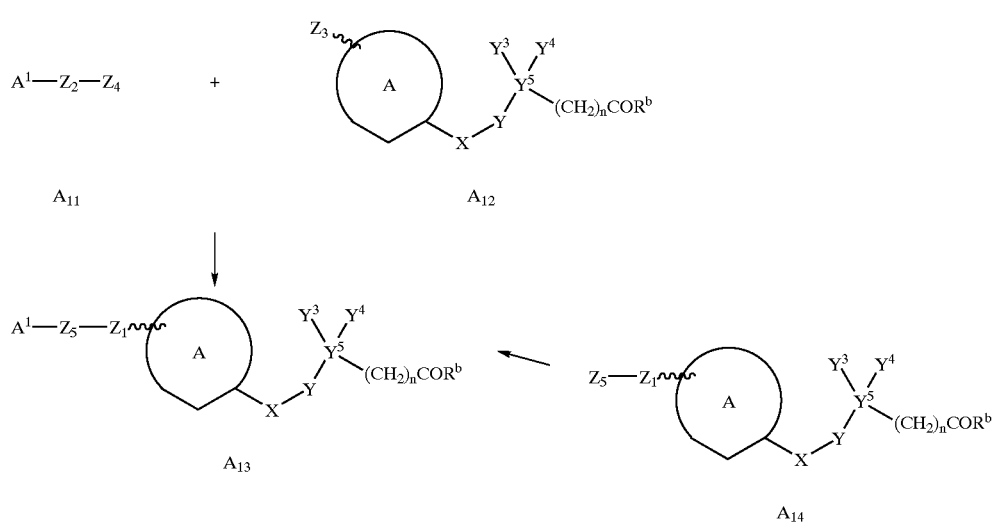

Scheme 1

The compounds of formula $A_{13}$, wherein the ring A is preferentially a 6-member heteroaryl or a bicyclic heteroaryl, can be prepared by reacting an intermediate of formula $A_{11}$ with a compound of the formula $A_{12}$. For example, when $Z_3$ is OH, SH or NHR, $A_{12}$ may be alkylated with $A_{11}$ ($Z_4$=Br or OMs) using base such as (sodium hydride, potassium hydride) preferably in a solvent such as dimethylsulfoxide or DMF. These reactions may preferentially be carried at 0° C. to approx. 40° C. Alternately, when $Z_3$ and $Z_4$ are both OH, the ether formation to product $A_{13}$ may be accomplished by using Mitsunobu reaction. This reaction may preferentially be carried out using triarylphosphine (such as triphenylphoshine) and azodicarboxylate (such as diethyl azodicarboxylate, di-tert-butyl azodicarboxylate, diisopropyl azodicarboxylate) in solvents such as DMF, methylene chloride, THF and the like. When $Z_3$ carries a carboxylic acid and $Z_4$ is an amine, the standard coupling conditions may be used to synthesize the carboxamide (CONH) containing targets $A_{13}$.

Alternately, the compounds of formula $A_{13}$ may be prepared by starting with compounds of general formula $A_{14}$. For example, when $Z_5$ in $A_{14}$ is $NH_2$, cyclic or acyclic guanidino containing compounds of formula $A_{13}$ may be synthesized by adopting the methodologies discussed in e.g. U.S. Pat. No. 5,852, 210, U.S. Pat. No. 5,773,646. Similarly, compounds of formula $A_{14}$ ($Z_5$=CHO) may be treated with amino containing heteroaromatic system (such as 2-aminopyridine) to give the target compounds $A_{13}$. This reaction may preferentially be carried out by reductive amination procedures using reducing agents such as sodium triacetoxyborohydride, sodium cyanoborohydride or sodium borohydride.

SCHEME 2

$A^1$—$Z_2$—$Z_1$—CN ⟶
$A_{15}$

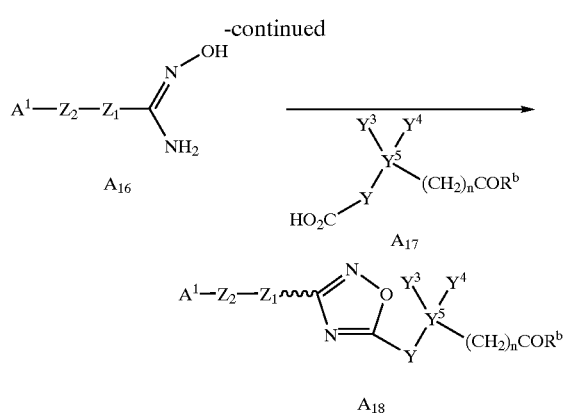

Scheme 2

Compounds of the formula $A_{18}$ containing an oxadiazole ring may be prepared by starting with intermediates $A_{15}$. The reaction of $A_{15}$ with hydroxylamine hydrochloride in the presence of base (such as sodium methoxide, sodium ethoxide) using solvents such as methanol, ethanol gives the amidoxime intermediate $A_{16}$. The reaction of $A_{16}$ with a carboxylic acid containing intermediate $A_{17}$ in the presence of a coupling reagent such as carbonyldiimidazole gives the compounds of formula $A_{18}$.

SCHEME 3

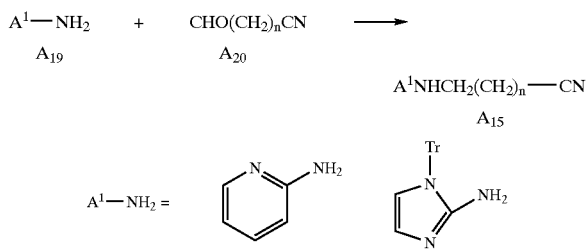

-continued

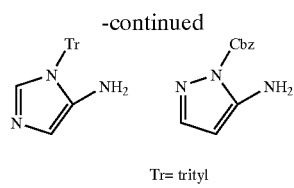

Tr= trityl

Scheme 3

Intermediates of the formula $A_{15}$ (scheme 2), containing a heteroarylamine can be prepared as shown in scheme 3. The reductive amination of arylamine ($A_{19}$) with an aliphatic aldehyde ($A_{20}$) gives the intermediate $A_{15}$ containing the aliphatic chain. This reaction may preferentially be carried out by using sodium triacetoxyborohydride, sodium cyanoborohydride or sodium borohydride as reducing agent and using methyene chloride, ethyl alcohol or tetrahydrofuran as solvent. Commercially accessible heteroarylamine such as 2-amnopyridine could be used directly. In certain cases, protected heteroaryls such as imidazole and pyrazole derived amines may be used as shown above. The reaction described in scheme 3 may also be used to synthesize other variants of $Z_1$–$Z_2$ in $A_{15}$ (scheme 2)

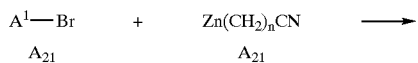

-continued

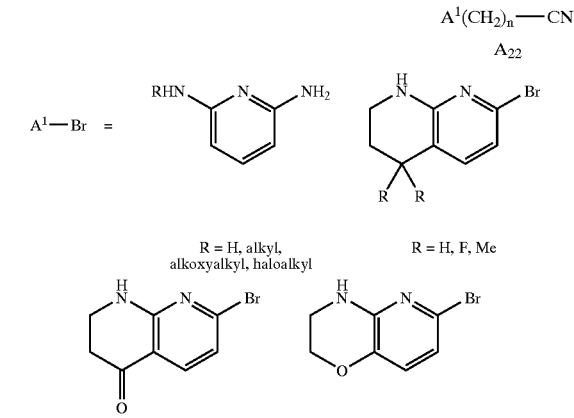

Scheme 4

Intermediates of the formula $A_{15}$ (Scheme 2), containing an aliphatic chain may be prepared by reacting the heteroaryl bromides with organometallic reagents in a cross coupling reaction, as shown in scheme 4. The coupling conditions described in e.g.; Heterocycles, 18, 117–121 (1982) and Tetrahedron 38, 3347–3354 (1982) may be used to accomplish the synthesis of $A_{22}$.

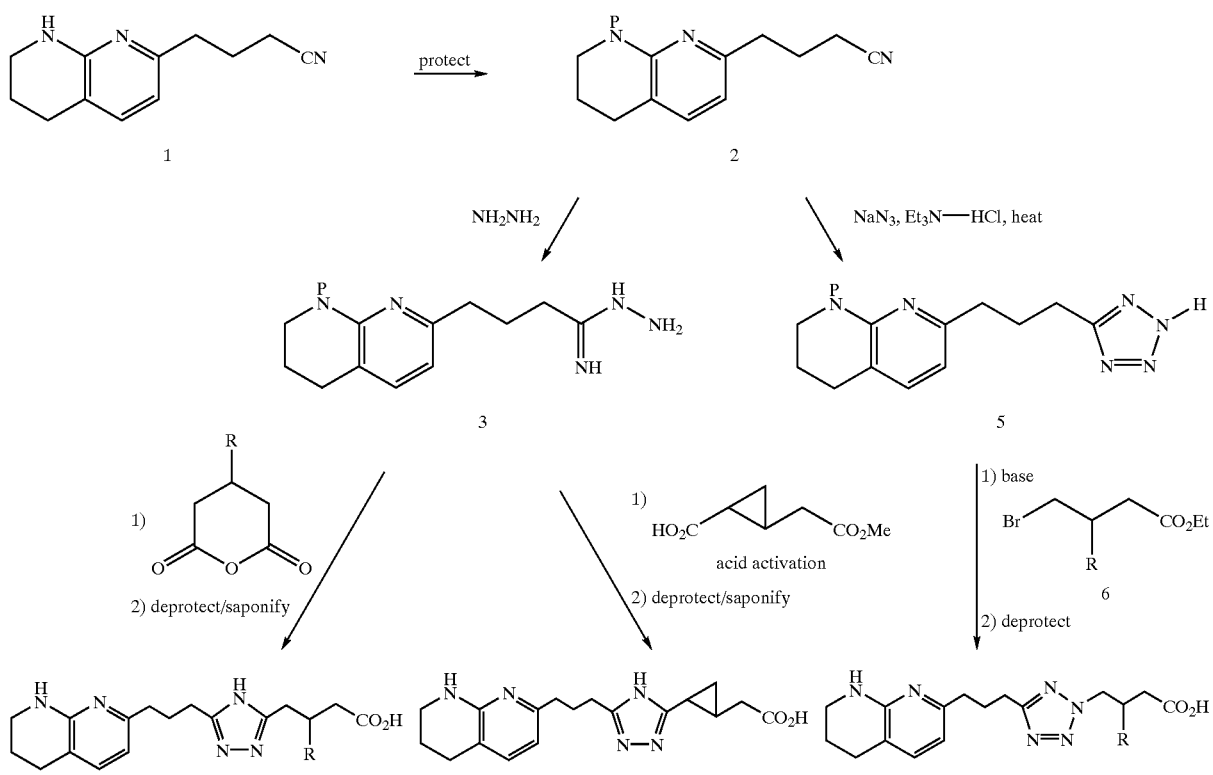

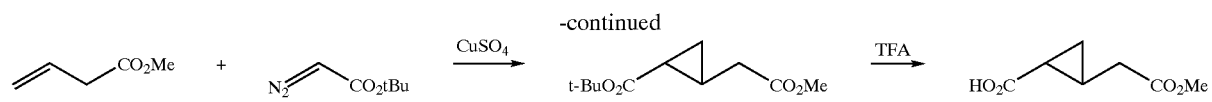

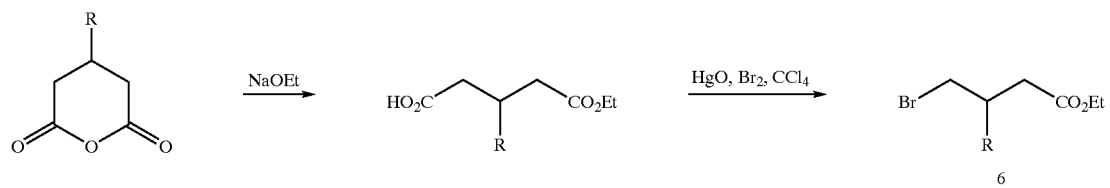

Scheme 5

The compounds containing a triazole and a tetrazole ring system can be prepared as shown in scheme 5. The nitrile 1 obtained using the literaure procedure (WO 99/30709) can be protected on nitrogen to give 2. Reaction with hydrazine would give aminoamidine 3. This can be reacted with a variety of cyclic anhydrides or activated esters to obtain, after deprotection, 1,2,4-triazoles 4a or 4b. Alternatively, nitrile 2 can be reacted with sodium azide to give tetrazole 5. This can be alkylated with bromide 6 (which is readily available from the respective cyclic anhydride) to give, after deprotection, tetrazole 7.

SCHEME 6

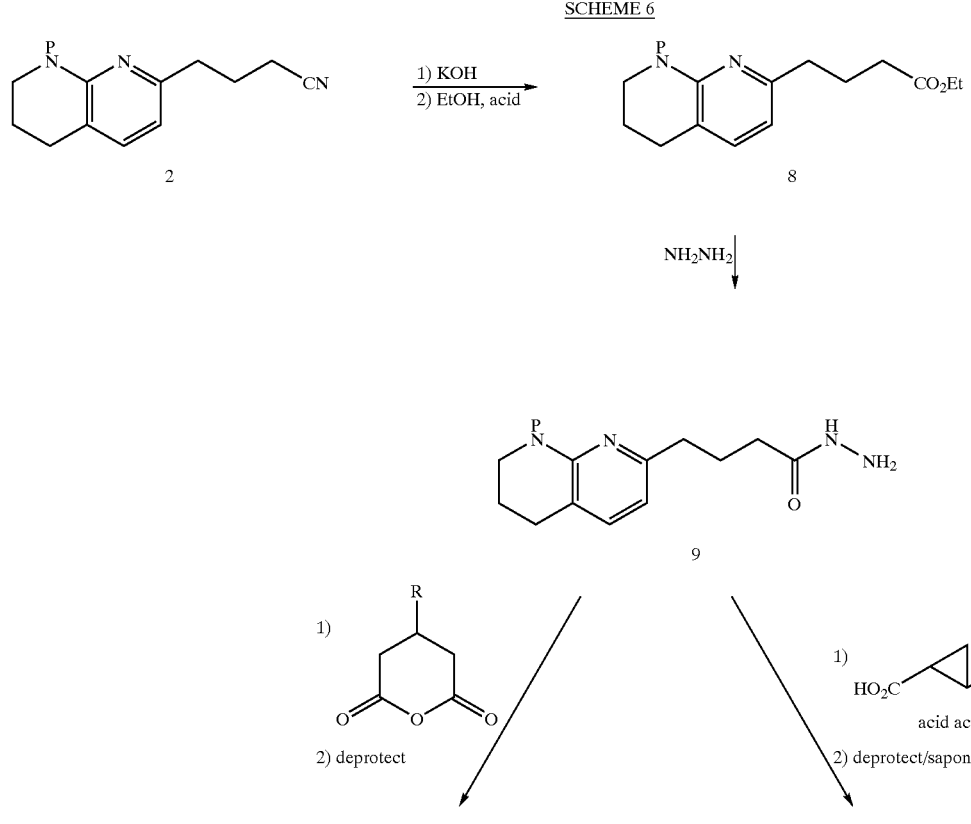

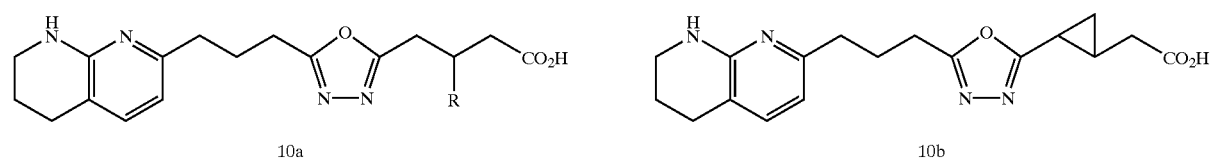

Scheme 6

Nitrile 2 can be hydrolyzed and esterified to give ester 8. Reaction with hydrazine would give acylhydrazine 9, which could be reacted with a variety of cyclic anhydrides or activated esters to give, after deprotection, 1,3,4-oxadiazoles 10a or 10b.

SCHEME 7

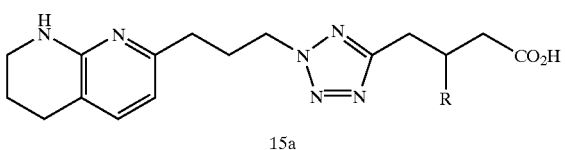

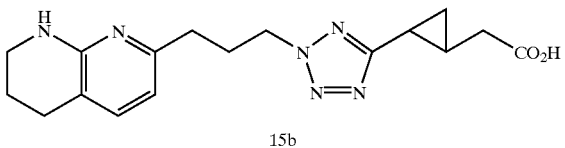

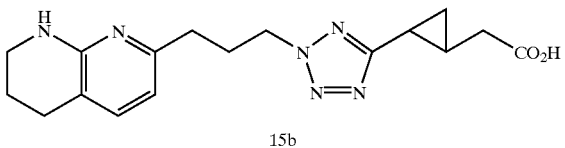

The compounds containing a tetrazole ring system can be prepared as shown in scheme 7. The aldehyde 11 obtained using the literaure procedure (WO 01/34602) can be homologated, and the resultant ester reduced and tosylated to give tosylate 12. Mono acids 13a or 13b can be converted to the corresponding nitriles via dehyration of the primary amides. Reaction of the nitrites with sodium azide would provide tetrazole 14a or 14b. Reaction of 14a or 14b with tosylate 12 would provide, after deprotection, tetrazoles 15a or 15b.

SCHEME 8

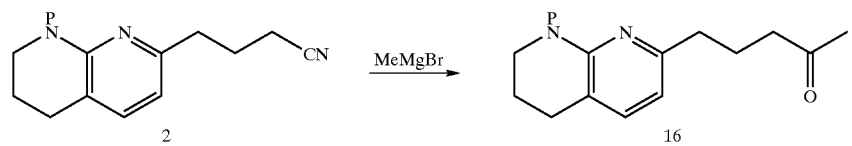

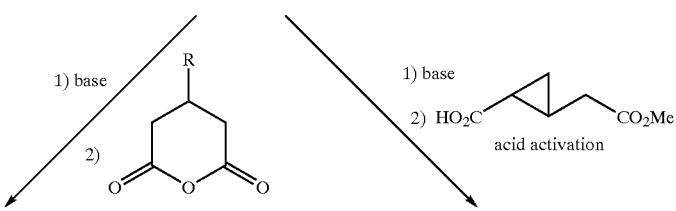

35 36

-continued

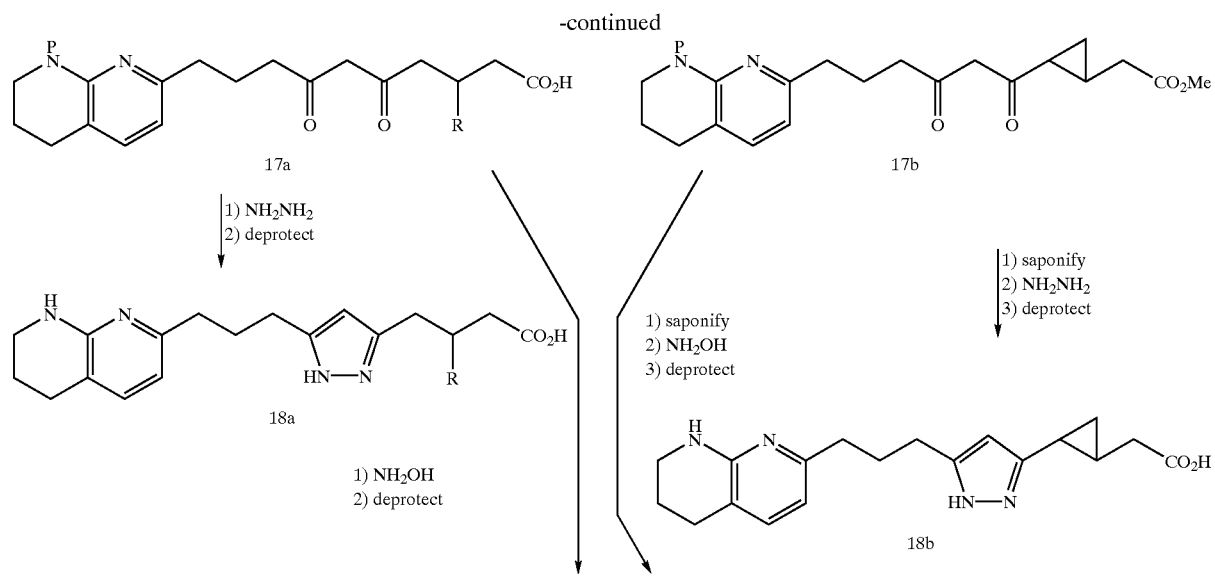

Scheme 8

Nitrile 2 can be converted to methyl ketone 16 using methyl magnesium bromide. Reaction with base, followed by a cyclic anhydride or activated ester would provide diketone 17a or 17b. Reaction with hydrazine would provide, after deprotection, pyrazole 18a or 18b. Alternatively, reaction of 17a or 17b with hydroxylamine would provide, after deprotection, isoxazoles 19a and 20a or 19b and 20b.

SCHEME 9

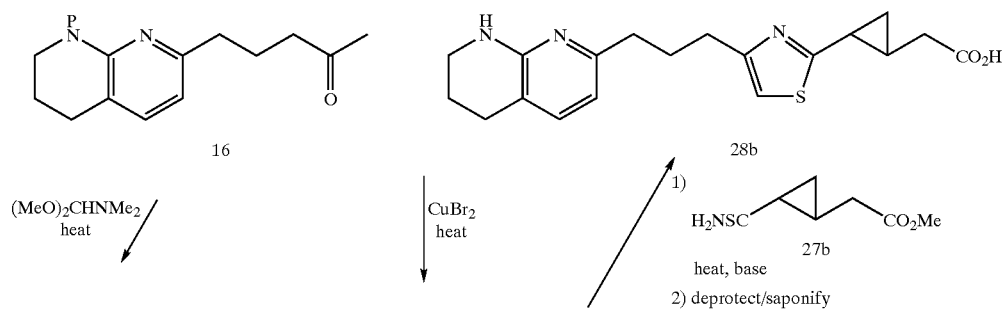

-continued

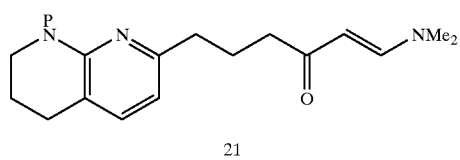
21

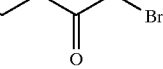
24

NH₂NH₂

1) 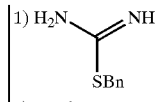
2) RaNi

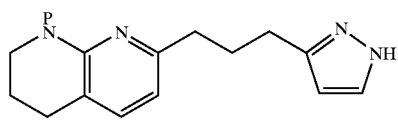
22

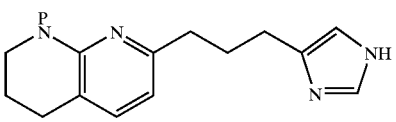
25

1) 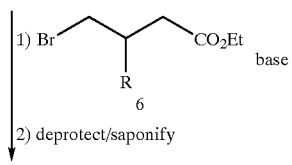
   6
   base
2) deprotect/saponify

1) 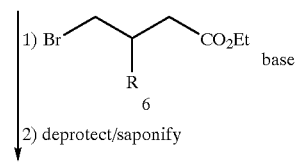
   6
   base
2) deprotect/saponify

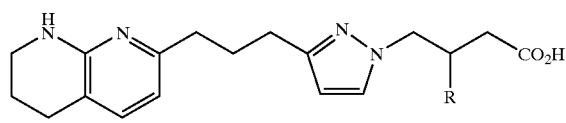
23

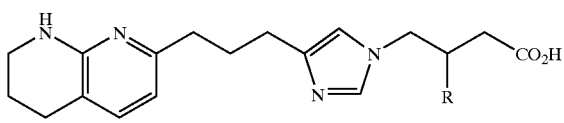
26

1) 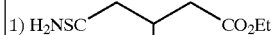
   27a
   heat, base
2) deprotect/saponify

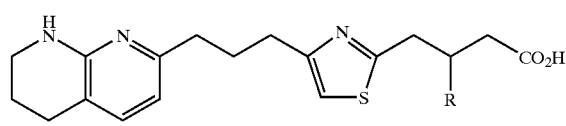
28a

Scheme 9

Methyl ketone 16 can be reacted with DMF-dimethylacetal to give enaminoketone 21. Reaction with hydrazine would provide pyrazole 22. Alkylation with bromide 6 would give, after deprotection, pyrazole 23. Alternatively, ketone 16 could be brominated to give bromoketone 24. Reaction with S-benzylthiourea would provide, after desulfurization with Raney nickel, imidazole 25. Alkylation with 6 and deprotection would provide imidazole 26. Bromoketone 24 could also be reacted with thioamides 27a or 27b (both readily accessible from the corresponding acids) to provide, after deprotection, thiazole 28a or 28b.

SCHEME 10
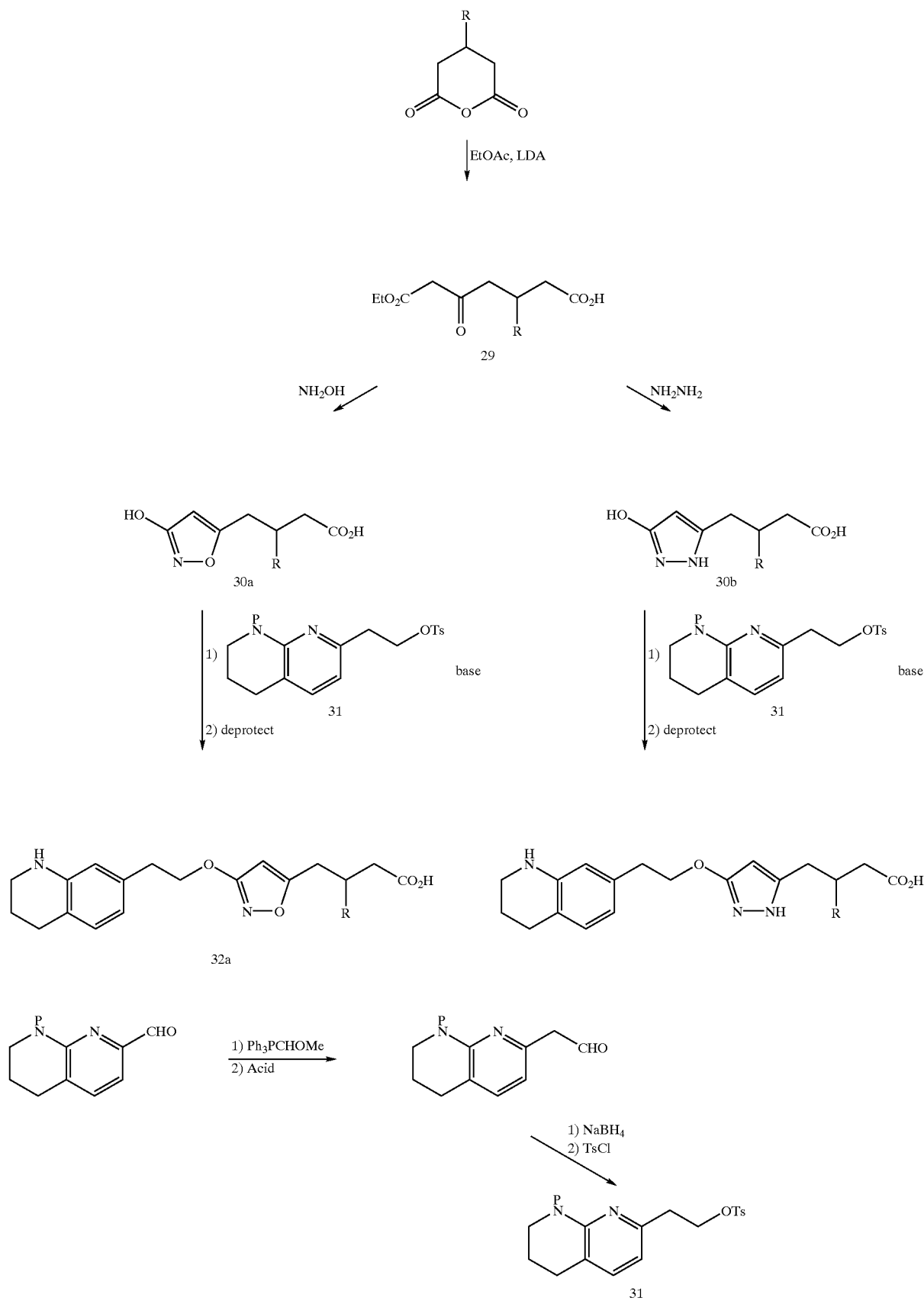

Scheme 10

A cyclic anhydride can be reacted with the lithium anion of ethyl acetate to give keto-ester 29. This can be reacted with hydroxylamine or hydrazine to give hydroxyisoxazole 30a or hydroxypyrazole 30b. Alkylation with tosylate 31 (which is available via homologation, reduction and tosylation of aldehyde 11) would provide, after deprotection, 32a or 32b.

SCHEME 11

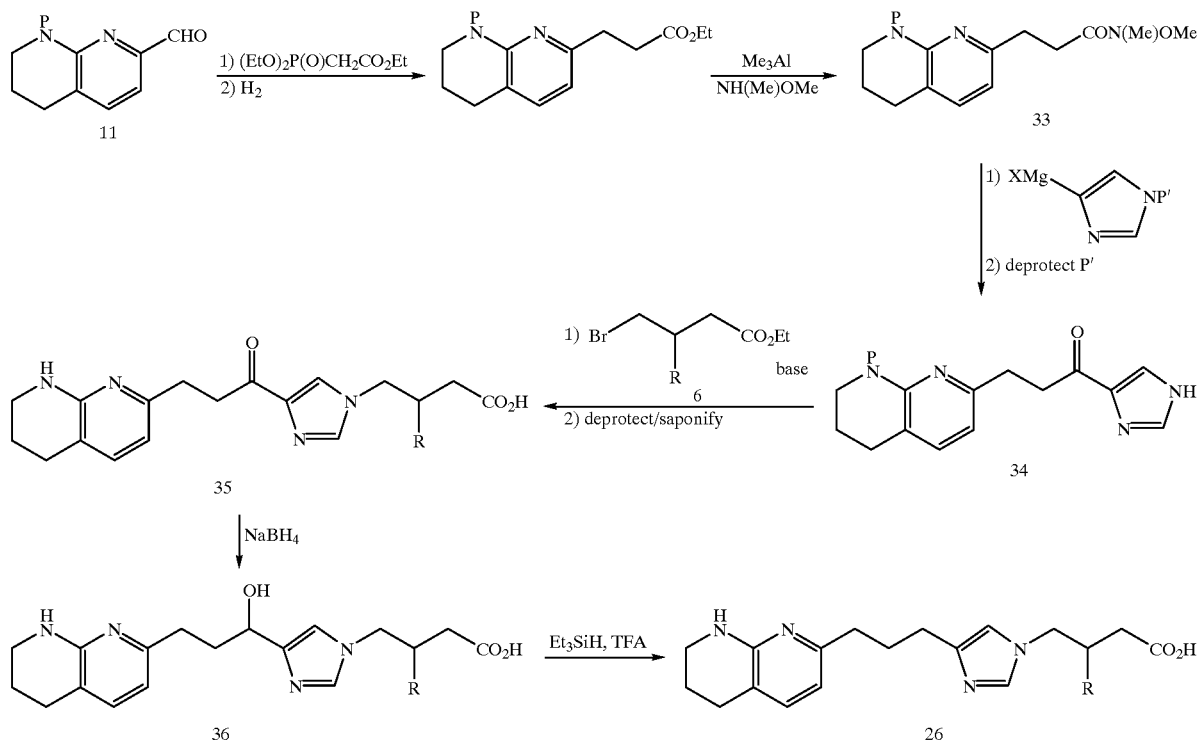

Scheme 11

Aldehyde 11 can be homologated, reduced and coupled to N, O-dimethylhydroxylamine to give amide 33. Reaction with a protected imidazole Grignard reagent would provide, after deprotection, acylimidazole 34. Alkylation with bromide 6 would give, after deprotection, acylimidazole 35. Reduction would provide the corresponding alcohol 36. Further reduction would provide imidazole analog 26.

SCHEME 12

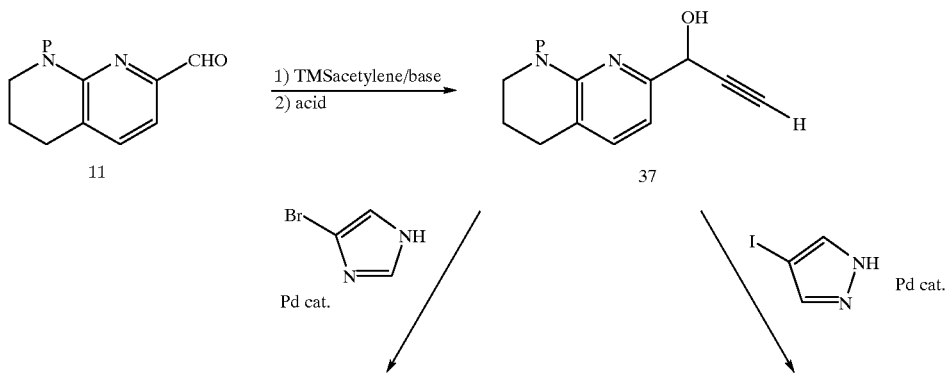

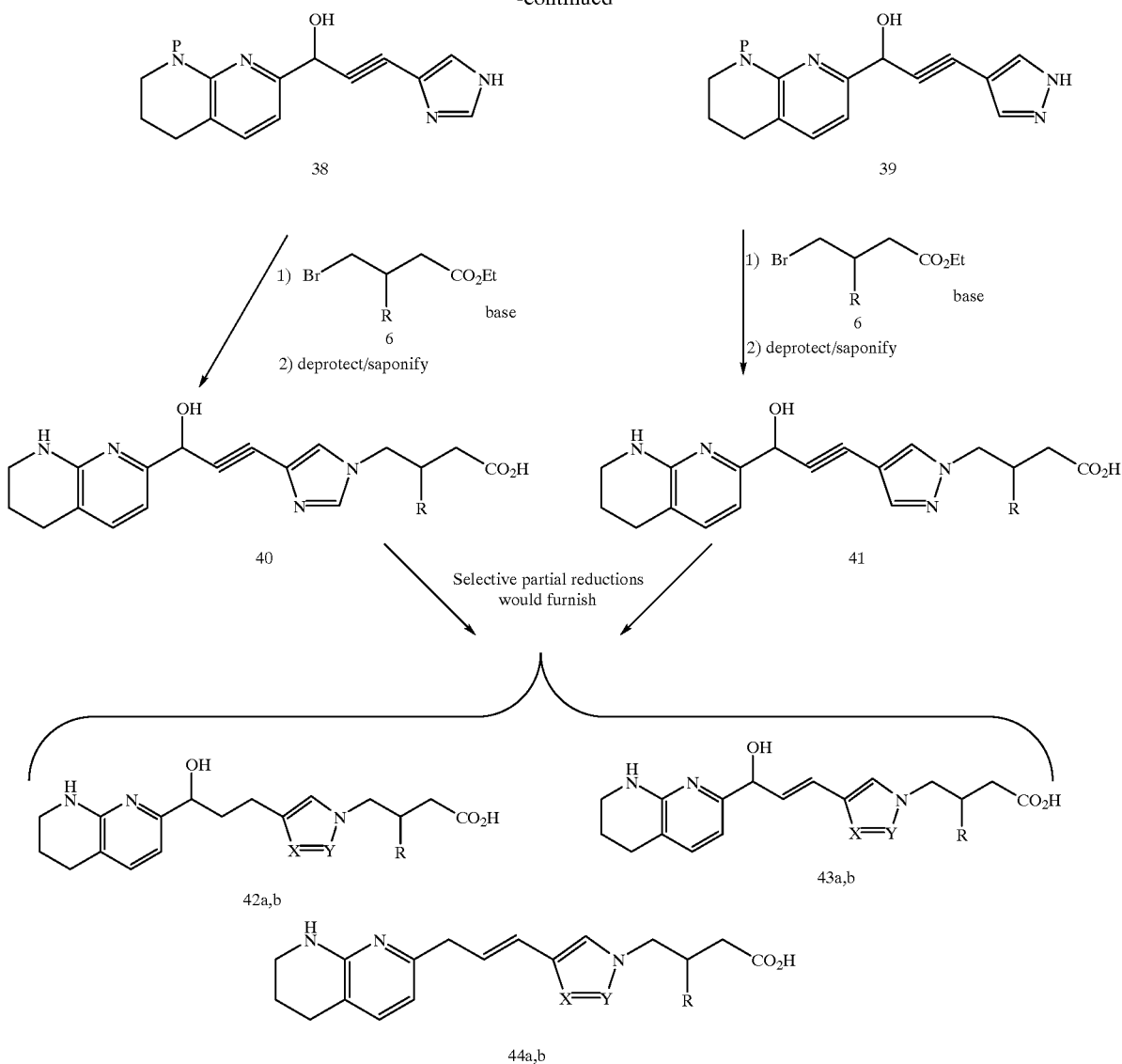

Scheme 12

Aldehyde 11 can be reacted with the lithium anion of TMS-acetylene to provide, after removal of the TMS group, acetylene 37. Palladium-catalyzed coupling with a halo-imidazole or pyrazole would provide 38 or 39. Alkylation with bromide 6 would give, after deprotection, 40 or 41. Selective partial reductions of these propargyl alcohols would provide alcohols 42a or 42b, allylic alcohols 43a or 43b, and alkenes 44a or 44b.

EXAMPLE A
(1Z)-N'-hydroxy-5-(pyridin-2-ylamino)pentanimidamide (A)

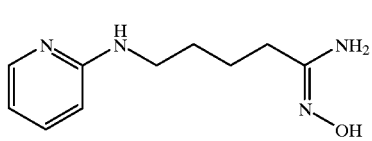

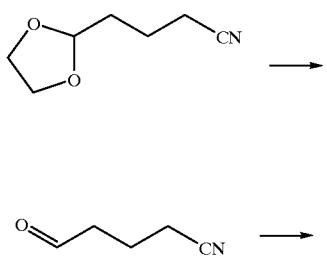

-continued

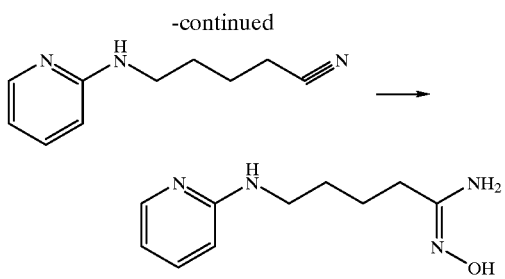

Step 1

4-(1,3-dioxolan-2-yl)-butanenitrile:

A mixture of 2-(3-chloropropyl)-1,3-dioxolane (15.88 g; 0.1054 moles), sodium cyanide (6.46 g; 0.132 moles) and sodium iodide (1.57 g; 0.0105 moles) in DMF (100 mL) was heated at 80° C., with magnetic stirring, under a nitrogen atmosphere for 15 hours. The mixture was allowed to cool, added to water (300 mL) and extracted with ethyl acetate (3×200 mL). The combined extracts were washed with water (200 mL) and saturated aqueous sodium chloride solution (100 mL) and then dried over sodium sulfate. Filtration and evaporation of solvent gave a crude yellow oil which was purified by chromatography on silica gel, eluting with hexane/ethyl acetate (5:2). Removal of solvent under vacuum gave the product 4-(1,3-dioxolan-2-yl)-butanenitrile (11.28 g; 76%) as a colorless oil. $^1$H NMR (CDCl$_3$) δ 4.89–4.91 (1H, m), 3.92–4.01 (2H, m), 3.82–3.90 (2H, m), 2.40–2.46 (2H, m), 1.77–1.85 (4H, m).

Step 2

5-(pyridin-2-ylamino)pentanenitrile:

4-(1,3-Dioxolan-2-yl)butanenitrile (6.26 g; 0.0443 moles) was dissolved in a mixture of acetone (50 mL) and water (50 mL) under nitrogen. p-Toluene-sulfonic acid (843 mg; 0.00443 moles) was added followed by sodium periodate (9.67 g; 0.0452 moles) and the mixture was heated at 40° C. for 32 hours with magnetic stirring. The mixture was filtered, washing the filter cake with ethyl acetate (100 mL). The filtrate was mixed with aqueous sodium bicarbonate solution (50 mL) and the phases were separated. The aqueous phase was extracted with ethyl acetate (3×100 mL). The combined organic phases were dried over sodium sulfate and filtered. Removal of solvent under vacuum gave the crude product (5-oxopentanenitrile). This material was dissolved in methylene chloride (150 mL). 2-Aminopyridine (4.17 g; 0.0443 moles) was added and the reaction mixture was magnetically stirred under nitrogen for 30 minutes. Sodium triacetoxyborohydride (14.1 g; 0.0665 moles) was added and the reaction mixture was stirred for 4 hours. The reaction mixture was added to aqueous sodium bicarbonate solution (50 mL) and the phases were separated. The aqueous phase was extracted with ethyl acetate (4×50 mL). The combined organic phases were dried over sodium sulfate and filtered. Removal of solvent under vacuum gave crude product which was purified by chromatography on silica gel, eluting with methylene chloride followed by methylene chloride/acetone (10:1). Removal of solvent under vacuum gave the product, 5-(pyridin-2-ylamino)pentane-nitrile, as an off white solid (4.30 g; 55%). $^1$H NMR (CDCl$_3$) δ 8.05–8.10 (1H, m), 7.38–7.43 (1H, m), 6.55–6.60 (1H, m), 6.38 (1H, d, J=8.5 Hz), 4.38–4.58 (1H, br), 3.30–3.40 (2H, m), 2.35–2.45 (2H, m), 1.70–1.85 (4H, m).

Step 3

(1Z)-N'-hydroxy-5-(pyridin-2-ylamino) pentanimidamide:

5-(Pyridin-2-ylamino)pentanenitrile (1.00 g; 5.71 mmoles) was dissolved in methanol (10 mL) and hydroxy-lamine (1.4 mL of a 50% aqueous solution; 22.83 mmoles) was added. The reaction mixture was stirred at 40° C. under nitrogen for 2 days. The solvent was removed under vacuum and the resulting oil was placed under vacuum at 40° C. for 6 hours. The product (1Z)-N'-hydroxy-5-(pyridin-2-ylamino)pentanimidamide (A) (1.16 g; 98%) was obtained as a pale yellow oil. $^1$H NMR (DMSO-d6) δ 8.68 (1H, s, br), 7.91–7.95 (1H, m), 7.29–7.35 (1H, m), 6.35–6.45 (3H, m), 5.25–5.35 (2H, s, br), 3.15–3.23 (2H, m), 1.97 (2H, t, J=7.5 Hz), 1.45–1.60 (4H, m).

EXAMPLE 1

3-methyl-4-(3-{3-[(pyridin-2-ylamino)methyl]phenyl}-1,2,4-oxadiazol-5-yl)butanoic acid

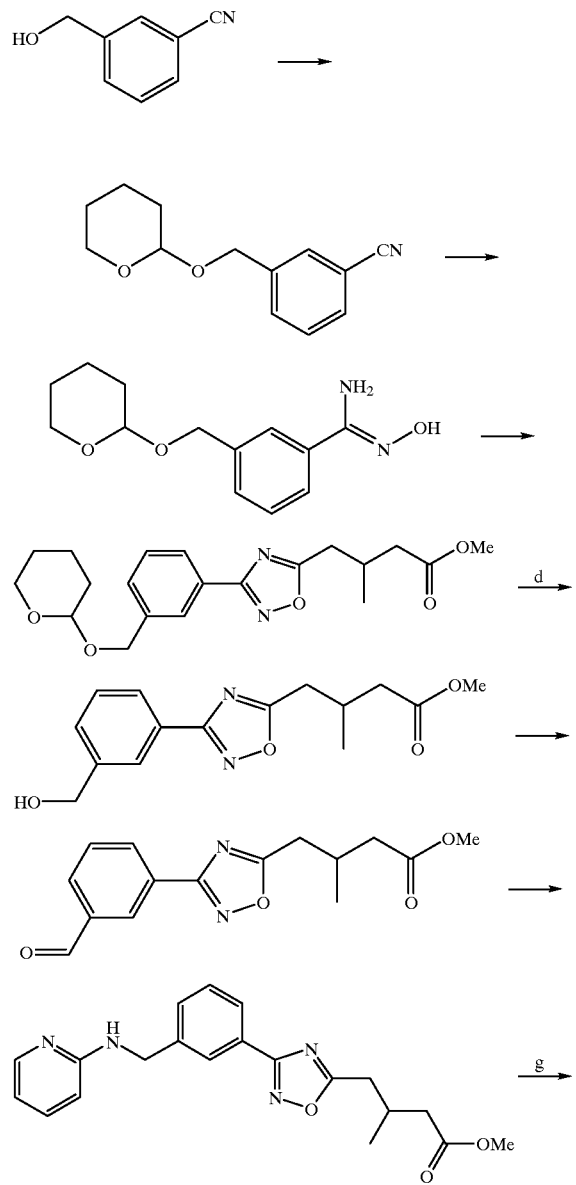

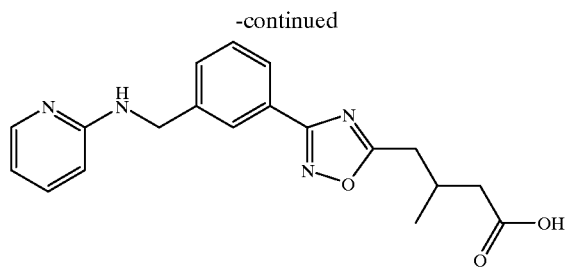

Step 1

3-[(tetrahydro-2H-pyran-2-yloxy)methyl]benzonitrile:

3-(Hydroxymethyl)benzonitrile (5.00 g; 37.6 mmoles) and 3,4-Dihydro-2H-pyran (3.77 mL; 41.4 mmoles) were dissolved in methylene chloride (25 mL) under nitrogen and the solution was cooled to 5° C. p-Toluenesulfonic acid monohydrate (74 mg; 0.37 mmoles) was added and the mixture was stirred for 2 hours at 25° C. The reaction mixture was diluted with methylene chloride (25 mL). The solution was washed with aqueous sodium bicarbonate solution (30 mL) and aqueous sodium chloride solution (30 mL). The solution was dried over sodium sulfate and filtered. The solvent was removed under vacuum to give the product, 3-[(tetrahydro-2H-pyran-2-yloxy)methyl]benzonitrile (7.34 g; 89%) as an oil. $^1$H NMR (400 MHz) CDCl$_3$ δ 7.68–7.70 (1H, m), 7.54–7.61 (2H, m), 7.42–7.48 (1H, m), 4.82 (1H, d, J=12.5 Hz), 4.72 (1H, t, J=3.3 Hz), 4.53 (1H, d, J=12.5 Hz), 3.84–3.92 (1H, m), 3.53–3.60 (1H, m), 1.60–1.95 (6H, m).

Step 2

N'-hydroxy-3-[(tetrahydro-2H-pyran-2-yloxy)methyl]benzenecarboximidamide:

The product from the previous reaction (4.0 g; 18.4 mmoles) was dissolved in methanol (20 mL) under nitrogen with stirring. Hydroxylamine hydrochloride (1.92 g; 27.6 mmoles) was added followed by sodium methoxide (6.3 mL of a 25 wt % solution; 27.6 mmoles). The mixture was heated to 65° C. for 4 hours and allowed to cool. The mixture was filtered and the methanol was removed under vacuum. The residue was dissolved in ethyl acetate and passed through a pad of silica gel. Following removal of solvent, the product, N'-hydroxy-3-[(tetrahydro-2H-pyran-2-yloxy)methyl]-benzenecarboximidamide (4.50 g; 98%) was obtained. $^1$H NMR (400 MHz) CDCl$_3$ δ 8.10 (1H, br, s), 7.62–7.64 (1H, m), 7.53–7.58 (1H, m), 7.42–7.46 (1H, m), 7.35–7.41 (1H, m), 4.91 (2H, br, s), 4.81 (1H, d, J=12.5 Hz), 4.72 (1H, t, J=3.3 Hz), 4.52 (1H, d, J=12.5 Hz), 3.88–3.96 (1H, m), 3.52–3.59 (1H, m), 1.50–1.95 (6H, m).

Step 3

Methyl 3-methyl-4-(3-{3-[(tetrahydro-2H-pyran-2-yloxy)methyl]phenyl}-1,2,4-oxadiazol-5-yl)butanoate:

The product from the previous reaction (3.75 g; 15.0 mmoles) and 3-methyl glutaric anhydride (1.92 mg; 15.0 mmoles) were dissolved in 1,4-dioxane (20 mL) under nitrogen and the mixture was heated to 95° C. for 24 hours. After allowing the mixture to cool, the solvent was removed under vacuum. The residue was dissolved in DMF (15 mL) under nitrogen. Potassium carbonate (2.50 g; 18.0 mmoles) and methyl iodide (1.10 mL; 18.0 mmoles) were added and the mixture was stirred for 24 hours at ambient temperature. The DMF was removed under reduced pressure and the residue was dissolved in ethyl acetate (50 mL) and filtered. The solution was washed with 1N aqueous potassium hydrogen sulfate (25 mL) and aqueous sodium bicarbonate (25 mL) and then dried over sodium sulfate and filtered. The solvent was removed under vacuum. The resulting product was purified by chromatography on silica gel, eluting with hexane/ethyl acetate (1:1). Removal of solvent gave the product, methyl 3-methyl-4-(3-{3-[(tetrahydro-2H-pyran-2-yloxy)methyl]phenyl}-1,2,4-oxadiazol-5-yl)butanoate (3.70 g; 64%) as an oil. $^1$H NMR (400 MHz) CDCl$_3$ δ 8.07–8.09 (1H, m), 7.98–8.02 (1H, m), 7.51–7.55 (1H, m), 7.43–7.49 (1H, m), 4.85 (1H, d, J=12.5 Hz), 4.74 (1H, t, J=3 Hz), 4.57 (1H, d, J=12.5 Hz), 3.89–3.97 (1H, m), 3.69 (3H, s), 3.53–3.61 (1H, m), 3.00–3.07 (1H, m), 2.89–2.97 (1H, m), 2.60–2.72 (1H, m), 2.48–2.55 (1H, m), 2.32–2.40 (1H, m), 1.50–1.96 (6H, m), 1.11 (3H, d, J=6 Hz).

Step 4

Methyl 4-{3-[3-(hydroxymethyl)phenyl]-1,2,4-oxadiazol-5-yl}-3-methylbutanoate:

The product from the previous reaction (2.00 g; 5.10 mmoles) was dissolved in methanol (25 mL) under nitrogen. p-Toluenesulfonic acid monohydrate (980 mg; 5.10 mmoles) was added and the mixture was stirred at 25° C. for 3 hours. The mixture was added to aqueous sodium bicarbonate solution (25 mL) and the methanol was removed under vacuum. The mixture was extracted with ethyl acetate (3×25 mL). The combined extracts were washed with saturated aqueous sodium chloride solution (50 mL), dried over sodium sulfate and filtered. The solvent was removed under vacuum to give the product, methyl 4-{3-[3-(hydroxymethyl)phenyl]-1,2,4-oxadiazol-5-yl}-3-methylbutanoate (1.53 g; 98%) as an oil. $^1$H NMR (400 MHz) CDCl$_3$ δ 8.07–8.09 (1H, m), 7.98–8.02 (1H, m), 7.45–7.55 (2H, m), 4.79 (2H, s), 3.69 (3H, s), 3.00–3.07 (1H, m), 2.89–2.96 (1H, m), 2.60–2.72 (1H, m), 2.48–2.55 (1H, m), 2.32–2.40 (1H, m), 1.11 (3H, d, J=6 Hz).

Step 5

Methyl 4-[3-(3-formylphenyl)-1,2,4-oxadiazol-5-yl]-3-methylbutanoate:

The product from the previous reaction (750 mg; 2.50 mmoles) was dissolved in methylene chloride (15 mL) under nitrogen. N-Methyl-morpholine-N-oxide (435 mg; 3.70 mmoles) and powdered 4 Å molecular sieves were added and the mixture was cooled to 5° C. with stirring. Tetra-n-propylammonium perruthenate (44 mg; 0.13 mmoles) was added and the mixture was stirred at ambient temperature for 2 hours. The mixture was diluted with methylene chloride (50 mL) and filtered through a pad of silica gel. The solvent was removed under vacuum to give the product, methyl 4-[3-(3-formylphenyl)-1,2,4-oxadiazol-5-yl]-3-methylbutanoate (650 mg) which was used directly in the next step without purification.

Step 6

3-methyl-4-(3-{3-[(pyridin-2-ylamino)methyl]phenyl}-1,2,4-oxadiazol-5-yl)butanoic acid trifluoroacetate:

The material was dissolved in methylene chloride (10 mL) with stirring under nitrogen. 2-Aminopyridine (222 mg; 2.37 mmoles) was added and the mixture was stirred for 30 minutes. Sodium triacetoxyborohydride (684 mg; 3.23 mmoles) was added and stirring was continued for 5 hours. The mixture was added to aqueous sodium bicarbonate solution (25 mL) and extracted into ethyl acetate (3×2 mL). The combined extracts were washed with saturated aqueous sodium chloride solution (20 mL) and dried over sodium sulfate. The solution was filtered and the solvent was evaporated. The residue was purified by chromatography on silica gel eluting with ethyl acetate/hexane (1:1). Solvent was removed and the resulting material, methyl 4-[3-(3-formylphenyl)-1,2,4-oxadiazol-5-yl]-3-methylbutanoate, was dissolved in tetrahydrofuran (3 mL). Aqueous sodium hydroxide (1N, 3 mL) was added and the mixture was stirred at ambient temperature for 12 hours. Hydrochloric acid (1N, 3 mL) was added and the solvent was removed under vacuum. The residue was purified by reverse phase HPLC (C18 column, eluting with water/acetonitrile, 9:1 to 1:1 gradient, TFA buffer). After removal of solvent the product, 3-methyl-4-(3-{3-[(pyridin-2-ylamino)methyl]phenyl}-1,2,4-oxadiazol-5-yl)butanoic acid trifluoroacetate (175 mg) was obtained. $^1$H NMR (400 MHz) DMSO-d6 δ 8.05 (1H, s), 7.93–8.00 (2H, m), 7.82–7.91 (1H, m), 7.55–7.63 (1H, m), 7.00–7.08 (1H, m), 6.82–6.89 (1H, m), 4.65–4.70 (2H, m), 3.03–3.11 (1H, m), 2.91–2.99 (1H, m), 2.20–2.53 (3H, m), 0.98 (3H, d, J=6 Hz). HPLC retention time 1.25 minutes (Column: YMC CombiScreen ODS-A, 50×4.6 mm I.D., particle s-5 µm, 12 nm; Eluent: Acetonitrile/phosphoric acid buffer, gradient 10:90 to 90:10).

EXAMPLE 2

Sodium 3-methyl-4-(3-{4-[(pyridin-2-ylamino)methyl]phenyl}-1,2,4-oxadiazol-5-yl)butanoate

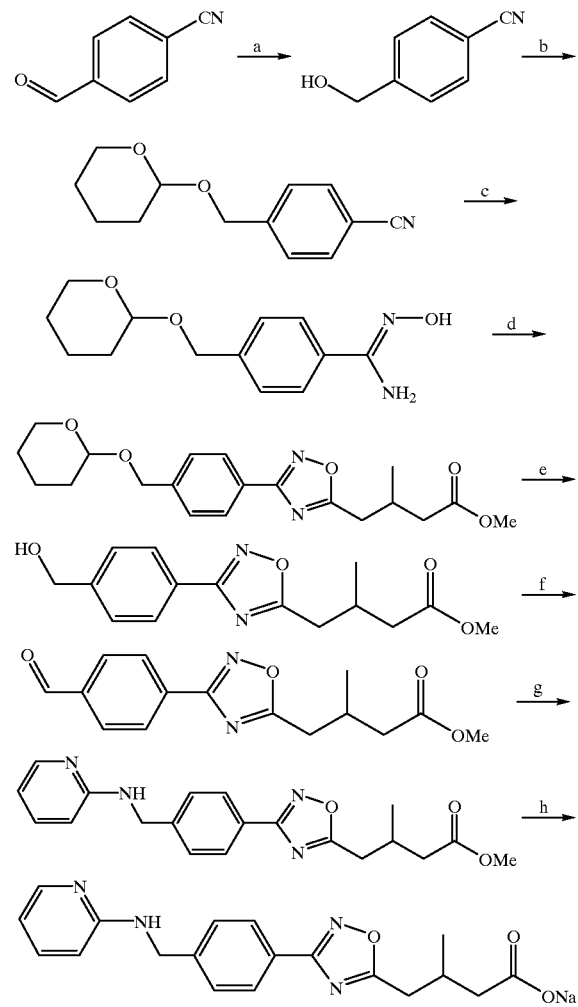

Step 1
4-(hydroxymethyl)benzonitrile:
A stirred suspension of 4-formylbenzonitrile (10.0 g; 0.0763 moles) in methanol (100 mL) under nitrogen was cooled to 5° C. Sodium borohydride (1.45 g; 0.0382 moles) was added. After 30 minutes the mixture was added to water (300 mL) and extracted with ethyl acetate (4×100 mL). The combined extracts were washed with aqueous sodium chloride solution (50 mL) and dried over sodium sulfate. Following filtration and removal of solvent under vacuum the product, 4-(hydroxymethyl)benzonitrile, (9.44 g; 93%) was obtained as a white solid. $^1$H NMR (400 MHz) CDCl$_3$ δ 7.61–7.66 (2H, m), 7.45–7.50 (2H, m), 4.78 (2H, d, J=5.5 Hz), 2.27 (1H, t, J=5.5 Hz).

Step 2
4-[(tetrahydro-2H-pyran-2-yloxy)methyl]benzonitrile:
The product from the previous reaction (9.26 g; 0.0695 moles) and 3,4-Dihydro-2H-pyran (7.0 mL; 0.077 mole) were dissolved in methylene chloride (100 mL) under nitrogen and the solution was cooled to 5° C. p-Toluene-sulfonic acid monohydrate (670 mg; 3.50 mmoles) was added and the mixture was stirred for 2 hours at 25° C. The solution was washed with aqueous sodium bicarbonate solution (30 mL) and aqueous sodium chloride solution (30 mL). The solution was dried over sodium sulfate and filtered. The solvent was removed under vacuum to give the crude product, which was purified by chromatography on silica gel eluting with hexane/ethyl acetate (4:1). Following removal of solvent the product, 4-[(tetrahydro-2H-pyran-2-yloxy)methyl]benzonitrile (13.98 g; 92%) was obtained as a straw colored oil. $^1$H NMR (400 MHz) CDCl$_3$ δ 7.62–7.67 (2H, m), 7.45–7.50 (2H, m), 4.84 (1H, d, J=12.5 Hz), 4.72 (1H, t, J=3 Hz), 4.57 (1H, d, J=12.5 Hz), 3.84–3.92 (1H, m), 3.52–3.59 (1H, m), 1.50–1.95 (6H, m).

Step 3
N'-hydroxy-4-[(tetrahydro-2H-pyran-2-yloxy)methyl]benzenecarboximidamide:
A solution of hydroxylamine hydrochloride (4.80 g; 0.0691 moles) in methanol (50 mL) under nitrogen was cooled to 5° C. Sodium methoxide (15.8 mL of a 25 wt % solution; 0.0691 moles) was added with stirring. The product from the previous reaction (10.0 g; 0.0460 moles) in methanol (50 mL) was added. The mixture was heated to 65° C. for 8 hours and allowed to cool. Methanol was removed under vacuum. The material was suspended in ether (100 mL) and filtered through celite. The solvent was removed under vacuum and the residue was purified by chromatography on silica gel eluting with ether/methanol (10:1). The material was further purified by chromatography on silica gel, eluting with ether. Following removal of solvent the product, N'-hydroxy-4-[(tetrahydro-2H-pyran-2-yloxy)-methyl]benzenecarboximidamide (8.69 g; 75%) was obtained as a white solid. $^1$H NMR (400 MHz) DMSO-d6 δ 9.62 (1H, s), 7.63–7.68 (2H, m), 7.31–7.36 (2H, m), 5.80 (1H, br, s), 4.65–4.70 (2H, m), 4.43–4.48 (1H, m), 3.75–3.83 (1H, m), 3.44–3.51 (1H, m), 1.60–1.80 (2H, m), 1.40–1.58 (4H, m).

Step 4
Methyl 3-methyl-4-(3-{4-[(tetrahydro-2H-pyran-2-yloxy)methyl]phenyl}-1,2,4-oxadiazol-5-yl)butanoate:
The product from the previous reaction (1.14 g; 4.54 mmoles) was dissolved in 1,4-dioxane (20 mL) under nitrogen. 3-Methyl glutaric anhydride (582 mg; 4.53 mmoles) was added and the mixture was stirred for one hour at ambient temperature and then heated to 95° C. for 30 hours. After allowing the mixture to cool, the solvent was removed under vacuum. The residue was dissolved in DMF (25 mL) under nitrogen. Potassium carbonate (879 mg; 6.36 mmoles) followed by methyl iodide (297 µL; 4.77 mmoles) was added and the mixture was stirred for 24 hours at ambient temperature. The mixture was diluted with water and extracted with ethyl acetate (3×50 mL). The combined extracts were washed with water (2×50 mL) and saturated aqueous sodium chloride solution (50 mL), dried over sodium sulfate, filtered and the solvent was removed under vacuum. The resulting product was purified by chromatography on silica gel, eluting with hexane/ethyl acetate (4:1). Removal of solvent gave the product, methyl 3-methyl-4-(3-{4-[(tetrahydro-2H-pyran-2-yloxy)methyl]phenyl}-1,2,4-oxadiazol-5-yl)-butanoate (1.528 g; 90%) as a colorless oil. $^1$H NMR (400 MHz) CDCl$_3$ δ 8.03–8.08 (2H, m), 7.45–7.50 (2H, m), 4.85 (1H, d, J=12.5 Hz), 4.73 (1H, t, J=3.7 Hz), 4.57 (1H, d, J=12.5 Hz), 3.89–3.97 (1H, m), 3.69 (3H, s), 3.52–3.60 (1H, m), 2.89–3.07 (2H, m), 2.60–2.72 (1H, m), 2.48–2.55 (1H, m), 2.32–2.40 (1H, m), 1.50–1.96 (6H, m), 1.11 (3H, d, J=6 Hz).

Step 5

Methyl 4-{3-[4-(hydroxymethyl)phenyl]-1,2,4-oxadiazol-5-yl}-3-methylbutanoate:

The product from the previous reaction (1.49 g; 3.98 mmoles) was dissolved in methanol (20 mL) under nitrogen. p-Toluenesulfonic acid monohydrate (76 mg; 0.40 mmoles) was added and the mixture was stirred at 25° C. for 3 hours. The mixture was added to aqueous sodium bicarbonate solution (20 mL) and extracted into ethyl acetate (3×50 mL). The combined extracts were washed with saturated aqueous sodium chloride solution (50 mL), dried over sodium sulfate and filtered. The solvent was removed under vacuum and the residue was purified by chromatography on silica gel, eluting with hexane/ethyl acetate (2:1 to 1:1). Following removal of solvent the product, methyl 4-{3-[4-(hydroxymethyl)phenyl]-1,2,4-oxadiazol-5-yl}-3-methylbutanoate (1.13 g; 98%) was obtained as a colorless oil. $^1$H NMR (400 MHz) CDCl$_3$ δ 8.04–8.09 (2H, m), 7.46–7.51 (2H, m), 4.78 (1H, d, J=5.5 Hz), 4.57 (1H, d, J=12.5 Hz), 3.69 (3H, s), 3.00–3.07 (1H, m), 2.89–2.96 (1H, m), 2.60–2.72 (1H, m), 2.48–2.55 (1H, m), 2.32–2.40 (1H, m), 1.87 (t, J=5.8 Hz), 1.11 (3H, d, J=6 Hz).

Step 6

Methyl 4-[3-(4-formylphenyl)-1,2,4-oxadiazol-5-yl]-3-methylbutanoate:

The product from the previous reaction (350 mg; 1.21 mmoles) was dissolved in methylene chloride (20 mL) under nitrogen. Magtrieve™(CrO$_2$) (1.8 g; 21.7 mmoles) was added and the mixture was mechanically stirred with heating to reflux for 6 hours. The mixture was diluted with ethyl acetate (100 mL) and filtered through a plug of silica and celite, washing with ethyl acetate. The solvent was removed under vacuum to give the product, methyl 4-[3-(4-formylphenyl)-1,2,4-oxadiazol-5-yl]-3-methylbutanoate (325 mg; 94%) as a colorless oil. $^1$H NMR (400 MHz) CDCl$_3$ δ 10.10 (1H, s), 8.24–8.29 (2H, m), 8.98–8.02 (2H, m), 3.69 (3H, s), 3.03–3.10 (1H, m), 2.92–2.99 (1H, m), 2.61–2.73 (1H, m), 2.48–2.56 (1H, m), 2.33–2.42 (1H, m), 1.12 (3H, d, J=6 Hz).

Step 7

Methyl 3-methyl-4-(3-{4-[(pyridin-2-ylamino)methyl]phenyl}-1,2,4-oxadiazol-5-yl)butanoate:

The product from the previous reaction (318 mg; 1.10 mmoles was dissolved in methylene chloride (5 mL) under nitrogen. 2-Aminopyridine (114 mg; 1.21 mmoles) was added and the mixture was stirred for 30 minutes. Sodium triacetoxyborohydride (408 mg; 1.93 mmoles) was added and stirring was continued for 5 hours. The mixture was added to aqueous ammonium chloride solution (50 mL) and extracted into ethyl acetate (3×20 mL). The combined extracts were washed with saturated aqueous sodium chloride solution (20 mL) and dried over sodium sulfate. The solution was filtered and the solvent was evaporated. The residue was purified by chromatography on silica gel eluting with methylene chloride/acetonitrile (10:1). After removal of solvent the product, methyl 3-methyl-4-(3-{4-[(pyridin-2-ylamino)methyl]phenyl}-1,2,4-oxadiazol-5-yl)butanoate (188 mg; 47%) was obtained as a colorless oil. $^1$H NMR (400 MHz) CDCl$_3$ δ 8.10–8.14 (1H, m), 8.02–8.07 (2H, m), 7.45–7.50 (2H, m), 7.38–7.44 (1H, m), 6.59–6.63 (1H, m), 6.38 (1H, d, J=8.5 Hz), 4.92–5.02 (1H, br, m), 4.59 (2H, d, J=5.5 Hz), 3.69 (3H, s), 2.99–3.06 (1H, m), 2.88–2.95 (1H, m), 2.59–2.72 (1H, m), 2.47–2.54 (1H, m), 2.32–2.40 (1H, m), 1.10 (3H, d, J=6 Hz).

Step 8

Sodium 3-methyl-4-(3-{4-[(pyridin-2-ylamino)methyl]phenyl}-1,2,4-oxadiazol-5-yl)butanoate:

The product from the previous reaction (164 mg; 0.448 mmoles) was dissolved in methanol (5 mL) under nitrogen. Aqueous sodium hydroxide solution (1.5 mL of a 1M solution; 1.5 mmoles) was added and the mixture was stirred for 5 hours at 25° C. and then for 30 minutes at 45° C. The mixture was allowed to cool and then adjusted to pH 7 by addition of hydrochloric acid (1N). The solvent was removed under vacuum and the residue was suspended in ethyl acetate/methanol (10:1) (20 mL). The inorganic salts were removed by filtration through celite. Removal of solvent gave the product, sodium 3-methyl-4-(3-{4-[(pyridin-2-ylamino)methyl]-phenyl}-1,2,4-oxadiazol-5-yl)butanoate as a white solid (167 mg; 100%). $^1$H NMR (400 MHz) DMSO-d6 δ 7.92–7.97 (2H, m), 7.47–7.52 (2H, m), 7.33–7.40 (1H, m), 7.17 (1H, t, J=6.3 Hz), 6.45–6.55 (2H, m), 4.55 (2H, d, J=5 Hz), 3.08–3.15 (1H, m), 2.75–2.83 (1H, m), 2.31–2.44 (1H, m), 1.92–2.10 (2H, m), 0.92 (3H, d, J=6 Hz). Anal. Calcd. for C$_{19}$H$_{19}$N$_4$O$_3$Na.0.3CH$_3$OH.0.8H$_2$O: C, 58.19; H, 5.52; N, 14.06. Found C, 58.28; H, 5.68; N, 13.70.

EXAMPLE 3

3,3-dimethyl-4-{4-[4-(pyridin-2-ylamino)butyl]-1,3-thiazol-2-yl}butanoic acid

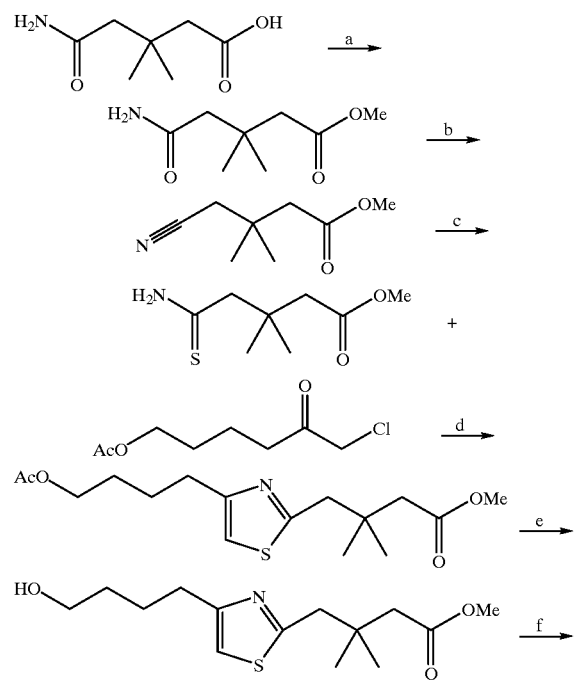

-continued

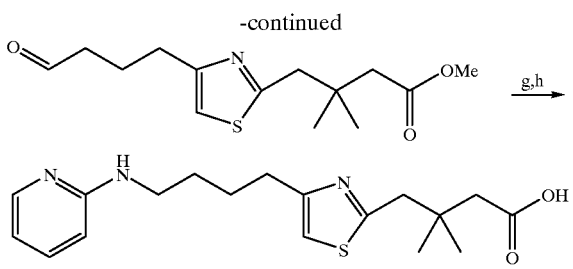

5-Amino-3,3-dimethyl-5-oxopentanoic acid was prepared according to the published procedure by Arrizabalaga, Philippe; Castan, Paule; Laurent, Jean-Pierre; J. Amer. Chem. Soc.; 106; 16; 1984; 4814–4818.

Step 1

Methyl 5-amino-3,3-dimethyl-5-oxopentanoate:

5-Amino-3,3-dimethyl-5-oxopentanoic acid (10.9 g; 68.6 mmoles) was dissolved in DMF (50 mL). Potassium carbonate (14.2 g; 103 mmoles) and methyl iodide (8.5 mL; 137.2 mmoles) were added and the reaction mixture was stirred overnight at room temperature. The reaction mixture was filtered, washing the filter cake with DMF. The DMF was removed under vacuum and the residue was suspended in ethyl acetate. The solids were removed by filtration and the ethyl acetate was removed under vacuum to give the product, methyl 5-amino-3,3-dimethyl-5-oxopentanoate, as a yellow oil (11.5 g; 97%). $^1$H NMR (400 MHz) DMSO-d6 δ 7.22 (1H, s, br), 6.73 (1H, s, br), 3.58 (3H, s), 2.39 (2H, s), 2.09 (2H, s), 1.02 (6H, s).

Step 2

Methyl 4-cyano-3,3-dimethylbutanoate:

Trifluoromethanesulfonic anhydride (5.4 mL; 31.8 mmoles) was added to an ice cooled solution of methyl 5-amino-3,3-dimethyl-5-oxopentanoate (5.00 g; 28.9 mmoles) in methylene chloride (250 mL) and triethylamine (8 mL; 57.8 mmoles), under nitrogen while keeping the temperature below 5° C. The reaction mixture was allowed to warm to room temperature and stirred for 30 minutes. Water (125 mL) was added and the phases were separated. The aqueous phase was extracted with methylene chloride (100 mL). The organic phases were combined, washed with saturated aqueous sodium chloride solution and dried over sodium sulfate. The solution was filtered and the solvent was removed under vacuum to give the product, methyl 4-cyano-3,3-dimethylbutanoate (3.1 g; 69%). $^1$H NMR (400 MHz) DMSO-d6 δ 3.60 (3H, s), 2.61 (2H, s), 2.35 (2H, s), 1.07 (6H, s).

Step 3

Methyl 5-Amino-3,3-Dimethyl-5-Thioxopentanoate:

Methyl 4-cyano-3,3-dimethylbutanoate (6.00 g; 38.7 mmoles) was dissolved in pyridine (15 mL) and triethylamine (1.5 mL). Hydrogen sulfide was bubbled into the solution until saturated, the flask was sealed and allowed to stand at ambient temperature for 12 days. The solvent was removed under a stream of nitrogen and the residue was dissolved in ethyl acetate and passed through a pad of silica gel. Removal of solvent under vacuum gave crude product which was purified by chromatography on silica gel, eluting with hexane/ethyl acetate (1:1). Following evaporation of solvent the product, methyl 5-amino-3,3-dimethyl-5-thioxopentanoate was obtained as an orange oil (1.4 g; 19%). $^1$H NMR (400 MHz) DMSO-d6 δ 3.58 (3H, s), 2.59 (2H, s), 2.46 (2H, s), 1.06 (6H, s).

Step 4

Methyl 4-{4-[4-(acetyloxy)butyl]-1,3-thiazol-2-yl}-3,3-dimethylbutanoate:

Methyl 5-amino-3,3-dimethyl-5-thioxopentanoate (500 mg; 2.64 mmoles) was dissolved in 1,4-dioxane (10 mL) under nitrogen and magnesium carbonate hydroxide pentahydrate (640 mg; 1.32 mmoles) was added. 6-Chloro-5-oxohexyl acetate (685 mg; 3.56 mmoles; Rieke, R. D.; Brown, J. D.; Wu, X. Synth. Commun. 1995, 25(23), 3923.) was added and the mixture was magnetically stirred for 10 hours with heating to 60° C. The mixture was allowed to cool, diluted with ethyl acetate and filtered. The solvent was removed under vacuum and the residue was purified by chromatography on silica gel, eluting with hexane/ethyl acetate (3:1). Following removal of solvent the product, methyl 4-{4-[4-(acetyloxy)butyl]-1,3-thiazol-2-yl}-3,3-dimethylbutanoate, was obtained as pale yellow oil. (820 mg). The material was impure, containing some 6-Chloro-5-oxohexyl acetate. $^1$H NMR (400 MHz) CDCl$_3$ δ 6.76 (1H, s), 4.04–4.11 (2H, m), 3.68 (3H, m), 3.05 (2H, s), 2.78 (2H, t, J=7.5 Hz), 2.33 (2H, s), 2.04 (3H, s), 1.61–1.82 (4H, m), 1.10 (6H, s).

Step 5

Methyl 4-[4-(4-hydroxybutyl)-1,3-thiazol-2-yl]-3,3-dimethylbutanoate:

The product from the previous reaction (800 mg; 2.44 mmoles) was dissolved in methanol and cooled to 5° C. Potassium carbonate (405 mg; 2.93 mmoles) was added and the mixture was magnetically stirred under nitrogen for 5 hours. The mixture was diluted with ethyl acetate (100 mL) and the mixture was filtered through celite. The solvent was removed under vacuum and the residue was purified by chromatography on silica gel, eluting with hexane/ethyl acetate (1:1). Solvent was removed to give the product, methyl 4-[4-(4-hydroxybutyl)-1,3-thiazol-2-yl]-3,3-dimethylbutanoate (220 mg; 32%) as an oil. $^1$H NMR (400 MHz) CDCl$_3$ δ 6.77 (1H, s), 3.68 (3H, s), 3.65–3.70 (2H, m), 3.04 (2H, s), 2.79 (2H, t, J=7.5 Hz), 2.33 (2H, s), 1.75–1.85 (2H, m), 1.59–1.68 (2H, m), 1.10 (6H, s). (Starting material, 41% was also isolated).

Step 6

Methyl 3,3-dimethyl-4-[4-(4-oxobutyl)-1,3-thiazol-2-yl]butanoate:

To a solution of DMSO (165 μL; 2.32 mmoles) in dry methylene (5 mL) chloride under nitrogen at −70° C. was added oxalyl chloride (0.55 mL of a 2.0 M solution in methylene chloride; 1.11 mmoles). The mixture was magnetically stirred for 1 hour. A solution of the product from the previous reaction (210 mg; 0.736 mmoles) in methylene chloride (5 mL) was added. After stirring for 40 minutes triethylamine (670 μL; 4.80 mmoles) was added and the reaction mixture was allowed to warm to ambient temperature. The mixture was diluted with ethyl acetate (50 mL) and the solution was washed with water (20 mL) and saturated sodium chloride solution (20 mL). The combined aqueous phases were extracted with methylene chloride (2×50 mL) and ethyl acetate (50 mL). The combined organic phases were dried over magnesium sulfate and filtered. The solvent was removed under vacuum to give the crude product as yellow oil. The material was purified by chromatography on silica gel, eluting with hexane/ethyl acetate (1:1). Following removal of solvent the product, methyl 3,3-dimethyl-4-[4-(4-oxobutyl)-1,3-thiazol-2-yl]butanoate, was obtained as a pale yellow oil (162 mg; 78%). $^1$H NMR (400 MHz) CDCl$_3$ δ 9.77 (1H, t, J=1.7 Hz), 6.78 (1H, s), 3.68 (3H, s), 3.04 (2H, s), 2.79 (2H, t, J=7.5 Hz), 2.49 (2H, dt, J=1.7, 7.3 Hz). 2.33 (2H, s), 2.01–2.09 (2H, m), 1.10 (6H, m).

Step 7

Methyl 3,3-dimethyl-4-{4-[4-(pyridin-2-ylamino)butyl]-1,3-thiazol-2-yl}butanoate:

The product from the previous reaction (160 mg; 0.565 mmoles) was dissolved in methylene chloride (10 mL) under nitrogen. 2-Aminopyridine (60 mg; 0.62 mmoles) was added and the mixture was magnetically stirred for 30 minutes. Sodium triacetoxyborohydride (180 mg; 0.85 mmoles) was added and stirring was continued for 4 hours. The reaction mixture was added to aqueous sodium bicarbonate solution (30 mL) and then extracted with ethyl acetate (3×30 mL). The combined extracts were washed with aqueous sodium chloride solution (10 mL) and dried over sodium sulfate. Following filtration, the solvent was removed under vacuum. The resulting product was purified by chromatography on silica gel, eluting with hexane/-ethyl acetate (1:1 to 1:2). The product, methyl 3,3-dimethyl-4-{4-[4-(pyridin-2-ylamino)butyl]-1,3-thiazol-2-yl}butanoate, was obtained as a pale yellow oil (153 mg; 75%). $^1$H NMR (400 MHz) CDCl$_3$ δ 8.04–8.08 (1H, m), 7.37–7.42 (1H, m), 6.75 (1H, s), 6.52–6.57 (1H, m), 6.36 (1H, d, J=8 Hz), 4.47–4.57 (1H, br), 3.68 (3H, s), 3.25–3.33 (2H, m), 3.04 (2H, s), 2.80 (2H, t, J=7.5 Hz), 2.33 (2H, s), 1.77–1.87 (2H, m), 1.60–1.75 (2H, m), 1.10 (6H, m).

Step 8

3,3-Dimethyl-4-{4-[4-(pyridin-2-ylamino)butyl]-1,3-thiazol-2-yl}butanoic acid:

The product from the previous reaction (150 mg; 0.415 mmoles) was dissolved in methanol (5 mL). Aqueous sodium hydroxide (1.5 mL of a 1M solution; 1.5 mmoles) was added and the mixture was stirred under nitrogen for 5 hours at ambient temperature and then heated at 40° C. for 5 hours. The mixture was allowed to cool and then the pH of the solution was adjusted to pH 7 by the addition of hydrochloric acid (2M). The solution was evaporated under vacuum and then dissolved in ethyl acetate/methanol (20:1, 30 mL) and filtered through celite. The solvent was removed under vacuum and the residue was dissolved in ethyl acetate and filtered to remove fine particulates. Removal of solvent under vacuum gave the product, 3,3-dimethyl-4-{4-[4-(pyridin-2-ylamino)butyl]-1,3-thiazol-2-yl}butanoic acid, as a pale yellow oil (153 mg; 92%). It contains 50 mole % ethyl acetate by NMR and analyzes for 0.2HCl. $^1$H NMR (400 MHz) DMSO-d6 δ 7.90–7.94 (1H, m), 7.29–7.34 (1H, m), 7.11 (1H, s), 6.38–6.45 (3H, m), 3.18–3.25 (2H, m), 2.99 (2H, s), 2.69 (2H, t, J=7.5 Hz), 2.20 (2H, s), 1.64–1.73 (2H, m), 1.48–1.58 (2H, m), 1.00 (6H, s). Anal. Calc. for C$_{18}$H$_{25}$N$_3$O$_2$S0.5ethyl acetate.0.2HCl: C, 60.23; H, 7.38; N, 10.54. Found C, 60.47; H, 7.13; N, 10.36.

EXAMPLE 4

[1-({3-[4-(pyridin-2-ylamino)butyl]-1,2,4-oxadiazol-5-yl}methyl)cyclopentyl]-acetic acid

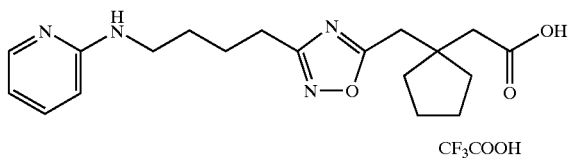

CF$_3$COOH

STEP 1

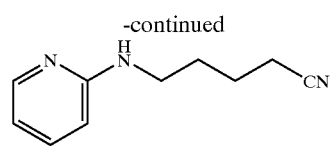

5-(pyridin-2-ylamino)pentanenitrile:

To a stirred solution of 2-aminopyridine (8.7 g, Aldrich) in DMF (75 mL) was added potassium hydride (12.6 g, 30 wt. % dispersion in mineral oil, Aldrich). After 1 hr, 4-bromobutyronitrile (15 g, Aldrich) was added. The mixture was heated to 60° C. for 16 hr. The mixture was quenched with water and the volatiles were removed in vacuo. The residue was extracted with ethyl acetate. The extract was filtered through a bed of silica gel and distilled in vacuo. The fraction boiling at 150° C. to 170° C. was collected to provide the title product as a white solid. $^1$H (CDCl$_3$) δ 1.78 (4H, m); 2.41 (2H, t); 3.36 (2H, q); 4.53 (2H, broad t); 6.38 (1H, dt); 6.57 (1H, ddd); 7.42 (1H, ddd); 8.08 (1H, ddd).

Step 2 (Alternate Procedure to Step 3, EXAMPLE A)

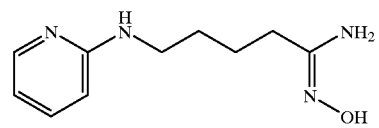

(1Z)-N'-hydroxy-5-(pyridin-2-ylamino)pentanimidamide:

To a solution of sodium (2.7 g, Aldrich) in methanol (100 mL) was added hydroxylamine hydrochloride (8.2 g, Aldrich). The mixture was stirred for 1 hr and filtered. To the filtrate was added the product of STEP1 (3 g). The solution was heated to 41° C. for 48 hrs. The volatiles were removed and the residue was extracted with ethyl acetate and aqueous saturated sodium bicarbonate solution. The organic phase was dried over MgSO$_4$ and concentrated in vacuo to provide the title product as a white solid. $^1$H (DMSOd$_6$) δ 1.53 (4H, m); 1.97 (2H, t); 3.19 (2H, q); 5.31 (2H, s); 0.42 (3H, m); 7.32 (1H, ddd); 0.93 (1H, dd); 8.78 (1H, s).

Step 3

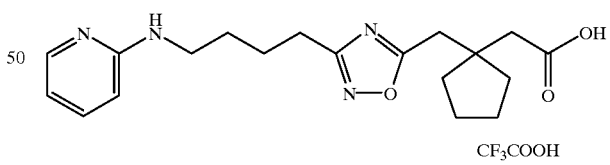

CF$_3$COOH

[1-({3-[4-(pyridin-2-ylamino)butyl]-1,2,4-oxadiazol-5-yl}methyl)cyclopentyl]-acetic acid trifluoroacetate:

A stirred mixture of the product of STEP2 (100 mg), 3,3-tetramethyleneglutaric anhydride (80 mg, Aldrich) and 1,4-dioxane (2 mL, Aldrich) was heated to 100° C. for 16 hrs. The resulting mixture was purified by HPLC to provide the title compound as a gum. $^1$H (CD$_3$OD) δ 1.65 (8H, m); 1.77 (2H, p); 1.89 (2H, p); 2.43 (2H, s); 2.81 (2H, t); 3.15 (2H, s); 3.39 (2H, t); 6.86 (1H, t); 7.03 (1H, d); 7.80 (1H, d); 7.88 (1H, t).

EXAMPLE 5

4-phenyl-4-{3-[4-(pyridin-2-ylamino)butyl]-1,2,4-oxadiazol-5-yl}butanoic acid

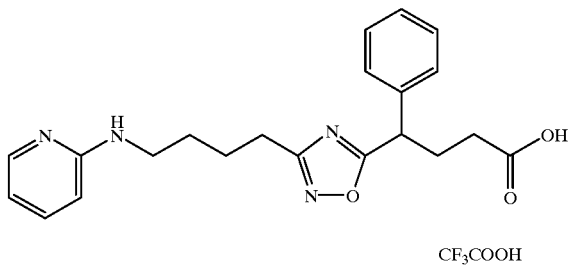

CF₃COOH

EXAMPLE 6

2-phenyl-4-{3-[4-(pyridin-2-ylamino)butyl]-1,2,4-oxadiazol-5-yl}butanoic acid

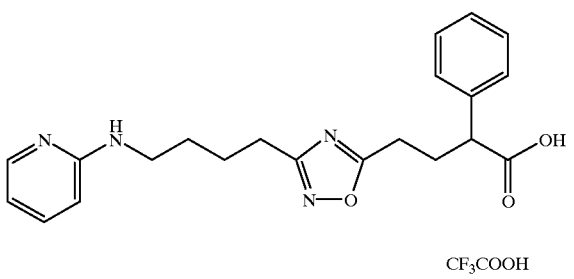

CF₃COOH

The procedure for the preparation of the product of EXAMPLE 4, STEP3 was repeated using 2-phenylglutaric anhydride (Aldrich) in the place of 3,3-tetramethyleneglutaric anhydride to provide a 55:45 mixture of the title products as a gum. $^1$H (CD$_3$OD) δ 1.78 (2H, p); 1.88 (2H, m); 2.15–2.36 (2H, comp. band); 2.42–2.54 (1H, comp. band); 2.75–2.90 (3H, comp. band); 3.39 (2H, t); 3.67 (4.38 (1H, t); 6.86 (1H, td); 7.03 (1H, d); 7.24–7.38 (5H, complex band); 7.80 (1H, d); 7.87 (1H, t).

EXAMPLE 7

3,3-dimethyl-4-{3-[2-(2-methyl-5,6,7,8-tetrahydro-1,8-naphthyridin-3-yl)ethyl]-1,2,4-oxadiazol-5-yl}butanoic acid

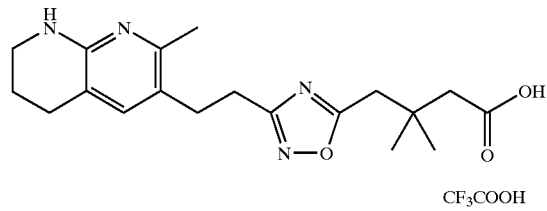

CF₃COOH

STEP 1

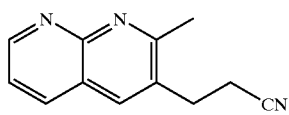

3-(2-methyl-1,8-naphthyridin-3-yl)propanenitrile:

A mixture of 5-oxo-hexanenitrile (5 mL, TCI-US), 2-amino-3-formylpyridine (7 g, J. Org. Chem. 1983, vol.48, p3401) and ethanol (100 mL) was heated to reflux for 12 hours. Following evaporation of the solvent, the residue was chromatographed (silica gel, ethyl acetate) to give 4-[1,8]naphthyridin-2-yl-butyronitirile and the title product as colorless solids. $^1$H (CDCl$_3$) δ 2.29 (3H, s); 2.83 (2H, t); 3.18 (2H, t); 7.48 (1H, dd); 8.04 (1H, s); 8.20 (1H, dd); 9.03 (1H, dd).

Step 2

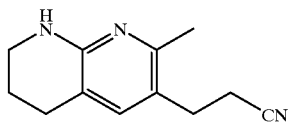

3-(2-methyl-5,6,7,8-tetrahydro-1,8-naphthyridin-3-yl)propanenitrile:

A mixture of the product of STEP1 (2 g), 10% Pd/C (250 mg) and ethanol (15 mL) was stirred under a balloon of hydrogen gas for 2 hr. Filtration and evaporation produced the title product. $^1$H (CDCl$_3$) δ 1.83 (2H, p); 2.24 (3H, s); 2.43 (2H, t); 2.62 (2H, t); 2.73 (2H, t); 3.31 (2H, m); 4.81 (1H, broad s); 6.88 (1H, s).

Step 3

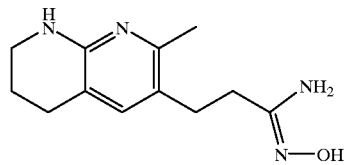

(1Z)-N'-hydroxy-3-(2-methyl-5,6,7,8-tetrahydro-1,8-naphthyridin-3-yl)-propanimidamide:

The procedure for the preparation of EXAMPLE 4, STEP 2 was repeated using the product of STEP 2 to provide the title compound as a colorless solid. $^1$H (DMSOd$_6$) δ 1.74 (2H, p); 2.09 (2H, t); 2.18 (3H, s); 2.58 (4H, m); 3.20 (2H, m); 5.38 (2H, s); 6.04 (1H, s); 6.91 (1H, s); 8.72 (1H, s).

Step 4

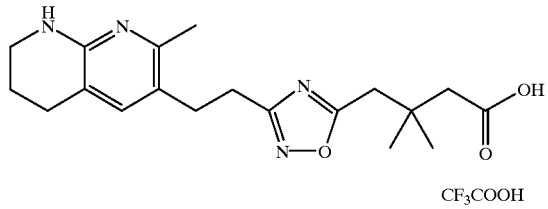

CF₃COOH 3,3-dimethyl-4-{3-[2-(2-methyl-5,6,7,8-tetrahydro-1,8-naphthyridin-3-yl)-ethyl]-1,2,4-oxadiazol-5-yl}butanoic acid trifluoroacetate:

A stirred mixture of the product of STEP 3 (100 mg), 3,3-dimethylglutaric anhydride (80 mg, Aldrich) and 1,4-dioxane (2 mL, Aldrich) was heated to 100° C. for 16 hrs. The resulting mixture was purified by HPLC to provide the title compound as a gum. $^1$H (CD$_3$OD) δ 1.10 (6H, s); 1.92 (2H, p); 2.35 (2H, s); 2.40 (3H, s); 2.77 (2H, t); 2.97 (2H, t); 3.01 (2H, t); 3.05 (2H, s); 3.46 (2H, t); 7.51 (1H, s).

EXAMPLE 8

[1-({3-[2-(2-methyl-5,6,7,8-tetrahydro-1,8-naphthyridin-3-yl)ethyl]-1,2,4-oxadiazol-5-yl}methyl)cyclopentyl]acetic acid

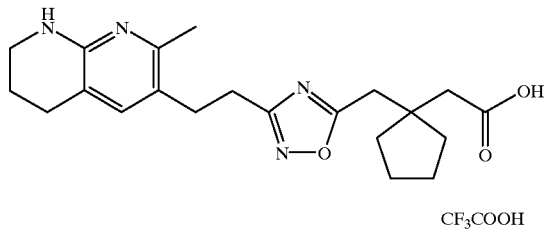

CF₃COOH

A stirred mixture of the product of EXAMPLE7, STEP3 (100 mg), 3,3-tetramethyleneglutaric anhydride (80 mg, Aldrich) and 1,4-dioxane (2 mL, Aldrich) was heated to 100° C. for 16 hrs. The resulting mixture was purified by HPLC to provide the title compound as a gum. $^1$H (CD₃OD) δ 1.66 (8H, m); 1.93 (2H, p); 2.40 (3H, s); 2.42 (2H, s); 2.77 (2H, t); 2.97 (2H, t); 3.00 (2H, t); 3.14 (2H, s); 3.46 (2H, t); 7.51 (1H, s).

EXAMPLE 9

4-{3-[2-(2-methyl-5,6,7,8-tetrahydro-1,8-naphthyridin-3-yl)ethyl]-1,2,4-oxadiazol-5-yl}-4-phenylbutanoic acid

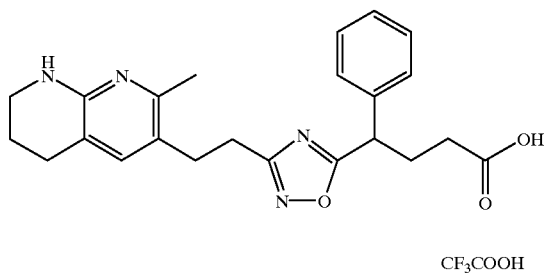

CF₃COOH

EXAMPLE 10

4-{3-[2-(2-methyl-5,6,7,8-tetrahydro-1,8-naphthyridin-3-yl)ethyl]-1,2,4-oxadiazol-5-yl}-2-phenylbutanoic acid

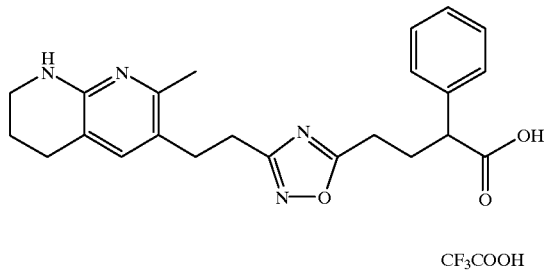

CF₃COOH

The procedure for the preparation of the product of EXAMPLE 8 was repeated using 2-phenylglutaric anhydride (Aldrich) in the place of 3,3-tetramethyleneglutaric anhydride to provide a 55:45 mixture of the title products as a gum. $^1$H (CD₃OD) δ 1.90 (2H, m); 2.15–2.35 (2H, comp. band); 2.32/2.40 (3H, s); 2.42–2.53 (1H, comp. band); 2.69/2.76 (2H, t); 2.85 (1H, m); 2.92–3.04 (4H, comp. band); 3.45 (2H, t); 3.66/4.39, (1H, t); 7.23–7.40 (5H, comp. band), 7.44/7.52 (1H, s).

EXAMPLE 11

4-{3-[2-(2-methyl-5,6,7,8-tetrahydro-1,8-naphthyridin-3-yl)ethyl]-1,2,4-oxadiazol-5-yl}-2-phenylbutanoic acid

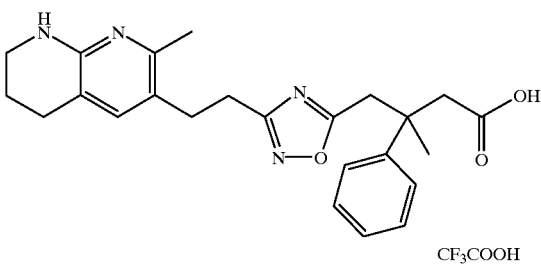

CF₃COOH

A stirred mixture of the product of EXAMPLE 7, STEP 3, (100 mg), 3-methyl-3-phenyl-glutaric anhydride (80 mg, Bruice, T. C.; Bradbury, W. C.; J. Amer. Chem. Soc.; EN; 87; 21; 1965; 4838–4845.) and 1,4-dioxane (2 mL, Aldrich) was heated to 100° C. for 16 hrs. The resulting mixture was purified by HPLC to provide the title compound as a gum. $^1$H (CD₃OD) δ 1.60 (3H, s); 1.92 (2H, p); 2.32 (3H, s); 2.75 (2H, t); 2.83 (1H, d); 2.85–2.95 (4H, comp. band); 3.12 (1H, d); 3.47 (2H, t); 3.48 (1H, d); 3.52 (1H, d); 7.18 (1H, t); 7.28 (2H, t); 7.36 (2H, d); 7.44 (1H, s).

EXAMPLE 12

3,3-dimethyl-4-{3-[3-(5,6,7,8-tetrahydro-1,8-naphthyridin-2-yl)propyl]-1,2,4-oxadiazol-5-yl}butanoic acid

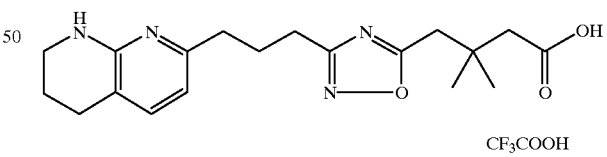

CF₃COOH

A stirred mixture of (1Z)-N'-hydroxy-4-(5,6,7,8-tetrahydro-1,8-naphthyridin-2-yl)butanimidamide (100 mg, WO 99/30709), 3,3-dimethylglutaric anhydride (80 mg, Aldrich) and 1,4-dioxane (2 mL, Aldrich) was heated to 100° C. for 16 hrs. The resulting mixture was purified by HPLC to provide the title compound as a gum. $^1$H (CD₃OD) δ 1.12 (6H, s); 1.96 (2H, p); 2.14 (2H, p); 2.36 (2H, s); 2.80 (6H, m); 3.05 (2H, s); 3.50 (2H, t); 6.63 (1H, d); 7.57 (1H, d).

EXAMPLE 13

[1-({3-[3-(5,6,7,8-tetrahydro-1,8-naphthyridin-2-yl)propyl]-1,2,4-oxadiazol-5-yl}methyl)cyclopentyl]acetic acid

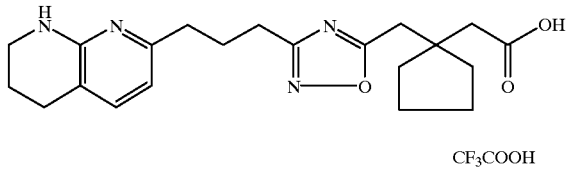

CF₃COOH

A stirred mixture of (1Z)-N'-hydroxy-4-(5,6,7,8-tetrahydro-1,8-naphthyridin-2-yl)butanimidamide (100 mg, WO 99/30709), 3,3-tetramethyleneglutaric anhydride (80 mg, Aldrich) and 1,4-dioxane (2 mL, Aldrich) was heated to 100° C. for 16 hrs. The resulting mixture was purified by HPLC to provide the title compound as a gum. $^1$H (CD$_3$OD) δ 1.68 (8H, m); 1.95 (2H, p); 2.13 (2H, p); 2.45 (2H, s); 2.80 (6H, m); 3.15 (2H, s); 3.50 (2H, t); 6.63 (1H, d);

EXAMPLE 14

4-phenyl-4-{3-[3-(5,6,7,8-tetrahydro-1,8-naphthyridin-2-yl)propyl]-1,2,4-oxadiazol-5-yl}butanoic acid

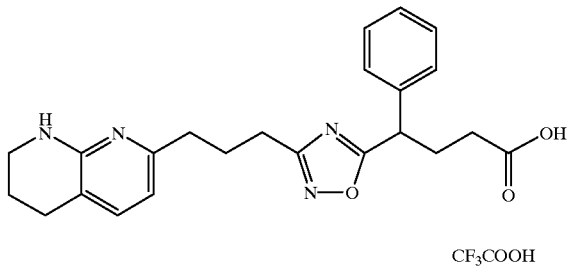

CF₃COOH

EXAMPLE 15

2-phenyl-4-{3-[3-(5,6,7,8-tetrahydro-1,8-naphthyridin-2-yl)propyl]-1,2,4-oxadiazol-5-yl}butanoic acid

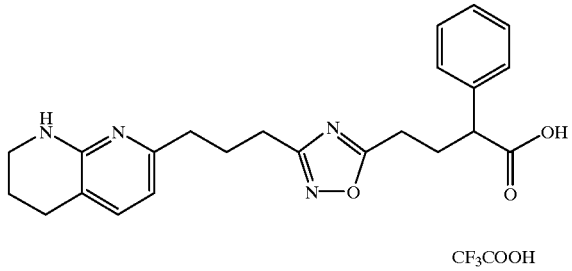

CF₃COOH

A stirred mixture of (1Z)-N'-hydroxy-4-(5,6,7,8-tetrahydro-1,8-naphthyridin-2-yl)butanimidamide (100 mg, WO 99/30709), 2-phenylglutaric anhydride (80 mg, Aldrich) and 1,4-dioxane (2 mL, Aldrich) was heated to 100° C. for 16 hrs. The resulting solution was purified by HPLC to provide the title compound as a gum. $^1$H (CD$_3$OD) δ 1.93 (2H, p); 2.12 (2H, m); 2.18–2.37 (2H, comp. band); 2.42–2.55 (1H, comp. band); 2.74–2.90 (7H, comp. band); 3.48 (2H, t); 3.66/4.38 (1H, t); 6.60/6.62 (1H, d); 7.23–7.39 (5H, comp. band); 7.51/7.55 (1H, d).

EXAMPLE 16

3-(1,3-benzodioxol-5-yl)-4-{3-[3-(5,6,7,8-tetrahydro-1,8-naphthyridin-2-yl)propyl]-1,2,4-oxadiazol-5-yl}butanoic acid

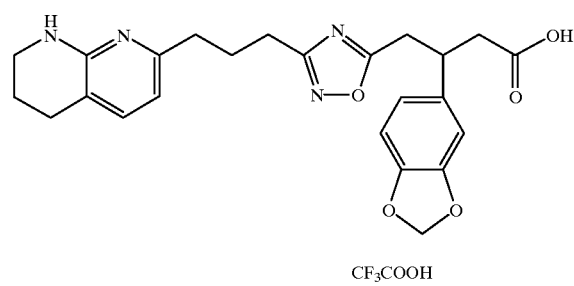

CF₃COOH

Step 1

Diethyl 2-(1,3-benzodioxol-5-yl)-4-hydroxy-4-methyl-6-oxocyclohexane-1,3-dicarboxylate:

Following the procedure of Brown, E.; Dhal, R.; Papin, N.; Tetrahedron, 1995, 51,13061–13072: piperonal (22.5 g; 150 mmoles), ethyl acetoacetate (38.24 ml; 300 mmoles), and piperidine (1.5 ml) were combined in a 500 ml round bottom flask and stirred at room temperature. After 72 hours, the mixture solidified and was re-crystallized using ethanol to give 42.4 g. of product (72%). $^1$H NMR (DMSO-d$_6$) δ 6.95 (m, 1H), 6.8 (m, J=7.5 Hz, 1H), 6.71 (m, J=7.5 Hz, 1H), 5.97 (s, 2H), 4.9 (s, 1H), 4.0–3.7 (m, 6H), 3.25 (d, J=11 Hz, 1H), 2.9 (d, J=14 Hz, 1H), 2.35 (d, J=14 Hz, 1H), 1.23 (s, 3H), 1.0 (t, 3H), 0.92 (t, 3H).

Step 2

3-(1,3-benzodioxol-5-yl)pentanedioic acid:

Diethyl 2-(1,3-benzodioxol-5-yl)-4-hydroxy-4-methyl-6-oxocyclohexane-1,3-dicarboxylate (19 g) was suspended in ethanol (140 ml) and an aqueous solution of NaOH (50%, 270 ml). The mixture was heated at reflux for one hour. After the mixture was cooled to room temperature, the ethanol was removed under reduced pressure. Then, concentrated HCl was added until pH 1 was achieved while maintaining the temperature below 50° C. The mixture was filtered. The solid was washed with ether. The two layers were separated. The aqueous layer was extracted with ether (3×). The ether layers were combined, dried, and concentrated to give product. $^1$H NMR (DMSO-d$_6$) δ 12.06 (br s, 2H), 6.88–6.68 (m, 3H), 5.98 (s, 2H), 3.4–3.3 (m, 1H), 2.62–2.42 (m, 4H).

Step 3

4-(1,3-benzodioxol-5-yl)dihydro-2H-pyran-2,6(3H)-dione:

3-(1,3-benzodioxol-5-yl)pentanedioic acid (2 g, 7.9 mmoles) was suspended in acetic anhydride (50 ml) and refluxed for two hours. The reaction mixture was allowed to cool to room temperature and the solvent was removed under reduced pressure. The residue was triturated with ether to give the product (1.3 g, 70%). $^1$H NMR (DMSO-d$_6$) δ 6.91 (m, 1H), 6.89 (m, 1H), 6.72 (m, 1H), 6.01 (s, 2H), 3.53–3.41 (m, 1H), 3.07–2.89 (m, 4H).

Step 4

3-(1,3-benzodioxol-5-yl)-4-{3-[3-(5,6,7,8-tetrahydro-1,8-naphthyridin-2-yl)-propyl]-1,2,4-oxadiazol-5-yl}butanoic acid trifluoroacetate:

The title compound was prepared using the following general procedure:

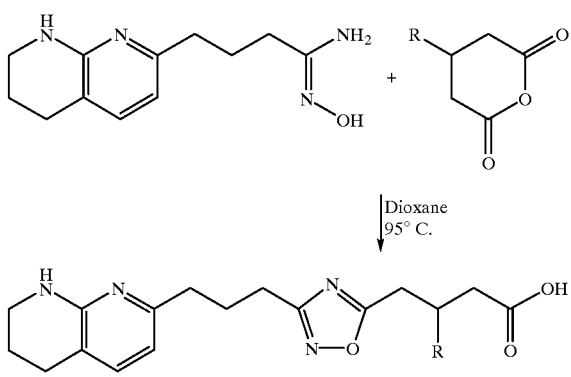

Dioxane
95° C.

100 mg of the amide oxime (prepared according to the method as described in WO 99/30709) was added to an equivalent of the anhydride suspended in dioxane (5 ml). The reaction mixture was heated to 95° C. overnight, the solvent was removed and the residue purified on HPLC (Gilson) using acetonitrile gradient 10–50% in 12 minutes for all compounds except the pyridine and quinoline derivatives used a gradient 5–35% in 12 minutes. $^1$H NMR (DMSO-$d_6$) δ 12.2 (br s, 1H), 8.13 (br s, 1H), 7.59 (d, J=7.5 Hz, 1H), 6.91–6.52 (m, 4H), 5.91 (s, 2H), 3.52–3.39 (m, 3H), 3.3–3.14 (m, 2H), 2.77–2.56 (m, 8H), 1.99–1.90 (m, 2H), 1.88–1.76 (m, 2H). Anal. Calcd. for $C_{24}H_{26}N_4O_5$ plus $1.2CF_3CO_2H$ and $1.0H_2O$: C, 52.38; H, 4.86; N, 9.26. Found: C, 52.47; H, 4.47; N, 9.27.

EXAMPLE 17

3-(1,3-benzodioxol-5-yl)-4-{3-[4-(pyridin-2-ylamino)butyl]-1,2,4-oxadiazol-5-yl}butanoic acid

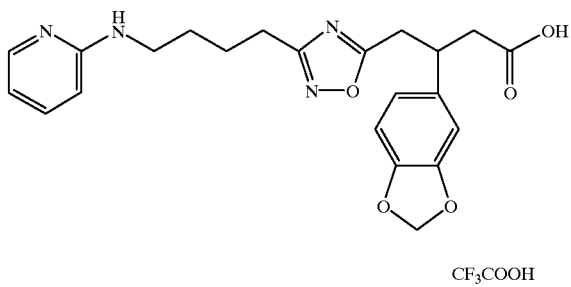

CF$_3$COOH

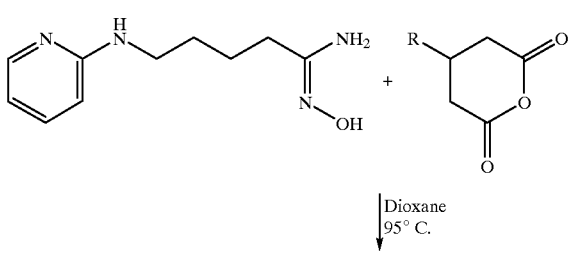

Dioxane
95° C.

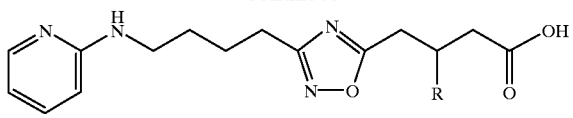

3-(1,3-benzodioxol-5-yl)-4-{3-[4-(pyridin-2-ylamino)butyl]-1,2,4-oxadiazol-5-yl}butanoic acid trifluoroacetate:

The title compound was prepared according to the method as described for preparing EXAMPLE 16 using the appropriate amide oxime: $^1$H NMR (DMSO-$d_6$) δ 12.15 (br s, 1H), 8.65 (br s, 1H), 7.92–7.82 (m, 2H), 7.00 (d, J=9.5 Hz, 1H), 6.9 (m, 1H), 6.83 (t, 1H), 6.73 (d, J=7.5 Hz, 1H), 6.63–6.61 (m, 1H), 5.93 (s, 2H), 3.55–3.15 (m, 5H), 2.76–2.55 (m, 4H), 1.73–1.63 (m, 2H), 1.61–1.52 (m, 2H). Mass Spectrum: (MH$^+$)=425.

EXAMPLE 18

3-quinolin-3-yl-4-{3-[3-(5,6,7,8-tetrahydro-1,8-naphthyridin-2-yl)propyl]-1,2,4-oxadiazol-5-yl}butanoic acid

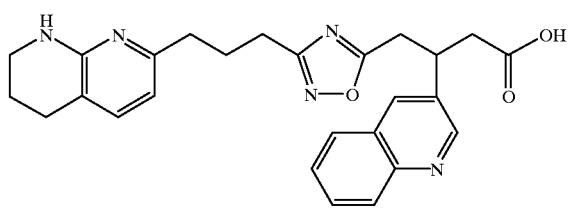

CF$_3$COOH

Step 1
Diethyl 4-hydroxy-4-methyl-6-oxo-2-quinolin-3-ylcyclohexane-1,3-dicarboxylate:

The compound was prepared according to the method as described for preparing EXAMPLE 16, STEP 1: $^1$H NMR (DMSO-$d_6$) δ 8.85 (m, 1H), 8.33 (m, 1H), 8.0 (d, J=7.5 Hz, 1H), 7.95 (d, J=7.5 Hz, 1H), 7.72 (t, J=7.5 Hz, 1H), 7.6 (t, J=7.5 Hz, 1H), 4.21 (d, J=14 Hz, 1H), 4.12 (t, J=14 Hz, 1H), 3.95–3.7 (m, 5H), 3.55 (d, J=10.5 Hz, 1H), 3.01 (d, J=14 Hz, 1H), 2.43 (d, J=14 Hz, 1H), 1.32 (s, 3H), 0.9 (t, 3H), 0.74 (t, 3H).

Step 2
3-quinolin-3-ylpentanedioic acid:

The compound was prepared according to the method as described for preparing EXAMPLE 16, STEP 2: $^1$H NMR (DMSO-$d_6$) δ 12.2 (br s, 2H), 8.85 (m, 1H), 8.23 (m, 1H), 7.98 (d, J=7.5 Hz, 1H), 7.91 (d, J=7.5 Hz, 1H), 7.71 (t, J=7.5 Hz, 1H), 7.59 (t, J=7.5 Hz, 1H), 3.68–3.59 (m, 1H), 2.84–2.66 (m, 4H).

Step 3:
4-quinolin-3-yldihydro-2H-pyran-2,6(3H)-dione:

The compound was prepared according to the method as described for preparing EXAMPLE 16, STEP 3: $^1$H NMR (DMSO-$d_6$) δ 8.91 (m, 1H), 8.26 (m, 1H), 8.02–7.97 (m, 2H), 7.8–7.74 (m, 1H), 7.66–7.6 (m, 1H), 3.9–3.8 (m, 1H), 3.28–3.1 (m, 4H).

Step 4
3-quinolin-3-yl-4-{3-[3-(5,6,7,8-tetrahydro-1,8-naphthyridin-2-yl)propyl]-1,2,4-oxadiazol-5-yl}butanoic acid bis trifluoroacetate:

The title compound was prepared according to the method as described for preparing EXAMPLE 16 using the appropriate anhydride: $^1$H NMR (DMSO-d$_6$) δ 12.2 (br s, 1H), 8.86 (m, 1H), 8.31 (m, 1H), 7.98–7.82 (m, 3H), 7.74–7.69 (m, 1H), 7.6–7.52 (m, 2H), 6.49 (d, J=7.5 Hz, 1H), 3.85–3.75 (m, 1H), 3.5–3.39 (m, 4H), 3.0–2.82 (m, 2H), 2.78–2.7 (m, 2H), 2.65–2.59 (m, 2H), 2.55–2.5 (m, 2H), 1.9–1.78 (m, 4H). Anal. Calcd. for C$_{26}$H$_{27}$N$_5$O$_3$ plus 2.0CF$_3$CO$_2$H: C, 52.56; H, 4.26; N, 10.22. Found: C, 52.42; H, 4.28; N, 10.38.

EXAMPLE 19

3-quinolin-3-yl-4-{3-[4-(pyridin-2-ylamino)butyl]-1,2,4-oxadiazol-5-yl}-butanoic acid

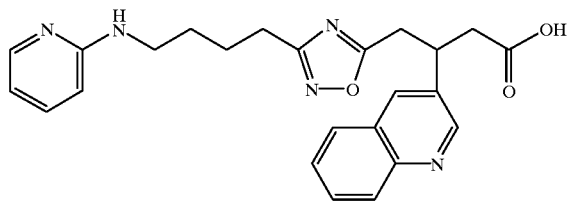

CF$_3$COOH

The title compound was prepared according to the method as described for preparing EXAMPLE 17 using the appropriate anhydride: $^1$H NMR (DMSO-d$_6$) δ 12.3 (br s, 1H), 8.83 (m, 1H), 8.68 (br s, 1H), 8.3 (m, 1H), 8.0–7.82 (m, 4H), 7.72–7.68 (m, 1H), 7.61–7.53 (m, 1H), 7.01 (d, J=14 Hz, 1H), 6.83 (t, J=7.5 Hz, 1H), 3.82–3.78 (m, 1H), 3.24–3.20 (m, 2H), 3.0–2.8 (m, 2H), 2.68–2.61 (m, 4H), 1.69–1.60 (m, 2H), 1.55–1.45 (m, 2H). Mass Spectrum: (MH$^+$)=432.

EXAMPLE 20

3-(3-methoxyphenyl)-4-{3-[3-(5,6,7,8-tetrahydro-1,8-naphthyridin-2-yl)propyl]-1,2,4-oxadiazol-5-yl}butanoic acid

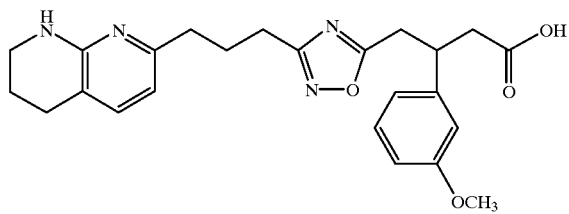

CF$_3$COOH

Step 1

Diethyl 4-hydroxy-2-(3-methoxyphenyl)-4-methyl-6-oxocyclohexane-1,3-dicarboxylate:

The compound was prepared according to the method as described for preparing EXAMPLE 16, STEP 1: $^1$H NMR (DMSO-d$_6$) δ 7.18 (t, 1H), 6.87 (m, 2H), 6.75 (m, 1H), 4.9 (s, 1H), 4.0–3.78 (m, 6H), 3.7 (s, 3H), 3.3 (d, J=10.5 Hz, 1H), 2.92 (d, J=14 Hz, 1H), 2.32 (d, J=14 Hz, 1H), 1.22 (s, 3H), 0.96 (t, 3H), 0.85 (t, 3H).

Step 2

3-(3-methoxyphenyl)pentanedioic acid:

The compound was prepared according to the method as described for preparing EXAMPLE 16, STEP 2: $^1$H NMR (DMSO-d$_6$) δ 12.08 (br s, 2H), 7.19 (t, J=7.5 Hz, 1H), 6.83–6.72 (m, 3H), 3.71 (s, 3H), 3.48–3.32 (m, 1H), 2.65–2.46 (m, 4H).

Step 3

4-(3-methoxyphenyl)dihydro-2H-pyran-2,6(3H)-dione:

The compound was prepared according to the method as described for preparing EXAMPLE 16, STEP 3: $^1$H NMR (DMSO-d$_6$) δ 7.28 (t, 7.5 Hz, 1H), 6.88–8.82 (m, 3H), 3.75 (s, 3H), 3.56–3.48 (m, 1H), 3.1–2.92 (m, 4H).

Step 4

3-(3-methoxyphenyl)-4-{3-[3-(5,6,7,8-tetrahydro-1,8-naphthyridin-2-yl)-propyl]-1,2,4-oxadiazol-5-yl}butanoic acid trifluoroacetate:

The title compound was prepared according to the method as described for preparing EXAMPLE 16 using the appropriate anhydride: $^1$H NMR (DMSO-d$_6$) δ 12.19 (br s, 1H), 7.99 (br s, 1H), 7.6 (d, J=7.5 Hz, 1H), 7.15 (t, 1H), 6.82–6.7 (m, 3H), 6.54 (d, J=7.5 Hz, 1H), 3.68 (s, 3H), 3.58–3.39 (m, 5H), 3.32–3.19 (m, 2H), 2.80–2.60 (m, 6H), 1.99–1.89 (m, 2H), 1.85–1.76 (m, 2H). Anal. Calcd. for C$_{24}$H$_{28}$N$_4$O$_4$ plus 1.0CF$_3$CO$_2$H and 1.0H$_2$O: C, 54.93; H, 5.50; N, 9.85. Found: C, 55.19; H, 5.93; N, 9.43.

EXAMPLE 21

3-(3-methoxyphenyl)-4-{3-[4-(pyridin-2-ylamino)butyl]-1,2,4-oxadiazol-5-yl}butanoic acid

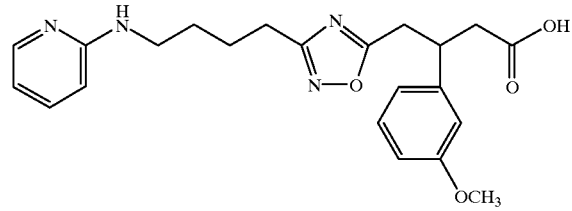

CF$_3$COOH

The title compound was prepared according to the method as described for preparing EXAMPLE 17 using the appropriate anhydride: $^1$H NMR (DMSO-d$_6$) δ 12.18 (br s, 1H), 8.65 (br s, 1H), 7.92–7.81 (m, 2H), 7.13 (d, J=9.5 Hz, 2H), 6.99 (d, J=9.5 Hz, 1H), 6.84–6.70 (m, 4H), 3.69 (s, 3H), 3.55–3.45 (m, 1H), 3.32–3.18 (m, 4H), 2.81–2.59 (m, 4H), 1.73–1.63 (m, 2H), 1.61–1.52 (m, 2H). Anal. Calcd. for C$_{22}$H$_{26}$N$_4$O$_4$ plus 1.45CF$_3$CO$_2$H: C, 51.94; H, 4.81; N, 9.73. Found: C, 52.27; H, 4.96; N, 9.33.

EXAMPLE 22

3-(4-methoxyphenyl)-4-{3-[3-(5,6,7,8-tetrahydro-1,8-naphthyridin-2-yl)propyl]-1,2,4-oxadiazol-5-yl}butanoic acid

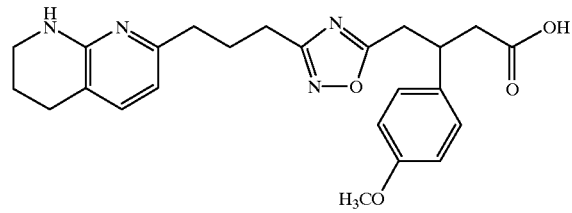

CF$_3$COOH

Step 1

Diethyl 4-hydroxy-2-(4-methoxyphenyl)-4-methyl-6-oxocyclohexane-1,3-dicarboxylate:

The compound was prepared according to the method as described for preparing EXAMPLE 16, STEP 1: $^1$H NMR (DMSO-d$_6$) δ 7.21 (d, J=7.5 Hz, 2H), 6.81 (d, J=7.5 Hz, 2H), 4.85 (s, 1H), 3.95–3.78 (m, 6H), 3.7 (s, 3H), 3.26 (d, J=10.5 Hz, 1H), 2.91 (d, J=14 Hz, 1H), 2.32 (d, J=14 Hz, 1H), 1.23 (s, 3H), 0.97 (t, 3H), 0.88 (t, 3H).

Step 2

3-(4-methoxyphenyl)pentanedioic acid:

The compound was prepared according to the method as described for preparing EXAMPLE 16, STEP 2: $^1$H NMR (DMSO-d$_6$) δ 12.02 (br s, 2H), 7.17 (d, J=9.5 Hz, 2H), 6.81 (d, J=9.5 Hz, 2H), 3.71 (s, 3H), 3.45–3.35 (m, 1H), 2.63–2.41 (m, 4H).

Step 3

4-(4-methoxyphenyl)dihydro-2H-pyran-2,6(3H)-dione:

The compound was prepared according to the method as described for preparing EXAMPLE 16, STEP 3: $^1$H NMR (DMSO-d$_6$) δ 7.21 (d, J=9.5 Hz, 2H), 6.91 (d, J=9.5 Hz, 2H), 3.71 (s, 3H), 3.55–3.45 (m, 1H), 3.06–2.9 (m, 4H).

Step 4

3-(4-methoxyphenyl)-4-{3-[3-(5,6,7,8-tetrahydro-1,8-naphthyridin-2-yl)-propyl]-1,2,4-oxadiazol-5-yl}butanoic acid trifluoroacetate:

The title compound was prepared according to the method as described for preparing EXAMPLE 16 using the appropriate anhydride: $^1$H NMR (DMSO-d$_6$) δ 12.19 (br s, 1H), 7.86 (br s, 1H), 7.6 (d, J=7.5 Hz, 1H), 7.15 (d, J=9.5 Hz, 2H), 6.79 (d, J=9.5 Hz, 2H), 6.55 (d, J=7.5 Hz, 1H), 3.67 (s, 3H), 3.54–3.39 (m, 5H), 3.31–3.16 (m, 2H), 2.73–2.55 (m, 6H), 1.99–1.89 (m, 2H), 1.85–1.76 (m, 2H). Mass Spectrum: (MH$^+$)=437.

EXAMPLE 23

3-(4-methoxyphenyl)-4-{3-[4-(pyridin-2-ylamino)butyl]-1,2,4-oxadiazol-5-yl}butanoic acid

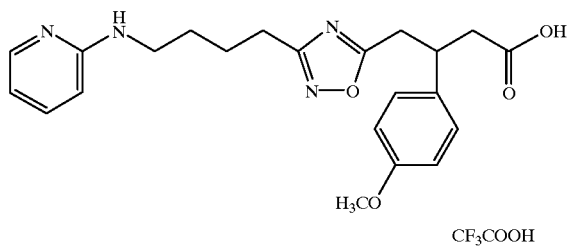

CF$_3$COOH

The title compound was prepared according to the method as described for preparing EXAMPLE 17 using the appropriate anhydride: $^1$H NMR (DMSO-d$_6$) δ 12.15 (br s, 1H), 8.65 (br s, 1H), 7.9–7.82 (m, 2H), 7.13 (d, J=9.5 Hz, 2H), 7.01 (d, J=9.5 Hz, 1H), 6.82 (t, 1H), 6.79 (d, J=9.5 Hz, 2H), 3.7 (s, 3H), 3.55–3.45 (m, 1H), 3.32–3.15 (m, 4H), 2.87–2.55 (m, 4H), 1.73–1.63 (m, 2H), 1.61–1.52 (m, 2H). Anal. Calcd. for C$_{22}$H$_{26}$N$_4$O$_4$ plus 1.4CF$_3$CO$_2$H: C, 52.25; H, 4.84; N, 9.83. Found: C, 52.08; H, 4.85; N, 9.61.

EXAMPLE 24

3-(3-fluorophenyl)-4-{3-[3-(5,6,7,8-tetrahydro-1,8-naphthyridin-2-yl)propyl]-1,2,4-oxadiazol-5-yl}butanoic acid

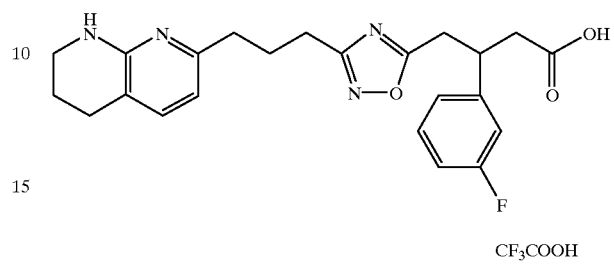

CF$_3$COOH

Step 1

Diethyl 2-(3-fluorophenyl)-4-hydroxy-4-methyl-6-oxocyclohexane-1,3-dicarboxylate:

The compound was prepared according to the method as described for preparing EXAMPLE 16, STEP 1: Mixture of diastereoisomers: $^1$H NMR (DMSO-d$_6$) δ 7.38–7.1 (m, 4H), 4.7–4.5 (m, 1H), 4.0–3.79 (m, 6H), 3.32–3.28 (m, 1H), 2.94–2.89 (m, 1H), 2.38–2.30 (m, 1H), 1.25 (s, 3H), 0.95 (t, 3H), 0.86 (t, 3H).

Step 2

3-(3-fluorophenyl)pentanedioic acid:

The compound was prepared according to the method as described for preparing EXAMPLE 16, STEP 2: $^1$H NMR (DMSO-d$_6$) δ 12.02 (br s, 2H), 7.33–7.29 (m, 1H), 7.15–7.11 (m, 2H), 7.0 (t, 1H), 3.47–3.38 (m, 1H), 2.7–2.5 (m, 4H).

Step 3

4-(3-fluorophenyl)dihydro-2H-pyran-2,6(3H)-dione:

The compound was prepared according to the method as described for preparing EXAMPLE 16, STEP 3: $^1$H NMR (DMSO-d$_6$) δ 7.41 (m, 1H), 7.2–7.09 (m, 3H), 3.66–3.56 (m, 1H), 3.11–2.94 (m, 4H).

Step 4

3-(3-fluorophenyl)-4-{3-[3-(5,6,7,8-tetrahydro-1,8-naphthyridin-2-yl)propyl]-1,2,4-oxadiazol-5-yl}butanoic acid trifluoroacetate:

The title compound was prepared according to the method as described for preparing EXAMPLE 16 using the appropriate anhydride: $^1$H NMR (DMSO-d$_6$) δ 12.28 (br s, 1H), 7.79 (br s, 1H), 7.59 (d, J=7.5 Hz, 1H), 7.31–7.24 (m, 1H), 7.18–6.96 (m, 3H), 6.55 (d, J=7.5 Hz, 1H), 3.61–3.55 (m, 2H), 3.4–3.2 (m, 5H), 2.82–2.6 (m, 6H), 1.99–1.89 (m, 2H), 1.86–1.78 (m, 2H). Mass Spectrum: (MH$^+$)=425.

EXAMPLE 25

3-(3-fluorophenyl)-4-{3-[4-(pyridin-2-ylamino)butyl]-1,2,4-oxadiazol-5-yl}butanoic acid trifluoroacetate

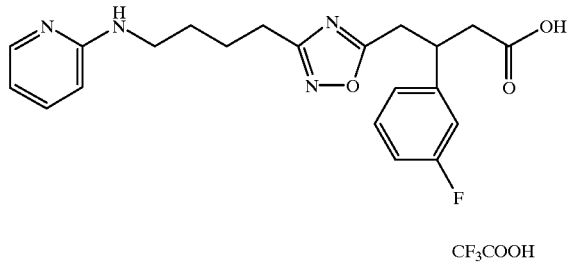

CF$_3$COOH

The title compound was prepared according to the method as described for preparing EXAMPLE 17 using the appropriate anhydride: $^1$H NMR (DMSO-d$_6$) δ 12.25 (br s, 1H), 8.69 (br s, 1H), 7.92–7.81 (m, 2H), 7.31–7.25 (m, 1H), 7.19–6.95 (m, 4H), 6.87–6.8 (m, 1H), 3.61–3.52 (m, 1H), 3.36–3.2 (m, 4H), 2.83–2.61 (m, 4H), 1.73–1.63 (m, 2H), 1.61–1.51 (m, 2H). Anal. Calcd. for C$_{21}$H$_{23}$N$_4$O$_3$F plus 1.0CF$_3$CO$_2$H and 1.0H$_2$O: C, 52.08; H, 4.94; N, 10.56. Found: C, 52.34; H, 4.56; N, 10.42.

EXAMPLE 26

3-(4-fluorophenyl)-4-{3-[3-(5,6,7,8-tetrahydro-1,8-naphthyridin-2-yl)propyl]-1,2,4-oxadiazol-5-yl}butanoic acid trifluoroacetate

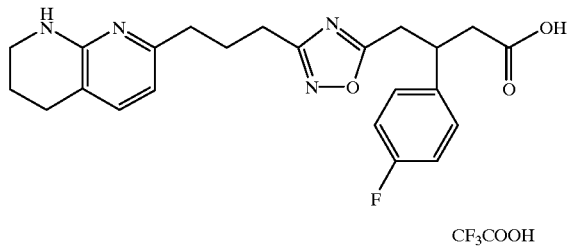

CF$_3$COOH

Step 1
Diethyl 2-(4-fluorophenyl)-4-hydroxy-4-methyl-6-oxocyclohexane-1,3-dicarboxylate:

The compound was prepared according to the method as described for preparing EXAMPLE 16, STEP 1: $^1$H NMR (DMSO-d$_6$) δ 7.36–7.31 (m, 2H), 7.17–7.08 (m, 2H), 4.94 (s, 1H), 4.0–3.77 (m, 6H), 2.91 (d, J=14 Hz, 1H), 2.35 (d, J=14 Hz, 1H), 2.34 (d, J=14 Hz, 1H), 1.24 (s, 3H), 0.94 (t, 3H), 0.86 (t, 3H).

Step 2
3-(4-fluorophenyl)pentanedioic acid:

The compound was prepared according to the method as described for preparing EXAMPLE 16, STEP 2: $^1$H NMR (DMSO-d$_6$) δ 12.09 (br s, 2H), 7.30 (dd, J=7.5, 2.5 Hz, 2H), 7.1 (t, J=7.5 Hz, 2H), 3.45–3.35 (m, 1H), 2.68–2.47 (m, 4H).

Step 3
4-(4-fluorophenyl)dihydro-2H-pyran-2,6(3H)-dione:

The compound was prepared according to the method as described for preparing EXAMPLE 16, STEP 3: $^1$H NMR (DMSO-d$_6$) δ 7.35–7.08 (m, 4H), 3.65–3.55 (m, 1H), 3.1–2.9 (m, 4H).

Step 4
3-(4-fluorophenyl)-4-{3-[3-(5,6,7,8-tetrahydro-1,8-naphthyridin-2-yl)propyl]-1,2,4-oxadiazol-5-yl}butanoic acid trifluoroacetate:

The title compound was prepared according to the method as described for preparing EXAMPLE 16 using the appropriate anhydride: $^1$H NMR (DMSO-d$_6$) δ 12.28 (br s, 1H), 7.72 (br s, 1H), 7.59 (d, J=7.5 Hz, 1H), 7.31–7.26 (m, 2H), 7.11–7.02 (m, 2H), 6.55 (d, J=7.5 Hz, 1H), 3.61–3.55 (m, 2H), 3.4–3.2 (m, 5H), 2.82–2.6 (m, 6H), 1.99–1.89 (m, 2H), 1.86–1.78 (m, 2H). Anal. Calcd. for C$_{23}$H$_{25}$N$_4$O$_3$F.1.2CF$_3$CO$_2$H: C, 54.35; H, 4.70; N, 9.98. Found: C, 54.02; H, 4.57; N, 9.66.

EXAMPLE 27

3-(4-fluorophenyl)-4-{3-[4-(pyridin-2-ylamino)butyl]-1,2,4-oxadiazol-5-yl}butanoic acid

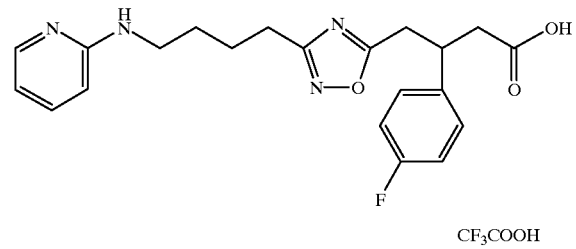

CF$_3$COOH

The title compound was prepared according to the method as described for preparing EXAMPLE 17 using the appropriate anhydride: $^1$H NMR (DMSO-d$_6$) δ 12.22 (br s, 1H), 8.65 (br s, 1H), 7.92–7.81 (m, 2H), 7.32–7.25 (m, 2H), 7.10–6.99 (m, 3H), 6.82 (t, J=7.5 Hz, 1H), 3.61–3.52 (m, 1H), 3.33–3.19 (m, 4H), 2.83–2.61 (m, 4H), 1.73–1.63 (m, 2H), 1.61–1.51 (m, 2H). Anal. Calcd. for C$_{21}$H$_{23}$N$_4$O$_3$F.1.2CF$_3$CO$_2$H: C, 52.51; H, 4.56; N, 10.47. Found: C, 52.21; H, 4.39; N, 10.20.

EXAMPLE 28

4-{3-[3-(5,6,7,8-tetrahydro-1,8-naphthyridin-2-yl)propyl]-1,2,4-oxadiazol-5-yl}-3-[3-(trifluoromethyl)phenyl]butanoic acid

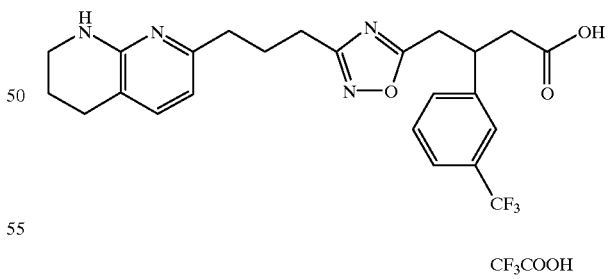

CF$_3$COOH

Step 1
Diethyl 4-hydroxy-4-methyl-6-oxo-2-[3-(trifluoromethyl)phenyl]cyclohexane-1,3-dicarboxylate:

The compound was prepared according to the method as described for preparing EXAMPLE 16, STEP 1: $^1$H NMR (DMSO-d$_6$) δ 7.7–7.51 (m, 4H), 5.03 (s, 1H), 4.1–3.83 (m, 4H), 3.80 (q, 2H), 3.41 (d, J=10.5 Hz, 1H), 2.94 (d, J=14 Hz, 1H), 2.38 (d, 14 Hz, 1H), 1.27 (s, 3H), 0.91 (t, 3H), 0.80 (t, 3H).

Step 2

3-[3-(trifluoromethyl)phenyl]pentanedioic acid:

The compound was prepared according to the method as described for preparing EXAMPLE 16, STEP 2: $^1$H NMR (DMSO-d$_6$) δ 12.15 (br s, 2H), 7.64–7.48 (m, 4H), 3.57–3.45 (m, 1H), 2.82–2.57 (m, 4H).

Step 3

4-[3-(trifluoromethyl)phenyl]dihydro-2H-pyran-2,6(3H)-dione:

The compound was prepared according to the method as described for preparing EXAMPLE 16, STEP 3: $^1$H NMR (DMSO-d$_6$) δ 7.7–7.5 (m, 4H), 3.96–3.89 (m, 1H), 3.16–2.96 (m, 4H).

Step 4

4-{3-[3-(5,6,7,8-tetrahydro-1,8-naphthyridin-2-yl)propyl]-1,2,4-oxadiazol-5-yl}-3-[3-(trifluoromethyl)phenyl]butanoic acid trifluoroacetate:

The title compound was prepared according to the method as described for preparing EXAMPLE 16 using the appropriate anhydride: $^1$H NMR (DMSO-d$_6$) δ 12.29 (br s, 1H), 7.92 (br s, 1H), 7.64–7.47 (m, 5H), 6.55 (d, J=7.5 Hz, 1H), 3.61–3.55 (m, 1H), 3.4–3.2 (m, 4H), 2.82–2.6 (m, 8H), 1.99–1.89 (m, 2H), 1.86–1.78 (m, 2H). Anal. Calcd. for C$_{24}$H$_{25}$F$_3$N$_4$O$_3$ plus 1.2CF$_3$CO$_2$H and 1.1H$_2$O: C, 50.24; H, 4.54; N, 8.88. Found: C, 50.26; H, 4.25; N, 8.90.

EXAMPLE 29

4-{3-[4-(pyridin-2-ylamino)butyl]-1,2,4-oxadiazol-5-yl}-3-[3-(trifluoromethyl)-phenyl]butanoic acid

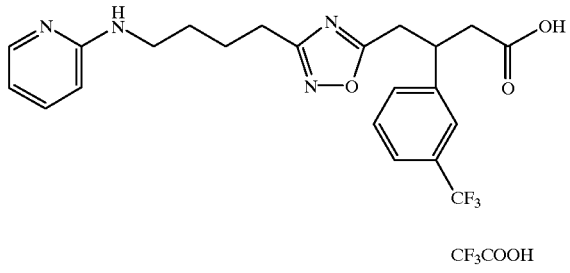

CF$_3$COOH

The title compound was prepared according to the method as described for preparing EXAMPLE 17 using the appropriate anhydride: $^1$H NMR (DMSO-d$_6$) δ 12.26 (br s, 1H), 8.55 (br s, 1H), 7.91 (d, J=5.5 Hz, 1H), 7.83 (t, J=7.5 Hz, 1H), 7.61–7.46 (m, 4H), 6.99 (d, J=7.5 Hz, 1H), 6.81 (t, J=7.5 Hz, 1H), 3.7–3.6 (m, 1H), 3.45–3.23 (m, 4H), 2.9–2.61 (m, 4H), 1.7–1.61 (m, 2H), 1.60–1.50 (m, 2H). Anal. Calcd. for C$_{22}$H$_{23}$F$_3$N$_4$O$_3$ plus 1.2CF$_3$CO$_2$H: C, 50.07; H, 4.17; N, 9.57. Found: C, 50.29; H, 4.00; N, 9.21.

EXAMPLE 30

3-(3-hydroxyphenyl)-4-{3-[3-(5,6,7,8-tetrahydro-1,8-naphthyridin-2-yl)propyl]-1,2,4-oxadiazol-5-yl}butanoic acid

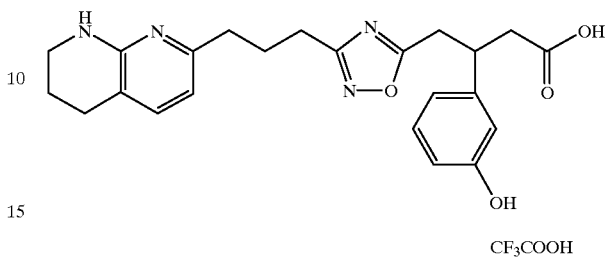

CF$_3$COOH

Step 1

Diethyl 4-hydroxy-2-(3-hydroxyphenyl)-4-methyl-6-oxocyclohexane-1,3-dicarboxylate:

The compound was prepared according to the method as described for preparing EXAMPLE 16, STEP 1: $^1$H NMR (DMSO-d$_6$) δ 9.26 (s, 1H), 7.03 (t, 1H), 6.74–6.6 (m, 2H), 6.58 (m, 1H), 4.86 (s, 1H), 3.98–3.71 (m, 6H), 3.24 (d, J=11 Hz, 1H), 2.93 (d, J=14 Hz, 1H), 2.31 (d, J=14 Hz, 1H), 1.23 (s, 3H), 0.98 (t, 3H), 0.89 (t, 3H).

Step 2

3-(3-hydroxyphenyl)pentanedioic acid:

The compound was prepared according to the method as described for preparing EXAMPLE 16, STEP 2: $^1$H NMR (DMSO-d$_6$) δ 12.1 (br s, 2H), 9.27 (s, 1H), 7.05 (t, 1H), 6.70–6.55 (m, 3H), 3.3 (m, 1H), 2.61–2.42 (m, 4H).

Step 3

4-(3-hydroxyphenyl)dihydro-2H-pyran-2,6(3H)-dione

The compound was prepared according to the method as described for preparing EXAMPLE 16, STEP 3 (acetate form): $^1$H NMR (DMSO-d$_6$) δ 7.41 (t, 1H), 7.2 (m, 1H), 7.1–7.03 (m, 2H), 3.65–3.55 (m, 1H), 3.1–2.95 (m, 4H), 2.28 (s, 3H).

Step 4

3-(3-hydroxyphenyl)-4-{3-[3-(5,6,7,8-tetrahydro-1,8-naphthyridin-2-yl)-propyl]-1,2,4-oxadiazol-5-yl}butanoic acid trifluoroacetate:

The title compound was prepared according to the method as described for preparing EXAMPLE 16 using the appropriate anhydride with minor modification: Amide oxime (100 mg) was added to an equivalent of the anhydride suspended in dioxane (5 ml). The reaction mixture was heated to 95° C. overnight and then the solvent was removed. The residue was dissolved in 1N NaOH (2 mL), MeOH (2 mL), and THF (2 mL) and stirred at room temperature until no more acetylated product was seen by LC/MS. The reaction was then neutralized with 1N HCl (2 mL), the solvent was removed under reduced pressure, and the residue was purified by reverse phase HPLC (Gilson): $^1$H NMR (DMSO-d$_6$) δ 7.81 (br s, 1H), 7.6 (d, J=7.5 Hz, 1H), 7.1 (t, J=14 Hz, 1H), 6.66–6.55 (m, 4H), 3.61–3.55 (m, 1H), 3.4–3.15 (m, 4H), 2.77–2.55 (m, 8H), 1.99–1.89 (m, 2H), 1.86–1.78 (m, 2H). Mass Spectrum: (MH$^+$)=423.

EXAMPLE 31

3-(3-hydroxyphenyl)-4-{3-[4-(pyridin-2-ylamino) butyl]-1,2,4-oxadiazol-5-yl}butanoic acid

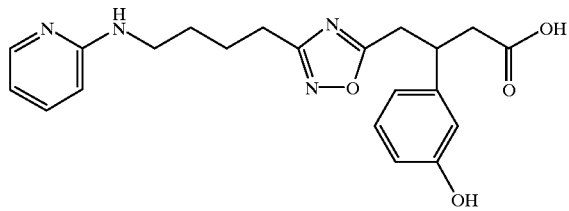

CF₃COOH

The title compound was prepared according to the method as described for preparing EXAMPLE 17 using the appropriate anhydride with minor modification: Amide oxime (100 mg) was added to an equivalent of the anhydride suspended in dioxane (5 ml). The reaction mixture was heated to 95° C. overnight and then the solvent was removed. The residue was dissolved in 1N NaOH (2 mL), MeOH (2 mL), and THF (2 mL) and stirred at room temperature until no more acetylated product was seen by LC/MS. The reaction was then neutralized with 1N HCl (2 mL), the solvent was removed under reduced pressure, and the residue was purified by reverse phase HPLC (Gilson). $^1$H NMR (DMSO-d$_6$) δ 9.3 (br s, 1H), 8.73 (br s, 1H), 7.91–7.85 (m, 2H), 7.05–6.98 (m, 2H), 6.84 (t, J=7.5 Hz, 1H), 6.63–6.53 (m, 3H), 3.52–3.4 (m, 1H), 3.33–3.14 (m, 4H), 2.71–2.54 (m, 4H), 1.73–1.63 (m, 2H), 1.61–1.51 (m, 2H). Mass Spectrum: (MH$^+$)=397.

EXAMPLE 32

3-pyridin-3-yl-4-{3-[3-(5,6,7,8-tetrahydro-1,8-naphthyridin-2-yl)propyl]-1,2,4-oxadiazol-5-yl}butanoic acid

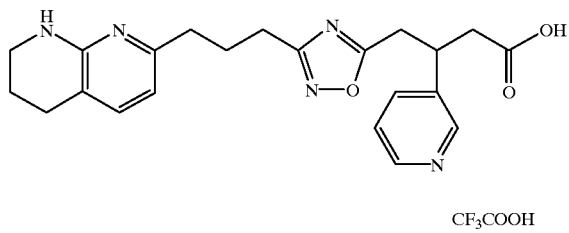

CF₃COOH

Step 1

3-pyridin-3-ylpentanedioic acid:

The diacid for this compound was synthesized according to the procedures outlined in Furschtatowa et al.; Zh. Obshch. Khim.; 28; 1958; 668, 670; engl. Ausg. S. 650, 652.

Step 2

4-pyridin-3-yldihydro-2H-pyran-2,6(3H)-dione:

The compound was prepared according to the method as described for preparing EXAMPLE 16, STEP 3: $^1$H NMR (DMSO-d$_6$) δ 8.83–8.77 (m, 2H), 8.35 (d, J=7.5 Hz, 1H), 7.95–7.89 (m, 1H), 3.9–3.78 (m, 1H), 3.26–3.08 (m, 4H).

Step 3

3-pyridin-3-yl-4-{3-[3-(5,6,7,8-tetrahydro-1,8-naphthyridin-2-yl)propyl]-1,2,4-oxadiazol-5-yl}butanoic acid bis(trifluoroacetate):

The title compound was prepared according to the method as described for preparing EXAMPLE 16 using the appropriate anhydride: $^1$H NMR (DMSO-d$_6$) δ 12.29 (br s, 1H), 8.55 (m, 1H), 8.5–8.46 (m, 1H), 7.92 (m, 2H), 7.61 (d, J=7.5 Hz, 1H), 7.5–7.4 (m, 1H), 6.57 (d, J=7.5 Hz, 1H), 3.70–3.55 (m, 1H), 3.47–2.60 (m, 4H), 2.77–2.55 (m, 8H), 1.99–1.89 (m, 2H), 1.86–1.78 (m, 2H). Anal. Calcd. for C$_{22}$H$_{25}$N$_5$O$_3$ plus 2.0CF$_3$CO$_2$H and 1.0H$_2$O: C, 47.78; H, 4.47; N, 10.72. Found: C, 47.36; H, 4.30; N, 10.67.

EXAMPLE 33

3-pyridin-3-yl-4-{3-[4-(pyridin-2-ylamino)butyl]-1,2,4-oxadiazol-5-yl}butanoic acid

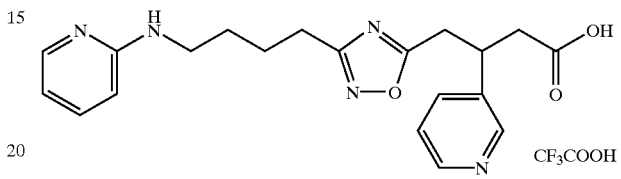

CF₃COOH

The title compound was prepared according to the method as described for preparing EXAMPLE 17 using the appropriate anhydride: $^1$H NMR (DMSO-d$_6$) δ 12.25 (br s, 1H), 8.78 (br s, 1H), 8.58 (m, 1H), 8.52–8.49 (m, 1H), 8.1–7.98 (m, 1H), 7.93–7.83 (m, 2H), 7.52–7.48 (m, 1H), 7.02 (d, J=7.5 Hz, 1H), 6.82 (t, J=7.5 Hz, 1H), 3.7–3.6 (m, 1H), 3.42–3.28 (m, 4H), 2.91–2.62 (m, 4H), 1.71–1.62 (m, 2H), 1.60–1.51 (m, 2H). Anal. Calcd. for C$_{20}$H$_{23}$N$_5$O$_3$ plus 2.0CF$_3$CO$_2$H and 1.0H$_2$O: C, 45.94; H, 4.34; N, 11.16. Found: C, 45.53; H, 4.27; N, 11.27.

EXAMPLE 34

3-phenyl-4-{3-[3-(5,6,7,8-tetrahydro-1,8-naphthyridin-2-yl)propyl]-1,2,4-oxadiazol-5-yl}butanoic acid trifluoroacetate

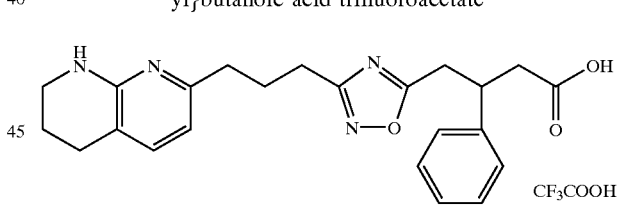

CF₃COOH

Step 1

4-phenyldihydro-2H-pyran-2,6(3H)-dione:

This compound was synthesized according to procedures outlined in Tokoroyama, Takashi; Kusaka, Hisashi; Can. J. Chem.; 74; 12; 1996; 2487–2502.

Step 2

3-phenyl-4-{3-[3-(5,6,7,8-tetrahydro-1,8-naphthyridin-2-yl)propyl]-1,2,4-oxadiazol-5-yl}butanoic acid trifluoroacetate:

The title compound was prepared according to the method as described for preparing EXAMPLE 16 using the appropriate anhydride: $^1$H NMR (DMSO-d$_6$) δ 12.19 (br s, 1H), 7.81 (br s, 1H), 7.59 (d, J=7.5 Hz, 1H), 7.22 (d, J=5 Hz, 4H), 7.20–7.12 (m, 1H), 6.55 (d, J=7.5 Hz, 1H), 3.61–3.52 (m, 1H), 3.4–3.2 (m, 4H), 2.81–2.6 (m, 8H), 1.98–1.88 (m, 2H), 1.84–1.78 (m, 2H). Mass Spectrum: (MH$^+$)=407.

EXAMPLE 35

3-phenyl-4-{3-[4-(pyridin-2-ylamino)butyl]-1,2,4-oxadiazol-5-yl}butanoic acid

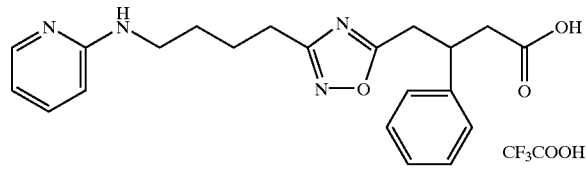

The title compound was prepared according to the method as described for preparing EXAMPLE 17 using the appropriate anhydride: $^1$H NMR (DMSO-d$_6$) d 12.15 (br s, 1H), 8.71 (br s, 1H), 7.92–7.84 (m, 2H), 7.29–7.12 (m, 5H), 7.02 (d, J=14 Hz, 1H), 6.82 (t, J=7.5 Hz, 1H), 3.60–3.51 (m, 1H), 3.45–3.19 (m, 4H), 2.81–2.60 (m, 4H), 1.73–1.63 (m, 2H), 1.61–1.51 (m, 2H). Mass Spectrum: (MH$^+$)=381.

EXAMPLE 36

3-methyl-3-({3-[4-(pyridin-2-ylamino)butyl]-1,2,4-oxadiazol-5-yl}methyl)pentanoic acid

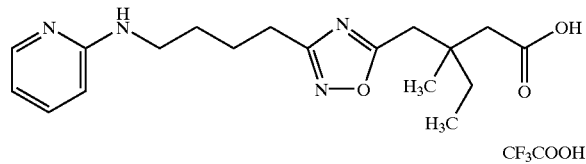

The title compound was prepared according to the method as described for preparing EXAMPLE 17 using the appropriate anhydride: $^1$H NMR (CD$_3$OD) δ 7.91 (m, 1H), 7.84 (d, 1H), 7.06 (d, 1H), 6.89 (m, 1H), 3.42 (t, 2H), 3.09 (dd, 2H), 2.84 (t, 2H), 2.39 (s, 2H), 1.92 (m, 2H), 1.80 (m, 2H), 1.51 (m, 2H), 1.09 (s, 3H), 0.95 (t, 3H); HRMS for C$_{18}$H$_{26}$N$_4$O$_3$ m/z found 347.2066 (M+H)$^+$. m/z calc (M+H)$^+$ 347.2083.

EXAMPLE 37

[1-({3-[4-(pyridin-2-ylamino)butyl]-1,2,4-oxadiazol-5-yl}methyl)cyclohexyl]-acetic acid

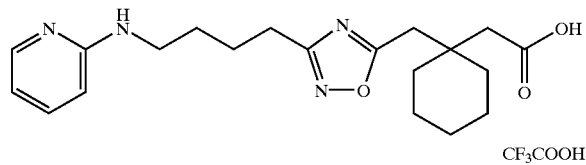

The title compound was prepared according to the method as described for preparing EXAMPLE 17 using the appropriate anhydride: $^1$H NMR (CD$_3$OD) δ 7.89 (m, 1H), 7.83 (d, 1H), 7.05 (d, 1H), 6.88 (m, 1H), 3.41 (t, 2H), 3.37 (s, 1H), 3.19 (s, 2H), 2.82 (t, 2H), 2.44 (s, 2H), 1.91 (m, 2H), 1.78 (m, 2H), 1.62–1.42 (series of m, 10H); HRMS for C$_{20}$H$_{28}$N$_4$O$_3$ m/z found 373.2230 (M+H)$^+$. m/z calc (M+H)$^+$ 373.2240.

EXAMPLE 38

3-methyl-3-({3-[4-(pyridin-2-ylamino)butyl]-1,2,4-oxadiazol-5-yl}methyl)-hexanoic acid

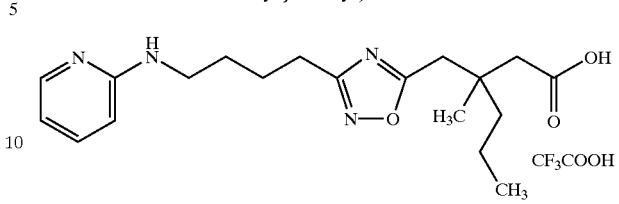

The title compound was prepared according to the method as described for preparing EXAMPLE 17 using the appropriate anhydride: $^1$H NMR (CD$_3$OD) δ 7.89 (m, 1H), 7.84 (d, 1H), 7.05 (d, 1H), 6.88 (m, 1H), 3.41 (t, 2H), 3.37 (s, 1H), 3.07 (dd, 2H), 2.83 (t, 2H), 2.38 (s, 2H), 1.92 (m, 2H), 1.80 (m, 2H), 1.49 (m, 4H), 1.08 (s, 3H), 0.92 (m, 3H); HRMS for C$_{19}$H$_{28}$N$_4$O$_3$ m/z found 361.2252 (M+H)$^+$. m/z calc (M+H)$^+$ 361.2240.

EXAMPLE 39

3,4-dimethyl-3-({3-[4-(pyridin-2-ylamino)butyl]-1,2,4-oxadiazol-5-yl}methyl)-pentanoic acid

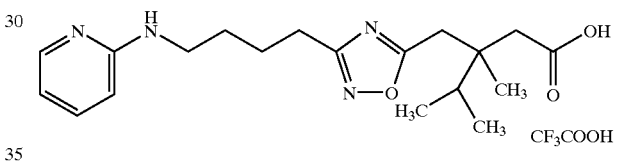

The title compound was prepared according to the method as described for preparing EXAMPLE 17 using the appropriate anhydride: $^1$H NMR (CD$_3$OD) δ 7.85 (d, 1H), 7.81 (m, 1H), 6.95 (d, 1H), 6.81 (m, 1H), 3.38 (t, 2H), 3.37 (s, 1H), 3.15 (m, 2H), 2.82 (t, 2H), 2.48 (d, 1H), 2.41 (m, 2H), 1.93–1.73 (series of m, 4H), 1.06 (s, 3H), 0.98–0.90 (series of m, 6H); HRMS for C$_{19}$H$_{28}$N$_4$O$_3$ m/z found 361.2260 (M+H)$^+$. m/z calc (M+H)$^+$ 361.2240.

EXAMPLE 40

3-ethyl-3-({3-[4-(pyridin-2-ylamino)butyl]-1,2,4-oxadiazol-5-yl}methyl)-pentanoic acid

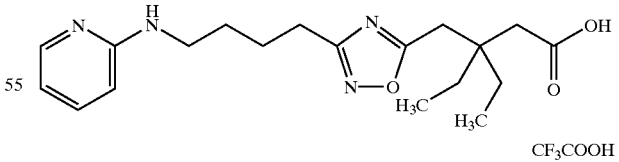

The title compound was prepared according to the method as described for preparing EXAMPLE 17 using the appropriate anhydride: $^1$H NMR (CD$_3$OD) δ 7.88 (d, 1H), 7.47 (m, 1H), 6.60–6.55 (series of m, 2H), 3.08 (s, 2H), 2.78 (t, 2H), 2.37 (s, 2H), 1.36 (m, 2H), 1.68 (m, 2H), 1.48 (m, 4H), 0.91 (t, 6H); HRMS for C$_{19}$H$_{28}$N$_4$O$_3$ m/z found 361.2242 (M+H)$^+$. m/z calc (M+H)$^+$ 361.2240.

EXAMPLE 41

4-{3-[4-(pyridin-2-ylamino)butyl]-1,2,4-oxadiazol-5-yl}butanoic acid

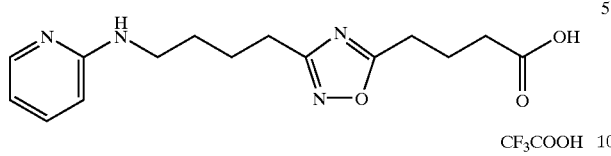

CF₃COOH

The title compound was prepared according to the method as described for preparing EXAMPLE 17 using the appropriate anhydride: $^1$H NMR (CD$_3$OD) δ 7.88 (m, 1H), 7.83 (d, 1H), 7.03 (d, 1H), 6.87 (m, 1H), 3.41 (t, 2H), 3.37 (s, 1H), 2.97 (t, 2H), 2.82 (t, 2H), 2.45 (t, 2H), 2.07 (m, 2H), 1.90 (m, 2H), 1.80 (m, 2H); HRMS for $C_{15}H_{20}N_4O_3$ m/z found 305.1611 (M+H)$^+$. m/z calc (M+H)$^+$ 305.1614.

EXAMPLE 42

3-methyl-3-phenyl-4-{3-[4-(pyridin-2-ylamino)butyl]-1,2,4-oxadiazol-5-yl}-butanoic acid

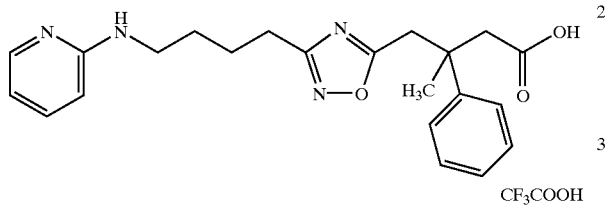

CF₃COOH

The title compound was prepared according to the method as described for preparing EXAMPLE 17 using the appropriate anhydride: $^1$H NMR (CD$_3$OD) δ 7.87 (m, 1H), 7.83 (d, 1H), 7.42–7.35 (series of m, 2H), 7.28 (t, 2H), 7.17 (t, 1H), 7.02 (d, 1H), 6.87 (m, 1H), 3.50 (m, 2H), 3.38–3.33 (series of m, 3H), 2.90 (s, 2H), 2.73 (t, 2H), 1.79 (m, 2H), 1.68 (m, 2H), 1.63 (s, 3H); HRMS for $C_{22}H_{26}N_4O_3$ m/z found 395.2089 (M+H)$^+$. m/z calc (M+H)$^+$ 395.2083.

EXAMPLE 43

3-Methyl-3-{3-[3-(5,6,7,8-tetrahydro-[1,8]naphthyridin-2-yl)-propyl]-[1,2,4]oxadiazol-5-ylmethyl}-pentanoic acid

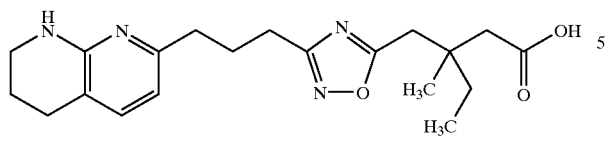

The title compound was prepared using the following general procedure:

Amide oxime (100 mg) was added to an equivalent of the anhydride suspended in dioxane (2 mL). The reaction mixture was heated to 95° C. for 16 hours. The reaction mixture was purified by reverse phase HPLC (Gilson, 5% to 70% acetonitrile in 0.05% aqueous trifluoroacetic acid, 12 minutes). $^1$H NMR (400 MHz, CD$_3$OD) δ 0.95 (t, 3H), 1.09 (s, 3H), 1.50 (m, 2H), 1.97 (m, 2H), 2.38 (m, 2H), 2.83 (m, 6H), 3.09 (dd, 2H), 3.37 (s, 1H), 3.53 (m, 2H), 6.63 (d, 1H), 7.59 (d, 1H); MS (ESI+) for $C_{20}H_{28}N_4O_3$ m/z 373.2230 (M+H)$^+$.

EXAMPLE 44

3-Methyl-3-{3-[3-(5,6,7,8-tetrahydro-[1,8]naphthyridin-2-yl)-propyl]-[1,2,4]oxadiazol-5-ylmethyl}-hexanoic acid

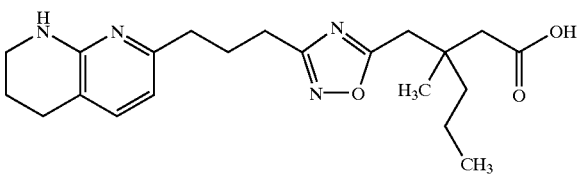

Step 1

4-Methyl-2,6-dioxo-4-propyl-piperidine-3,5-dicarbonitrile:

Following the procedure of Vogel, A. I.; J. Chem. Soc., 1934; 1758–1765: Pentan-2-one, ethyl cyanoacetate, and saturated ethanolic ammonia were combined in a 250 mL round bottomed flask. The flask was sealed with a rubber septum and allowed to sit at 0° C. After 120 hrs, the mixture had solidified and was filtered. The solid was dissolved in a minimum of hot water and acidified with concentrated hydrochloric acid. After 16 hours the crystals were collected. MS (ESI+) for $C_{11}H_{13}N_3O_2$ m/z 220.2 (M+H)$^+$.

Step 2

4-Methyl-4-propyl-dihydro-pyran-2,6-dione:

Following the procedure of Vogel, A. I.; J. Chem. Soc., 1934; 1758–1765: 4-Methyl-2,6-dioxo-4-propyl-piperidine-3,5-dicarbonitrile was dissolved in 50 mL of sulfuric acid and stirred for 16 hrs. Water (50 mL) was added and the solution was refluxed for 18 hrs. Upon cooling, the crystals were collected. The crystals were suspended in 10 mL of acetic anhydride. The suspension was heated to 130° C. and stirred for 16 hrs. The solvent was removed under reduced pressure. The residue was partitioned between saturated aqueous sodium bicarbonate and diethyl ether. The ether fraction was treated with anhydrous magnesium sulfate and concentrated under reduced pressure to give the product MS (ESI+) for $C_9H_{14}O_3$ m/z 171.2 (M+H)$^+$.

Step 3

3-Methyl-3-{3-[3-(5,6,7,8-tetrahydro-[1,8]naphthyridin-2-yl)-propyl]-[1,2,4]oxadiazol-5-ylmethyl}-hexanoic acid The title compound was prepared according to the method as described for preparing EXAMPLE 43. $^1$H NMR (400 MHz, CD$_3$OD) δ 0.93 (m, 3H), 1.11 (s, 3H), 1.40 (m, 4H), 1.97 (m, 2H), 2.15 (m, 2H), 2.40 (s, 2H), 2.83 (m, 8H), 3.09 (dd, 2H), 3.53 (m, 2H), 6.63 (d, 1H), 7.59 (d, 1H); MS (ESI+) for $C_{21}H_{30}N_4O_3$ m/z 387.2393 (M+H)$^+$.

EXAMPLE 45

3-Ethyl-3-{3-[3-(5,6,7,8-tetrahydro-[1,8] naphthyridin-2-yl)-propyl]-[1,2,4]oxadiazol-5-ylmethyl}-pentanoic acid

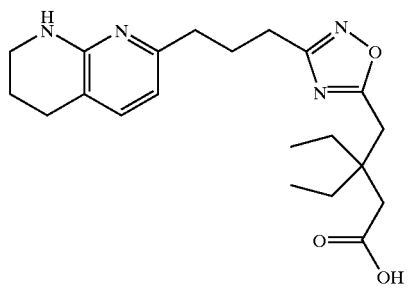

Step 1
4,4-Diethyl-2,6-dioxo-piperidine-3,5-dicarbonitrile
The compound was prepared according to the method as described for preparing EXAMPLE 44, STEP1: MS (ESI+) for $C_{11}H_{13}N_3O_2$ m/z 220.2 (M+H)$^+$.

Step 2
4,4-Diethyl-dihydro-pyran-2,6-dione
The compound was prepared according to the method as described for preparing EXAMPLE 44, STEP 2: MS (ESI+) for $C_9H_{14}O_3$ m/z 171.2 (M+H)$^+$.

Step 3
3-Ethyl-3-{3-[3-(5,6,7,8-tetrahydro-[1,8]naphthyridin-2-y)-propyl]-[1,2,4]oxadiazol-5-ylmethyl}-pentanoic acid
The title compound was prepared according to the method as described for preparing EXAMPLE 43. $^1$H NMR (400 MHz, CD$_3$OD) δ 0.95 (m, 8H), 1.84 (m, 1H), 1.95 (m, 2H), 2.15 (m, 2H), 2.43 (m, 2H), 2.83 (m, 6H), 3.15 (m, 2H), 3.37 (s, 2H), 3.52 (m, 2H), 6.63 (d, 1H), 7.59 (d, 1H); MS (ESI+) for $C_{21}H_{30}N_4O_3$ m/z 387.2413 (M+H)$^+$.

EXAMPLE 46

3,4-Dimethyl-3-{3-[3-(5,6,7,8-tetrahydro-[1,8] naphthyridin-2-yl)-propyl]-[1,2,4]oxadiazol-5-ylmethyl}-pentanoic acid

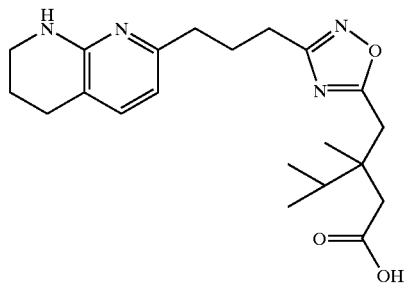

Step 1
4-Isopropyl-4-methyl-2,6-dioxo-piperidine-3,5-dicarbonitrile
The compound was prepared according to the method as described for preparing EXAMPLE 44, STEP 1: MS (ESI+) for $C_{11}H_{13}N_3O_2$ m/z 220.2 (M+H)$^+$.

Step 2
4-Isopropyl-4-methyl-dihydro-pyran-2,6-dione
The compound was prepared according to the method as described for preparing EXAMPLE 44, STEP 2: MS (ESI+) for $C_9H_{14}O_3$ m/z 171.2 (M+H)$^+$.

Step 3
3,4-Dimethyl-3-{3-[3-(5,6,7,8-tetrahydro-[1,8] naphthyridin-2-yl)-propyl]-[1,2,4]oxadiazol-5-ylmethyl}-pentanoic acid
The title compound was prepared according to the method as described for preparing EXAMPLE 43. $^1$H NMR (400 MHz, CD$_3$OD) δ 0.93 (t, 6H), 1.50 (m, 4H), 1.97 (m, 2H), 2.15 (m, 2H), 2.39 (s, 2H), 2.83 (m, 6H), 3.09 (s, 2H), 3.37 (s, 1H), 3.52 (m, 2H), 6.63 (d, 1H), 7.59 (d, 1H); MS (ESI+) for $C_{21}H_{30}N_4O_3$ m/z 387.2379 (M+H)$^+$.

EXAMPLE 47

3-Methyl-3-phenyl-4-{3-[3-(5,6,7,8-tetrahydro-[1,8] naphthyridin-2-yl)-propyl]-[1,2,4]oxadiazol-5-yl}-butyric acid

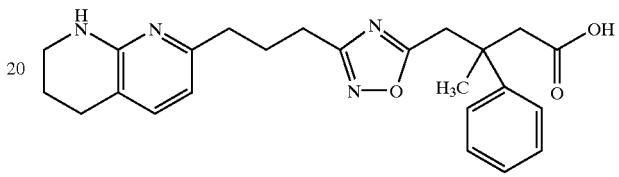

Step 1
4-Methyl-4-phenyl-dihydro-pyran-2,6-dione
The compound was prepared according to the method as described for preparing EXAMPLE 44, STEP 2: MS (ESI+) for $C_{12}H_{12}O_3$ m/z 205.2 (M+H)$^+$.

Step 2
3-Methyl-3-phenyl-4-{3-[3-(5,6,7,8-tetrahydro-[1,8] naphthyridin-2-yl)-propyl]-[1,2,4]oxadiazol-5-yl}-butyric acid
The title compound was prepared according to the method as described for preparing EXAMPLE 43. $^1$H NMR (400 MHz, CD$_3$OD) δ 1.65 (s, 3H), 1.99 (m, 2H), 2.07 (m, 2H), 2.70 (m, 4H), 2.83 (m, 2H), 2.92 (s, 2H), 3.38 (s, 2H), 3.52 (m, 4H), 6.56 (d, 1H), 7.18 (m, 1H), 7.28 (m, 2H), 7.39 (m, 2H), 7.58 (d, 1H); MS (ESI+) for $C_{24}H_{28}N_4O_3$ m/z 421.2227 (M+H)$^+$.

EXAMPLE 48

3-Phenyl-3-{3-[3-(5,6,7,8-tetrahydro-[1,8] naphthyridin-2-yl)-propyl]-[1,2,4]oxadiazol-5-ylmethyl}-pentanoic acid

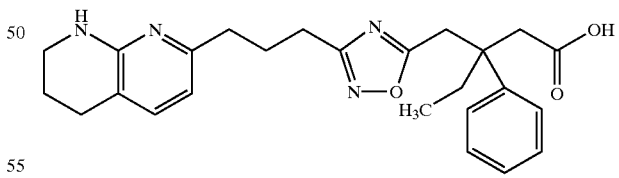

Step 1
4-Ethyl-4-phenyl-dihydro-pyran-2,6-dione
The compound was prepared according to the method as described for preparing EXAMPLE 44, STEP 2: MS (ESI+) for $C_{13}H_{14}O_3$ m/z 219.2 (M+H)$^+$.

Step 2
3-Phenyl-3-{3-[3-(5,6,7,8-tetrahydro-[1,8]naphthyridin-2-yl)-propyl]-[1,2,4]oxadiazol-5-ylmethyl}-pentanoic acid
The title compound was prepared according to the method as described for preparing EXAMPLE 43. $^1$H NMR (400

MHz, CD₃OD) δ 0.72 (t, 3H), 1.95 (m, 6H), 2.59 (m, 2H), 2.68 (t, 2H), 2.74 (m, 2H), 2.82 (d, 1H), 3.01 (d, 1H), 3.40 (m, 2H), 3.63 (d, 1H), 3.77 (d, 1H), 6.43 (d, 1H), 7.17 (m, 1H), 7.29 (m, 2H), 7.38 (m, 3H); MS (ESI+) for $C_{25}H_{30}N_4O_3$ m/z 435.2386 (M+H)⁺.

EXAMPLE 49

3-Phenyl-3-{3-[3-(5,6,7,8-tetrahydro-[1,8]naphthyridin-2-yl)-propyl]-[1,2,4]oxadiazol-5-ylmethyl}-hexanoic acid

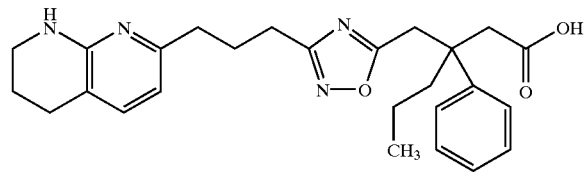

Step 1

4-Phenyl-4-propyl-dihydro-pyran-2,6-dione

The compound was prepared according to the method as described for preparing EXAMPLE 44, STEP 2: MS (ESI+) for $C_{14}H_{16}O_3$ m/z 233.2 (M+H)⁺.

Step 2

3-Phenyl-3-{3-[3-(5,6,7,8-tetrahydro-[1,8]naphthyridin-2-yl)-propyl]-[1,2,4]oxadiazol-5-ylmethyl}-hexanoic acid The title compound was prepared according to the method as described for preparing EXAMPLE 43. ¹H NMR (400 MHz, CD₃OD) δ 0.83 (t, 3H), 1.14 (m, 2H), 1.95 (m, 6H), 2.59 (t, 2H), 2.69 (t, 2H), 2.76 (m, 2H), 2.83 (d, 1H), 3.01 (d, 1H), 3.43 (m, 2H), 3.59 (d, 1H), 3.72 (d, 1H), 6.48 (d, 1H), 7.18 (m, 1H), 7.31 (m, 2H), 7.38 (m, 1H), 7.41 (m, 1H); MS (ESI+) for $C_{26}H_{33}N_4O_3$ m/z 449.2552 (M+H)⁺.

EXAMPLE 50

4-{3-[3-(5,6,7,8-Tetrahydro-[1,8]naphthyridin-2-yl)-propyl]-[1,2,4]oxadiazol-5-yl}-butyric acid

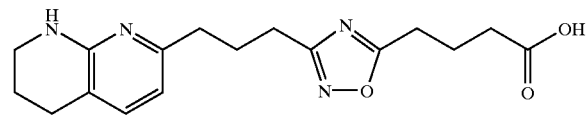

4-{3-[3-(5,6,7,8-Tetrahydro-[1,8]naphthyridin-2-yl)-propyl]-[1,2,4]oxadiazol-5-yl}-butyric acid:

The title compound was prepared according to the method as described for preparing EXAMPLE 43. ¹H NMR (400 MHz, DMSO-d₆) δ 1.82 (m, 2H), 1.92 (m, 2H), 2.01 (m, 2H), 2.34 (t, 2H), 2.72 (m, 6H), 2.92 (t, 2H), 3.41 (m, 3H), 6.59 (d, 1H), 7.58 (d, 1H), 8.26 (s, 1H); MS (ESI+) for $C_{17}H_{22}N_4O_3$ m/z 331.5 (M+H)⁺.

EXAMPLE 51

3-Methyl-3-pyridin-3-yl-4-{3-[3-(5,6,7,8-tetrahydro-[1,8]naphthyridin-2-yl)-propyl]-[1,2,4]oxadiazol-5-yl}-butyric acid

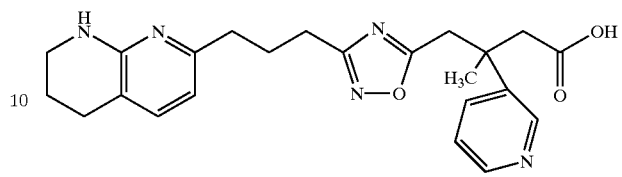

Step 1

2-Cyano-3-pyridin-3-yl-but-2-enoic acid ethyl ester

1-Pyridin-3-yl-ethanone, ethyl cyanoacetate, benzene, ammonium acetate, and acetic acid were refluxed for 16 hrs in a 250 mL round bottomed flask fitted with a Dean-Stark trap. The solutions were washed with water and brine, dried over magnesium sulfate, and concentrated. The residue was purified by silica gel chromatography to yield the product as an oil. MS (ESI+) for $C_{12}H_{12}N_2O_2$ m/z 217.2 (M+H)⁺.

Step 2

4'-Methyl-2',6'-dioxo-1',2',3',4',5',6'-hexahydro-[3,4']bipyridinyl-3',5'-dicarbonitrile Cyanoacetamide was stirred with sodium ethoxide in ethanol for 30 minutes. 2-Cyano-3-pyridin-3-yl-but-2-enoic acid ethyl ester was added and allowed to sit for 16 hours. The solution was acidified to pH 4 and partially concentrated under reduced pressure, causing precipitation of product. The product was filtered and allowed to dry. MS (ESI+) for $C_{13}H_{10}N_4O_2$ m/z 255.2 (M+H)⁺.

Step 3

3,4,5-Trimethyl-4-pyridin-3-yl-dihydro-pyran-2,6-dione

The compound was prepared according to the method as described for preparing EXAMPLE 44, STEP 2: MS (ESI+) for $C_{11}H_{11}NO_3$ m/z 206.2 (M+H)⁺.

Step 4

3-Methyl-3-pyridin-3-yl-4-{3-[3-(5,6,7,8-tetrahydro-[1,8]naphthyridin-2-yl)-propyl]-[1,2,4]oxadiazol-5-yl}-butyric acid The title compound was prepared according to the method as described for preparing EXAMPLE 43. ¹H NMR (400 MHz, CD₃CN) δ 1.62 (s, 3H), 1.96 (m, 2H), 2.05 (m, 2H), 2.68 (m, 4H), 2.79 (m, 2H), 2.96 (d, 1H), 3.11 (d, 1H), 3.49 (m, 4H), 6.47 (d, 1H), 7.48 (d, 1H), 7.70 (dd, 1H), 8.27 (m, 1H), 8.61 (m, 1H), 8.78 (m, 1H), 9.62 (m, 1H); MS (ESI+) for $C_{23}H_{27}N_5O_3$ m/z 422.5 (M+H)⁺.

EXAMPLE 52

(1-Acetyl-4-{3-[3-(5,6,7,8-tetrahydro-[1,8]naphthyridin-2-yl)-propyl]-[1,2,4]oxadiazol-5-ylmethyl}-piperidin-4-yl)-acetic acid

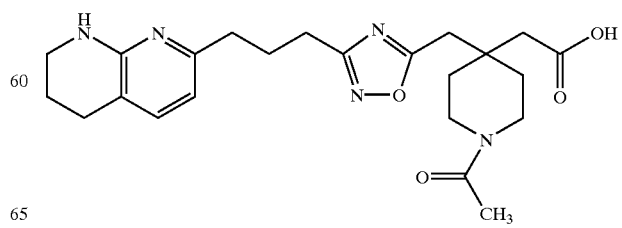

Step 1

9-Acetyl-2,4-dioxo-3,9-diaza-spiro[5.5]undecane-1,5-dicarbonitrile

The compound was prepared according to the method as described for preparing EXAMPLE 44, STEP 1: MS (ESI+) for $C_{13}H_{14}N_4O_3$ m/z 275.3 $(M+H)^+$.

Step 2

9-Acetyl-3-oxa-9-aza-spiro[5.5]undecane-2,4-dione

The compound was prepared according to the method as described for preparing EXAMPLE 44, STEP 2: MS (ESI+) for $C_{11}H_{15}NO_4$ m/z 226.3 $(M+H)^+$.

Step 3

(1-Acetyl-4-{3-[3-(5,6,7,8-tetrahydro-[1,8]naphthyridin-2-yl)-propyl]-[1,2,4]oxadiazol-5-ylmethyl}-piperidin-4-yl)-acetic acid The title compound was prepared according to the method as described for preparing EXAMPLE 43. $^1$H NMR (400 MHz, $CD_3CN$) δ 1.6 (m, 4H), 1.92 (m, 2H), 2.02 (s, 3H), 2.11 (m, 2H), 2.48 (s, 2H), 2.77 (m, 2H), 3.19 (s, 2H), 3.5 (m, 6H), 6.49 (d, 1H), 7.46 (d, 1H); MS (ESI+) for $C_{23}H_{31}N_5O_4$ m/z 442.6 $(M+H)^+$.

EXAMPLE 53

[4-{3-[3-(5,6,7,8-Tetrahydro-[1,8]naphthyridin-2-yl)-propyl]-[1,2,4]oxadiazol-5-ylmethyl}-1-(2,2,2-trifluoro-acetyl)-piperidin-4-yl]-acetic acid

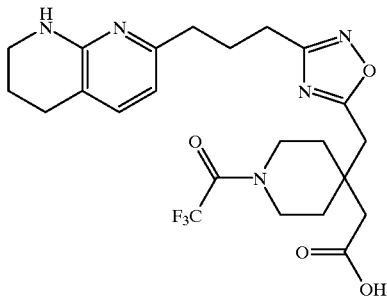

Step 1

9-Acetyl-2,4-dioxo-3,9-diaza-spiro[5.5]undecane-1,5-dicarbonitrile

The compound was prepared according to the method as described for preparing EXAMPLE 44, STEP 1: MS (ESI+) for $C_{13}H_{14}N_4O_3$ m/z 275.3 $(M+H)^+$.

Step 2

9-(2,2,2-Trifluoro-acetyl)-3-oxa-9-aza-spiro[5.5]undecane-2,4-dione

9-Acetyl-2,4-dioxo-3,9-diaza-spiro[5.5]undecane-1,5-dicarbonitrile was dissolved in concentrated hydrochloric acid and refluxed for 18 hrs. Upon cooling, the crystals were collected. The crystals were suspended in 10 mL of trifluoroacetic anhydride. The suspension was refluxed and stirred for 16 hrs. The solvent was removed under reduced pressure to give the product. $^1$H NMR ($CDCl_3$) δ 1.66 (m, 4H), 2.79 (m, 4H), 3.64 (m, 2H), 3.72 (m, 2H);

Step 3

[4-{3-[3-(5,6,7,8-Tetrahydro-[1,8]naphthyridin-2-yl)-propyl]-[1,2,4]oxadiazol-5-ylmethyl}-1-(2,2,2-trifluoro-acetyl)-piperidin-4-yl]-acetic acid The title compound was prepared according to the method as described for preparing EXAMPLE 43. $^1$H NMR ($CDCl_3$) δ 1.78 (m, 5H), 1.93 (m, 2H), 2.08 (m, 2H), 2.53 (s, 2H), 2.78 (m, 6H), 3.23 (s, 2H), 3.47 (m, 2H), 3.58–3.85 (m, 5H), 6.59 (d, 1H), 7.53 (d, 1H); MS (ESI+) for $C_{23}H_{28}F_3N_5O_4$ m/z 496.6 $(M+H)^+$.

EXAMPLE 54

(1-Benzoyl-4-{3-[3-(5,6,7,8-tetrahydro-[1,8]naphthyridin-2-yl)-propyl]-[1,2,4]oxadiazol-5-ylmethyl}-piperidin-4-yl)-acetic acid

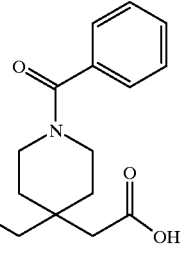

Step 1

9-Acetyl-2,4-dioxo-3,9-diaza-spiro[5.5]undecane-1,5-dicarbonitrile

The compound was prepared according to the method as described for preparing EXAMPLE 44, STEP 1: MS (ESI+) for $C_{13}H_{14}N_4O_3$ m/z 275.3 $(M+H)^+$.

Step 2

(4-Ethoxycarbonylmethyl-piperidin-4-yl)-acetic acid ethyl ester

9-Acetyl-2,4-dioxo-3,9-diaza-spiro[5.5]undecane-1,5-dicarbonitrile was dissolved in concentrated hydrochloric acid and refluxed for 18 hrs. Upon cooling, the crystals were collected. The crystals were refluxed for 18 hours with 4 M HCl in Dioxane (5 mL) and ethanol (50 mL). The solution was concentrated to yield an oil. $^1$H NMR ($CD_3OD$) δ 1.18 (t, 6H), 1.81 (m, 4H), 2.54 (s, 4H), 3.08 (m, 4H), 4.04 (q, 4H).

Step 3

The oil, polystyrene bound diisopropylethylamine, benzoyl chloride and dichloromethane were combined and stirred for 18 hours. The solution was filtered and concentrated to yield an oil. The oil, 4 M NaOH, and methanol were combined and stirred overnight. The solution was acidified with 1M HCl and extracted with ethyl acetate. The organic layer was dried with magnesium sulfate and concentrated to yield an oil. The oil and acetic anhydride were combined, heated (130° C.) and stirred for 18 hours. The solution was concentrated to yield product.

Step 4

(1-Benzoyl-4-{3-[3-(5,6,7,8-tetrahydro-[1,8]naphthyridin-2-yl)-propyl]-[1,2,4]oxadiazol-5-ylmethyl}-piperidin-4-yl)-acetic acid The title compound was prepared according to the method as described for preparing EXAMPLE 43. $^1$H NMR ($CD_3OD$) δ 1.70–1.96 (m, 4H), 2.03 (m, 2H), 2.21 (m, 2H), 2.64 (s, 2H), 2.88 (m, 6H), 3.44 (s, 2H), 3.58 (m, 4H), 3.83 (m, 1H), 3.98 (m, 1H), 6.71 (d, 1H), 7.48 (m, 2H), 7.55 (m, 3H), 7.65 (m, 1H); MS (ESI+) for $C_{28}H_{33}N_5O_4$ m/z 504.7 $(M+H)^+$.

EXAMPLE 55

4-Carboxymethyl-4-{3-[3-(5,6,7,8-tetrahydro-[1,8]naphthyridin-2-yl)-propyl]-[1,2,4]oxadiazol-5-ylmethyl}-piperidine-1-carboxylic acid tert-butyl ester

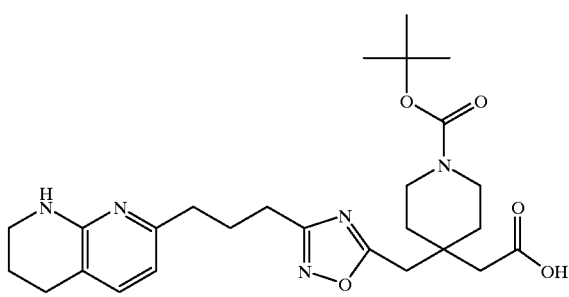

Step 1

9-Acetyl-2,4-dioxo-3,9-diaza-spiro[5.5]undecane-1,5-dicarbonitrile

The compound was prepared according to the method as described for preparing EXAMPLE 44, STEP 1: MS (ESI+) for $C_{13}H_{14}N_4O_3$ m/z 275.3 (M+H)+.

Step 2

(4-Ethoxycarbonylmethyl-piperidin-4-yl)-acetic acid ethyl ester

The compound was prepared as EXAMPLE 54, STEP 2

Step 3

2,4-Dioxo-3-oxa-9-aza-spiro[5.5]undecane-9-carboxylic acid tert-butyl ester

The oil, polystyrene bound diisopropylethylamine, di-t-butyl dicarbonate and dichloromethane were combined and stirred for 18 hours. The solution was filtered and concentrated to yield an oil. The oil, 4 M NaOH, and methanol were combined and stirred overnight. The solution was acidified with 1M HCl and extracted with ethyl acetate. The organic layer was dried with magnesium sulfate and concentrated to yield an oil. The oil and acetic anhydride were combined, heated (130° C.) and stirred for 18 hours. The solution was concentrated to yield product.

Step 4

4-Carboxymethyl-4-{3-[3-(5,6,7,8-tetrahydro-[1,8]naphthyridin-2-yl)-propyl]-[1,2,4]oxadiazol-5-ylmethyl}-piperidine-1-carboxylic acid tert-butyl ester The title compound was prepared according to the method as described for preparing EXAMPLE 43. $^1$H NMR (CD$_3$OD) δ 1.47 (s, 9H), 1.57–1.73 (m, 3H), 1.98 (m, 3H), 2.14 (m, 2H), 2.50–2.69 (m, 3H), 2.83 (m, 6H), 3.27 (s, 2H), 3.40–3.62 (m, 4H), 6.64 (d, 1H), 7.60 (d, 1H); MS (ESI+) for $C_{26}H_{37}N_5O_5$ m/z 500.7 (M+H)+.

EXAMPLE 56

(1-{3-[3-(5,6,7,8-Tetrahydro-[1,8]naphthyridin-2-yl)-propyl]-[1,2,4]oxadiazol-5-ylmethyl}-cyclohexyl)-acetic acid

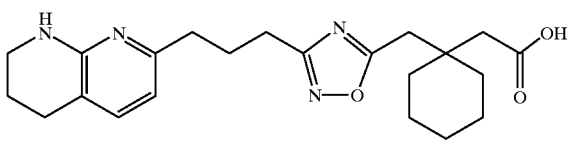

Step 1

2,4-Dioxo-3-aza-spiro[5.5]undecane-1,5-dicarbonitrile

The compound was prepared according to the method as described for preparing EXAMPLE 44, STEP 1: MS (ESI+) for $C_{12}H_{13}N_3O_2$ m/z 232.2 (M+H)+.

Step 2

3-Oxa-spiro[5.5]undecane-2,4-dione

The compound was prepared according to the method as described for preparing EXAMPLE 44, STEP 2: MS (ESI+) for $C_{10}H_{14}O_3$ m/z 183.2 (M+H)+.

Step 3

(1-{3-[3-(5,6,7,8-Tetrahydro-[1,8]naphthyridin-2-yl)-propyl]-[1,2,4]oxadiazol-5-ylmethyl}-cyclohexyl)-acetic acid The title compound was prepared according to the method as described for preparing EXAMPLE 43. $^1$H NMR (400 MHz, CD$_3$OD) δ 1.55 (m, 10H), 1.97 (m, 2H), 2.15 (m, 2H), 2.45 (s, 2H), 2.82 (m, 6H), 3.19 (s, 2H), 3.37 (s, 2H), 3.52 (m, 2H), 6.63 (d, 1H), 7.59 (d, 1H); MS (ESI+) for $C_{22}H_{30}N_4O_3$ m/z 399.2392 (M+H)+.

EXAMPLE 57

3-Methyl-3-pyridin-3-yl-4-{3-[4-(pyridin-2-ylamino)-butyl]-[1,2,4]oxadiazol-5-yl}-butyric acid

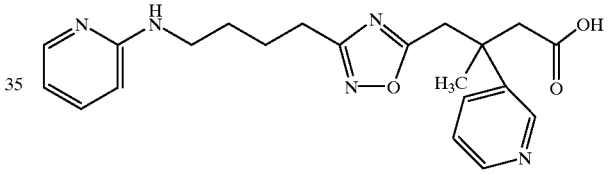

Step 1

2-Cyano-3-pyridin-3-yl-but-2-enoic acid ethyl ester

The compound was prepared as in EXAMPLE 51, STEP1

Step 2

4'-Methyl-2',6'-dioxo-1',2',3',4',5',6'-hexahydro-[3,4']bipyridinyl-3',5'-dicarbonitrile The compound was prepared as in EXAMPLE 51, STEP2

Step 3

3,4,5-Trimethyl-4-pyridin-3-yl-dihydro-pyran-2,6-dione

The compound was prepared according to the method as described for preparing EXAMPLE 44, STEP 2: MS (ESI+) for $C_{11}H_{11}NO_3$ m/z 206.2 (M+H)+.

Step 4

3-Methyl-3-pyridin-3-yl-4-{3-[4-(pyridin-2-ylamino)-butyl]-[1,2,4]oxadiazol-5-yl}-butyric acid The title compound was prepared according to the method as described for preparing EXAMPLE 43. $^1$H NMR (400 MHz, CD$_3$CN) δ 1.60 (m, 5H), 1.72 (m, 2H), 2.68 (t, 2H), 2.92 (d, 1H), 3.05 (d, 1H), 3.32 (m, 2H), 3.45 (dd, 2H), 6.79 (m, 1H), 6.95 (d, 1H), 7.55 (dd, 1H), 7.78 (m, 1H), 7.88 (m, 1H), 8.18 (m, 1H), 8.53 (m, 1H), 8.67 (m, 1H); MS (ESI+) for $C_{21}H_{25}N_5O_3$ m/z 396.5 (M+H)+.

EXAMPLE 58

4-(benzyloxy)-3-({3-[4-(pyridin-2-ylamino)butyl]-1,2,4-oxadiazol-5-yl}methyl)-butanoic acid

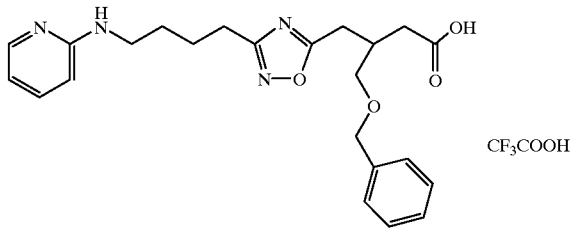

4-(benzyloxy)-3-({3-[4-(pyridin-2-ylamino)butyl]-1,2,4-oxadiazol-5-yl}methyl)-butanoic acid trifluoroacetate:

The title compound was prepared according to the method as described for preparing EXAMPLE 17 using the appropriate anhydride: $^1$H NMR (400 MHz, CD$_3$OD) δ 7.88 (m, 1H), 7.37–7.24 (m, 5H), 7.04 (d, 1H), 6.88 (t, 1H), 4.46 (s, 2H), 3.50 (m, 2H), 3.38 (t, 2H), 3.09 (dd, 1H), 3.01 (dd, 1H), 2.77 (t, 2H), 2.70 (m, 1H), 2.53 (dd, 1H), 2.46 (dd, 1H), 1.85 (m, 2H), 1.76 (m, 2H); MS (ESI+) for m/z 425 (M+H)$^+$.

EXAMPLE 59

4-[4-(N-pyridin-2-yl-beta-alanyl)piperazin-1-yl]butanoic acid

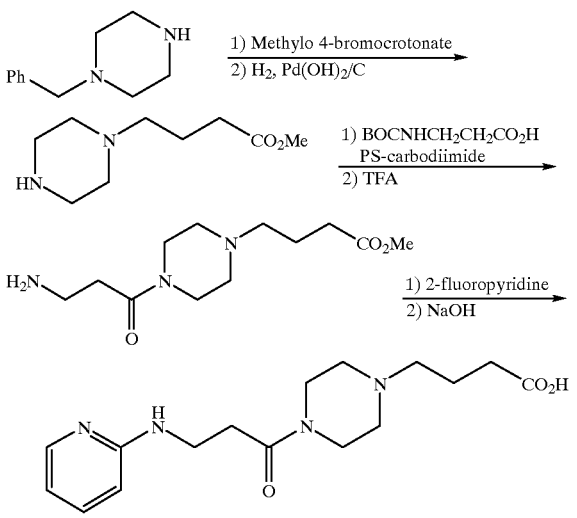

Step 1

Methyl 4-(4-benzylpiperazin-1-yl)but-2-enoate:

To a ice chilled solution of 1-benylpiperazine (25.0 g, 0.14 moles) in 140 mL dimethylformamide was added potassium carbonate (24.0 g, 1.25 eq.) and methyl 4-bromocrotonate (18.6 mL, 0.99 eq.). The solution was warmed to room temperature and stirred 24 h. The solution was filtered. Water was added and extracted with ethyl acetate. The organics were washed with water twice and brine, dried over sodium sulfate, filtered and evaporatated to afford methyl -4-(4-benzylpiperazin-1-yl)but-2-enoate (35.2 g, 92%) as a brown-orange liquid. MS (ESI+) for m/z 275 (M+H)$^+$.

Step 2

Methyl 4-(4-benzylpiperazin-1-yl)butanoate:

A solution of methyl 4-(4-benzylpiperazin-1-yl)but-2-enoate (10.2 g, 0.04 moles) in methanol was added to 20% palladium hydroxide on carbon and placed under 40 psi hydrogen gas for 7 h. The resulting solution was filtered through celite and evaporated to afford methyl 4-(4-benzylpiperazin-1-yl)butanoate (6.70 g, 97%). MS (ESI+) for m/z 187 (M+H)$^+$.

Step 3

Methyl 4-{4-[N-(tert-butoxycarbonyl)-beta-alanyl]piperazin-1-yl}butanoate:

To a suspension of PS-carbodiimide (1.7 g, 1.5 mmoles) in dichloromethane (2 mL) was added 4-(tert-butoxycarbonylamino)butyric acid (305 mg, 1.5 mmoles) and HOBT (230 mg, 1.7 mmoles). After 20 min 186 mg of methyl 4-(4-benzylpiperazin-1-yl)butanoate (186 mg, 1.0 mmol) was added to the reaction mixture and stirred 24 h. PS-trisamine (1.08 g, 5 eq.) was added and stirred 16 h. The reaction mixture was filtered and evaporated to afford methyl 4-{4-[N-(tert-butoxycarbonyl)-beta-alanyl]piperazin-1-yl}butanoate (290 mg, 77%).

Step 4

Methyl 4-(4-beta-alanylpiperazin-1-yl)butanoate:

To methyl 4-{4-[N-(tert-butoxycarbonyl)-beta-alanyl]piperazin-1-yl}-butanoate (290 mg, 0.8 mmoles) in 2 mL dichloromethane was added 2 mL trifluoroacetic acid. After 1 hour the solvents were evaporated. The residue was dissolved in 10% DMF/DCM and MP-carbonate (0.8 g) was added. After 16 h the solution was filtered and evaporated to afford methyl 4-(4-beta-alanylpiperazin-1-yl)butanoate (87 mg, 41%) as an oil. MS (ESI+) for m/z 272 (M+H)$^+$.

Step 5

4-[4-(N-pyridin-2-yl-beta-alanyl)piperazin-1-yl]butanoic acid bis(trifluoroacetate):

A solution of methyl 4-(4-beta-alanylpiperazin-1-yl)butanoate, 2-fluoropyridine (2.5 mL) and diisopropylethylamine (125 uL) was heated to 105° C. for 22 h. The solvents were evaporated and methanol (2 mL) and 1M aq. NaOH (3 mL) were added. Adjusted to neutral pH with 12M HCl and evaporated. Purified by RP-HPLC to afford 4-[4-(N-pyridin-2-yl-beta-alanyl)-piperazin-1-yl]butanoic acid bis(trifluoroacetate) (38.9 mg). $^1$H NMR (400 MHz, CD$_3$CN) δ 7.92 (m, 1H), 7.81 (d, 1H), 7.02 (d, 1H), 6.82 (t, 1H), 3.63 (t, 4H), 3.10 (dd, 4H), 2.73 (t, 2H), 2.44 (t, 4H), 1.95 (m, 4H); MS (ESI+) for m/z 321 (M+H)$^+$.

EXAMPLE 60

4-{4-[3-(pyridin-2-ylamino)propyl]piperazin-1-yl}butanoic acid

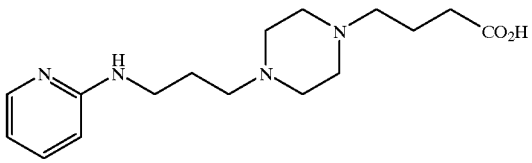

Step 1

Methyl 4-(4-{3-[(tert-butoxycarbonyl)amino]propyl}piperazin-1-yl)butanoate:

To a solution of methyl 4-(4-benzylpiperazin-1-yl)butanoate (500 mg, 2.68 mmoles) in dichloromethane (5 mL) was added tert-butyl 4-oxobutyl-carbamate (505 mg, 2.68 mmoles) and sodium triacetoxyborohydride (900 mg, 1.5 eq) and stirred 20 h. To the reaction mixture water was added followed by 1M aqueous sodium bicarbonate solution. The solution was extracted with ethyl acetate. The organics were evaporated to afford methyl 4-(4-{3-[(tert-butoxycarbonyl)amino]propyl}-piperazin-1-yl)butanoate (0.72 g, 75%). MS (ESI+) for m/z 358 (M+H)$^+$.

Step 2

4-{4-[3-(pyridin-2-ylamino)propyl]piperazin-1-yl}butanoic acid tris(trifluoroacetate):

Prepared in an analogous manner to 4-[4-(N-pyridin-2-yl-beta-alanyl)-piperazin-1-yl]butanoic acid bis (trifluoroacetate) using methyl 4-(4-{3-[(tertbutoxycarbonyl)amino]propyl}piperazin-1-yl) butanoate in the place of methyl 4-{4-[N-(tert-butoxycarbonyl)-beta-alanyl]piperazin-1-yl}butanoate. $^1$H NMR (400 MHz, CD$_3$CN) δ 7.91 (dt, 1H), 7.82 (d, 1H), 6.97 (d, 1H), 6.86 (m, 1H), 3.60–3.42 (m, 8H), 3.19–3.03 (m, 6H), 2.44 (t, 2H), 2.08 (t, 2H), 1.95 (d, 2H); MS (ESI+) for m/z 307 (M+H)$^+$.

EXAMPLE 61

β,β-dimethyl-3-[5-(2-pyridinylamino)pentyl]-1,2,4-oxadiazole-5-butanoic acid

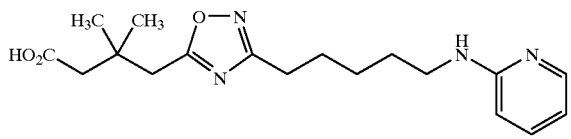

Step 1

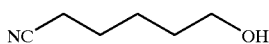

5-chloro-pentan-1-ol (25 g, 0.204 moles), potassium cyanide (15.94 g, 0.248 moles), and potassium iodide (1.69 g, 0.01 moles) were dissolved in ethanol (200 mL) and heated. After two days, an additional amount of potassium cyanide (2.66 g, 0.041 moles) was added, and the reaction was heated for another two days. The reaction mixture was then diluted with ether (200 mL) and filtered through celite. The solvent was removed under reduced vacuum. Water was added to the residue and extracted with ether (6×200 mL). The aqueous phase was concentrated, diluted with brine (200 mL) and further extracted with ether (3×100 mL). The ether fractions were combined, dried (Na$_2$SO$_4$), and concentrated. The crude product was purified by flash chromatography (2:1 hexane:ethyl acetate) to give a pale yellow oil (13.13 g, 57%). $^1$H NMR (400 MHz, CDCl$_3$) 3.7–3.6 (m, 2H), 2.38 (t, 2H), 1.8–1.5 (m, 6H).

Step 2

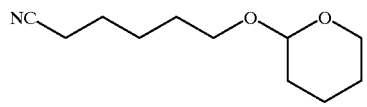

A solution of dihydropyran (11.5 mL, 0.126 moles) in methylene chloride (80 mL) was added to an ice-cooled solution of 6-hydroxyhexanitrile as prepared in Step 1 (13 g, 0.115 moles) and p-toluenesulfonic acid (50 mg) in methylene chloride (100 mL). The reaction mixture was allowed to warm up to room temperature and stirred overnight. The solvent was removed under vacuum. The residue was partioned between ether (100 mL) and aqueous sodium bicarbonate (100 mL). The aqueous layer was extracted with ether (100 mL). The combined organic layers were washed with brine (50 mL) and dried (Na$_2$SO$_4$). The crude product was purified by flash chromatography (3:1 hexane:ethyl acetate) to give an oil (19.9 g, 88%). $^1$H NMR (400 MHz, CDCl$_3$) δ 4.6 (t, 1H), 3.9–3.7 (m, 2H), 3.55–3.35 (m, 2H), 2.35 (t, 2H), 1.9–1.5 (m, 12H).

Step 3

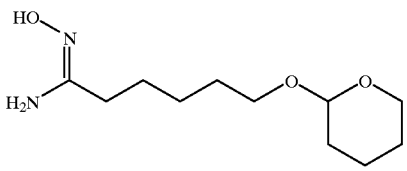

To the compound produced in Step 2 in methanol (25 mL) was added hydroxylamine hydrochloride (2.74 g, 39.5 mmoles) and sodium methoxide 25% wt. solution in methanol (9 mL, 39.5 mmoles). The reaction mixture was heated at 60° C. overnight. The solvent was removed under vacuum. The residue was dissolved in ethyl acetate (150 mL) and extracted with brine (50 mL), dried (Na$_2$SO$_4$), and concentrated. The crude product was purified by flash chromatography (1:1 hexane:ethyl acetate to 100% ethyl acetate) to give an oil (3.1 g, 53%). $^1$H NMR (400 MHz, DMSO) δ 8.65 (s, 1H), 5.3 (bs, 2H), 4.55 (t, 1H), 3.75–3.7 (m, 1H), 3.62–3.55 (m, 1H), 3.42–3.38 (m, 1H), 3.32–3.28 (m, 1H), 1.95 (t, 2H), 1.72–1.25 (m, 12H).

Step 4

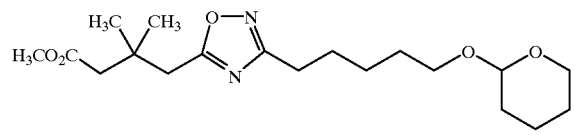

To 3,3-dimethyl-glutaric acid monomethyl ester (1.2 g, 6.9 mmoles) in DMF (7 mL) was added carbonyldiimidazole (1.1 g, 6.8 mmoles) and the mixture was stirred for twenty minutes at room temperature. Then, a solution of the compound produced in Step 3 (1.5 g, 6.8 mmoles) in DMF (5 mL) was added. The reaction mixture was stirred overnight. The solvent was removed under vacuum. Ethyl acetate (100 mL) was added to the residue and washed with saturated sodium bicarbonate, 1N KHSO$_4$, and brine. The organic layer was separated, dried (Na$_2$SO$_4$), and concentrated. The crude product was purified by flash chromatography (1:1 hexane:ethyl acetate to 100% ethyl acetate) to give an oil (2 g, 80%). $^1$H NMR (400 MHz, DMSO) δ 6.25 (bs, 2H), 4.55 (t, 1H), 3.75–3.7 (m, 1H), 3.62–3.55 (m, 1H), 3.58 (s, 3H), 3.42–3.38 (m, 1H), 3.32–3.28 (m, 1H), 2.39 (s, 2H), 2.38 (s, 2H), 2.2 (t, 2H), 1.72–1.3 (m, 12H), 1.02 (s, 6H). The product (1.9 g, 5 mmol) was dissolved in dioxane (30 mL) and refluxed for 5 days. The reaction mixture was then cooled to room temperature and the solvent removed under vacuum. The residue was dissolved in ethyl acetate and passed through a pad of silica to give the product (1.74 g, 97% yield). $^1$H NMR (400 MHz, DMSO) δ 4.55 (t, 1H), 3.75–3.7 (m, 1H), 3.62–3.55 (m, 1H), 3.58 (s, 3H), 3.42–3.38 (m, 1H), 3.32–3.28 (m, 1H), 2.9 (s, 2H), 2.68 (t, 2H), 2.38 (s, 2H), 1.72–1.3 (m, 12H), 1.02 (s, 6H).

Step 5

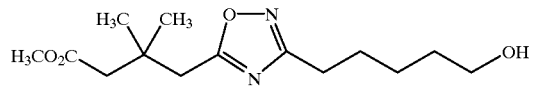

To a solution of the compound produced in Step 4 in methanol (15 mL) was added p-toluenesulfonic acid (890 mg, 4.7 mmoles) and the reaction mixture was stirred at room temperature for three hours. The solvent was removed and the residue was dissolved in ethyl acetate. The ethyl acetate was washed with saturated sodium bicarbonate, brine, and dried (Na$_2$SO$_4$). The ethyl acetate was removed to give the product (1.23 g, 95% yield). $^1$H NMR (400 MHz, CDCl$_3$) δ 3.68 (s, 3H), 3.68–3.6 (m, 2H), 3.0 (s, 2H), 2.73 (t, 2H), 2.38 (s, 2H), 1.85–1.75 (m, 2H), 1.65–1.59 (m, 2H), 1.5–1.37 (m, 2H), 1.12 (s, 6H).
Step 6

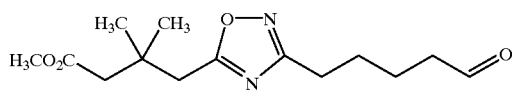

To a solution of the compound produced in Step 5 (500 mg, 1.8 mmoles), N-methyl morpholine N-oxide (317 mg, 2.7 mmoles), and 4 A molecular sieves (900 mg) in methylene chloride (20 mL) was added tetrapropylammonium perruthenate (32 mg, 0.9 mmoles). The reaction mixture was stirred at room temperature until no starting material present by TLC. The reaction mixture was then diluted with methylene chloride (100 mL) and passed through a pad of silica. The methylene chloride was removed under vacuum to give product (450 mg, 91% yield). $^1$H NMR (400 MHz, CDCl$_3$) δ 9.78 (s, 1H), 3.68 (s, 3H), 3.0 (s, 2H), 2.73 (t, 2H), 2.49 (t, 2H), 2.38 (s, 2H), 1.85–1.68 (m, 4H), 1.12 (s, 6H).
Step 7

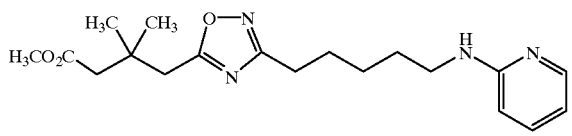

A solution of the compound produced in Step 6 (440 mg, 1.6 mmoles) in methylene chloride (3 mL) was cooled in an ice bath and 2-aminopyridine (165 mg, 1.8 mmoles) was added followed by the addition of sodium triacetoxyborohydride (510 mg, 2.4 mmoles). The ice bath was removed and the reaction mixture was stirred at room temperature overnight. The reaction mixture was then poured into a saturated solution of sodium bicarbonate (10 mL) and extracted with ethyl acetate. The ethyl acetate was dried (Na$_2$SO$_4$), filtered, and concentrated under vacuum to give the product (485 mg, 87% yield) which was not purified further. $^1$H NMR (400 MHz, CDCl$_3$) δ 8.05 (m, 1H), 7.45–7.38 (m, 1H), 6.63–6.53 (m, 1H), 6.52–6.33 (m, 1H), 3.68 (s, 3H), 3.3–3.2 (m, 2H), 3.0 (s, 2H), 2.73 (t, 2H), 2.38 (s, 2H), 1.85–1.78 (m, 2H), 1.7–1.6 (m, 2H), 1.52–1.45 (m, 2H), 1.12 (s, 6H).
Step 8
β,β-dimethyl-3-[5-(2-pyridinylamino)pentyl]-1,2,4-oxadiazole-5-butanoic acid, mono(trifluoroacetate)

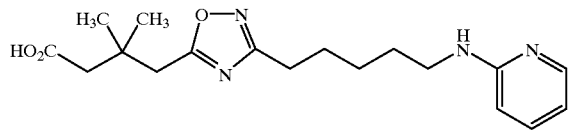

The compound produced in Step 7 was dissolved in CH$_3$OH (2.5 mL), THF (2.5 mL), 1N NaOH (2.5 mL) and stirred at room temperature until hydrolysis complete. The reaction mixture was then diluted with 1N HCl (2.5 mL) and the solvent removed under vacuum. The crude product was purified by reverse phase HPLC to give the product (470 mg, 78% yield). $^1$H NMR (400 MHz, DMSO) 7.9–7.8 (m, 2H), 7.1 (d, 1H), 6.83 (t, 1H), 3.3–3.2 (m, 2H), 3.0 (s, 2H), 2.7 (t, 2H), 2.25 (s, 2H), 1.75–1.58 (m, 4H), 1.45–1.35 (m, 2H), 1.02 (s, 6H). The compound was analyzed for (C$_{18}$H$_{26}$N$_4$O$_3$·TFA·0.9H$_2$O): C, 50.40, H, 6.09, N, 11.75. Found: C, 50.72, H, 6.05, N, 11.44.

EXAMPLE 62

β,β-dimethyl-3-[4-(2-pyridinylamino)butyl]-1,2,4-oxadiazole-5-butanoic acid

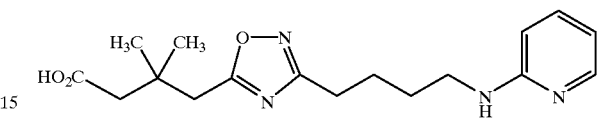

Step 1
2-(4-bromo-butoxy)-tetrahydro-pyran

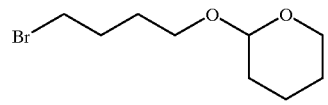

The above compound was prepared in analogous fashion to the published procedure in Snider, Barry B.; Lu, Qing; J. Org. Chem.; 61; 8; 1996; 2839–2844.
Step 2
5-(tetrahydro-pyran-2-yloxy)-pentanenitrile

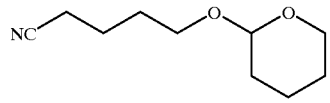

A mixture of the bromide of Step 1 (27.0 g, 0.114 moles) and sodium cyanide (6.4 2 g, 0.131 moles) in DMF (200 mL) was heated under nitrogen at 80° C. for 16 hours with magnetic stirring. After allowing to cool the majority of the DMF was removed under vacuum by rotary evaporation (oil pump vacuum, 50° C.). The mixture was partitioned between water (100 mL) and ether (100 mL). The phases were separated and the aqueous phase was further extracted with ether (2×50 mL). The combined organic phases were washed with water (2×50 mL) and brine (50 mL) and then dried over sodium sulfate. The solution was filtered and evaporated under vacuum to give a yellow oil (22 g). Purification by chromatography on silica gel, eluting with hexane/ethyl acetate (3:1) gave a straw colored oil (17.65 g, 85% yield). $^1$H NMR (400 MHz) CDCl$_3$ δ 4.55–4.60 (m, 1H), 3.74–3.90 (m, 2H), 3.48–3.55 (m, 1H), 3.40–3.48 (m, 1H), 2.41 (dd, J=6.0, 7.5 Hz, 2H), 1.65–1.90 (m, 6H), 1.45–1.63 (m, 4H).
Step 3
5-(tetrahydro-pyran-2-yloxy)-N-hydroxy-pentaneamidine (3)

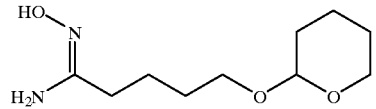

To a suspension of hydroxylamine hydrochloride (1.14 g, 0.0164 moles) under nitrogen at 0° C. was added a solution of sodium methoxide (3.75 mL of a 25 wt. % solution, 0.0164 moles) with magnetic stirring. A solution of the nitrile produced in Step 2 (3.00 g, 0.0164 moles) in methanol (10 mL) was added. After stirring at 25° C. for 1 day and at 40° C. for 1 day the mixture was heated at 65° C. for 2 days and then allowed to cool. The methanol was removed by rotary evaporation. The mixture was diluted with ether and filtered. Removal of the ether gave a crude oil (3.34 g). Purification by chromatography on silica gel eluting with ether followed by ether/methanol (10:1) gave a colorless oil (2.73 g, 77%). $^1$H NMR (400 MHz) DMSO-d$_6$ δ 8.68 (s, 1H), 5.30 (br, s, 2H), 4.50–4.55 (m, 1H), 3.68–3.77 (m, 1H), 3.56–3.64 (m, 1H), 3.38–3.46 (m, 1H), 3.28–3.36 (m, 1H), 1.91–1.99 (m, 2H), 1.35–1.78 (m, 10H).
Step 4

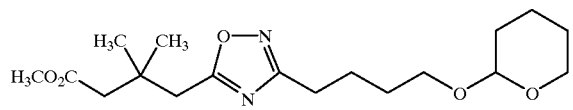

To a solution of the compound produced in Step 3 (1.732 g, 8.008 mmoles) in 1,4-dioxane (30 mL) under nitrogen was added a solution of 3,3-dimethylglutaric anhydride (1.138 g, 8.008 mmoles) in 1,4-dioxane (10 mL) with magnetic stirring at ambient temperature (20° C.). After 1 hour the mixture was heated to 95° C. for 48 hours. The mixture was allowed to cool and the solvent was removed by rotary evaporation. The residue was dissolved in DMF (40 mL) and potassium carbonate (1.55 g, 11.2 mmoles) was added. The mixture was magnetically stirred under nitrogen. Methyl iodide (523 μL, 8.41 mmoles) was added and the mixture was stirred for 24 hours at 20° C. The reaction mixture was added to water (100 mL) and extracted into ethyl acetate (3×50 mL). The combined extracts were washed with water (3×20 mL) and saturated sodium chloride solution (20 mL). The solution was dried over sodium sulfate, filtered and evaporated under vacuum to give a crude oil. The product was purified by chromatography on silica gel, eluting with hexane/ethyl acetate (3:1) to give a pale yellow oil (2.52 g; 89% yield). $^1$H NMR (400 MHz) CDCl$_3$ δ 4.55–4.60 (m, 1H), 3.81–3.90 (m, 1H), 3.73–3.81 (m, 1H), 3.68 (s, 3H), 3.47–3.53 (m, 1H), 3.38–3.47 (m, 1H), 3.00 (s, 2H), 2.77 (t, J=7.5 Hz, 2H), 2.39 (s, 2H), 1.45–1.90 (m, 10H), 1.12 (s, 6H).
Step 5

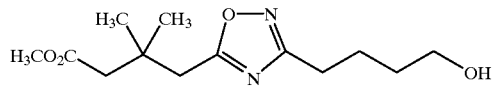

To a solution of the compound produced in Step 4 (2.47 g, 6.97 mmoles) in methanol (40 mL) was added p-toluenesulfonic acid monohydrate (133 mg, 0.700 mmoles). The mixture was magnetically stirred under nitrogen at 20° C. for 2 hours. The majority of the methanol was removed by rotary evaporation. The mixture was diluted with water (40 mL) and saturated sodium bicarbonate solution (10 mL). The mixture was extracted with ethyl acetate (3×30 mL), and the combined extracts were washed with saturated sodium chloride solution (20 mL). The solution was dried over sodium sulfate, filtered and evaporated under vacuum to give a residual oil which was purified by chromatography on silica gel, eluting with hexane/ethyl acetate (4:1 to 1:2). This gave a colorless oil (1.642 g, 87%). $^1$H NMR (400 MHz) CDCl$_3$ δ 3.65–3.72 (m, 2H), 3.69 (s, 3H), 3.00 (s, 2H), 2.78 (t, J=7.5 Hz, 2H), 2.40 (s, 2H), 1.80–1.90 (m, 2H), 1.60–1.70 (m, 2H), 1.52 (t, J=5 Hz, 1H), 1.12 (s, 6H).
Step 6

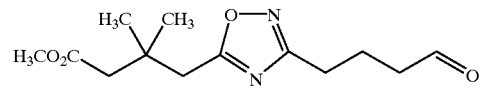

To a solution of the compound produced in Step 5 (500 mg, 1.85 mmoles) in methylene chloride (10 mL) was added powdered 4 A molecular sieves (925 mg) and N-methylmorpholine-N-oxide (325 mg, 2.78 mmoles). The mixture was cooled to 10° C. under nitrogen with magnetic stirring. Tetrapropylammonium perruthenate (33 mg, 0.093 mmoles) was added and the mixture was stirred for 2 hours at 22° C. The mixture was diluted with ethyl acetate/hexane (2:1, 40 mL) and filtered through a pad of silica gel, washing with ethyl acetate/hexane (2:1). The solvent was removed under vacuum to give a pale yellow oil (390 mg; 79% yield). $^1$H NMR (400 MHz) CDCl$_3$ δ 9.79 (t, J=1.2 Hz, 1H), 3.69 (s, 3H), 3.01 (s, 2H), 2.79 (t, J=7.5 Hz, 2H), 2.58 (td, J=7.5, 1.2 Hz, 2H), 2.40 (s, 2H), 2.05–2.13 (m, 2H), 1.12 (s, 6H).
Step 7

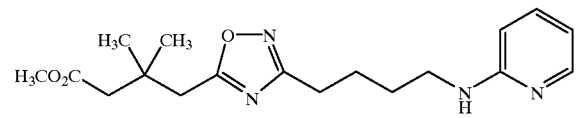

To a solution of the compound produced in Step 6 (380 mg, 1.42 mmoles) in methylene chloride (10 mL) was added 2-aminopyridine (147 mg, 1.56 mmoles). The mixture was magnetically stirred under nitrogen for 30 minutes. Sodium triacetoxyborohydride (450 mg, 2.12 mmoles) was added and the mixture was stirred at 20° C. for 4.5 hours. The mixture was added to aqueous sodium bicarbonate solution (30 mL) and extracted into ethyl acetate (3×30 mL). The combined extracts were washed with saturated sodium chloride solution (30 mL), dried over sodium sulfate and filtered. The solvent was removed under vacuum to give a crude oil which was purified by chromatography on silica gel, eluting with ethyl acetate/hexane (2:1). The product was obtained as a colorless oil (343 mg, 70%). $^1$H NMR (400 MHz) CDCl$_3$ δ 8.05–8.09 (m, 1H), 7.38–7.43 (m, 1H), 6.53–6.58 (m, 1H), 6.37 (d, J=8.7 Hz, 1H), 4.49 (br, m, 1H), 3.69 (s, 3H), 3.31 (dt, J=6.2, 6.2 Hz, 2H), 3.00 (s, 2H), 2.79 (t, J=7.5 Hz, 2H), 2.39 (s, 2H), 1.82–1.92 (m, 2H), 1.65–1.75 (m, 2H), 1.12 (s, 6H).
Step 8
β,β-dimethyl-3-[4-(2-pyridinylamino)butyl]-1,2,4-oxadiazole-5-butanoic acid

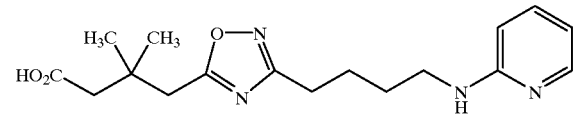

To a solution of the compound produced in Step 7 (307 mg, 0.886 mmoles) in methanol (10 mL) was added 1N sodium hydroxide solution (3 mL) and the mixture was stirred at 20° C. for 16 hours. 2N hydrochloric acid was added to adjust the pH to 7.0 and the solvent was then removed under vacuum. The material was put under high vacuum to remove residual water. The remaining gum was dissolved in a mixture of ethyl acetate/methanol (10:1) and the inorganic salts were removed by filtration through celite. The solvent was removed under vacuum. The material was placed under high vacuum at 65° C. for 16 hours to yield a pale yellow gum (320 mg). This material contains 20mole % ethyl acetate. $^1$H NMR (400 MHz) DMSO-d$_6$ δ 7.90–7.93 (m, 1H), 7.29–7.34 (m, 1H), 6.45–6.52 (br, m, 1H), 6.39–6.44 (m, 2H), 3.22 (br, q, J=5 Hz, 2H), 3.05 (s, 2H), 2.70 (t, J=7.5 Hz, 2H), 2.11 (s, 2H), 1.65–1.77 (br, m, 2H), 1.49–1.59 (br, m, 2H), 0.99 (s, 6H). The material was analyzed as follows: Found C, 57.81; H, 6.93; N, 15.07; $C_{17}H_{24}N_4O_{3+0.45}HCl+0.2H_2O+0.2$ethyl acetate requires C, 57.78; H, 7.20; N, 15.14.

EXAMPLE 63

β,β-dimethyl-3-[[[2-(2-pyridinylamino)ethyl]thio]methyl]-1,2,4-oxadiazole-5-butanoic acid Step 1

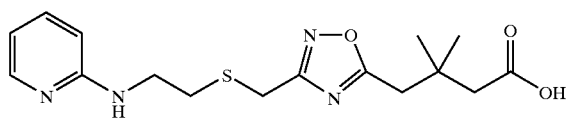

STEP 1

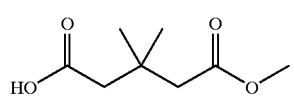

A solution of 3,3-dimethyl glutaric anhydride (4.0 g, 28.1 mmoles) in MeOH (30 mL) was heated to reflux overnight. The solution was concentrated to afford a colorless liquid (4.84 g; 99% yield). $^1$H NMR (CDCl$_3$) δ 3.57 (3H, s), 2.40 (2H, s), 2.3 (2H, s), 1.05 (6H, s).

Step 2

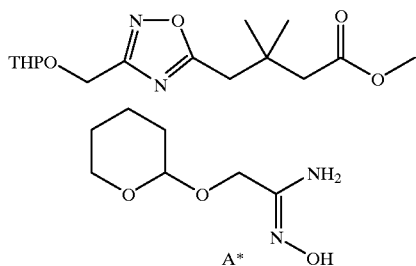

To a solution of the product of Step 1 (207 mg, 1.18 mmoles) in DMF (3 mL) was added solid CDI (193 mg, 1 equivalent). The reaction was stirred at ambient temperature for 15 minutes and a solution of A* (207 mg, 1 equivalent) [produced as described in Showell, Graham A.; Gibbons, Tracey L.; Kneen, Clare O.; MacLeod, Angus M.; Merchant, Kevin; et al.; J. Med. Chem.; 34; 3; 1991; 1086–1094] in DMF (0.5 mL) was added. The reaction was stirred at ambient temperature for 16 hours, diluted with water and extracted with ethyl acetate (3×). The combined organic extracts were washed with water, 1N NaHCO$_3$ and brine and dried over Na$_2$SO$_4$. The solution was filtered and concentrated to afford a colorless oil (375 mg; 95% yield). This material was taken up in dioxane (5 mL) and heated to 100° C. for 16 hours. The mixture was concentrated and purified by flash chromatography (SiO$_2$, hexanes:ethyl acetate, 7:1) to afford an oil (173 mg; 49% yield). $^1$H NMR (DMSO-d$_6$)

δ 4.75 (1H, t), 4.69 (1H, d, J=13 Hz), 4.61 (1H, d, J=13 Hz), 3.75 (1H, m), 3.59 (3H, s), 3.46 (1H, m), 3.04 (2H, s), 2.40 (2H, s), 1.75–1.11 (6H, m), 1.04 (6H, s).

Step 3

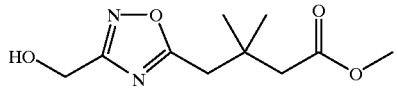

To a solution of the product of Step 2 (2.1 g, 6.72 mmoles) in MeOH (10 mL) was added p-toluenesulfonic acid (1.27 g, 1 equivalent). The mixture was stirred at room temperature for 1 hour. The reaction was concentrated, diluted with water and extracted with ethyl acetate (3×). The combined extracts were washed with 1N NaHCO$_3$, water and brine and dried (Na$_2$SO$_4$). After concentrating, the resulting residue was purified by flash chromatography (SiO$_2$, hexane:ethyl acetate, 2:1) to afford a colorless oil (1.42 g; 93% yield). $^1$H NMR (DMSO-d$_6$) δ 5.65 (1H, t, J=11 Hz), 4.53 (2H, d, J=10Hz), 3.59 (3H, s), 3.02 (2H, s), 2.40 (2H, s), 1.05 (6H, s).

Step 4

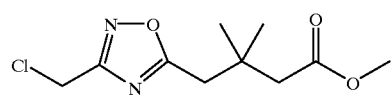

A solution of the product of Step 3 (1.41 g, 6.18 mmoles) and TEA (0.95 mL, 1.1 equivalent) in CH$_2$Cl$_2$ (10 mL) was cooled to 5° C. in an ice bath and methanesulfonyl chloride (0.53 mL, 1.1 equivalent) was added dropwise. The resulting mixture was stirred at ambient temperature overnight. The reaction was applied to a SiO$_2$ column and the product was eluted with hexane:ethyl acetate (4:1) to afford a colorless oil (1.24 g; 82% yield). $^1$H NMR (CDCl$_3$) δ 4.60 (2H, s), 3.68 (3H, s), 3.07 (2H, s), 2.40 (2H, s), 1.15 (6H, s); MS s/z 247 (MH$^+$).

Step 5

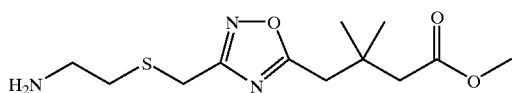

To a solution of N-Boc aminoethanethiol (517 mg, 1 eq.) in MeOH (5 mL) was added NaOMe (25% wt solution in MeOH, 0.68 mL). The reaction stirred at room temperature for 5 minutes followed by the addition of the product of Step 4 (720 mg, 2.92 mmoles). After 10 minutes, the mixture was diluted with water and extracted with ethyl acetate (3×). The combined organics were washed with water and brine and dried over Na$_2$SO$_4$. The resulting residue (1.1 g) was taken up in ethyl acetate (15 mL) and cooled to 5° C. in an ice bath. HCl (gas) was bubbled until saturated. The solution was stirred at 5° C. for 30 minutes, concentrated and the residue triturated with hexane. The supernatant liquid was decanted and the resulting residue was dried under vacuum to afford the above compound (902 mg; 98% yield) as the HCl salt. $^1$H NMR (DMSO-d$_6$) δ 3.92 (2H, s), 3.60 (3H, s), 3.07–2.90 (2H, s, 2H m), 2.79 (2H, t, J=7.5 Hz), 2.40 (2H, s), 1.05 (6H, s).

Step 6

β,β-dimethyl-3-[[[2-(2-pyridinylamino)ethyl]thio]methyl]-1,2,4-oxadiazole-5-butanoic acid, monohydrochloride

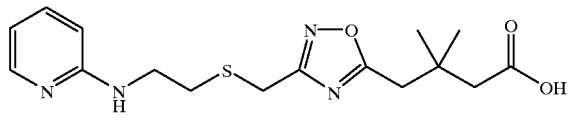

A mixture of the product of Step 5 (323 mg, 1 mmoles), 4-methyl-morpholine (0.92 mL, 2 equivalents) and 2-fluoropyridine (3 mL) was heated to 105° C. for 16 hours. The reaction was cooled to room temperature and concentrated to remove the excess 2-fluoropyridine. The residue was applied to a short bed of $SiO_2$, washed with hexane and then eluted with ethyl acetate. The ethyl acetate fraction was concentrated to afford a slightly yellow oil (270 mg; 74% yield). This material was taken up in THF (2 mL) and water (2 mL) and 1N NaOH (0.5 mL) was added. The mixture was stirred at room temperature for 14 hours. Purification of the material by RPHPLC afforded the above compound as the HCl salt (210 mg; 84% yield). Calculated for $C_{16}H_{22}N_4O_3SHCl1.5H_2O$: C, 46.43, H, 6.33, N, 13.54; Found: C, 46.74, H, 6.24, N, 13.40. $^1$H NMR ($CD_3OD$) δ 7.95–7.7.84 (2H, m), 7.16–6.91 (2H m), 3.90 (2H, s), 3.68 (2H, t, J=6.25 Hz), 3.09 (2H, s), 2.96 (2H, t, J=7.5 Hz), 2.38 (2H, s), 1.13 (6H, s).

EXAMPLE 64

2-methyl-6-[3(2-pyridylamino)propoxy)-3-pyridinebutanoic acid

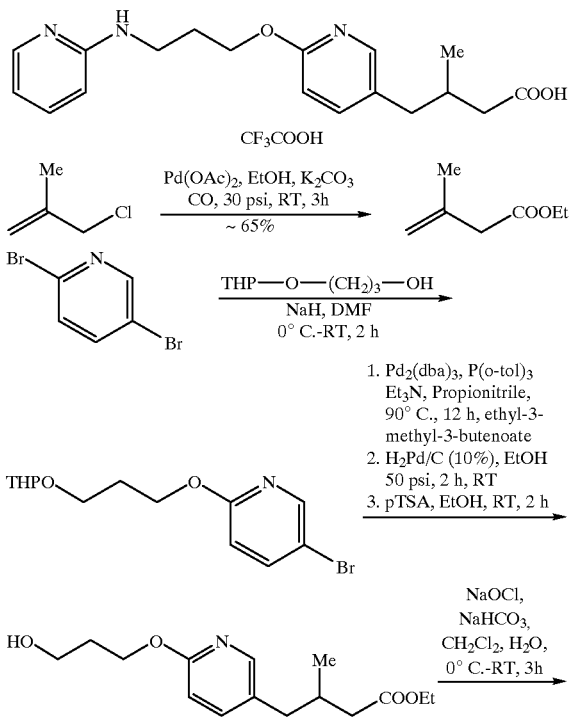

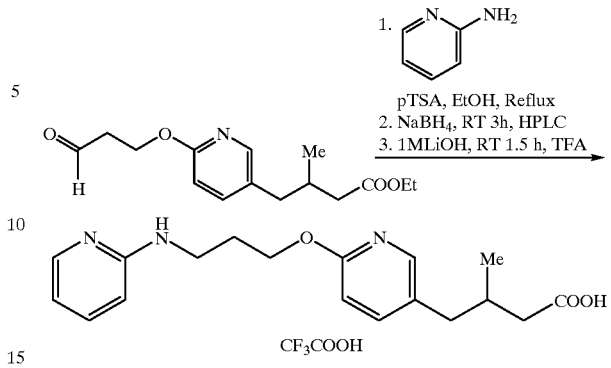

Step 1

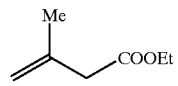

Ethyl-3-methyl-3-butenoate:

An oven dried Fisher-Porter bottle was charged with 3-chloro-2-methyl propene (15.7 g, 173. 4 mmol), potassium carbonate (13.0 g, 93.5 mmol), and ethanol (13.0 mL). The bottle was capped with a pressure head and the system was degassed on the vacuum line. The bottle was opened under an atmosphere of nitrogen and $Pd(OAc)_2$ (0.6 g, 2.67 mmol) was added. The system was capped and evacuated. The system was pressurized with carbon monoxide to 30 psi and the reactants were stirred at 10° C. After 30 minutes, the reaction mixture was stirred at room temperature for 2.5 hours. The system was then opened. The reaction mixture was diluted with ether (100 mL), and filtered. The yellow colored filtrate was concentrated under reduced pressure and the residue was purified by silica gel flash chromatography using 10% EtOAc in hexane to afford ethyl-3-methyl-3-butenoate (9.0 g) as a yellow liquid. $^1$H-NMR and mass spectral data were consistent with the structure.

Step 2

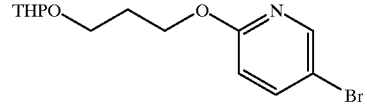

5-Bromo-2-[(3-tetrahydro-2H-pyran-2-yl)propoxy]pyridine.

To a solution of 3-tetrahydropyranyloxy-1-propanol (1.0 g, 6.25 mmol) in DMF (10.0 mL) was added NaH (0.17 g, 95%) and stirred at 0° C. After 30 minutes, 2,5 dibromopyridine (1.0 g, 4.22 mmol) was added and the mixture was stirred at room temperature for 2 hours. The mixture was then poured into 5% cold citric acid (10.0 mL) and extracted with EtOAc (3×15 mL). The combined organic extracts were washed with water (3×15 mL), dried ($Na_2SO_4$), and concentrated to dryness. The resulting material was purified by silica gel flash chromatography using 20% EtOAc in hexane containing 0.5% triethyl amine. The appropriate fractions (monitored by TLC in 30% EtOAc in hexane) were combined and concentrated to give the desired product (1.1 g) as a colorless syrup. $^1$H-NMR and mass spectral data were consistent with the structure.

HRMS: Calcd. for $C_{13}H_{19}NO_3Br$, 316.0553($MH^+$), found 316.0548.

Step 3

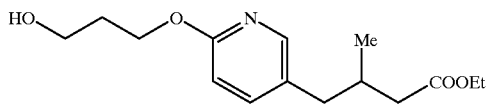

An oven-dried Fisher-Porter bottle was charged with 5-bromo-2-[(3-tetrahydro-2H-pyran-2-yl)propoxy]pyridine (0.8 g, 2.54 mmol), ethyl-3-methyl-3-butenoate (0.5 g, 3.9 mmol), and propionitrile (20 mL). The bottle was capped with a pressure head and the system was degassed on the vacuum line. The system was opened under an atmosphere of nitrogen, and Pd(dba)$_2$ (0.025 g), P(o-tol)$_3$ (0.07 g), and triethyl amine (0.4 ml) were added. The bottle was again capped with the pressure head, degassed, pressurized with nitrogen up to 5 psi, and heated at 100° C. for 20 hours. The dark reaction mixture was cooled and concentrated to dryness. The residue was purified by flash chromatography using 30% EtOAc in hexane as the eluent to provide the desired product (0.45 g, MH$^+$ m/z=366) as a pale yellow syrup. This material was dissolved in EtOH (15.0 mL), and hydrogenated at 50 psi in the presence of Pd/C (10%, 0.5 g) for 3 hours at room temperature. The mixture was filtered and the filtrate was concentrated to dryness. The resulting residue was dissolved in EtOH (5.0 mL), and p-toluenesulphonic acid (0.1 g) was added, and the reaction mixture was stirred at 50° C. for 3 hours. During this period the removal of the tetrahydropyranyl group was complete. The solution was concentrated to dryness under reduced pressure and the residue was treated with water (15 mL), NaHCO$_3$ (0.5 g), and extracted with EtOAc (2×15 mL). The combined organic extracts were washed with water (2×10 mL), dried (Na$_2$SO$_4$) and concentrated to dryness under reduced pressure to give ethyl b-methyl-6-(3-hydroxypropoxy)-3-pyridinebutanoate (0.17 g) as a pale yellow syrup. $^1$H-NMR and mass spectral data were consistent with the structure.

HRMS: Calcd. for C$_{15}$H$_{24}$NO$_4$, 282.1705 (MH$^+$), found 282.1705.

Step 4

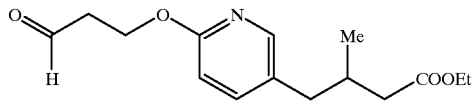

To a solution of the product of Step 3 (0.39 g, 1.39 mmol) in dichloromethane (7 mL), and THF (2.0 mL) at 0° C., 2,2,6,6-tetramethyl-1-piperidinyloxy-radical, (TEMPO) (0.005 g), KBr (16.7 mg), NaHCO$_3$ (0.015 g), and 18-crown-6 (0.005 g) were added. To this reaction mixture, was added dropwise a solution of NaOCl (5%, 2.5 mL) and then stirred at 0° C. for 1 hour. After stirring for 1 hour at room temperature, sodium bisulphite solution (5%, 1 mL), dichloromethane (20 mL), and water (10 mL) were added. The organic phase was washed with water (2×20 mL), dried (Na$_2$SO$_4$), and concentrated to dryness under reduced pressure to give ethyl β-methyl-6-(3-oxopropoxy)-3-pyridinebutanoate as a light brown liquid (0.34 g). $^1$H-NMR and mass spectral data were consistent with the structure. This material was used without purification in the following step.

Step 5

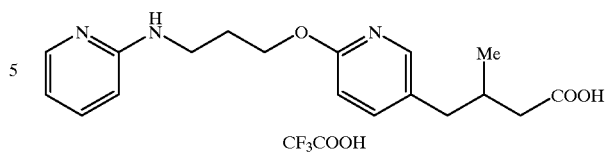

A solution of the crude aldehyde produced in Step 3 (0.4 g, 1.43 mmoles) and 2-aminopyridine (0.16 g, 1.7 mmoles) in EtOH (5.0 mL) containing p-toluenesulfonic acid (0.005 g) was heated to reflux for 4 hours. The reaction mixture was cooled, sodium borohydride (0.06 g) was added and the reactants were stirred at room temperature for 3 hours. The mixture was then cooled, glacial acetic acid (1.0 mL) was added, and the mixture was concentrated under reduced pressure. The resulting residue was purified by reverse-phase HPLC using 5–70% CH$_3$CN/H$_2$O (30 min gradient) at flow rate of 70 mL/min. The appropriate fractions as revealed by ES-mass-spectra of fractions [m/z 358 (MH$^+$)] were combined and lyophilized to give the desired ester (0.09 g). This material was treated with 1M LiOH (1.0 mL), CH$_3$CN (2.0 mL), and heated at 70° C. for 1.5 hours. The solution was cooled, diluted with water (5.0 mL), acidified with trifluoroacetic acid, and the desired product was isolated by reverse-phase HPLC using 5–50% CH$_3$CN/H$_2$O (30 min gradient) at flow rate of 70 mL/min. The appropriate fractions as revealed by ES-mass-spectra of fractions [m/z 330 (MH$^+$)] were combined and lyophilized to give β-methyl-6-[3(2-pyridylamino)propoxy)-3-pyridinebutanoic acid mono(trifluoroacetate) as a glassy substance (0.035 g). $^1$H-NMR and mass spectral data were consistent with the structure.

HRMS: Calcd. for C$_{18}$H$_{24}$N$_3$O$_3$ (MH$^+$), 330.1818, found 330.1826.

EXAMPLE 65

4-(phenylthio)-3-({3-[4-(pyridin-2-ylamino)butyl]-1,2,4-oxadiazol-5-yl}methyl)butanoic acid

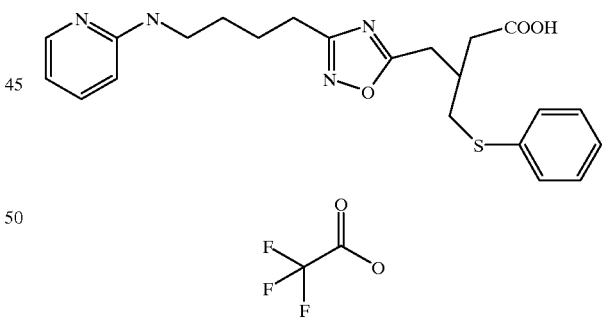

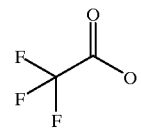

Step 1
tert-butyl(5-oxotetrahydrofuran-3-yl)acetate:
Tetrahydrofuran (50 mL) and Lithium diisopropylamide mono tetrahydrofuran complex (20 mL of 1.5 M in cyclohexane) was cooled in a dry ice/Isopropanol bath for 10 min. Tert-butyl acetate (3.5 mL 26 mmoles) was added via syringe and stirred at −78° C. for 30 min. 2(5H)-Furanone (1.59 g, 19 mmoles) was added dropwise and the reaction was stirred for 1 h at −78° C. The reaction was poured into water and extracted with ether 2×150 mL The ether extracts were combined and washed with water 100 mL then brine 3×100 mL, dried and the ether removed under reduced pressure to give 2.74 g of product (72%). MS (ESI+) for $C_{10}H_{16}O_4$ m/z 223 (M+Na)$^+$.

Step 2

5-tert-butoxy-5-oxo-3-[(phenylthio)methyl]pentanoic acid:

The product from step 1 (200 mg, 1.0 mmoles) and thio phenol (110 mg, 1 mmoles) were combined in dimethyl formamide (1.5 mL) at room temperature. Lithium(bis trimethyl silyl)amide (1.25 mL of a 1M solution in THF) was added and the reaction heated at 80° C. for 18 h. Reaction was diluted with water, made acidic with acetic acid and extracted with dichloromethane 2×40 mL. The combined extracts were washed with water 2×50 mL, brine 1×50 mL, dried and the solvent removed under pressure. The crude was chromatographed to give the product 108 mg (35%). MS (ESI+) for $C_{16}H_{22}O_4S$ m/z 333 (M+Na)$^+$.

Step 3 tert-butyl 4-(phenylthio)-3-({3-[4-(pyridin-2-ylamino)butyl]-1,2,4-oxadiazol-5-yl}methyl)butanoate The product from step 2 (54 mg, 0.175 mmoles), N'-hydroxy-5-(pyridin-2-ylamino)pentanimidamide (40 mg, 0.192 mmoles) and carbonyl diimidazole (45 mg, 0.28 mmoles) were combined in DMF 1.5 mL and stirred at RT for 4 h then heated at 65° C. overnight. N'-hydroxy-5-(pyridin-2-ylamino)pentanimidamide (36 mg 0.175 mmoles) and carbonyl diimidazole (50 mg, 0.31 mmoles) were added in and reaction was stirred at RT for 2 h followed by heating to 80° C. for 24 h. Reaction was cooled, diluted with a sodium bicarbonate solution (6 ml, 1:1 saturated bicarbonate solution and water) and extracted with ethyl acetate 3×3 mL. The combined organics were washed with water 2×3 mL, brine 3 mL, dried and passed through a pad of silica eluting with a further 10 mL of ethyl acetate. The solvent was removed under reduced pressure to give the product 50.4 mg (60%). MS (ESI+) for $C_{26}H_{34}N_4O_3S$ m/z 483 (M+H)$^+$.

Step 4

4-(phenylthio)-3-({3-[4-(pyridin-2-ylamino)butyl]-1,2,4-oxadiazol-5-yl}methyl)butanoic acid trifluoroacetate The product from step 3 (50.4 mg, 0.10 mmoles) was stirred at RT in 1:1 mix of TFA and dichloromethane (2 mL) for 30 min. The solvent was removed under reduced pressure to give the product 56.2 mg (99%). $^1$H NMR (CD$_3$OD) δ 7.84–7.79 (m, 2H), 7.39–7.35 (m, 2H), 7.32–7.26 (m, 2H), 7.22–7.17 (t, 1H), 6.95 (d, 1H), 6.82 (t, 1H), 3.37 (t, 2H), 3.22–3.02 (series of m, 4H), 2.81 (t, 2H), 2.65–2.57 (series of m, 2H), 2.49 (t, 1H), 1.92–1.82 (series of m, 2H), 1.80–1.72 (series of m, 2H); MS (ESI+) for $C_{22}H_{26}N_4O_3S$ m/z 427 (M+H)$^+$.

EXAMPLE 66

4-(phenylthio)-3-({3-[3-(5,6,7,8-tetrahydro-1,8-naphthyridin-2-yl)propyl]-1,2,4-oxadiazol-5-yl}methyl)butanoic acid

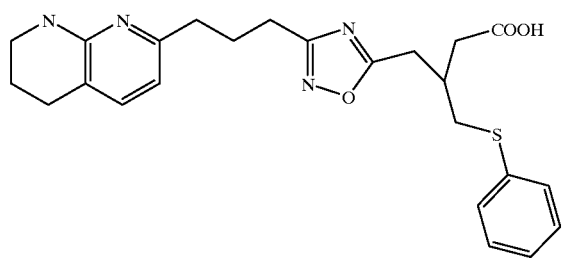

-continued

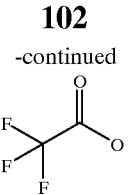

Step 1 tert-butyl 4-(phenylthio)-3-({3-[3-(5,6,7,8-tetrahydro-1,8-naphthyridin-2-yl)propyl]-1,2,4-oxadiazol-5-yl}methyl)butanoate The compound was prepared according to the method in step 3 in the previous example substituting N'-hydroxy-4-(5,6,7,8-tetrahydro-1,8-naphthyridin-2-yl)butanimidamide for N'-hydroxy-5-(pyridin-2-ylamino)pentanimidamide. MS (ESI+) for $C_{28}H_{36}N_4O_3S$ m/z 509 (M+H)$^+$.

Step 2

4-(phenylthio)-3-({3-[3-(5,6,7,8-tetrahydro-1,8-naphthyridin-2-yl)propyl]-1,2,4-oxadiazol-5-yl}methyl)butanoic acid trifluoroacetate The compound was prepared according to the method in step 4 in the previous example. $^1$H NMR (CD$_3$OD) δ 7.55 (d, 1H), 7.41–7.38 (m, 2H), 7.32–7.28 (m, 2H), 7.22–7.18 (m, 1H), 6.61 (d, 1H), 3.48 (t, 2H), 3.26–3.00 (series of m, 4H), 2.83–2.73 (series of m, 6H), 2.67–2.59 (m, 2H), 2.49–2.42 (m, 1H), 2.16–2.08 (m, 2H), 1.98–1.92 (m, 2H); MS (ESI+) for $C_{24}H_{28}N_4O_3S$ m/z 453 (M+H)$^+$.

EXAMPLE 67

3-hydroxy-4-{3-[3-(5,6,7,8-tetrahydro-1,8-naphthyridin-2-yl)propyl]-1,2,4-oxadiazol-5-yl}butanoic acid

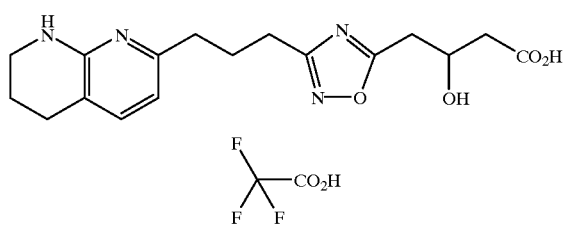

A solution of 3-(tert-butyldimethylsilyloxy)glutaric anhydride (0.50 g, 2.0 mmol) and (1Z)-N'-hydroxy-4-(5,6,7,8-tetrahydro-1,8-naphthyridin-2-yl)butanimidamide (479 mg, 2.0 mmol) in 1,4-dioxane (5 mL) was heated at 100 C for 16 h. The sample was filtered and partially concentrated. The solution was purified by RPHPLC (5–75% acetonitrile/water(TFA)) and the solvent evaporated to afford a yellow oil (0.22 g) The oil was treated with trifluoroacetic acid (4 mL) and water (0.1 mL) and allowed to stand 16 h. The solvents were evaporated to afford 0.21 g of the product as a yellow oil (30%). $^1$H NMR (400 MHz, CD$_3$OD) δ 7.58 (d, 1H), 6.63 (d, 1H), 4.52 (m, 1H), 3.52 (dd, 2H), 3.17 (dd, 1H), 3.10 (dd, 1H), 2.70 (m, 6H), 2.66 (dd, 1H), 2.59 (dd, 1H), 2.15 (m, 2H), 1.98 (m, 2H); MS (ESI+) for m/z 347 M+H)$^+$.

EXAMPLE 68

3-hydroxy-4-{3-[4-(pyridin-2-ylamino)butyl]-1,2,4-oxadiazol-5-yl}butanoic acid

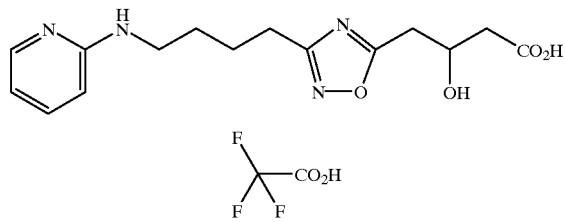

The title compound was prepared by a method analogous to the method described for Example PHA-665009E. $^1$H NMR (400 MHz, CD$_3$OD) δ 7.9 (m, 1H), 7.83 (d, 1H), 7.08 (d, 1H), 6.89 (m, 1H), 4.51 (m, 1H), 3.42 (t, 2H), 3.19 (dd, 1H), 3.1 (dd, 1H), 2.82 (t, 2H), 2.65 (dd, 1H), 2.6 (dd, 1H), 1.9 (m, 2H), 1.81 (m, 2H); MS (ESI+) for m/z 321 (M+H)$^+$.

EXAMPLE 69

3-methyl-4-{3-[4-(pyridin-2-ylamino)butyl]-1,2,4-oxadiazol-5-yl}butanoic acid

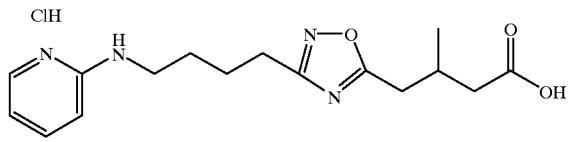

The title compound was prepared according to the method as described for preparing EXAMPLE 17 using the appropriate anhydride. $^1$H NMR (400 MHz) DMSO-d$_6$ δ 8.83 (1H, s, br), 7.82–7.92 (2H, m), 7.05 (1H, d, J=9.5 Hz), 6.80–6.86 (1H, m), 3.35–3.43 (2H, m), 2.91–2.99 (1H, m), 2.78–2.87 (1H, m), 2.74 (2H, t, J=7.5 Hz), 2.30–2.40 (1H, m), 2.15–2.25 (1H, m), 1.71–1.82 (2H, m), 1.59–1.70 (2H, m), 0.92 (3H, d, J=6 Hz). The material analyzed as follows: Found C, 51.79; H, 6.79; N, 14.77; C$_{16}$H$_{22}$N$_4$O$_3$+HCl+H$_2$O requires C, 51.54; H, 6.76; N, 15.03.

EXAMPLE 70

3-methyl-4-{3-[3-(5,6,7,8-tetrahydro-1,8-naphthyridin-2-yl)propyl]-1,2,4-oxadiazol-5-yl}butanoic acid

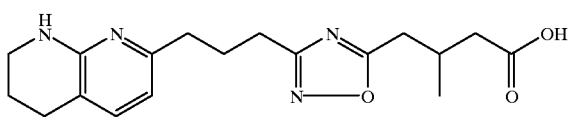

The title compound was prepared according to the method as described for preparing EXAMPLE 17 using the appropriate anhydride. $^1$H NMR (DMSO-d$_6$) 12.2 (br s, 1H), 7.92 (s, 1H), 7.60 (d, J=7.5 Hz, 1H), 6.61 (d, J=7.5 Hz, 1H), 3.5–3.3 (m, 2H), 3.0–2.8 (m, 2H), 2.78–2.7 (m, 6H), 2.4–2.13 (m, 3H), 2.06–1.98 (m, 2H), 1.87–1.79 (m, 2H), 0.93 (d, J=7.5 Hz, 3H). Anal. Calcd. for C$_{18}$H$_{24}$N$_4$O$_3$ plus 1.2CF$_3$CO$_2$H and 1.0H$_2$O: C, 49.08; H, 5.49; N, 11.22. Found: C, 49.30; H, 5.23; N, 11.12.

EXAMPLE 71

((1S,2R)-2-{3-[3-(5,6,7,8-tetrahydro-1,8-naphthyridin-2-yl)propyl]-1,2,4-oxadiazol-5-yl}cyclopropyl)acetic acid

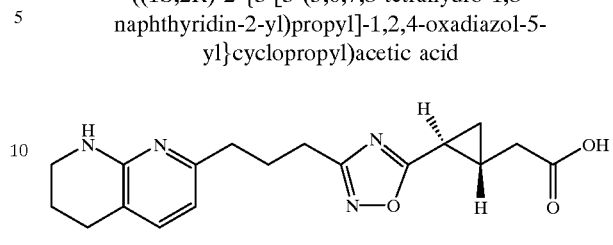

Step 1

Tert-butyl (1S,2R)-2-(2-methoxy-2-oxoethyl)cyclopropanecarboxylate and Tert-butyl (1S,2S)-2-(2-methoxy-2-oxoethyl)cyclopropanecarboxylate

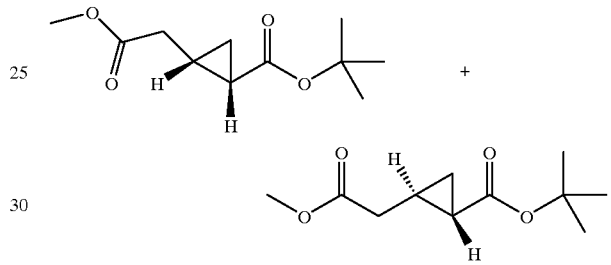

The compounds were prepared according to the procedure of Choi, S.; Newcomb, M.; Tetrahedron, 1995, 51, 657–663. The compounds were purified by flash chromatography 9:1 hexane:ethyl acetate. The trans isomer was isolated as a 20:1 mixture. $^1$H NMR (DMSO-d$_6$) δ 3.70 (s, 3H), 2.46–2.16 (m, 2H), 1.68–1.6 (m, 1H), 1.44 (s, 9H), 1.43–1.36 (m, 1H), 1.21–1.15 (m, 1H), 0.76–0.69 (m, 1H). The cis isomer was isolated as a 10:1 mixture. $^1$H NMR (DMSO-d$_6$) δ 3.68 (s, 3H), 2.71–2.56 (m, 2H), 1.77–1.69 (m, 1H), 1.55–1.48 (m, 1H), 1.44 (s, 9H), 1.10–1.02 (m, 1H), 0.92–0.88 (m, 1H).

Step 2

(1S,2R)-2-(2-methoxy-2-oxoethyl)cyclopropanecarboxylic acid

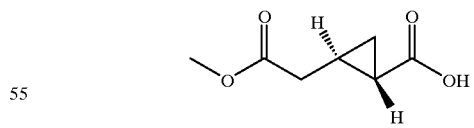

Tert-butyl (1S,2R)-2-(2-methoxy-2-oxoethyl)cyclopropanecarboxylate was dissolved in a mixture of trifluoroacetic acid:methylene chloride (7:3) and stirred at room temperature until the t-butyl ester was removed. The solvent was removed under reduced pressure to give product. $^1$H NMR (CDCl$_3$) δ 3.70 (s, 3H), 2.35 (d, J=7.5 Hz, 2H), 1.85–1.70 (m, 1H), 1.52–1.49 (m, 1H), 1.39–1.30 (m, 1H), 0.93–0.87 (m, 1H).

Step 3
(1S,2S)-2-(2-methoxy-2-oxoethyl)cyclopropanecarboxylic acid

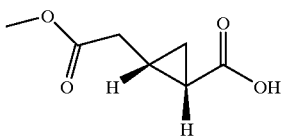

The compound was prepared using the same procedure as described above. ¹H NMR (CDCl₃) δ 3.68 (s, 3H), 2.75–2.6 (m, 2H), 1.87–1.79 (m, 1H), 1.70–1.59 (m, 1H), 1.27–1.19 (m, 1H), 1.06–0.99 (m, 1H).

Step 4
((1S,2R)-2-{3-[3-(5,6,7,8-tetrahydro-1,8-naphthyridin-2-yl)propyl]-1,2,4-oxadiazol-5-yl}cyclopropyl)acetic acid Hydrochloride

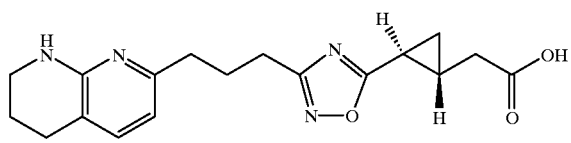

(1S,2R)-2-(2-methoxy-2-oxoethyl)cyclopropanecarboxylic acid (100 mg, 0.64 mmoles) was dissolved in DMF (4 ml) and carbonyldiimidazole (105 mg, 0.64 mmoles) was added. The mixture was stirred at room temperature for 30 minutes and then the amide oxime (150 mg, 0.64 mmoles) was added. The mixture was stirred at room temperature overnight. Then, the mixture was heated to 90° C. overnight. LC/MS: (MH⁺)=357. The solvent was removed and the residue dissolved in MeOH (2 mL), THF (2 mL), and 1N NaOH (2 mL) and stirred at room temperature overnight. 1N HCl (2 mL) was added and the solvent was removed. The residue was purified by reverse phase HPLC. ¹H NMR (DMSO-d₆) δ 7.95 (s, 1H), 7.6 (d, J=7.5 Hz, 1H), 6.6 (d, J=7.5 Hz, 1H), 3.43–3.39 (m, 2H), 2.77–2.62 (m, 6H), 2.5–2.31 (m, 2H), 2.21–2.18 (m, 1H), 2.03–1.97 (m, 2H), 1.82–78 (m, 2H), 1.71–1.61 (m, 1H), 1.31–1.25 (m, 1H), 1.20–1.14 (m, 1H). Mass Spectrum: (MH⁺)=343.

EXAMPLE 72

((1S,2S)-2-{3-[3-(5,6,7,8-tetrahydro-1,8-naphthyridin-2-yl)propyl]-1,2,4-oxadiazol-5-yl}cyclopropyl)acetic acid

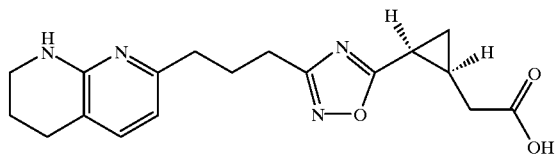

The title compound was prepared according to the procedure as described for EXAMPLE 69: ¹H NMR (DMSO-d₆) δ 12.13 (br s, 1H), 7.89 (s, 1H), 7.59 (d, J=7.5 Hz, 1H), 6.58 (d, J=7.5 Hz, 1H), 3.50–3.45 (m, 2H), 2.75–2.62 (m, 6H), 2.6–2.30 (m, 3H), 2.08–1.93 (m, 2H), 1.86–1.70 (m, 3H), 1.48–1.4 (m, 1H), 1.05–0.99 (m, 1H). Mass Spectrum: (MH⁺)=343.

EXAMPLE 73

3-(1,3-benzodioxol-5-yl)-4-{3-[(5,6,7,8-tetrahydro-1,8-naphthyridin-2-ylmethoxy)methyl]-1,2,4-oxadiazol-5-yl}butanoic acid

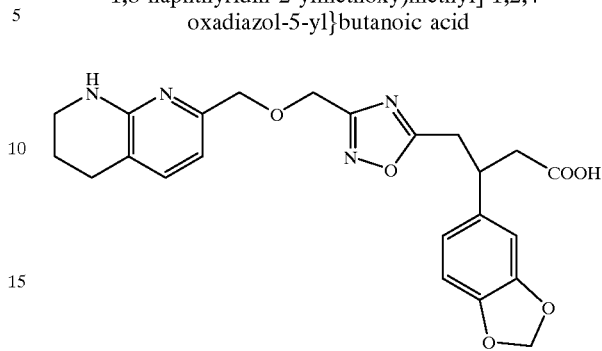

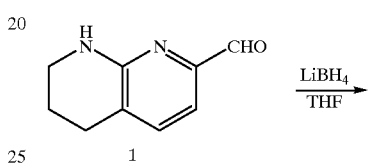

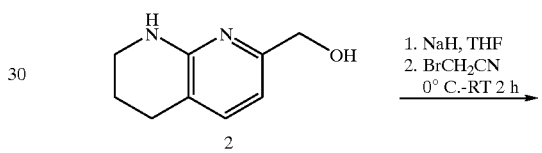

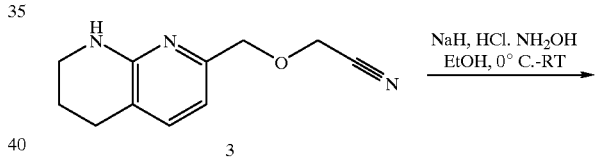

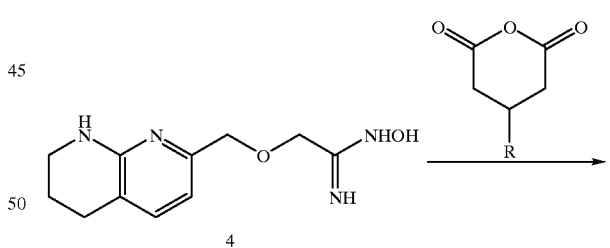

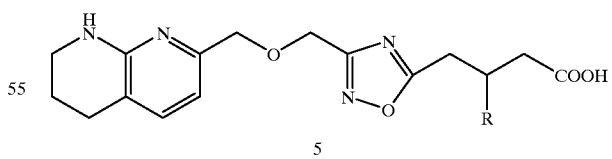

R =

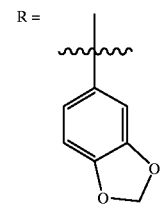

Step 1
Preparation of 1-(5,6,7,8-Tetrahydro-1,8-naphthyridin-2-yl)-methanol

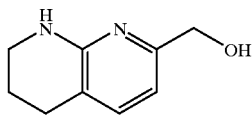

A mixture of 5,6,7,8-tetrahydro-[1,8]naphthyridine-2-carboxaldehyde 1 (0.5 g) and lithhiumborohydride (3.0 mL, 2.0 M) in THF (5.0 ML) was stirred at 5° C. for 1 h. The reaction mixture was then allowed to warm to room temperature over a period of another hour, quenched with acetic acid (2.0 mL) and concentrated under reduced pressure. The residue was partitioned between 1N NaOH (20.0 mL)and EtOAc (25 mL). The organic phase was washed with brine (2×0 mL), dried (Na2SO4), and concentrated to dryness. The resulting residue was purified by silica gel flash chromatography using EtOAc containing 10% methanol to give 0.3 g of the title compound as a pale yellow solid: $^1$H-NMR δ (CD3OD) 7.18 (d, 1H, J=7.6 Hz), 6.58 (d, 1H, J=7.6 Hz), 4.40 (s, 2H), 3.34 (m, 2H), 2.69 (t, 2H, J=6.0 Hz), 1.85 (t, 2H, J=6.0 Hz); ES-MS, m/z =165 (MH$^+$).

Step 2
2-(5,6,7,8-Tetrahydro-1,8-naphthyridin-2-yl)-methyleneoxy-acetonitrile

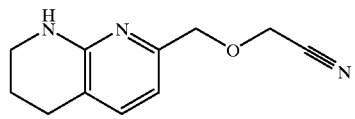

To a solution of 1-(5,6,7,8-Tetrahydro-1,8-naphhyridin-2-yl)-methanol (0.5 g) in THF (10.0 mL) at 0° C., was added NaH (0.08 g) and stirred for 15 min. Then added dropwise, a solution of bromoacetonitrile (0.25 mL) in THF (5.0 mL). The resulting mixture was stirred at 0° C. for 1 h and at room temperature for another 1 h. The reaction mixture was concentrated to dryness and the residue was purified by reverse-phase HPLC using 5–90% acetonitrile/water gradient at flow rate of 100 mL/min. The appropriate fractions were combined and freeze dried to give 0.5 g of the title compound: $^1$H-NMR δ (CDCl3) 7.37 (d, 1H, J=9.6 Hz), 6.56 (d, 1H, 9.6 Hz), 4.62 (s, 2H), 4.46 (s, 2H), 3.52 (t, 2H, J=7.2 Hz), 2.79 (t, 2H, J=9.2 Hz), 1.94 (m, 2H); ES-MS, m/z =204 (MH$^+$).

Step 3

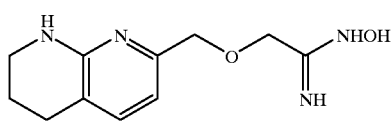

To a mixture of Compound from step 2 (0.1 g), and hydroxylamine hydrochloride (0.07 g) in dry EtOH (3.0 mL) was added NaH (0.04 g) and stirred at 5° C. under argon for 30 min. The reaction mixture was then stirred at room temperature for 3 h, and added acetic acid (0.5 mL) The resulting mixture was concentrated to dryness and the amidoxime was isolated by reverse-phase HPLC using 10–90% acetonitrile/water gradient at flow rate of 70 mL/min. The appropriate fractions (MH$^+$ m/z =237) were combined and freeze dried to give (0.025 g) the desired product: $^1$H-NMR δ (CD3OD) 7.61 (d, 1H, J=7.5 Hz), 6.73 (d, 1H, J=7.5 Hz), 4.62 (s, 2H), 4.41 (s, 2H), 3.5 (t, 2H, J=6.0 Hz), 2.85 (t, 2H, J=6.0 Hz), and 1.96 (m, 2H), ES-MS: MH$^+$ m/z =237.

Step 4
3-(1,3-benzodioxol-5-yl)-4-{3-[(5,6,7,8-tetrahydro-1,8-naphthyridin-2-ylmethoxy)methyl]-1,2,4-oxadiazol-5-yl}butanoic acid, trifluroacetate.

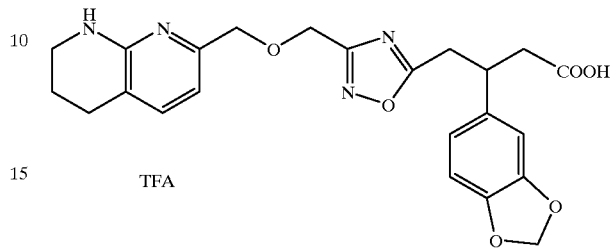

A mixture of amidoxime (0.174 g, 0.737 mmol) and anhydride (0.189, 0.8107 mmol) in dioxane (5 mL) was heated overnight under argon at 95° C. The reaction was monitored by electro spray MS (M+H 453). The reaction mixture was cooled to room temperature, diluted with acetonitrile (5 mL) and purified by RP HPLC using a gradient of 90–10% H2O/acetonitrile/0.05% TFA in 30 min, to afford the title compound (60 mg), m/z=453 (MH$^+$).

EXAMPLE 74

3,3-dimethyl-4-{5-[4-(pyridin-2-ylamino)butyl]-1,2,4-oxadiazol-3-yl}butanoic acid trifluoroacetate

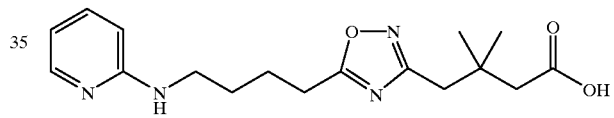

Step 1:
5-tert-butoxy-3,3-dimethyl-5-oxopentanoic acid

3,3-Dimethylglutaric anhydride (6.5 g, 45.7 mmol) was dissolved in THF (75 mL) and the t-BuOK, 1M in THF (52.5 mL, 52.5 mmol) was added and the mixture was stirred at room temperature for one hour. The reaction mixture was then diluted with ether, washed with 1N HCl, brine (3×), dried (MgSO$_4$), and concentrated to give 6.8 g (69%) of the desired product as a colorless oil. $^1$H NMR (DMSO-d$_6$) 12.0 (br s, 1H), 2.22 (s, 4H), 1.39 (s, 9H), 1.03 (s, 6H).

Step 2:
Tert-butyl 5-amino-3,3-dimethyl-5-oxopentanoate

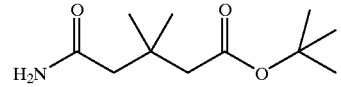

5-Tert-butoxy-3,3-dimethyl-5-oxopentanoic acid (6 g, 27.8 mmol) was dissolved in DMF (111 mL) and benzotriazol-1-yloxytris(pyrrolidino)phosphonium hexafluorophosphate (21.68 g, 41.7 mmol), 1-hydroxybenzotriazole (5.6 g, 41.7 mmol), diisopropyl-ethylamine (19.3 mL, 111 mmol) and ammonium chloride (3 g, 55.6 mmol) were added. The mixture was stirred at room temperature for two hours. The DMF was removed under reduced pressure and the residue dissolved in ethyl acetate. The ethyl acetate was washed with 1N $KHSO_4$, saturated sodium bicarbonate, brine, dried ($Na_2SO_4$) and concentrated. The residue was again dissolved in ethyl acetate, washed with 0.1N HCl, 0.1N NaOH, $H_2O$, dried ($Na_2SO_4$), passed through a pad of silica and concentrated to give 4.9 g (82%) of the desired product. $^1$H NMR (DMSO-$d_6$) 7.19 (br s, 1H), 6.71 (br s, 1H), 2.23 (s, 2H), 2.08 (s, 2H), 1.4 (s, 9H), 1.02 (s, 6H).

Step 3:

Tert-butyl 4-cyano-3,3-dimethylbutanoate

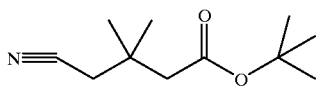

Tert-butyl 5-amino-3,3-dimethyl-5-oxopentanoate (3.17 g, 14.7 mmol) was dissolved in dioxane (32 mL) containing pyridine (8 mL) and the solution was cooled to 0° C. Trifluoroacetic anhydride was added dropwise over 25 minutes keeping the temperature between 0–5° C. The mixture was stirred at 0° C. for one hour and then at room temperature overnight. A few chips of ice were added, followed by ethyl acetate (250 mL). The ethyl acetate was washed with brine, dried ($Na_2SO_4$) and removed under reduced pressure. The residue was purified by flash chromatography 7:3 (hexane:ethyl acetate) to give 2.1 g (72%) of the desired product. $^1$H NMR (CDCl$_3$) 2.44 (s, 2H), 2.21 (s, 2H), 1.39 (s, 9H), 1.10 (s, 6H).

Step 4:

Tert-butyl-5-amino-5-(hydroxyimino)-3,3-dimethylpentanoate

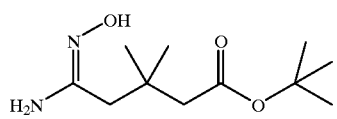

Hydroxylamine hydrochloride (353 mg, 5 mmol) and NaOMe 25% in MeOH (1.14 mL, 5 mmol) were mixed together in MeOH (3 mL), filtered, and washed with MeOH (2 mL). Tert-butyl 4-cyano-3,3-dimethylbutanoate (500 mg, 2.5 mmol) was dissolved in the above solution. The mixture was refluxed overnight. The solvent was removed under reduced pressure. The residue was dissolved in ethyl acetate, passed through a pad of silica, concentrated, and used directly in next reaction. Mass Spectrum: (MH$^+$)=231.

Step 5:

Methyl 5-hydroxypentanoate

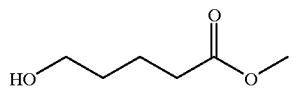

This compound was synthesized following the procedure of: Fleming, I.; Higgins, D.; Journal Chemical Society Perkin Trans. 1, 1998, 17, 2673–2678.

Step 6:

Methyl 5-oxopentanoate

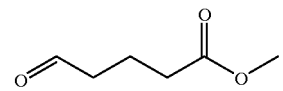

This compound was synthesized following the procedure of: Fleming, I.; Higgins, D.; Journal Chemical Society Perkin Trans. 1, 1998, 17, 2673–2678.

Step 7:

Methyl 5-(pyridin-2-ylamino)pentanoate

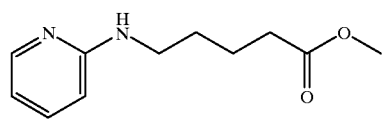

To a solution of methyl 5-oxopentanoate (3.0 g, 23 mmol) in methylene chloride (75 mL) was added 2-aminopyridine (2.38 g, 25.3 mmol). The mixture was stirred at room temperature for 30 minutes. Then, the sodium triacetoxy borohydride (7.31 g, 34.5 mmol) was added and the mixture was stirred at room temperature for 4.5 hours. A saturated solution of sodium bicarbonate (40 mL) was added and the reaction mixture was extracted with ether (4×30 mL). The organic layer was washed with 0.1 N NaOH, water (2×40 mL), dried (MgSO$_4$) and concentrated. The residue was purified by flash chromatography 1:1 (Acetone:methylene chloride) to obtain 2.31 g (48%) of the product. $^1$H NMR (CDCl$_3$) 8.09–8.06 (m, 1H), 7.42–7.38 (m, 1H), 6.59–6.52 (m, 1H), 6.37 (d, J=9 Hz, 1H), 4.52 (br s, 1H), 3.68 (s, 3H), 3.29 (q, J=6 Hz, 2H), 2.40–2.31 (m, 2H), 1.8–1.61 (m, 4H).

Step 8:

Methyl 5-[(tert-butoxycarbonyl)(pyridin-2-yl)amino]pentanoate

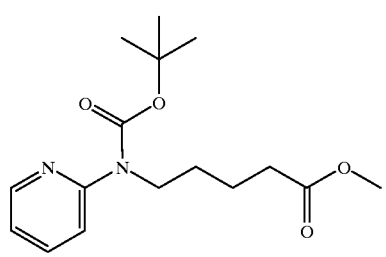

To a mixture of methyl 5-(pyridin-2-ylamino)pentanoate (300 mg, 1.44 mmol) in methylene chloride (10 mL) was added DMAP (17.6 mg, 0.144 mmol) and di-tert-butyl dicarbonate (1.57 g, 7.2 mmol). The mixture was stirred at room temperature overnight. The reaction was diluted with water and the organic layer separated, dried (MgSO$_4$), and concentrated. The residue was purified by flash chromatography 1:2 (ethyl acetate:hexane) to obtain 213 mg (48%) of the product as a colorless oil. $^1$H NMR (CDCl$_3$) 8.36–8.34 (m, 1H), 7.65–7.55 (m, 2H), 7.02–6.98 (m, 1H), 3.97–3.92 (m, 2H), 3.65 (s, 3H), 2.36–2.30 (m, 2H), 1.67–1.62 (m, 4H), 1.51 (s, 9H).

Step 9:

5-[(tert-butoxycarbonyl)(pyridin-2-yl)amino]pentanoic acid

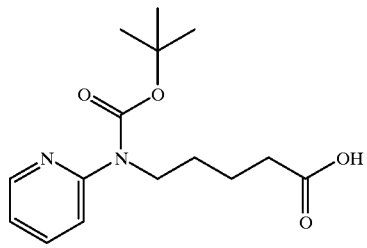

NaOH (240 mg, 6 mmol) was dissolved in water (3 mL) and MeOH (10 mL). This solution was added to methyl 5-[(tert-butoxycarbonyl)(pyridin-2-yl)amino]pentanoate (200 mg, 0.64 mmol) dissolved in MeOH (15 mL). The mixture was stirred at room temperature overnight. The reaction mixture was neutralized with 2N HCl to pH 7. The solvent was removed under reduced pressure. A citric acid solution (10 mL) was added and the mixture was extracted with ethyl acetate, dried (MgSO$_4$) and concentrated to give 128 mg (68%) of the product. $^1$H NMR (CDCl$_3$) 8.36–8.34 (m, 1H), 7.65–7.52 (m, 2H), 7.02–6.98 (m, 1H), 3.97–3.91 (m, 2H), 2.38–2.32 (m, 2H), 1.69–1.62 (m, 4H), 1.50 (s, 9H).

Step 10:

3,3-dimethyl-4-{5-[4-(pyridin-2-ylamino)butyl]-1,2,4-oxadiazol-3-yl}butanoic acid trifluoroacetate

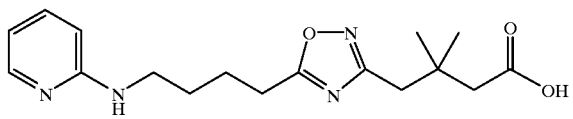

5-[(Tert-butoxycarbonyl)(pyridin-2-yl)amino]pentanoic acid (128 mg, 0.44 mmoles) was dissolved in DMF (4 ml) and carbonyldiimidazole (71 mg, 0.64 mmoles) was added. The mixture was stirred at room temperature for 30 minutes and then tert-butyl-5-amino-5-(hydroxyimino)-3,3-dimethylpentanoate (151 mg, 0.66 mmoles) was added. The mixture was stirred at room temperature overnight. Then, the solvent was removed under reduced pressure, the residue was dissolved in ethyl acetate, and passed through a pad of silica. The ethyl acetate was removed under reduced pressure and the residue was dissolved in dioxane (5 mL). The mixture was heated at 90° C. overnight. LC/MS: (MH$^+$)= 489. The solvent was removed and the residue was purified by flash chromatography 7:3 (hexane:ethyl acetate). The desired fractions were combined and the residue was dissolved in a 7:3 mixture of trifluroacetic acid:methylene chloride (10 mL) and stirred at room temperature for one hour. The solvent was removed to give 70 mg(36%) of the desired product. $^1$H NMR (DMSO-d$_6$) 8.82 (br s, 1H), 7.92–7.84 (m, 2H), 7.04 (d, J=9.5 Hz, 1H), 6.88–6.81 (m, 1H), 3.39–3.30 (m, 2H), 2.97 (t, J=6 Hz, 2H), 2.75 (s, 2H), 2.25 (s, 2H), 1.87–1.78 (m, 2H), 1.70–1.60 (m, 2H), 1.01 (s, 6H). Mass Spectrum: (MH$^+$)=333.

EXAMPLE 75

3-Phenyl-4-{5-[3-(5,6,7,8-tetrahydro-[1,8] naphthyridin-2-yl)-propyl]-tetrazol-2-yl}-butyric acid

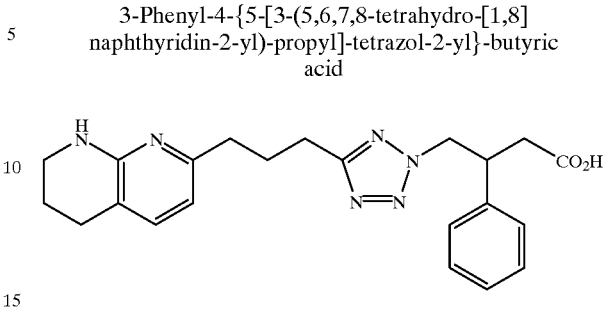

The title compound is prepared according to the general procedures described in SCHEME 5.

EXAMPLE 76

3-(2,3-Dihydro-benzofuran-6-yl)-4-{5-[3-(5,6,7,8-tetrahydro[1,8]naphthyridin-2-yl)-propyl]-tetrazol-2-yl}-butyric acid

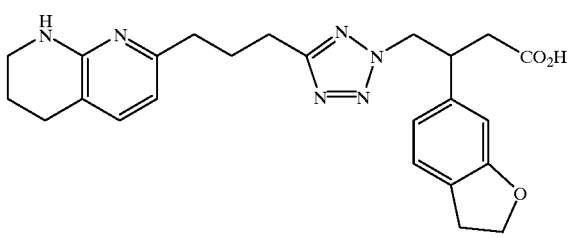

The title compound is prepared according to the general procedures described in SCHEME 5.

EXAMPLE 77

3-(3-Fluoro-phenyl)-4-{5-[3-(5,6,7,8-tetrahydro-[1,8]naphthyridin-2-yl)-propyl]-tetrazol-2-yl}-butyric acid

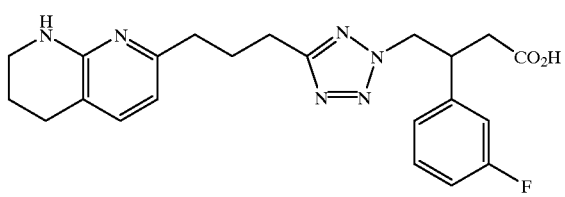

The title compound is prepared according to the general procedures described in SCHEME 5.

EXAMPLE 78

3-Pyridin-3-yl-4-{5-[3-(5,6,7,8-tetrahydro-[1,8]naphthyridin-2-yl)-propyl]-tetrazol-2-yl}-butyric acid

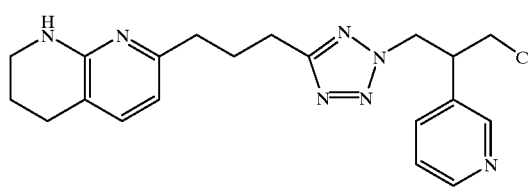

The title compound is prepared according to the general procedures described in SCHEME 5.

EXAMPLE 79

3-Benzo[1,3]dioxol-5-yl-4-{5-[3-(5,6,7,8-tetrahydro-[1,8]naphthyridin-2-yl)-propyl]-tetrazol-2-yl}-butyric acid

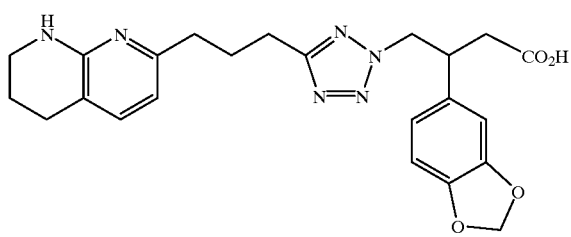

The title compound is prepared according to the general procedures described in SCHEME 5.

EXAMPLE 80

(2-{5-[3-(5,6,7,8-Tetrahydro-[1,8]naphthyridin-2-yl)-propyl]-[1,3,4]oxadiazol-2-yl}-cyclopropyl)-acetic acid

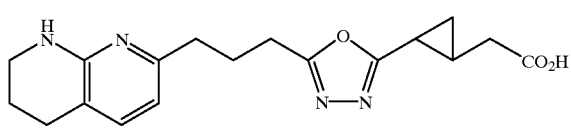

The title compound is prepared according to the general procedures described in SCHEME 6.

EXAMPLE 81

3-Phenyl-4-{5-[3-(5,6,7,8-tetrahydro-[1,8]naphthyridin-2-yl)-propyl]-[1,3,4]oxadiazol-2-yl}-butyric acid

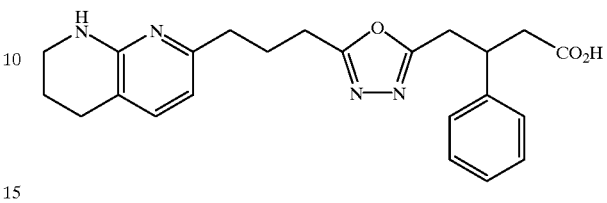

The title compound is prepared according to the general procedures described in SCHEME 6.

EXAMPLE 82

3-(2,3-Dihydro-benzofuran-6-yl)-4-{5-[3-(5,6,7,8-tetrahydro-[1,8]naphthyridin-2-yl)-propyl]-[1,3,4]oxadiazol-2-yl}-butyric acid

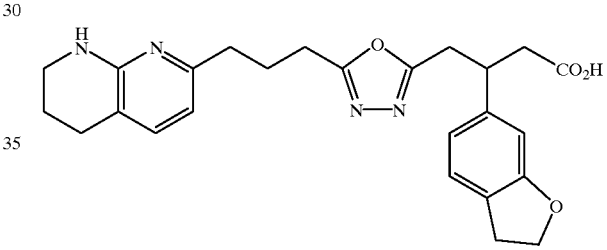

The title compound is prepared according to the general procedures described in SCHEME 6.

EXAMPLE 83

3-(3-Fluoro-phenyl)-4-{5-[3-(5,6,7,8-tetrahydro-[1,8]naphthyridin-2-yl)-propyl]-[1,3,4]oxadiazol-2-yl}-butyric acid

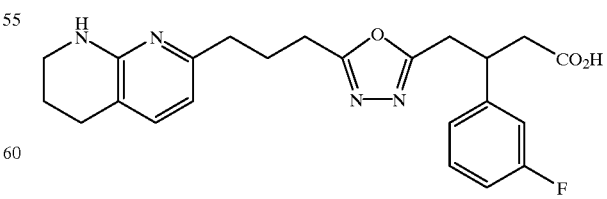

The title compound is prepared according to the general procedures described in SCHEME 6.

EXAMPLE 84

3-Benzo[1,3]dioxol-5-yl-4-{5-[3-(5,6,7,8-tetrahydro-[1,8]naphthyridin-2-yl)-propyl]-[1,3,4]oxadiazol-2-yl}-butyric acid

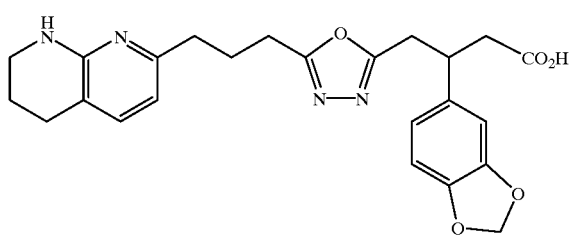

The title compound is prepared according to the general procedures described in SCHEME 6.

EXAMPLE 85

(2-{2-[3-(5,6,7,8-Tetrahydro-[1,8]naphthyridin-2-yl)-propyl]-2H-tetrazol-5-yl}-cyclopropyl)-acetic acid

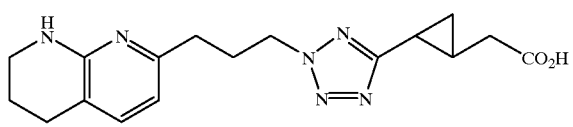

The title compound is prepared according to the general procedures described in SCHEME 7.

EXAMPLE 86

3-Phenyl-4-{2-[3-(5,6,7,8-tetrahydro-[1,8]naphthyridin-2-yl)-propyl]-2H-tetrazol-5-yl}-butyric acid

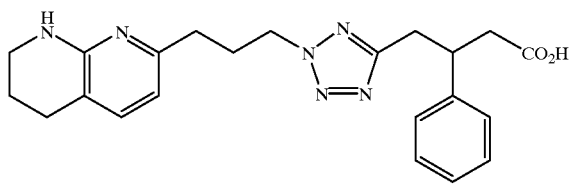

The title compound is prepared according to the general procedures described in SCHEME 7.

EXAMPLE 87

3-(2,3-Dihydro-benzofuran-6-yl)-4-{2-[3-(5,6,7,8-tetrahydro-[1,8]naphthyridin-2-yl)-propyl]-2H-tetrazol-5-yl}-butyric acid

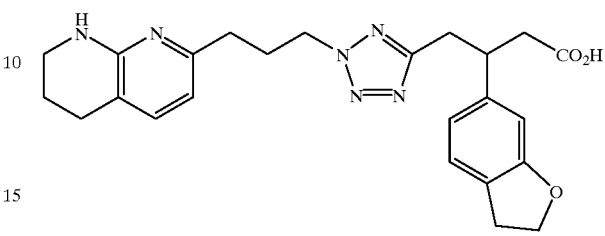

The title compound is prepared according to the general procedures described in SCHEME 7.

EXAMPLE 88

3-(3-Fluoro-phenyl)-4-{2-[3-(5,6,7,8-tetrahydro-[1,8]naphthyridin-2-yl)-propyl]-2H-tetrazol-5-yl}-butyric acid

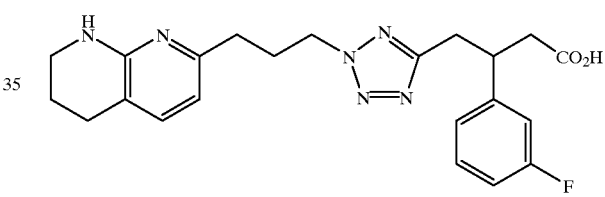

The title compound is prepared according to the general procedures described in SCHEME 7.

EXAMPLE 89

3-Pyridin-3-yl-4-{2-[3-(5,6,7,8-tetrahydro-[1,8]naphthyridin-2-yl)-propyl]-2H-tetrazol-5-yl}-butyric acid

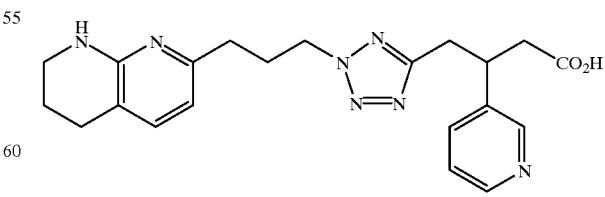

The title compound is prepared according to the general procedures described in SCHEME 7.

EXAMPLE 90

3-Benzo[1,3]dioxol-5-yl-4-{2-[3-(5,6,7,8-tetrahydro-[1,8]naphthyridin-2-yl)-propyl]-2H-tetrazol-5-yl}-butyric acid

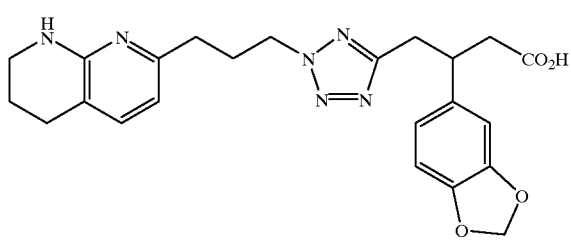

The title compound is prepared according to the general procedures described in SCHEME 7.

EXAMPLE 91

(2-{5-[3-(5,6,7,8-Tetrahydro-[1,8]naphthyridin-2-yl)-propyl]-isoxazol-3-yl}-cyclopropyl)-acetic acid

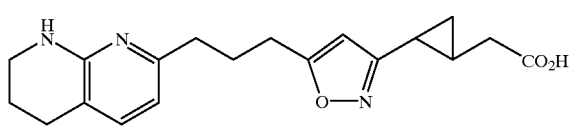

The title compound is prepared according to the general procedures described in SCHEME 8.

EXAMPLE 92

3-Phenyl-4-{5-[3-(5,6,7,8-tetrahydro-[1,8]naphthyridin-2-yl)-propyl]-isoxazol-3-yl}-butyric acid

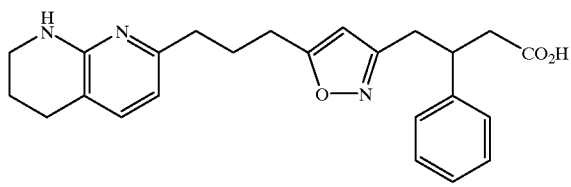

The title compound is prepared according to the general procedures described in SCHEME 8.

EXAMPLE 93

3-(2,3-Dihydro-benzofuran-6-yl)-4-{5-[3-(5,6,7,8-tetrahydro-[1,8]naphthyridin-2-yl)-propyl]-isoxazol-3-yl}-butyric acid

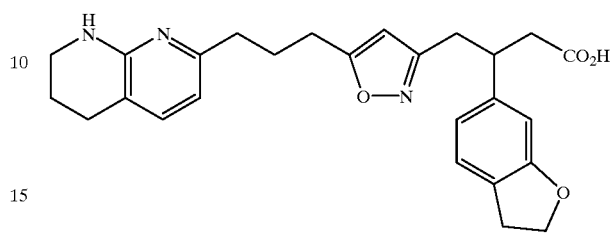

The title compound is prepared according to the general procedures described in SCHEME 8.

EXAMPLE 94

3-(3-Fluoro-phenyl)-4-{5-[3-(5,6,7,8-tetrahydro-[1,8]naphthyridin-2-yl)-propyl]-isoxazol-3-yl}-butyric acid

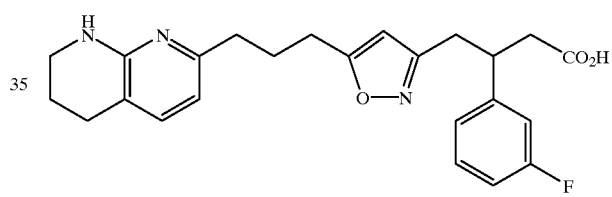

The title compound is prepared according to the general procedures described in SCHEME 8.

EXAMPLE 95

3-Pyridin-3-yl-4-{5-[3-(5,6,7,8-tetrahydro-[1,8]naphthyridin-2-yl)-propyl]-isoxazol-3-yl}-butyric acid

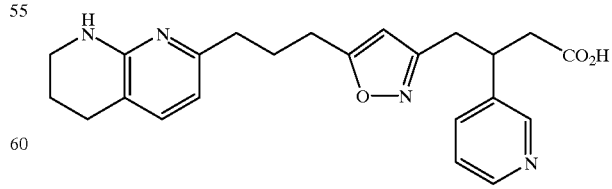

The title compound is prepared according to the general procedures described in SCHEME 8.

EXAMPLE 96

3-Benzo[1,3]dioxol-5-yl-4-{5-[3-(5,6,7,8-tetrahydro-[1,8]naphthyridin-2-yl)-propyl]-isoxazol-3-yl}-butyric acid

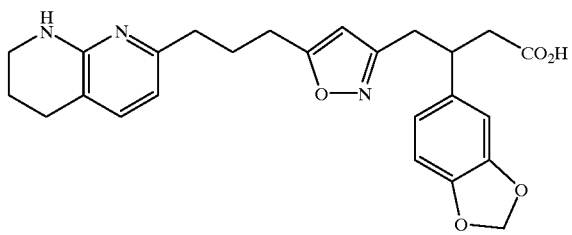

The title compound is prepared according to the general procedures described in SCHEME 8.

EXAMPLE 97

3-Benzo[1,3]dioxol-5-yl-4-{5-[3-(5,6,7,8-tetrahydro-[1,8]naphthyridin-2-yl)-propyl]-isoxazol-3-yl}-butyric acid

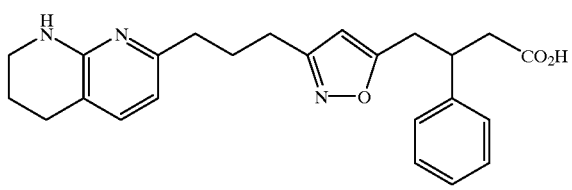

The title compound is prepared according to the general procedures described in SCHEME 8.

EXAMPLE 98

3-(2,3-Dihydro-benzofuran-6-yl)-4-{3-[3-(5,6,7,8-tetrahydro-[1,8]naphthyridin-2-yl)-propyl]-isoxazol-5-yl}-butyric acid

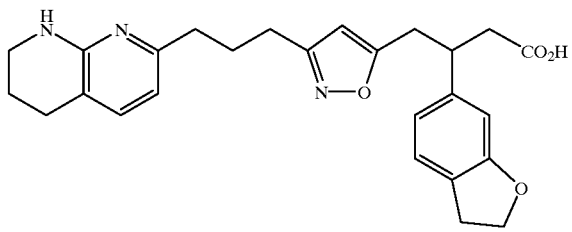

The title compound is prepared according to the general procedures described in SCHEME 8.

EXAMPLE 99

3-(3-Fluoro-phenyl)-4-{3-[3-(5,6,7,8-tetrahydro-[1,8]naphthyridin-2-yl)-propyl]-isoxazol-5-yl}-butyric acid

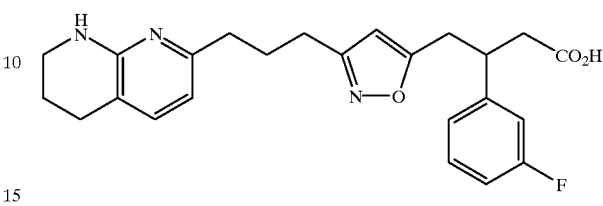

The title compound is prepared according to the general procedures described in SCHEME 8.

EXAMPLE 100

3-Pyridin-3-yl-4-{3-[3-(5,6,7,8-tetrahydro-[1,8]naphthyridin-2-yl)-propyl]-isoxazol-5-yl}-butyric acid

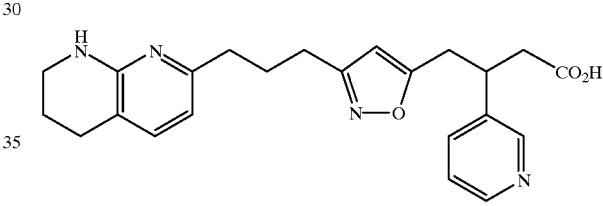

The title compound is prepared according to the general procedures described in SCHEME 8.

EXAMPLE 101

3-Benzo[1,3]dioxol-5-yl-4-{3-[3-(5,6,7,8-tetrahydro-[1,8]naphthyridin-2-yl)-propyl]-isoxazol-5-yl}-butyric acid

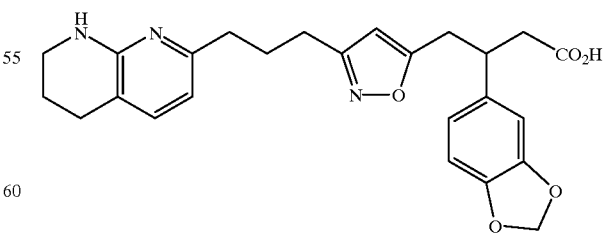

The title compound is prepared according to the general procedures described in SCHEME 8.

EXAMPLE 102

3-Phenyl-4-{5-[3-(5,6,7,8-tetrahydro-[1,8]
naphthyridin-2-yl)-propyl]-1H-pyrazol-3-yl}-butyric
acid

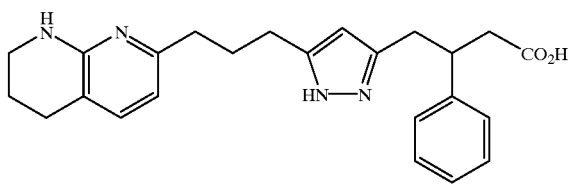

The title compound is prepared according to the general procedures described in SCHEME 8.

EXAMPLE 103

3-(2,3-Dihydro-benzofuran-6-yl)-4-{5-[3-(5,6,7,8-tetrahydro-[1,8]naphthyridin-2-yl)-propyl]-1H-pyrazol-3-yl}-butyric acid

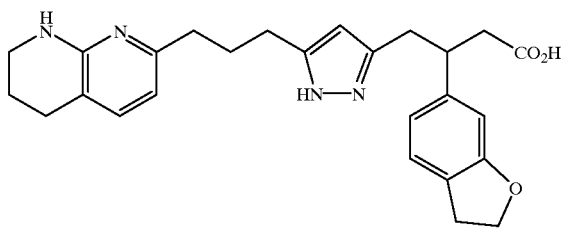

The title compound is prepared according to the general procedures described in SCHEME 8.

EXAMPLE 104

3-(3-Fluoro-phenyl)-4-{5-[3-(5,6,7,8-tetrahydro-[1,8]naphthyridin-2-yl)-propyl]-1H-pyrazol-3-yl}-butyric acid

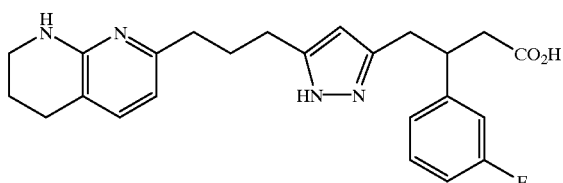

The title compound is prepared according to the general procedures described in SCHEME 8.

EXAMPLE 105

3-Pyridin-3-yl-4-{5-[3-(5,6,7,8-tetrahydro-[1,8]
naphthyridin-2-yl)-propyl]-1H-pyrazol-3-yl}-butyric
acid

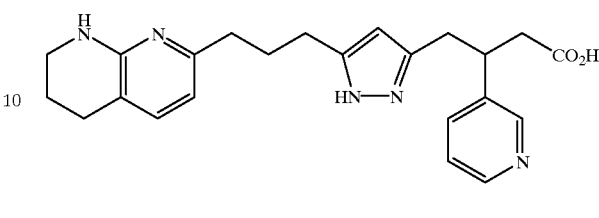

The title compound is prepared according to the general procedures described in SCHEME 8.

EXAMPLE 106

3-Benzo[1,3]dioxol-5-yl-4-{5-[3-(5,6,7,8-tetrahydro-[1,8]naphthyridin-2-yl)-propyl]-1H-pyrazol-3-yl}-butyric acid

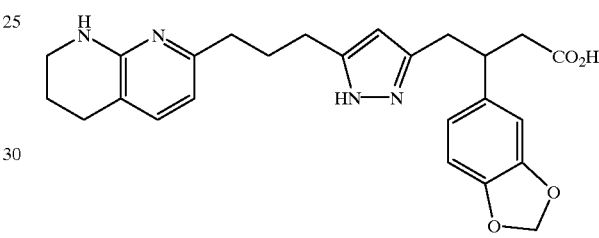

The title compound is prepared according to the general procedures described in SCHEME 8.

EXAMPLE 107

(2-{3-[3-(5,6,7,8-Tetrahydro-[1,8]naphthyridin-2-yl)-propyl]-isoxazol-5-yl}-cyclopropyl)-acetic acid

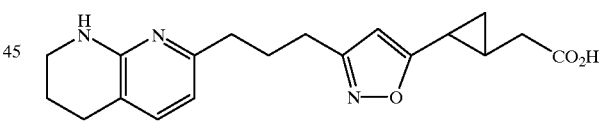

The title compound is prepared according to the general procedures described in SCHEME 8.

EXAMPLE 108

(2-{5-[3-(5,6,7,8-Tetrahydro-[1,8]naphthyridin-2-yl)-propyl]-1H-pyrazol-3-yl}-cyclopropyl)-acetic acid

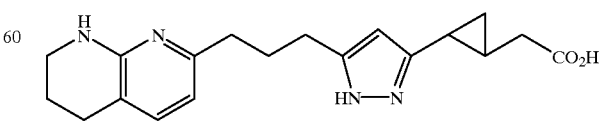

The title compound is prepared according to the general procedures described in SCHEME 8.

EXAMPLE 109

(2-{4-[3-(5,6,7,8-Tetrahydro-[1,8]naphthyridin-2-yl)-propyl]-thiazol-2-yl}-cyclopropyl)-acetic acid

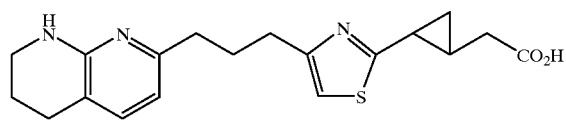

The title compound is prepared according to the general procedures described in SCHEME 9.

EXAMPLE 110

3-Phenyl-4-{4-[3-(5,6,7,8-tetrahydro-[1,8]naphthyridin-2-yl)-propyl]-thiazol-2-yl}-butyric acid

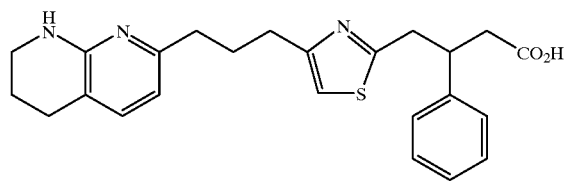

The title compound is prepared according to the general procedures described in SCHEME 9.

EXAMPLE 111

3-(2,3-Dihydro-benzofuran-6-yl)-4-{4-[3-(5,6,7,8-tetrahydro-[1,8]naphthyridin-2-yl)-propyl]-thiazol-2-yl}-butyric acid

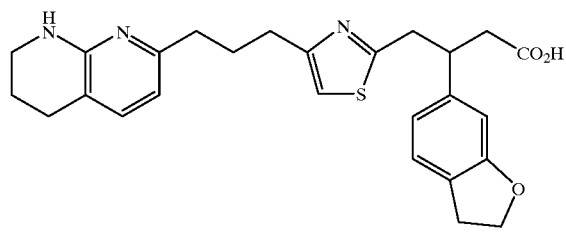

The title compound is prepared according to the general procedures described in SCHEME 9.

EXAMPLE 112

3-(3-Fluoro-phenyl)-4-{4-[3-(5,6,7,8-tetrahydro-[1,8]naphthyridin-2-yl)-propyl]-thiazol-2-yl}-butyric acid

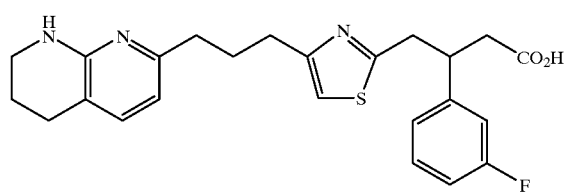

The title compound is prepared according to the general procedures described in SCHEME 9.

EXAMPLE 113

3-Pyridin-3-yl-4-{4-[3-(5,6,7,8-tetrahydro-[1,8]naphthyridin-2-yl)-propyl]-thiazol-2-yl}-butyric acid

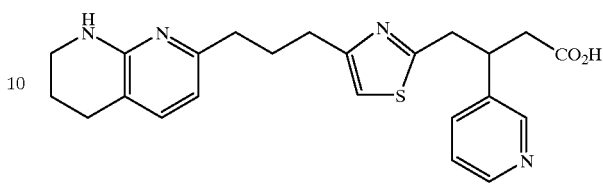

The title compound is prepared according to the general procedures described in SCHEME 9.

EXAMPLE 114

3-Benzo[1,3]dioxol-5-yl-4-{4-[3-(5,6,7,8-tetrahydro-[1,8]naphthyridin-2-yl)-propyl]-thiazol-2-yl}-butyric acid

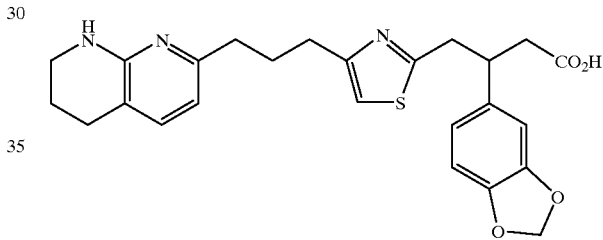

The title compound is prepared according to the general procedures described in SCHEME 9.

EXAMPLE 115

3-Phenyl-4-{3-[3-(5,6,7,8-tetrahydro-[1,8]naphthyridin-2-yl)-propyl]-pyrazol-1-yl}-butyric acid

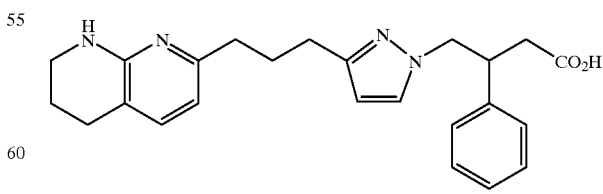

The title compound is prepared according to the general procedures described in SCHEME 9.

EXAMPLE 116

3-(2,3-Dihydro-benzofuran-6-yl)-4-{3-[3-(5,6,7,8-tetrahydro-[1,8]naphthyridin-2-yl)-propyl]-pyrazol-1-yl}-butyric acid

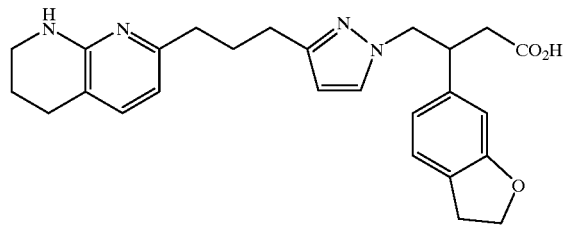

The title compound is prepared according to the general procedures described in SCHEME 9.

EXAMPLE 117

3-(3-Fluoro-phenyl)-4-{3-[3-(5,6,7,8-tetrahydro-[1,8]naphthyridin-2-yl)-propyl]-pyrazol-1-yl}-butyric acid

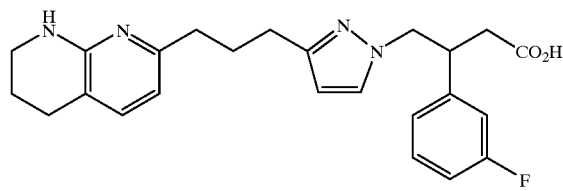

The title compound is prepared according to the general procedures described in SCHEME 9.

EXAMPLE 118

3-Pyridin-3-yl-4-{3-[3-(5,6,7,8-tetrahydro-[1,8]naphthyridin-2-yl)-propyl]-pyrazol-1-yl}-butyric acid

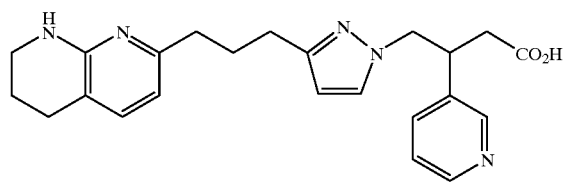

The title compound is prepared according to the general procedures described in SCHEME 9.

EXAMPLE 119

3-Benzo[1,3]dioxol-5-yl-4-{3-[3-(5,6,7,8-tetrahydro-[1,8]naphthyridin-2-yl)-propyl]-pyrazol-1-yl}-butyric acid

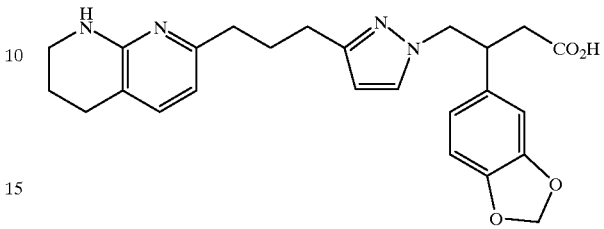

The title compound is prepared according to the general procedures described in SCHEME 9.

EXAMPLE 120

3-Phenyl-4-{4-[3-(5,6,7,8-tetrahydro-[1,8]naphthyridin-2-yl)-propyl]-imidazol-1-yl}-butyric acid

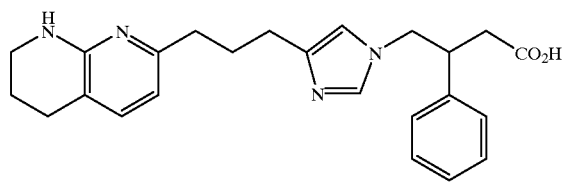

The title compound is prepared according to the general procedures described in SCHEME 9.

EXAMPLE 121

3-(2,3-Dihydro-benzofuran-6-yl)-4-{4-[3-(5,6,7,8-tetrahydro-[1,8]naphthyridin-2-yl)-propyl]-imidazol-1-yl}-butyric acid

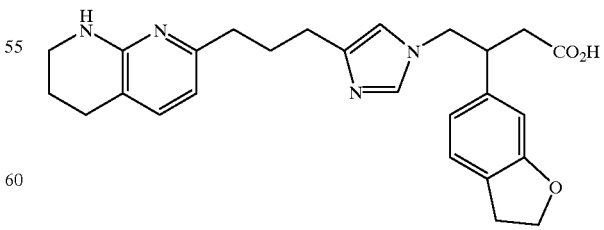

The title compound is prepared according to the general procedures described in SCHEME 9.

EXAMPLE 122

3-(3-Fluoro-phenyl)-4-{4-[3-(5,6,7,8-tetrahydro-[1,8]naphthyridin-2-yl)-propyl]-imidazol-1-yl}-butyric acid

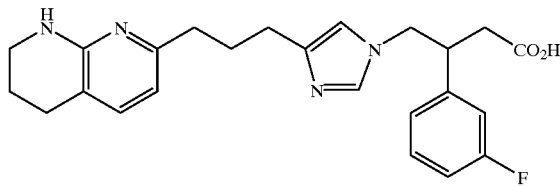

The title compound is prepared according to the general procedures described in SCHEME 9.

EXAMPLE 123

3-Pyridin-3-yl-4-{4-[3-(5,6,7,8-tetrahydro-[1,8]naphthyridin-2-yl)-propyl]-imidazol-1-yl}-butyric acid

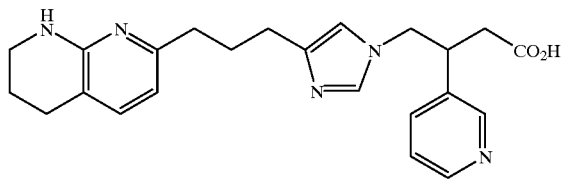

The title compound is prepared according to the general procedures described in SCHEME 9.

EXAMPLE 124

3-Benzo[1,3]dioxol-5-yl-4-{4-[3-(5,6,7,8-tetrahydro-[1,8]naphthyridin-2-yl)-propyl]-imidazol-1-yl}-butyric acid

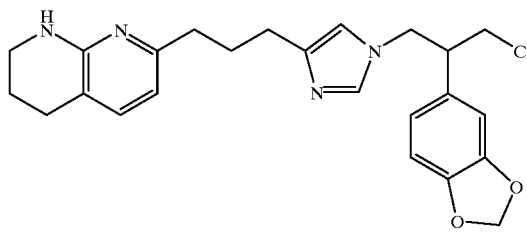

The title compound is prepared according to the general procedures described in SCHEME 9.

EXAMPLE 125

3-Phenyl-4-{3-[2-(5,6,7,8-tetrahydro-[1,8]naphthyridin-2-yl)-ethoxy]-isoxazol-5-yl}-butyric acid

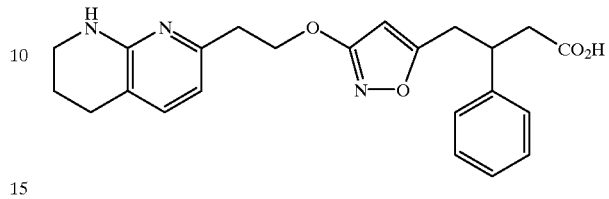

The title compound is prepared according to the general procedures described in SCHEME 10.

EXAMPLE 126

3-(2,3-Dihydro-benzofuran-6-yl)-4-{3-[2-(5,6,7,8-tetrahydro-[1,8]naphthyridin-2-yl)-ethoxy]-isoxazol-5-yl}-butyric acid

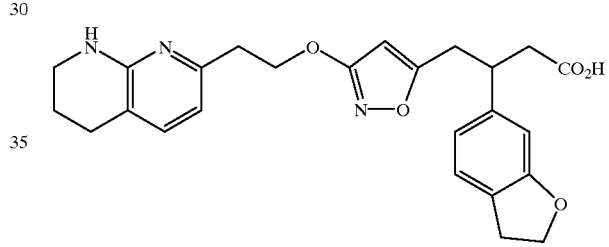

The title compound is prepared according to the general procedures described in SCHEME 10.

EXAMPLE 127

3-(3-Fluoro-phenyl)-4-{3-[2-(5,6,7,8-tetrahydro-[1,8]naphthyridin-2-yl)-ethoxy]-isoxazol-5-yl}-butyric acid

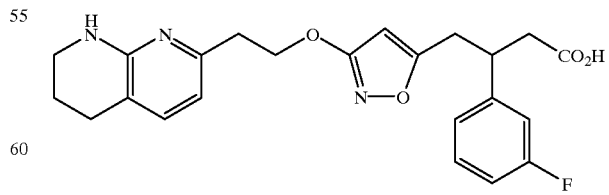

The title compound is prepared according to the general procedures described in SCHEME 10.

EXAMPLE 128

3-Pyridin-3-yl-4-{3-[2-(5,6,7,8-tetrahydro-[1,8]naphthyridin-2-yl)-ethoxy]-isoxazol-5-yl}-butyric acid

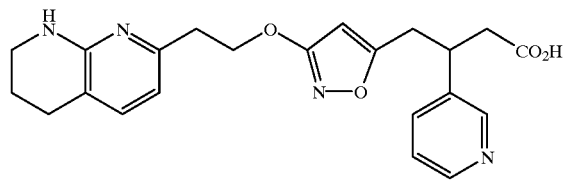

The title compound is prepared according to the general procedures described in SCHEME 10.

EXAMPLE 129

3-Benzo[1,3]dioxol-5-yl-4-{3-[2-(5,6,7,8-tetrahydro-[1,8]naphthyridin-2-yl)-ethoxy]-isoxazol-5-yl}-butyric acid

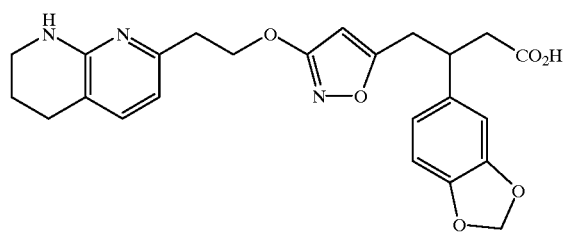

The title compound is prepared according to the general procedures described in SCHEME 10.

EXAMPLE 130

3-(3-Fluoro-phenyl)-4-{5-[2-(5,6,7,8-tetrahydro-[1,8]naphthyridin-2-yl)-ethoxy]-2H-pyrazol-3-yl}-butyric acid

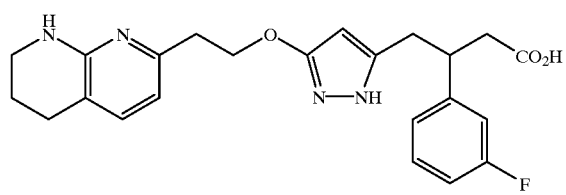

The title compound is prepared according to the general procedures described in SCHEME 10.

EXAMPLE 131

3-(2,3-Dihydro-benzofuran-6-yl)-4-{5-[2-(5,6,7,8-tetrahydro-[1,8]naphthyridin-2-yl)-ethoxy]-2H-pyrazol-3-yl}-butyric acid

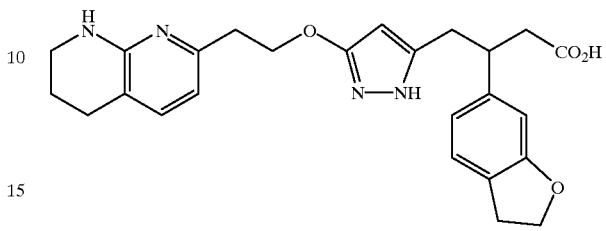

The title compound is prepared according to the general procedures described in SCHEME 10.

EXAMPLE 132

3-Phenyl-4-{5-[2-(5,6,7,8-tetrahydro-[1,8]naphthyridin-2-yl)-ethoxy]-2H-pyrazol-3-yl}-butyric acid

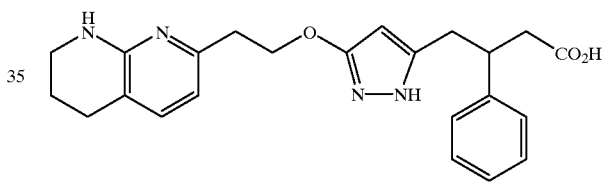

The title compound is prepared according to the general procedures described in SCHEME 10.

EXAMPLE 133

3-Pyridin-3-yl-4-{5-[2-(5,6,7,8-tetrahydro-[1,8]naphthyridin-2-yl)-ethoxy]-2H-pyrazol-3-yl}-butyric acid

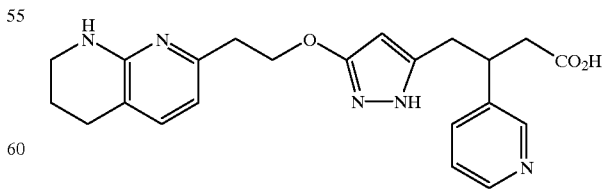

The title compound is prepared according to the general procedures described in SCHEME 10.

EXAMPLE 134

3-Benzo[1,3]dioxol-5-yl-4-{5-[2-(5,6,7,8-tetrahydro-[1,8]naphthyridin-2-yl)-ethoxy]-2H-pyrazol-3-yl}-butyric acid

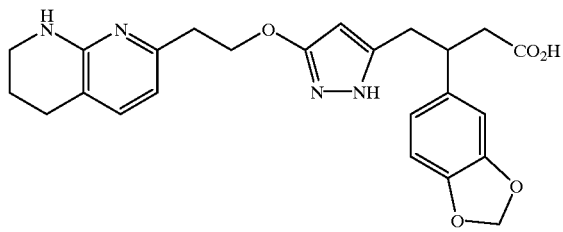

The title compound is prepared according to the general procedures described in SCHEME 10.

EXAMPLE 135

3-Phenyl-4-[4-(3-5,6,7,8-tetrahydro-[1,8]naphthyridin-2-yl-propionyl)-imidazol-1-yl]-butyric acid

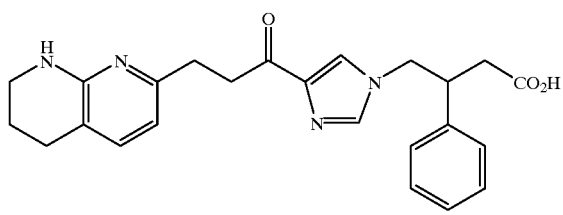

The title compound is prepared according to the general procedures described in SCHEME 11.

EXAMPLE 136

3-(2,3-Dihydro-benzofuran-6-yl)-4-[4-(3-5,6,7,8-tetrahydro-[1,8]naphthyridin-2-yl-propionyl)-imidazol-1-yl]-butyric acid

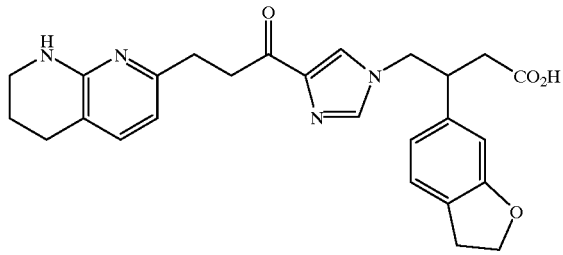

The title compound is prepared according to the general procedures described in SCHEME 11.

EXAMPLE 137

3-(3-Fluoro-phenyl)-4-[4-(3-5,6,7,8-tetrahydro-[1,8]naphthyridin-2-yl-propionyl)-imidazol-1-yl]-butyric acid

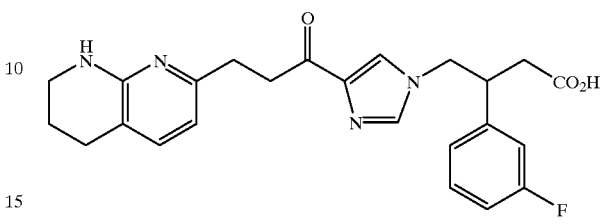

The title compound is prepared according to the general procedures described in SCHEME 11.

EXAMPLE 138

3-Pyridin-3-yl-4-[4-(3-5,6,7,8-tetrahydro-[1,8]naphthyridin-2-yl-propionyl)-imidazol-1-yl]-butyric acid

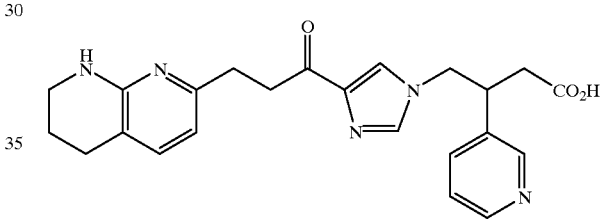

The title compound is prepared according to the general procedures described in SCHEME 11.

EXAMPLE 139

3-Benzo[1,3]dioxol-5-yl-4-[4-(3-5,6,7,8-tetrahydro-[1,8]naphthyridin-2-yl-propionyl)-imidazol-1-yl]-butyric acid

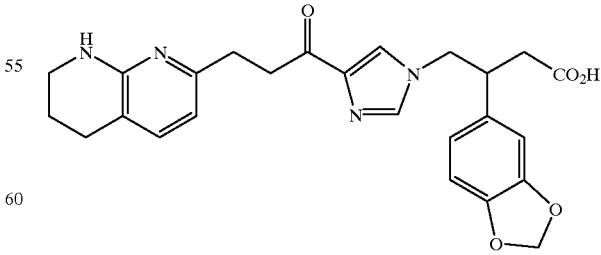

The title compound is prepared according to the general procedures described in SCHEME 11.

EXAMPLE 140

4-{4-[1-Hydroxy-3-(5,6,7,8-tetrahydro-[1,8]naphthyridin-2-yl)-propyl]-imidazol-1-yl}-3-phenyl-butyric acid

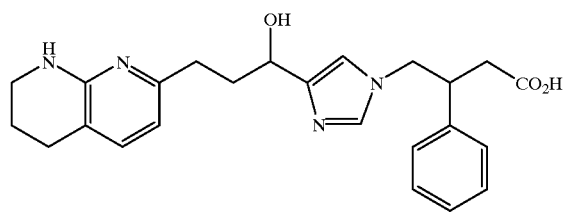

The title compound is prepared according to the general procedures described in SCHEME 11.

EXAMPLE 141

3-(2,3-Dihydro-benzofuran-6-yl)-4-{4-[1-hydroxy-3-(5,6,7,8-tetrahydro-[1,8]naphthyridin-2-yl)-propyl]-imidazol-1-yl}-butyric acid

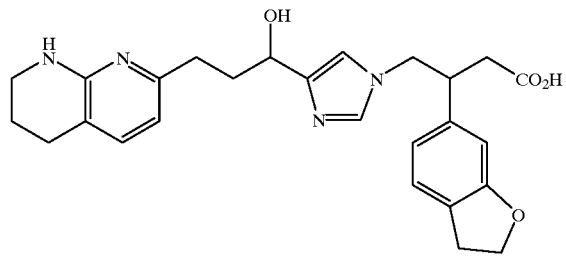

The title compound is prepared according to the general procedures described in SCHEME 11.

EXAMPLE 142

3-(3-Fluoro-phenyl)-4-{4-[1-hydroxy-3-(5,6,7,8-tetrahydro-[1,8]naphthyridin-2-yl)-propyl]-imidazol-1-yl}-butyric acid

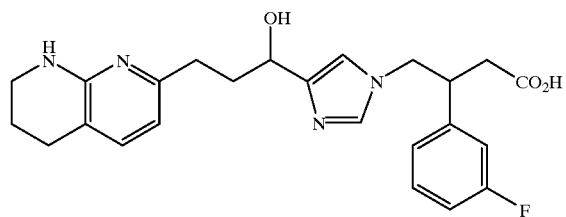

The title compound is prepared according to the general procedures described in SCHEME 11.

EXAMPLE 143

4-{4-[1-Hydroxy-3-(5,6,7,8-tetrahydro-[1,8]naphthyridin-2-yl)-propyl]-imidazol-1-yl}-3-pyridin-3-yl-butyric acid

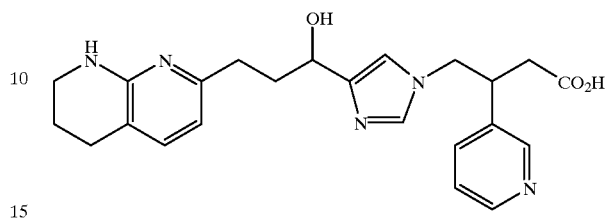

The title compound is prepared according to the general procedures described in SCHEME 11.

EXAMPLE 144

4-{4-[1-Hydroxy-3-(5,6,7,8-tetrahydro-[1,8]naphthyridin-2-yl)-propyl]-imidazol-1-yl}-3-pyridin-3-yl-butyric acid

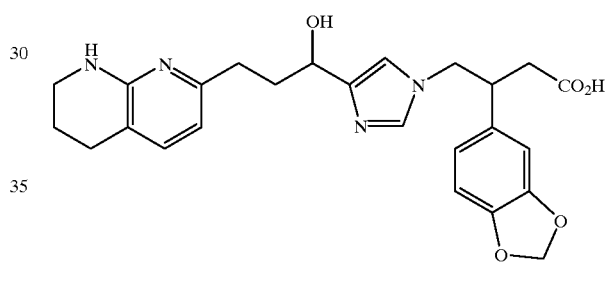

3-Benzo[1,3]dioxol-5-yl-4-{4-[1-hydroxy-3-(5,6,7,8-tetrahydro-[1,8]naphthyridin-2-yl)-propyl]-imidazol-1-yl}-butyric acid The title compound is prepared according to the general procedures described in SCHEME 11.

EXAMPLE 145

4-{4-[1-Hydroxy-3-(5,6,7,8-tetrahydro-[1,8]naphthyridin-2-yl)-propyl]-imidazol-1-yl}-3-pyridin-3-yl-butyric acid

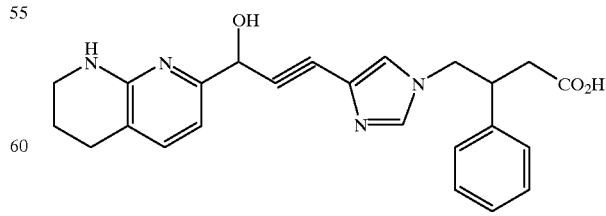

The title compound is prepared according to the general procedures described in SCHEME 12.

EXAMPLE 146

3-(2,3-Dihydro-benzofuran-6-yl)-4-{4-[3-hydroxy-3-(5,6,7,8-tetrahydro-[1,8]naphthyridin-2-yl)-prop-1-ynyl]-imidazol-1-yl}-butyric acid

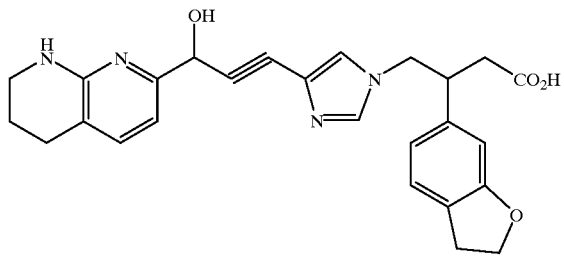

The title compound is prepared according to the general procedures described in SCHEME 12.

EXAMPLE 147

3-(3-Fluoro-phenyl)-4-{4-[3-hydroxy-3-(5,6,7,8-tetrahydro-[1,8]naphthyridin-2-yl)-prop-1-ynyl]-imidazol-1-yl}-butyric acid

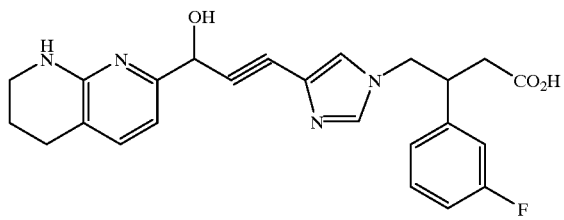

The title compound is prepared according to the general procedures described in SCHEME 12.

EXAMPLE 148

4-{4-[3-Hydroxy-3-(5,6,7,8-tetrahydro-[1,8]naphthyridin-2-yl)-prop-1-ynyl]-imidazol-1-yl}-3-pyridin-3-yl-butyric acid

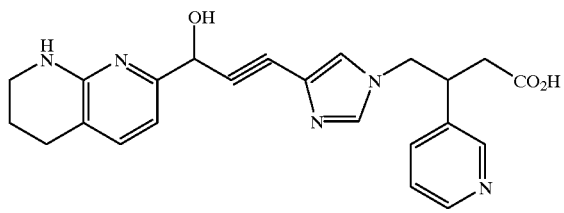

The title compound is prepared according to the general procedures described in SCHEME 12.

EXAMPLE 149

3-Benzo[1,3]dioxol-5-yl-4-{4-[3-hydroxy-3-(5,6,7,8-tetrahydro-[1,8]naphthyridin-2-yl)-prop-1-ynyl]-imidazol-1-yl}-butyric acid

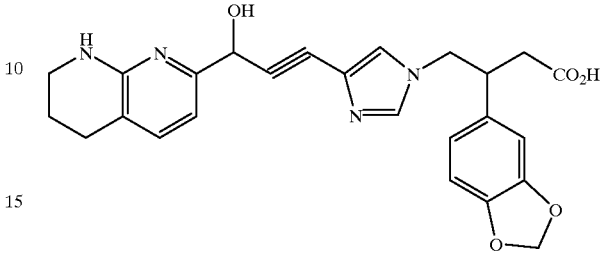

The title compound is prepared according to the general procedures described in SCHEME 12.

EXAMPLE 150

4-{4-[3-Hydroxy-3-(5,6,7,8-tetrahydro-[1,8]naphthyridin-2-yl)-prop-1-ynyl]-pyrazol-1-yl}-3-phenyl-butyric acid

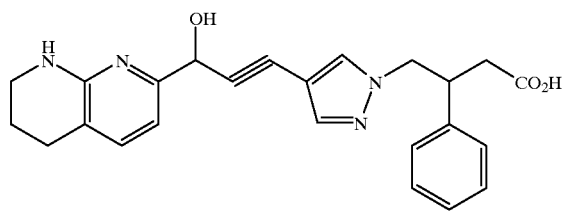

The title compound is prepared according to the general procedures described in SCHEME 12.

EXAMPLE 151

3-(2,3-Dihydro-benzofuran-6-yl)-4-{4-[3-hydroxy-3-(5,6,7,8-tetrahydro-[1,8]naphthyridin-2-yl)-prop-1-ynyl]-pyrazol-1-yl}-butyric acid

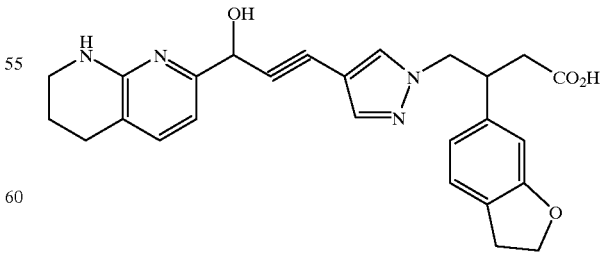

The title compound is prepared according to the general procedures described in SCHEME 12.

EXAMPLE 152

3-(3-Fluoro-phenyl)-4-{4-[3-hydroxy-3-(5,6,7,8-tetrahydro-[1,8]naphthyridin-2-yl)-prop-1-ynyl]-pyrazol-1-yl}-butyric acid

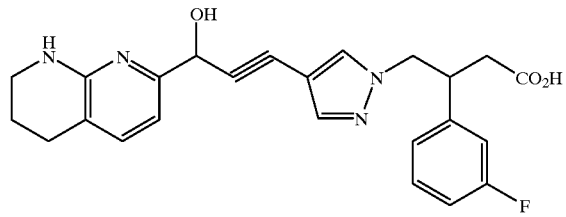

The title compound is prepared according to the general procedures described in SCHEME 12.

EXAMPLE 153

4-{4-[3-Hydroxy-3-(5,6,7,8-tetrahydro-[1,8]naphthyridin-2-yl)-prop-1-ynyl]-pyrazol-1-yl}-3-pyridin-3-yl-butyric acid

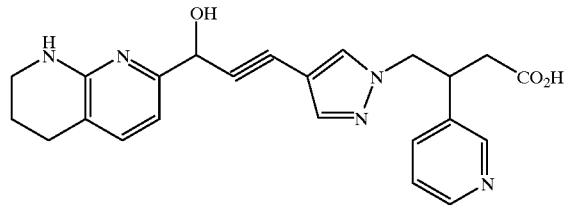

The title compound is prepared according to the general procedures described in SCHEME 12.

EXAMPLE 154

3-Benzo[1,3]dioxol-5-yl-4-{4-[3-hydroxy-3-(5,6,7,8-tetrahydro-[1,8]naphthyridin-2-yl)-prop-1-ynyl]-pyrazol-1-yl}-butyric acid

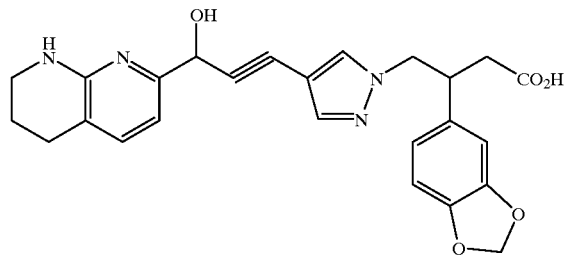

The title compound is prepared according to the general procedures described in SCHEME 12.

EXAMPLE 155

4-{4-[3-Hydroxy-3-(5,6,7,8-tetrahydro-[1,8]naphthyridin-2-yl)-propenyl]-pyrazol-1-yl}-3-phenyl-butyric acid

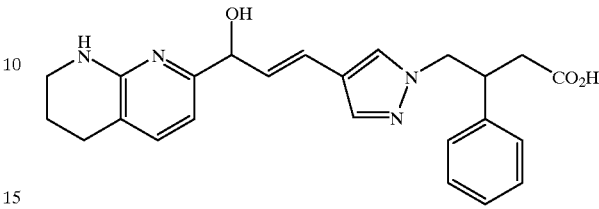

The title compound is prepared according to the general procedures described in SCHEME 12.

EXAMPLE 156

3-(2,3-Dihydro-benzofuran-6-yl)-4-{4-[3-hydroxy-3-(5,6,7,8-tetrahydro-[1,8]naphthyridin-2-yl)-propenyl]-pyrazol-1-yl}-butyric acid

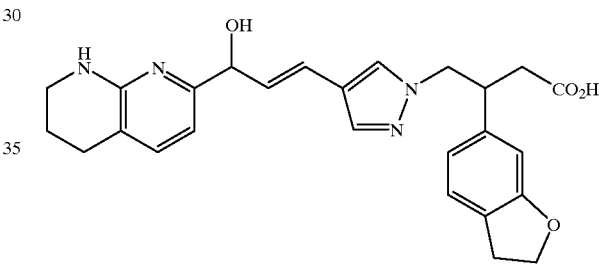

The title compound is prepared according to the general procedures described in SCHEME 12.

EXAMPLE 157

3-(3-Fluoro-phenyl)-4-{4-[3-hydroxy-3-(5,6,7,8-tetrahydro-[1,8]naphthyridin-2-yl)-propenyl]-pyrazol-1-yl}-butyric acid

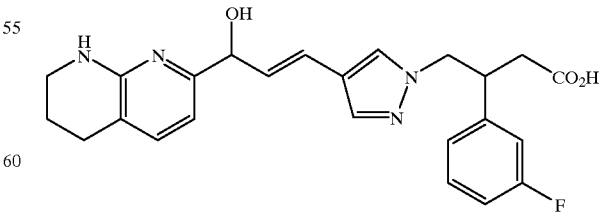

The title compound is prepared according to the general procedures described in SCHEME 12.

EXAMPLE 158

4-{4-[3-Hydroxy-3-(5,6,7,8-tetrahydro-[1,8]naphthyridin-2-yl)-propenyl]-pyrazol-1-yl}-3-pyridin-3-yl-butyric acid

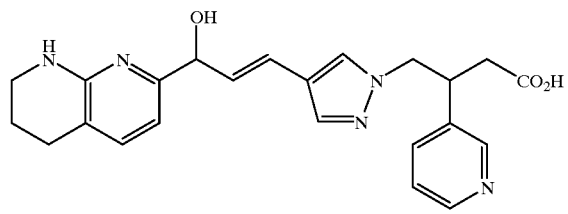

The title compound is prepared according to the general procedures described in SCHEME 12.

EXAMPLE 159

3-Benzo[1,3]dioxol-5-yl-4-{4-[3-hydroxy-3-(5,6,7,8-tetrahydro-[1,8]naphthyridin-2-yl)-propenyl]-pyrazol-1-yl}-butyric acid

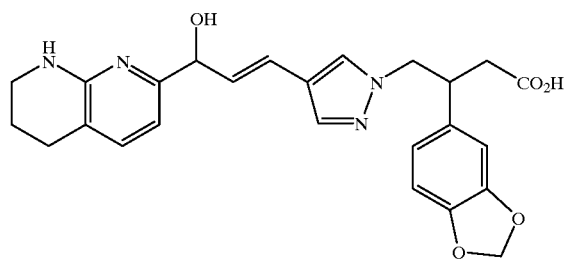

The title compound is prepared according to the general procedures described in SCHEME 12.

EXAMPLE 160

3-Benzo[1,3]dioxol-5-yl-4-{4-[3-hydroxy-3-(5,6,7,8-tetrahydro-[1,8]naphthyridin-2-yl)-propenyl]-pyrazol-1-yl}-butyric acid

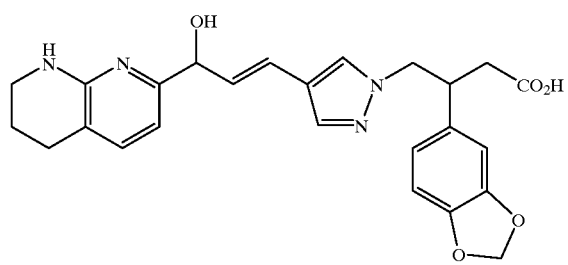

The title compound is prepared according to the general procedures described in SCHEME 12.

EXAMPLE 161

4-{4-[3-Hydroxy-3-(5,6,7,8-tetrahydro-[1,8]naphthyridin-2-yl)-propenyl]-imidazol-1-yl}-3-phenyl-butyric acid

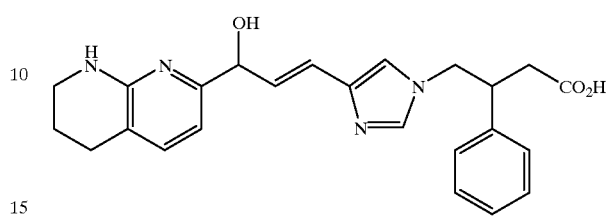

The title compound is prepared according to the general procedures described in SCHEME 12.

EXAMPLE 162

3-(2,3-Dihydro-benzofuran-6-yl)-4-{4-[3-hydroxy-3-(5,6,7,8-tetrahydro-[1,8]naphthyridin-2-yl)-propenyl]-imidazol-1-yl}-butyric acid

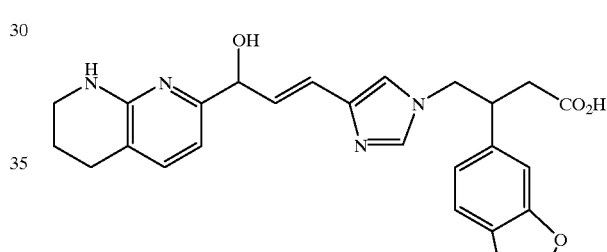

The title compound is prepared according to the general procedures described in SCHEME 12.

EXAMPLE 163

3-(3-Fluoro-phenyl)-4-{4-[3-hydroxy-3-(5,6,7,8-tetrahydro-[1,8]naphthyridin-2-yl)-propenyl]-imidazol-1-yl}-butyric acid

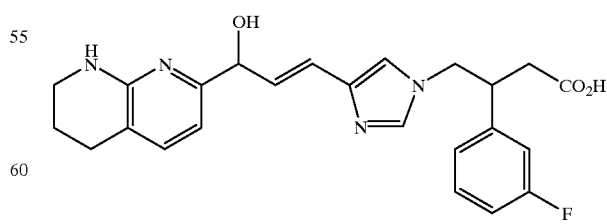

The title compound is prepared according to the general procedures described in SCHEME 12.

EXAMPLE 164

4-{4-[3-Hydroxy-3-(5,6,7,8-tetrahydro-[1,8]naphthyridin-2-yl)-propenyl]-imidazol-1-yl}-3-pyridin-3-yl-butyric acid

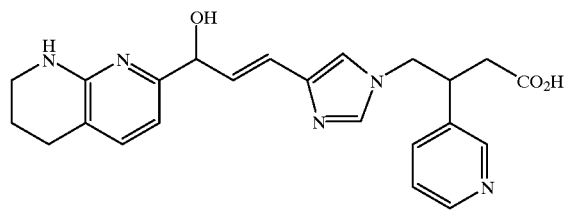

The title compound is prepared according to the general procedures described in SCHEME 12.

EXAMPLE 165

3-Benzo[1,3]dioxol-5-yl-4-{4-[3-hydroxy-3-(5,6,7,8-tetrahydro-[1,8]naphthyridin-2-yl)-propenyl]-imidazol-1-yl}-butyric acid

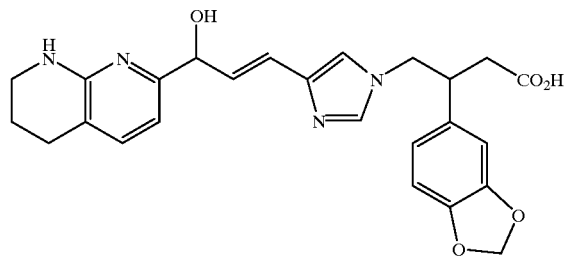

The title compound is prepared according to the general procedures described in SCHEME 12.

EXAMPLE 166

4-{4-[3-Hydroxy-3-(5,6,7,8-tetrahydro-[1,8]naphthyridin-2-yl)-propyl]-imidazol-1-yl}-3-phenyl-butyric acid

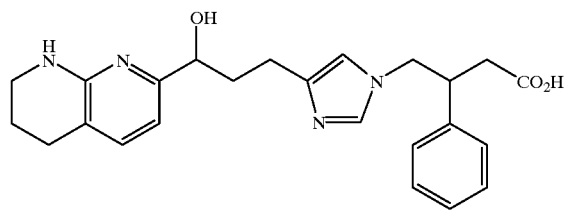

The title compound is prepared according to the general procedures described in SCHEME 12.

EXAMPLE 167

3-(2,3-Dihydro-benzofuran-6-yl)-4-{4-[3-hydroxy-3-(5,6,7,8-tetrahydro-[1,8]naphthyridin-2-yl)-propyl]-imidazol-1-yl}-butyric acid

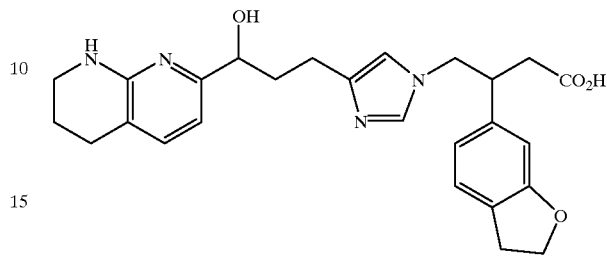

The title compound is prepared according to the general procedures described in SCHEME 12.

EXAMPLE 168

3-(3-Fluoro-phenyl)-4-{4-[3-hydroxy-3-(5,6,7,8-tetrahydro-[1,8]naphthyridin-2-yl)-propyl]-imidazol-1-yl}-butyric acid

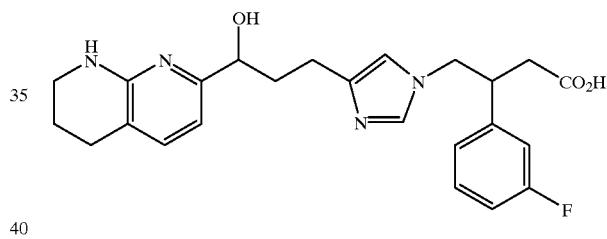

The title compound is prepared according to the general procedures described in SCHEME 12.

EXAMPLE 169

4-{4-[3-Hydroxy-3-(5,6,7,8-tetrahydro-[1,8]naphthyridin-2-yl)-propyl]-imidazol-1-yl}-3-pyridin-3-yl-butyric acid

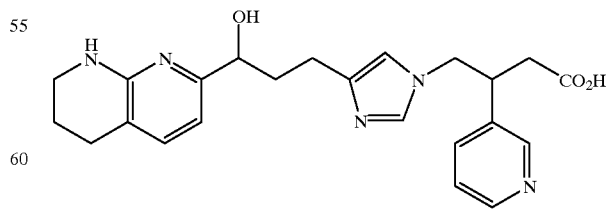

The title compound is prepared according to the general procedures described in SCHEME 12.

EXAMPLE 170

3-Benzo[1,3]dioxol-5-yl-4-{4-[3-hydroxy-3-(5,6,7,
8-tetrahydro-[1,8]naphthyridin-2-yl)-propyl]-
imidazol-1-yl}-butyric acid

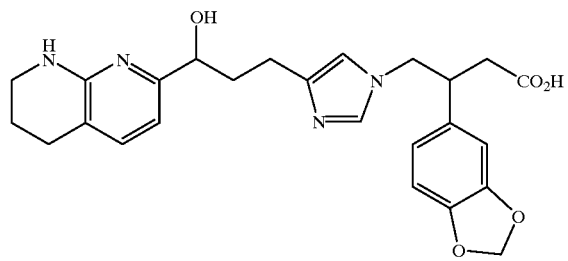

The title compound is prepared according to the general procedures described in SCHEME 12.

EXAMPLE 171

4-{4-[3-Hydroxy-3-(5,6,7,8-tetrahydro-[1,8]
naphthyridin-2-yl)-propyl]-pyrazol-1-yl}-3-phenyl-
butyric acid

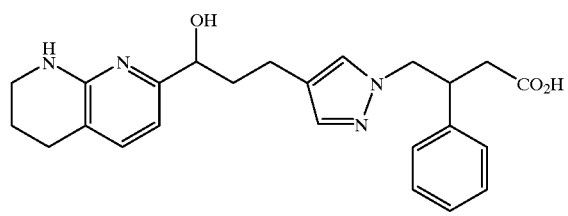

The title compound is prepared according to the general procedures described in SCHEME 12.

EXAMPLE 172

3-(2,3-Dihydro-benzofuran-6-yl)-4-{4-[3-hydroxy-3-
(5,6,7,8-tetrahydro-[1,8]naphthyridin-2-yl)-propyl]-
pyrazol-1-yl}-butyric acid

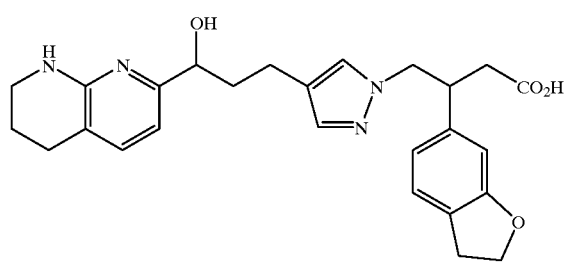

The title compound is prepared according to the general procedures described in SCHEME 12.

EXAMPLE 173

3-(3-Fluoro-phenyl)-4-{4-[3-hydroxy-3-(5,6,7,8-
tetrahydro-[1,8]naphthyridin-2-yl)-propyl]-pyrazol-
1-yl}-butyric acid

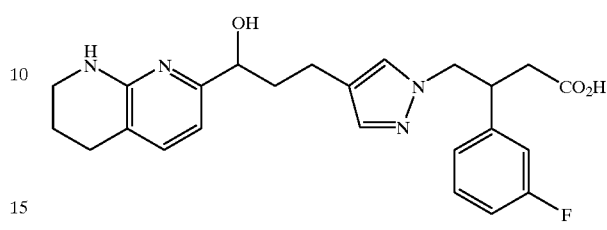

The title compound is prepared according to the general procedures described in SCHEME 12.

EXAMPLE 174

3-Benzo[1,3]dioxol-5-yl-4-{4-[3-hydroxy-3-(5,6,7,
8-tetrahydro-[1,8]naphthyridin-2-yl)-propyl]-
pyrazol-1-yl}-butyric acid

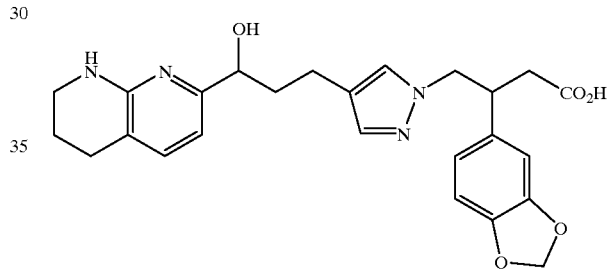

The title compound is prepared according to the general procedures described in SCHEME 12.

EXAMPLE 175

4-{4-[3-Hydroxy-3-(5,6,7,8-tetrahydro-[1,8]
naphthyridin-2-yl)-propyl]-pyrazol-1-yl}-3-pyridin-
3-yl-butyric acid

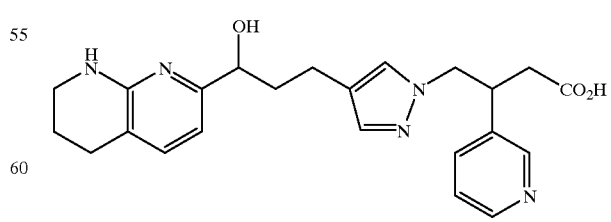

The title compound is prepared according to the general procedures described in SCHEME 12.

EXAMPLE 176

3-Phenyl-4-{4-[3-(5,6,7,8-tetrahydro-[1,8]
naphthyridin-2-yl)-propenyl]-imidazol-1-yl}-butyric
acid

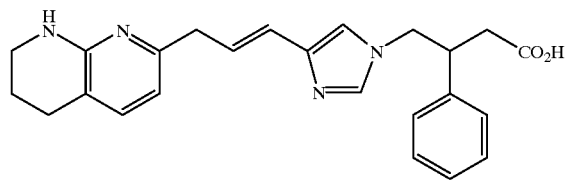

The title compound is prepared according to the general procedures described in SCHEME 12.

EXAMPLE 177

3-(2,3-Dihydro-benzofuran-6-yl)-4-{4-[3-(5,6,7,8-
tetrahydro-[1,8]naphthyridin-2-yl)-propenyl]-
imidazol-1-yl}-butyric acid

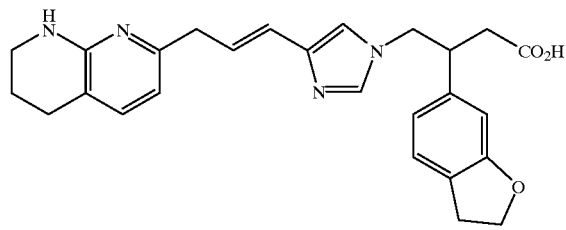

The title compound is prepared according to the general procedures described in SCHEME 12.

EXAMPLE 178

3-(3-Fluoro-phenyl)-4-{4-[3-(5,6,7,8-tetrahydro-[1,
8]naphthyridin-2-yl)-propenyl]-imidazol-1-yl}-
butyric acid

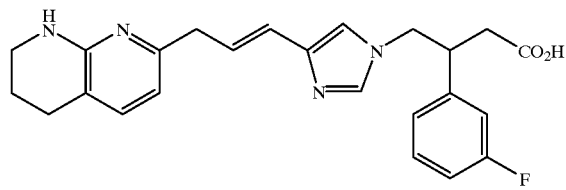

The title compound is prepared according to the general procedures described in SCHEME 12.

EXAMPLE 179

3-Pyridin-3-yl-4-{4-[3-(5,6,7,8-tetrahydro-[1,8]
naphthyridin-2-yl)-propenyl]-imidazol-1-yl}-butyric
acid

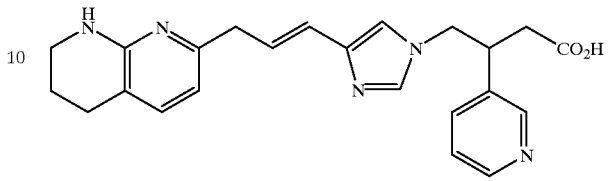

The title compound is prepared according to the general procedures described in SCHEME 12.

EXAMPLE 180

3-Benzo[1,3]dioxol-5-yl-4-{4-[3-(5,6,7,8-tetrahydro-
[1,8]naphthyridin-2-yl)-propenyl]-imidazol-1-yl}-
butyric acid

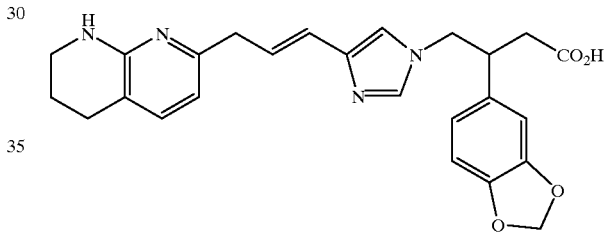

The title compound is prepared according to the general procedures described in SCHEME 12.

EXAMPLE 181

3-Benzo[1,3]dioxol-5-yl-4-{4-[3-(5,6,7,8-tetrahydro-
[1,8]naphthyridin-2-yl)-propenyl]-pyrazol-1-yl}-
butyric acid

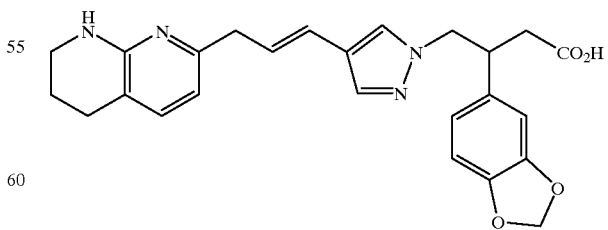

The title compound is prepared according to the general procedures described in SCHEME 12.

EXAMPLE 182

3-Pyridin-3-yl-4-{4-[3-(5,6,7,8-tetrahydro-[1,8] naphthyridin-2-yl)-propenyl]-pyrazol-1-yl}-butyric acid

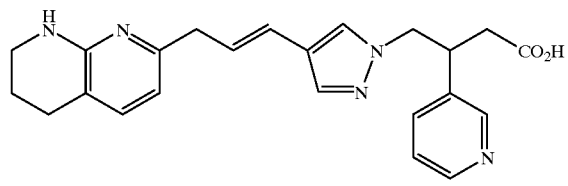

The title compound is prepared according to the general procedures described in SCHEME 12.

EXAMPLE 183

3-(3-Fluoro-phenyl)-4-{4-[3-(5,6,7,8-tetrahydro-[1, 8]naphthyridin-2-yl)-propenyl]-pyrazol-1-yl}-butyric acid

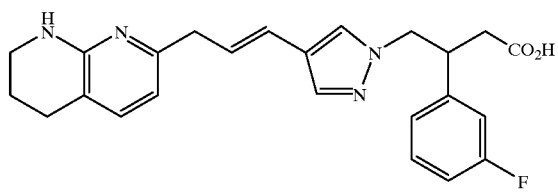

The title compound is prepared according to the general procedures described in SCHEME 12.

EXAMPLE 184

3-(2,3-Dihydro-benzofuran-6-yl)-4-{4-[3-(5,6,7,8-tetrahydro-[1,8]naphthyridin-2-yl)-propenyl]-pyrazol-1-yl}-butyric acid

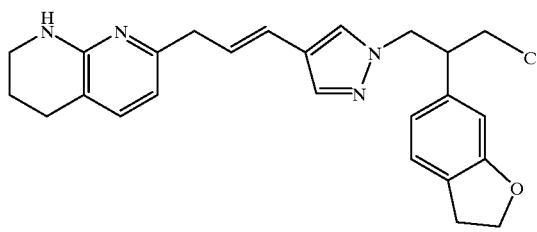

The title compound is prepared according to the general procedures described in SCHEME 12.

EXAMPLE 185

3-Phenyl-4-{4-[3-(5,6,7,8-tetrahydro-[1,8] naphthyridin-2-yl)-propenyl]-pyrazol-1-yl}-butyric acid

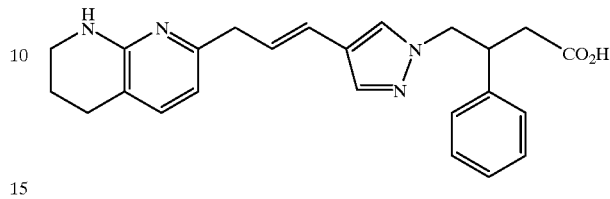

The title compound is prepared according to the general procedures described in SCHEME 12.

EXAMPLE 186

3-Benzo[1,3]dioxol-5-yl-4-{3-[4-(1H-imidazol-2-ylamino)-butyl]-[1,2,4]oxadiazol-5-yl}-butyric acid

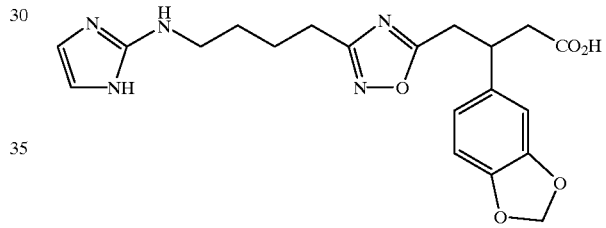

The title compound is prepared following the general Scheme 3 and using the intermediate and the methodology shown in Example 16.

EXAMPLE 187

3-(3-Fluoro-phenyl)-4-{3-[4-(1H-imidazol-2-ylamino)-butyl]-[1,2,4]oxadiazol-5-yl}-butyric acid

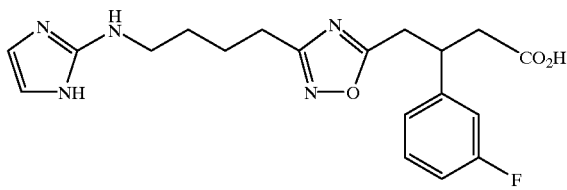

The title compound is prepared following the general Scheme 3 and using the intermediate and the methodology shown in Example 26.

EXAMPLE 188

3-Benzo[1,3]dioxol-5-yl-4-{3-[4-(2H-pyrazol-3-ylamino)-butyl]-[1,2,4]oxadiazol-5-yl}-butyric acid

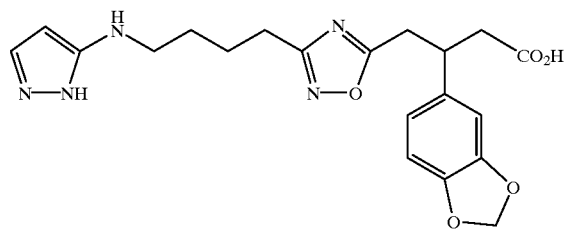

The title compound is prepared following the general Scheme 3 and using the intermediate and the methodology shown in Example 16.

EXAMPLE 189

3-(3-Fluoro-phenyl)-4-{3-[4-(2H-pyrazol-3-ylamino)-butyl]-[1,2,4]oxadiazol-5-yl}-butyric acid

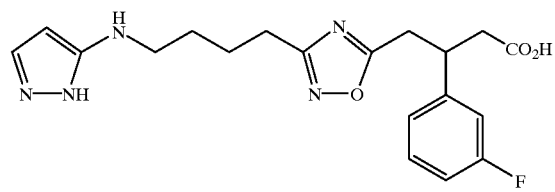

The title compound is prepared following the general Scheme 3 and using the intermediate and the methodology shown in Example 26.

EXAMPLE 190

3-Benzo[1,3]dioxol-5-yl-4-{3-[4-(3H-imidazol-4-ylamino)-butyl]-[1,2,4]oxadiazol-5-yl}-butyric acid

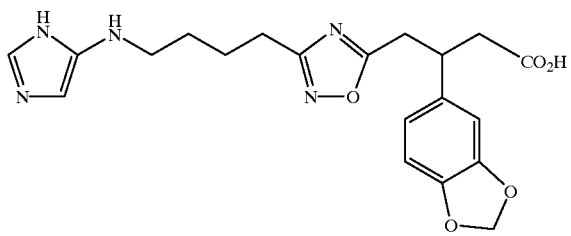

The title compound is prepared following the general Scheme 3 and using the intermediate and the methodology shown in Example 16.

EXAMPLE 191

3-(3-Fluoro-phenyl)-4-{3-[4-(3H-imidazol-4-ylamino)-butyl]-[1,2,4]oxadiazol-5-yl}-butyric acid

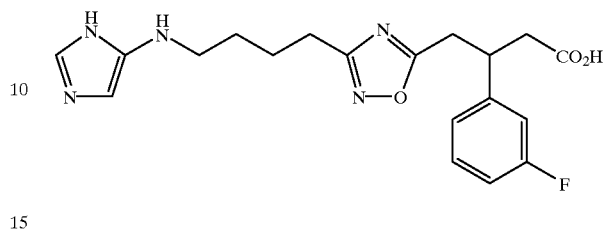

The title compound is prepared following the general Scheme 3 and using the intermediate and the methodology shown in Example 26.

EXAMPLE 192

3-Benzo[1,3]dioxol-5-yl-4-{3-[3-(6-methylamino-pyridin-2-yl)-propyl]-[1,2,4]oxadiazol-5-yl}-butyric acid

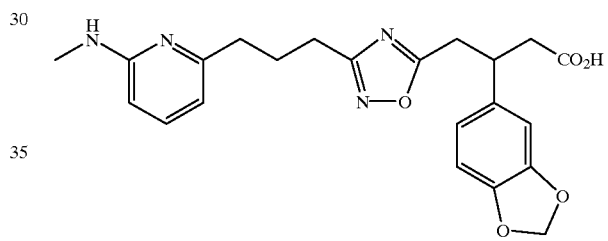

The title compound is prepared following the general Scheme 4 and using the intermediate and the methodology shown in Example 16.

EXAMPLE 193

3-(3-Fluoro-phenyl)-4-{3-[3-(6-methylamino-pyridin-2-yl)-propyl]-[1,2,4]oxadiazol-5-yl}-butyric acid

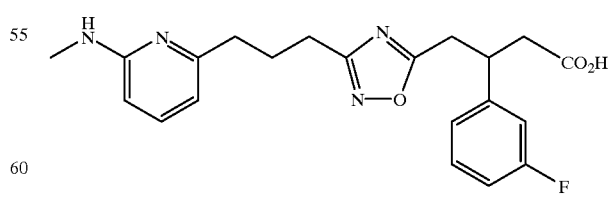

The title compound is prepared following the general Scheme 4 and using the intermediate and the methodology shown in Example 26.

EXAMPLE 194

4-{3-[3-(6-Ethylamino-pyridin-2-yl)-propyl]-[1,2,4]oxadiazol-5-yl}-3-(3-fluoro-phenyl)-butyric acid

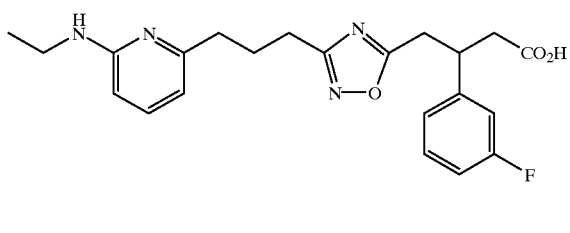

The title compound is prepared following the general Scheme 4 and using the intermediate and the methodology shown in Example 26.

EXAMPLE 195

3-(3-Fluoro-phenyl)-4-(3-{3-[6-(2-methoxy-ethylamino)-pyridin-2-yl]-propyl}-[1,2,4]oxadiazol-5-yl)-butyric acid

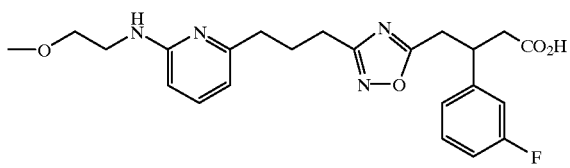

The title compound is prepared following the general Scheme 4 and using the intermediate and the methodology shown in Example 26.

EXAMPLE 196

3-(3-Fluoro-phenyl)-4-(3-{3-[6-(3-methoxy-propylamino)-pyridin-2-yl]-propyl}-[1,2,4]oxadiazol-5-yl)-butyric acid

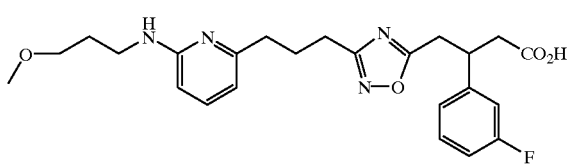

The title compound is prepared following the general Scheme 4 and using the intermediate and the methodology shown in Example 26.

EXAMPLE 197

3-(3-Fluoro-phenyl)-4-(3-{3-[6-(2,2,2-trifluoro-ethylamino)-pyridin-2-yl]-propyl}-[1,2,4]oxadiazol-5-yl)-butyric acid

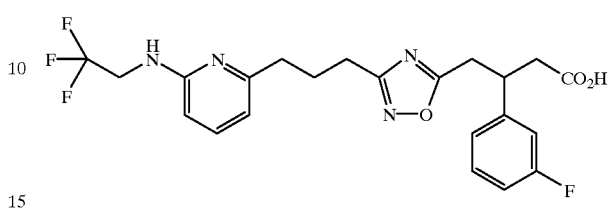

The title compound is prepared following the general Scheme 4 and using the intermediate and the methodology shown in Example 26.

EXAMPLE 198

3-(3-Fluoro-phenyl)-4-{3-[3-(5-oxo-5,6,7,8-tetrahydro-[1,8]naphthyridin-2-yl)-propyl]-[1,2,4]oxadiazol-5-yl}-butyric acid

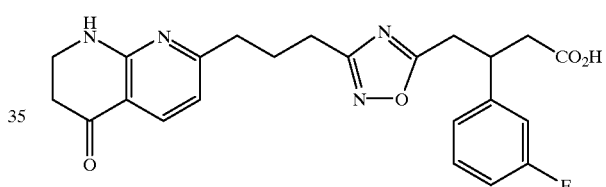

The title compound is prepared following the general Scheme 4 and using the intermediate and the methodology shown in Example 26.

EXAMPLE 199

4-{3-[3-(5,5-Dimethyl-5,6,7,8-tetrahydro-[1,8]naphthyridin-2-yl)-propyl]-[1,2,4]oxadiazol-5-yl}-3-(3-fluoro-phenyl)-butyric acid

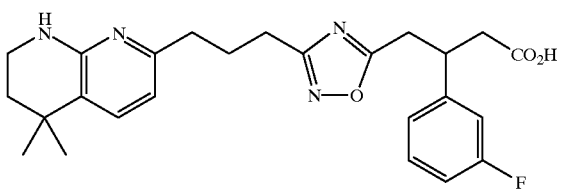

The title compound is prepared following the general Scheme 4 and using the intermediate and the methodology shown in Example 26.

EXAMPLE 200

4-{3-[3-(5,5-Difluoro-5,6,7,8-tetrahydro-[1,8]naphthyridin-2-yl)-propyl]-[1,2,4]oxadiazol-5-yl}-3-(3-fluoro-phenyl)-butyric acid

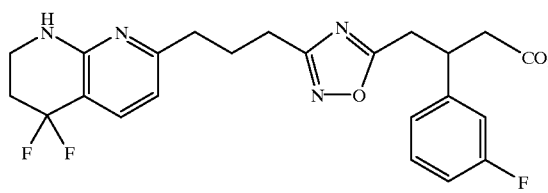

The title compound is prepared following the general Scheme 4 and using the intermediate and the methodology shown in Example 26.

EXAMPLE 201

3-Pyridin-3-yl-4-{5-[3-(5,6,7,8-tetrahydro-[1,8]naphthyridin-2-yl)-propyl]-4H-[1,2,4]triazol-3-yl}-butyric acid

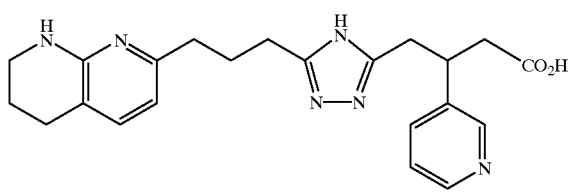

The title compound is prepared according to the general procedures described in SCHEME 5.

EXAMPLE 202

3-(2,3-Dihydro-benzofuran-6-yl)-4-{5-[3-(5,6,7,8-tetrahydro-[1,8]naphthyridin-2-yl)-propyl]-4H-[1,2,4]triazol-3-yl}-butyric acid

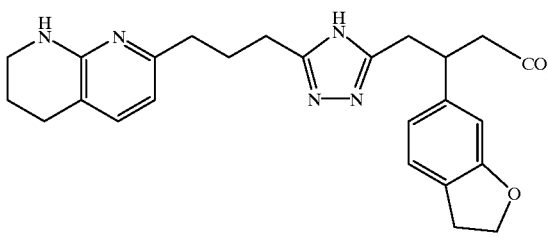

The title compound is prepared according to the general procedures described in SCHEME 5.

EXAMPLE 203

3-(3-Fluoro-phenyl)-4-{5-[3-(5,6,7,8-tetrahydro-[1,8]naphthyridin-2-yl)-propyl]-4H-[1,2,4]triazol-3-yl}-butyric acid

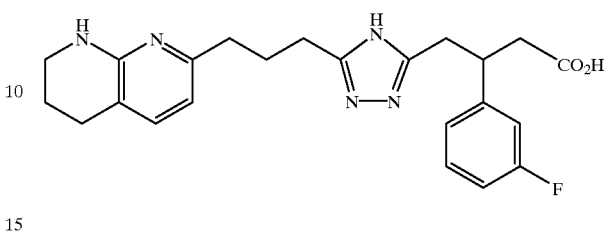

The title compound is prepared according to the general procedures described in SCHEME 5.

EXAMPLE 204

3-Benzo[1,3]dioxol-5-yl-4-{5-[3-(5,6,7,8-tetrahydro-[1,8]naphthyridin-2-yl)-propyl]-4H-[1,2,4]triazol-3-yl}-butyric acid

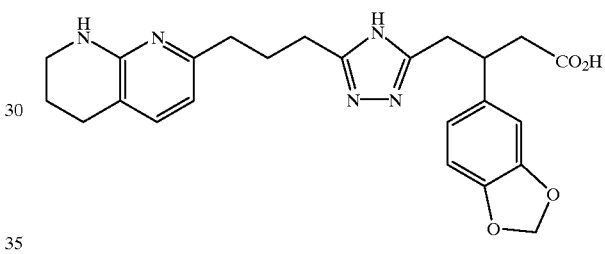

The title compound is prepared according to the general procedures described in SCHEME 5.

EXAMPLE 205

3-Benzo[1,3]dioxol-5-yl-4-{3-[3-(3,4-dihydro-2H-pyrido[3,2-b][1,4]oxazin-6-yl)-propyl]-[1,2,4]oxadiazol-5-yl}-butyric acid

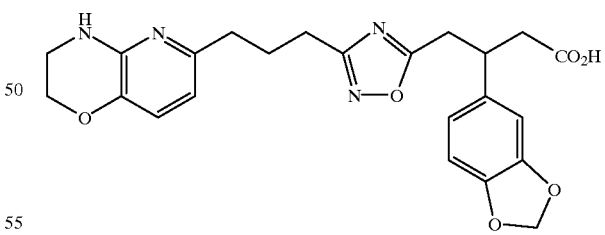

The title compound is prepared following the general Scheme 4 and using the intermediate and the methodology shown in Example 26.

The activity of the compounds of the present invention was tested in the following assays. Compounds of the present invention antagonize the $\alpha_v\beta_3$ integrin with an $IC_{50}$ between 0.1 nM to 100 µM in the 293-cell assay. Similarly these compounds antagonize the $\alpha_v\beta_5$ integrin with an $IC_{50}$ of <50 µM in the cell adhesion assay.

Vitronectin Adhesion Assay

Materials

Human vitronectin receptors $\alpha_v\beta_3$ and $\alpha_v\beta_5$ were purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Sigma (St. Louis, Mo.). Nalge Nunc-Immuno microtiter plates were obtained from Nalge Company (Rochester, N.Y.).

Methods

Solid Phase Receptor Assays

This assay was essentially the same as previously reported [Niiya et al., *Blood*, 70:475–483 (1987)]. The purified human vitronectin receptors $\alpha_v\beta_3$ and $\alpha_v\beta_5$ were diluted from stock solutions to 1.0 µg/mL in Tris-buffered saline containing 1.0 mM $Ca^{++}$, $Mg^{++}$, and $Mn^{++}$, pH 7.4 ($TBS^{+++}$). The diluted receptors were immediately transferred to Nalge Nunc-Immuno microtiter plates at 100 µL/well (100 ng receptor/well). The plates were sealed and incubated overnight at 4° C. to allow the receptors to bind to the wells. All remaining steps were at room temperature. The assay plates were emptied and 200 µL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in $TBS^{+++}$/BSA and 125 µL was added to each well. After 45 minutes, the plates were washed and incubated with $OPD/H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Pat. No. 5,602,155 Example 1] which is a potent $\alpha_v\beta_3$ antagonist ($IC_{50}$ in the range 3–10 nM) was included on each plate as a positive control.

Purified IIb/IIIa Receptor Assay

Materials

Human fibrinogen receptor (IIb/IIIa) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, IL) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Sigma (St. Louis, Mo.). Nalge Nunc-Immuno microtiter plates were obtained from (Rochester, N.Y.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor (IIb/IIIa) was diluted from stock solutions to 1.0 µg/mL in Tris-buffered saline containing 1.0 mM $Ca^{++}$, $Mg^{++}$, and $Mn^{++}$, pH 7.4 ($TBS^{+++}$). The diluted receptor was immediately transferred to Nalge Nunc-Immuno microtiter plates at 100 µL/well (100 ng receptor/well). The plates were sealed and incubated overnight at 4° C. to allow the receptors to bind to the wells. All remaining steps were at room temperature. The assay plates were emptied and 200 µL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in $TBS^{+++}$/BSA and 125 µL were added to each well. After 45 minutes, the plates were washed and incubated with $ODD/H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCELJ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Pat. No. 5,602,155 Example 1] which is a potent $\alpha_v\beta_3$ antagonist ($IC_{50}$ in the range 3–10 nM) was included on each plate as a positive control.

Human Platelet Rich Plasma Assays

Healthy aspirin free donors were selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200×g to sediment non-platelet cells. Platelet rich plasma was removed to a polyethylene tube and stored at room temperature until used. Platelet poor plasma was obtained from a second centrifugation of the remaining blood at 2000×g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and the concentration of half-maximal inhibition ($IC_{50}$) was calculated graphically from the dose response curve for those compounds which exhibited 50% or greater inhibition at the highest concentration tested; otherwise, the $IC_{50}$ is reported as being greater than the highest concentration tested.

Cell Assays for Potency and Selectivity

While the $\beta_3$ subunit of $\alpha_v\beta_3$ is only known to complex with $\alpha_V$ or $\alpha_{IIb}$, the $\alpha_V$ subunit complexes with multiple β subunits. The three $\alpha_V$ integrins most homologous with $\alpha_v\beta_3$ are $\alpha_v\beta_1$, $\alpha_v\beta_5$ and $\alpha_v\beta_6$, with 43%, 56% and 47% amino acid identity in the β subunits, respectively. To evaluate the selectivity of compounds between the integrins $\alpha_v\beta_3$ and $\alpha_v\beta_6$, cell-based assays were established using the 293 human embryonic kidney cell line. 293 cells express $\alpha_v\beta_1$, but little to no detectable $\alpha_v\beta_3$ or $\alpha_v\beta_6$. cDNAs for $\beta_3$ and $\beta_6$ were transfected separately into 293 cells to generate 293-$\beta_3$ and 293-$\beta_6$ cells, respectively. High surface expression of $\alpha_v\beta_3$ and $\alpha_v\beta_6$ was confirmed by flow cytometry. Conditions were established for each cell line in which cell adhesion to immobilized human vitronectin was mediated by the appropriate integrin, as determined by a panel of integrin-specific, neutralizing monoclonal antibodies. Briefly, cells were incubated with inhibitor in the presence of 200 uM $Mn^{2+}$, allowed to adhere to immobilized vitronectin, washed, and adherent cells are detected endogenous alkaline phosphatase and para-nitrophenyl phosphate. An 8-point dose-response curve using either 10-fold or 3-fold dilutions of compound was evaluated by fitting a four-parameter logistic, nonlinear model (using SAS).

To evaluate compound potency for membrane-bound $\alpha_v\beta_6$ an additional cell-based adhesion assay was established using the HT-29 human colon carcinoma cell line. High surface expression of $\alpha_v\beta_6$ on HT-29 cells was confirmed by flow cytometry. Conditions were established in which cell adhesion to immobilized human latency associated peptide (LAP) was mediated by the $\alpha_v\beta_6$, as determined by a panel of integrin-specific, neutralizing monoclonal antibodies. Briefly, cells were incubated with inhibitor in the presence of 200 uM $Mn^{2+}$, allowed to adhere to immobilized LAP, washed, and adherent cells are detected by quantifying endogenous alkaline phosphatase using para-nitrophenyl phosphate. An 8-point dose-response curve using either 10-fold or 3-fold dilutions of compound was evaluated by fitting a four-parameter logistic, nonlinear model (using SAS). The compounds evaluated were relatively ineffective at inhibition of $\alpha_v\beta_6$-mediated cell adhesion. The selective antagonism of the $\alpha_v\beta_3$ integrin is viewed as desirable in this class of compounds, as $\alpha_v\beta_6$ may also play a role in normal physiological processes of tissue repair and cellular turnover that routinely occur in the skin and pulmonary tissues.

What is claimed is:

1. A compound or a pharmaceutically acceptable salt thereof, wherein:

the compound corresponds in structure to Formula I:

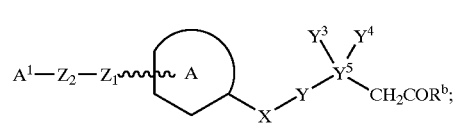

the structure:

is a thiazole or isoxazole, wherein:

the thiazole or isoxazole is optionally substituted with one or more substituents independently selected from the group consisting of alkyl, haloalkyl, aryl, heteroaryl, halogen, alkoxyalkyl, aminoalkyl, hydroxy, nitro, alkoxy, hydroxyalkyl, alkylthio, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —$(CH_2)_m COR$;

each m is independently zero, 1, or 2;

each R is independently selected from the group consisting of hydroxy, alkoxy, alkyl, amino, and sulfone;

$A^1$ is selected from the group consisting of:

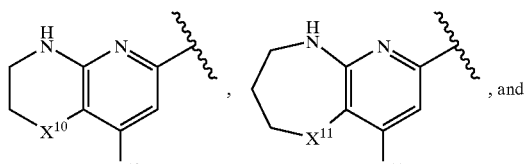
, and

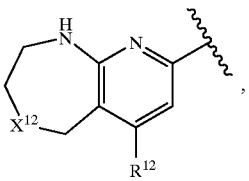
, wherein any such substituent is optionally substituted by one or more substituents independently selected from the group consisting of hydroxy, alkyl, alkoxy, alkoxyalkyl, alkylthio, haloalkyl, cyano, amino, alkylamino, halogen, acylamino, sulfonamide, and —$COR^4$;

$X^{10}$ is $CH_2$, O, S, $SO_2$, CO, $CF_2$, or $C(CH_3)_2$;
$X^{11}$ is $CH_2$, O, S, $SO_2$, CO, $CF_2$, or $C(CH_3)_2$;
$X^{12}$ is $CH_2$, O, S, $SO_2$, CO, or $C(CH_3)_2$;
$R^{10}$ is H, $CH_3$, $OCH_3$, or OH;
$R^{11}$ is H, $CH_3$, $OCH_3$, or OH;
$R^{12}$ is H, $CH_3$, $OCH_3$, or OH;
each $R^4$ is independently hydroxy, alkoxy, alkyl, or amino;
$Z_1$ is selected from the group consisting of $CH_2$, O, $CH_2O$, NH, CO, S, SO, CH(OH), and $SO_2$;
$Z_2$ is a 1–5 carbon linker optionally containing one or more heteroatoms independently selected from the group consisting of O, S, and N;
each $R^c$ is independently selected from the group consisting of alkyl, haloalkyl, aryl, heteroaryl, halogen, alkoxyalkyl, aminoalkyl, hydroxy, alkoxy, carboxamide, and cyano;
any carbon and nitrogen atoms of $Z_1$ and $Z_2$ are optionally substituted by a moiety selected from the group consisting of alkyl, alkoxy, alkylthio, alkylsulfone, aryl, alkoxyalkyl, hydroxy, alkylamino, heteroaryl, alkenyl, alkynyl, carboxyalkyl, halogen, haloalkyl, and acylamino;
X is selected from the group consisting of —$CHR^e$—, —$NR^f$—, —O—, —S—, —$SO_2$—, and —CO—;
Y is selected from the group consisting of —$(CH_2)_p$—, —$CHR^g$—, —$NR^g$—, —CO—, and —$SO_2$—;
$R^e$ is selected from the group consisting of H, lower alkyl, alkoxy, cycloalkyl, alkoxyalkyl, hydroxy, alkynyl, alkenyl, haloalkyl, alkylthio, and aryl, wherein:
the hydroxy can optionally form a lactone with the $COR^b$ of the $CH_2COR^b$ moiety bonded to $Y^5$;
$R^f$ is selected from the group consisting of H, alkyl, aryl, benzyl, and haloalkyl;
each $R^g$ is independently selected from the group consisting of H, alkyl, haloalkyl, alkoxyalkyl, alkynyl, aryl, heteroaryl, aralkyl, hydroxy, alkoxy, and carboxyalkyl;
p is zero or 1;
as to $Y^3$, $Y^4$, and $Y^5$:
$Y^5$ is carbon, and $Y^3$ and $Y^4$ are independently selected from the group consisting of H, alkyl, haloalkyl, halogen, aryl, arakyl, heteroaralkyl, heteroaryl, alkenes, hydroxyalkyl, and alkyne, wherein:
the alkyl optionally contains one or more moieties independently selected from the group consisting of N, O, S, sulfone, sulfonamide sulfonamide, nitrile, carboxamide, carboalkoxy, and carboxyl, and
the aryl and heteroaryl rings:
are monocyclic or bicyclic optionally containing 1–5 heteroatoms, and
may optionally be substituted by one or more $R^c$ substituents;
$Y^5$ is nitrogen, $Y^4$ is absent, and $Y^3$ is selected from the group consisting of H, alkyl, haloalkyl, halogen, aryl, arakyl, heteroaralkyl, heteroaryl, alkenes, hydroxyalkyl, and alkyne, wherein:
the alkyl chain optionally contains one or more moieties independently selected from the group consisting of N, O, S, sulfone, sulfonamide sulfonamide, nitrile, carboxamide, carboalkoxy, and carboxyl, and
the aryl and heteroaryl rings:
are monocyclic or bicyclic optionally containing 1–5 heteroatoms, and
may optionally be substituted by one or more $R^e$ substituents: or
$Y^5$ is carbon, and $Y^3$, $Y^4$, and $Y^5$ together form a 3–8 membered monocyclic or a 7–11 membered bicyclic ring, wherein the ring:
optionally contains one or more moieties independently selected from the group consisting of O, $NR^g$, S, CO, and $SO_2$, and
optionally is substituted with one or more substituents selected from the group consisting of alkyl, haloalkyl, halogen, haloalkyl, alkoxy, alkyne, cyano, alkylsulfone, sulfonamide, carboalkoxy, and carboxyalkyl;
$R^b$ is $X_2$—$R^h$;
$X^2$ is selected from the group consisting of O, S, and $NR^j$; and
$R^h$ and $R^j$ are independently selected from the group consisting of H, alkyl, aryl, aralkyl, acyl, and alkoxyalkyl.

2. A compound or salt according to claim 1, wherein:
X is —$CH_2$—;
Y is a bond;
$Y^5$ is a carbon; and
$R^b$ is OH.

3. A compound or a pharmaceutically acceptable salt thereof, wherein:
the compound corresponds in structure to the following formula:

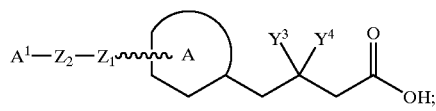

the structure:

is a thiazole or isoxazole, wherein:

the thiazole or isoxazole is optionally substituted with one or more substituents independently selected from the group consisting of alkyl, haloalkyl, aryl, heteroaryl, halogen, alkoxyalkyl, aminoalkyl, hydroxy, nitro, alkoxy, hydroxyalkyl, alkylthio, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and $-(CH_2)_m COR$;

each m is independently zero, 1, or 2;

each R is independently selected from the group consisting of hydroxy, alkoxy, alkyl, amino, and sulfone;

$A^1$ is selected from the group consisting of:

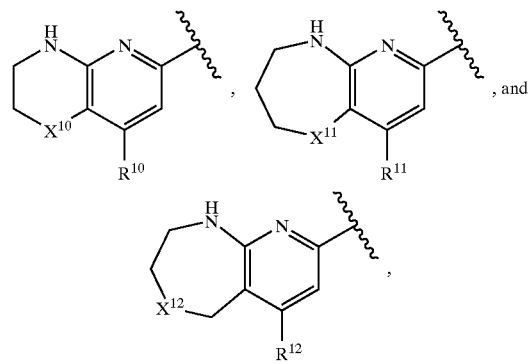

wherein any such substituent is optionally substituted by one or more substituents independently selected from the group consisting of hydroxy, alkyl, alkoxy, alkoxyalkyl, alkylthio, haloalkyl, cyano, amino, alkylamino, halogen, acylamino, sulfonamide, and $-COR^4$;

$X^{10}$ is $CH_2$, O, S, $SO_2$, CO, $CF_2$, or $C(CH_3)_2$;

$X^{11}$ is $CH_2$, O, S, $SO_2$, CO, $CF_2$, or $C(CH_3)_2$;

$X^{12}$ is $CH_2$, O, S, $SO_2$, CO, or $C(CH_3)_2$;

$R^{10}$ is H, $CH_3$, $OCH_3$, or OH;

$R^{11}$ is H, $CH_3$, $OCH_3$, or OH;

$R^{12}$ is H, $CH_3$, $OCH_3$, or OH;

each $R^4$ is independently hydroxy, alkoxy, alkyl, or amino;

$Z_1$ is selected from the group consisting of $CH_2$, O, $CH_2O$, NH, CO, S, SO, CH(OH), and $SO_2$; and $Z_2$ is a 1-5 carbon linker optionally containing one or more heteroatoms independently selected from the group consisting of O, S, and N;

each $R^c$ is independently selected from the group consisting of alkyl, haloalkyl, aryl, heteroaryl, halogen, alkoxyalkyl, aminoalkyl, hydroxy, alkoxy, carboxamide, and cyano;

any carbon and nitrogen atoms of $Z_1$ and $Z_2$ are optionally substituted by a moiety selected from the group consisting of alkyl, alkoxy, alkylthio, alkylsulfone, aryl, alkoxyalkyl, hydroxy, alkylamino, heteroaryl, alkenyl, alkynyl, carboxyalkyl, halogen, haloalky, and acylamino;

$Y^3$ is selected from the group consisting of H, alkyl, $CH_2Z^3R^{20}$, $CH_2OH$, $C{\equiv}C-R^{21}$,

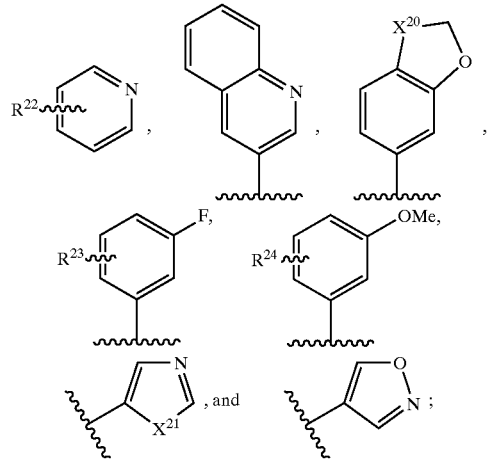

$Z^3$ is O, $SO_2$, S, or CO;

$R^{20}$ is alkyl or aryl;

$R^{21}$ is alkyl, aryl, or alkoxyalkyl;

$R^{22}$ is H, alkyl, $OCH_3$, OH, halogen, amino, or CN;

$R^{23}$ is H, alkyl, $OCH_3$, OH, halogen, amino, or CN;

$R^{24}$ is H, alkyl, $OCH_3$, OH, or halogen;

$X^{20}$ is $CH_2$ or O;

$X^{21}$ is NH, $NCH_3$, O, or S; and $Y^4$ is selected from the group consisting of H, alkyl, haloalkyl, halogen, aryl, arakyl, heteroaralkyl, heteroaryl, alkenes, hydroxyalkyl, and alkyne, wherein:
the alkyl optionally contains one or more moieties independently selected from the group consisting of N, O, S, sulfone, sulfonamide sulfonamide, nitrile, carboxamide, carboalkoxy, and carboxyl, and
the aryl and heteroaryl rings:
are monocyclic or bicyclic optionally containing 1-5 heteroatoms, and
may optionally be substituted by one or more $R^c$ substituents.

4. A compound or a pharmaceutically acceptable salt thereof, wherein:

the compound corresponds in structure to the following formula:

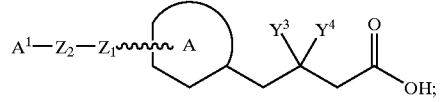

the structure:

is a thiazole or isoxazole, wherein:
the thiazole or isoxazole is optionally substituted with one or more substituents independently selected from the group consisting of alkyl, haloalkyl, aryl, heteroaryl, halogen, alkoxyalkyl, aminoalkyl, hydroxy, nitro, alkoxy, hydroxyalkyl, alkylthio, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —(CH$_2$)$_m$COR;

each m is independently zero, 1, or 2;

each R is independently selected from the group consisting of hydroxy, alkoxy, alkyl, amino, and sulfone;

A$^1$ is selected from the group consisting of:

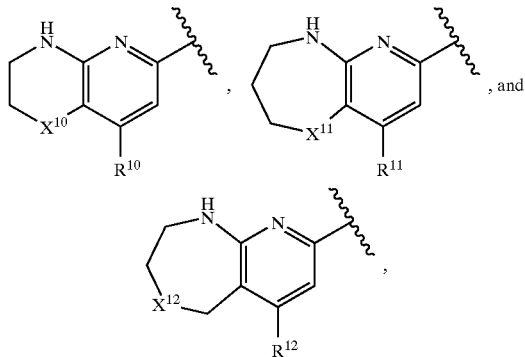

wherein any such substituent is optionally substituted by one or more substituents independently selected from the group consisting of hydroxy, alkyl, alkoxy, alkoxyalkyl, alkylthio, haloalkyl, cyano, amino, alkylamino, halogen, acylamino, sulfonamide, and —COR$^4$;

X$^{10}$ is CH$_2$, O, S, SO$_2$, CO, CF$_2$, or C(CH$_3$)$_2$;

X$^{11}$ is CH$_2$, O, S, SO$_2$, CO, CF$_2$, or C(CH$_3$)$_2$;

X$^{12}$ is CH$_2$, O, S, SO$_2$, CO, or C(CH$_3$)$_2$;

R$^{10}$ is H, CH$_3$, OCH$_3$, OH, or OH;

R$^{11}$ is H, CH$_3$, OCH$_3$, OH, or OH;

R$^{12}$ is H, CH$_3$, OCH$_3$, or OH;

each R$^4$ is independently hydroxy, alkoxy, alkyl, or amino;

Z$_1$ is selected from the group consisting of CH$_2$, O, CH$_2$O, NH, CO, S, SO, CH(OH), and SO$_2$;

Z$_2$ is a 1–5 carbon linker optionally containing one or more heteroatoms independently selected from the group consisting of O, S, and N;

each R$^c$ is independently selected from the group consisting of alkyl, haloalkyl, aryl, heteroaryl, halogen, alkoxyalkyl, aminoalkyl, hydroxy, alkoxy, carboxamide, and cyano;

any carbon and nitrogen atoms of Z$_1$ and Z$_2$ are optionally substituted by a moiety selected from the group consisting of alkyl, alkoxy, alkylthio, alkylsulfone, aryl, alkoxyalkyl, hydroxy, alkylamino, heteroaryl, alkenyl, alkynyl, carboxyalkyl, halogen, haloalky, and acylamino;

Y$^3$ is selected from the group consisting of H, methyl, phenyl, ethyl, propyl, isopropyl, phenylmethoxymethyl,

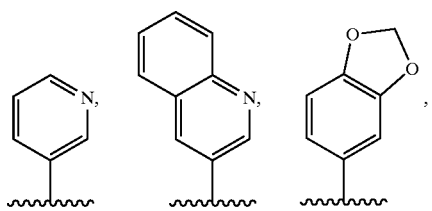

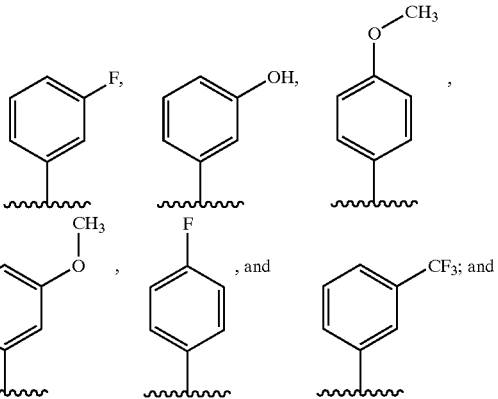

Y$^4$ is selected from the group consisting of H, alkyl, haloalkyl, halogen, aryl, arakyl, heteroaralkyl, heteroaryl, alkenes, hydroxyalkyl, and alkyne, wherein:
the alkyl optionally contains one or more moieties independently selected from the group consisting of N, O, S, sulfone, sulfonamide sulfonamide, nitrile, carboxamide, carboalkoxy, and carboxyl, and
the aryl and heteroaryl rings:
are monocyclic or bicyclic optionally containing 1–5 heteroatoms, and
may optionally be substituted by one or more R$^c$ substituents.

5. A compound or salt according to claim 4, wherein A$^1$ is:

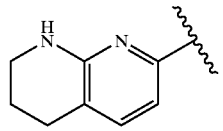

6. A compound or a pharmaceutically acceptable salt thereof, wherein the compound is selected from the group consisting of:

(2-{5-[3-(5,6,7,8-Tetrahydro-[1,8]naphthyridin-2-yl)-propyl]-isoxazol-3-yl}-cyclopropyl)-acetic acid;

3-Phenyl-4-{5-[3-(5,6,7,8-tetrahydro-[1,8]naphthyridin-2-yl)-propyl]-isoxazol-3-yl}-butyric acid;

3-(2,3-Dihydro-benzofuran-6-yl)-4-{5-[3-(5,6,7,8-tetrahydro-[1,8]naphthyridin-2-yl)-propyl]-isoxazol-3-yl}-butyric acid;

3-(3-Fluoro-phenyl)-4-{5-[3-(5,6,7,8-tetrahydro-[1,8] naphthyridin-2-yl)-propyl]-isoxazol-3-yl}-butyric acid;

3-Pyridin-3-yl-4-{5-[3-(5,6,7,8-tetrahydro-[1,8] naphthyridin-2-yl)-propyl]-isoxazol-3-yl}-butyric acid;

3-Benzo[1,3]dioxol-5-yl-4-{5-[3-(5,6,7,8-tetrahydro-[1, 8]naphthyridin-2-yl)-propyl]-isoxazol-3-yl}-butyric acid;

3-(2,3-Dihydro-benzofuran-6-yl)-4-{3-[3-(5,6,7,8-tetrahydro-[1,8]naphthyridin-2-yl)-propyl]-isoxazol-5-yl}-butyric acid;

3-(3-Fluoro-phenyl)-4-{3-[3-(5,6,7,8-tetrahydro-[1,8] naphthyridin-2-yl)-propyl]-isoxazol-5-yl)-butyric acid;

3-Pyridin-3-yl-4-{3-[3-(5,6,7,8-tetrahydro-[1,8] naphthyridin-2-yl)-propyl]-isoxazol-5-yl}-butyric acid;

3-Benzo[1,3]dioxol-5-yl-4-{3-[3-(5,6,7,8-tetrahydro-[1,8]naphthyridin-2-yl)-propyl]-isoxazol-5-yl}-butyric acid;

(2-{3-[3-(5,6,7,8-Tetrahydro-[1,8]naphthyridin-2-yl)-propyl]-isoxazol-5-yl)-cyclopropyl)-acetic acid;

(2-{4-[3-(5,6,7,8-Tetrahydro-[1,8]naphthyridin-2-yl)-propyl]-thiazol-2-yl}-cyclopropyl)-acetic acid;

3-Phenyl-4-{4-[3-(5,6,7,8-tetrahydro-[1,8]naphthyridin-2-yl)-propyl]-thiazol-2-yl}-butyric acid;

3-(2,3-Dihydro-benzofuran-6-yl)-4-{4-[3-(5,6,7,8-tetrahydro-[1,8]naphthyridin-2-yl)-propyl]-thiazol-2-yl}-butyric acid;

3-(3-Fluoro-phenyl)-4-{4-[3-(5,6,7,8-tetrahydro-[1,8]naphthyridin-2-yl)-propyl]-thiazol-2-yl}-butyric acid;

3-Pyridin-3-yl-4-{4-[3-(5,6,7,8-tetrahydro-[1,8]naphthyridin-2-yl)-propyl]-thiazol-2-yl}-butyric acid;

3-Benzo[1,3]dioxol-5-yl-4-{4-[3-(5,6,7,8-tetrahydro-[1,8]naphthyridin-2-yl)-propyl]-thiazol-2-yl}-butyric acid;

3-Phenyl-4-{3-[2-(5,6,7,8-tetrahydro-[1,8]naphthyridin-2-yl)-ethoxy]-isoxazol-5-yl}-butyric acid;

3-(2,3-Dihydro-benzofuran-6-yl)-4-{3-[2-(5,6,7,8-tetrahydro-[1,8]naphthyridin-2-yl)-ethoxy]-isoxazol-5-yl}-butyric acid;

3-(3-Fluoro-phenyl)-4-{3-[2-(5,6,7,8-tetrahydro-[1,8]naphthyridin-2-yl)-ethoxy]-isoxazol-5-yl}-butyric acid;

3-Pyridin-3-yl-4-{3-[2-(5,6,7,8-tetrahydro-[1,8]naphthyridin-2-yl)-ethoxy]-isoxazol-5-yl}-butyric acid;

3-Benzo[1,3]dioxol-5-yl-4-{3-[2-(5,6,7,8-tetrahydro-[1,8]naphthyridin-2-yl)-ethoxy]-isoxazol-5-yl}-butyric acid (2-(5-[3-(5,6,7,8-Tetrahydro-[1,8]naphthyridin-2-yl)-propyl]-isoxazol-3-yl}-cyclopropyl)-acetic acid;

3-Phenyl-4-{5-[3-(5,6,7,8-tetrahydro-[1,8]naphthyridin-2-yl)-propyl]-isoxazol-3-yl}-butyric acid;

3-(2,3-Dihydro-benzofuran-6-yl)-4-{5-[3-(5,6,7,8-tetrahydro-[1,8]naphthyridin-2-yl)-propyl]-isoxazol-3-yl}-butyric acid;

3-(3-Fluoro-phenyl)-4-{5-[3-(5,6,7,8-tetrahydro-[1,8]naphthyridin-2-yl)-propyl]-isoxazol-3-yl}-butyric acid;

3-Pyridin-3-yl-4-(5-[3-(5,6,7,8-tetrahydro-[1,8]naphthyridin-2-yl)-propyl]-isoxazol-3-yl)-butyric acid;

3-Benzo[1,3]dioxol-5-yl-4-{5-[3-(5,6,7,8-tetrahydro-[1,8]naphthyridin-2-yl)-propyl]-isoxazol-3-yl}-butyric acid;

3-(2,3-Dihydro-benzofuran-6-yl)-4-{3-[3-(5,6,7,8-tetrahydro-[1,8]naphthyridin-2-yl)-propyl]-isoxazol-5-yl}-butyric acid;

3-(3-Fluoro-phenyl)-4-{3-[3-(5,6,7,8-tetrahydro-[1,8]naphthyridin-2-yl)-propyl]-isoxazol-5-yl}-butyric acid;

3-Pyridin-3-yl-4-{3-[3-(5,6,7,8-tetrahydro-[1,8]naphthyridin-2-yl)-propyl]-isoxazol-5-yl}-butyric acid;

3-Benzo[1,3]dioxol-5-yl-4-{3-[3-(5,6,7,8-tetrahydro-[1,8]naphthyridin-2-yl)-propyl]-isoxazol-5-yl}-butyric acid;

(2-{3-[3-(5,6,7,8-Tetrahydro-[1,8]naphthyridin-2-yl)-propyl]-isoxazol-5-yl}-cyclopropyl)-acetic acid;

(2-{4-[3-(5,6,7,8-Tetrahydro-[1,8]naphthyridin-2-yl)-propyl]-thiazol-2-yl}-cyclopropyl)-acetic acid;

3-Phenyl-4-{4-[3-(5,6,7,8-tetrahydro-[1,8]naphthyridin-2-yl)-propyl]-thiazol-2-yl}-butyric acid;

3-(2,3-Dihydro-benzofuran-6-yl)-4-{4-[3-(5,6,7,8-tetrahydro-[1,8]naphthyridin-2-yl)-propyl]-thiazol.2-yl}-butyric acid;

3-(3-Fluoro-phenyl)-4-{4-[3-(5,6,7,8-tetrahydro-[1,8]naphthyridin-2-yl)-propyl]-thiazol-2-yl}-butyric acid;

3-Pyridin-3-yl-4-{4-[3-(5,6,7,8-tetrahydro-[1,8]naphthyridin-2-yl)-propyl]-thiazol-2-yl}-butyric acid;

3-Benzo[1,3]dioxol-5-yl-4-{4-[3-(5,6,7,8-tetrahydro-[1,8]naphthyridin-2-yl)-propyl]-thiazol-2-yl}-butyric acid;

Phenyl-4-{3-[2-(5,6,7,8-tetrahydro-[1,8]naphthyridin-2-yl)-ethoxy]-isoxazol-5-yl}-butyric acid;

3-(2,3-Dihydro-benzofuran-6-yl)-4-{3-[2-(5,6,7,8-tetrahydro-[1,8]naphthyridin-2-yl)-ethoxy]-isoxazol-5-yl}-butyric acid;

3-(3-Fluoro-phenyl)-4-{3-[2-(5,6,7,8-tetrahydro-[1,8]naphthyridin-2-yl)-ethoxy]-isoxazol-5-yl}-butyric acid;

3-Pyridin-3-yl-4-{3-[2-(5,6,7,8-tetrahydro-[1,8]naphthyridin-2-yl)-ethoxy]-isoxazol-5-yl}-butyric acid; and 3-Benzo[1,3]dioxol-5-yl-4-{3-[2-(5,6,7,8-tetrahydro-[1,8]naphthyridin-2-yl)-ethoxy]-isoxazol-5-yl}-butyric acid.

7. A pharmaceutical composition comprising a therapeutically effective amount of a compound or salt of claim 1 and a pharmaceutically acceptable carrier.

8. A pharmaceutical composition comprising a therapeutically effective amount of a compound or salt of claim 6 and a pharmaceutically acceptable carrier.

9. A pharmaceutical composition comprising a therapeutically effective amount of at least one compound or salt of claim 1 and a pharmaceutically acceptable carrier and a cytotoxic agent.

10. A pharmaceutical composition comprising a therapeutically effective amount of at least one compound or salt of claim 6 and a pharmaceutically acceptable carrier and a cytotoxic agent.

11. A method for treating a condition mediated by $\alpha_V\beta_3$ integrin selected from the group consisting of tumor metastasis, solid tumor growth, angiogenesis, osteoporosis, humoral hypercalcemia of malignancy, smooth muscle cell migration, restenosis, atheroscelorosis, macular degeneration, retinopathy and arthritis in a mammal in need of such treatment comprising administering an effective $\alpha_V\beta_3$ inhibiting amount of a compound or salt of claim 1.

12. A method for treating a condition mediated by $\alpha_V\beta_3$ integrin selected from the group consisting of tumor metastasis, solid tumor growth, angiogenesis, osteoporosis, humoral hypercalcemia of malignancy, smooth muscle cell migration, restenosis, atheroscelorosis, macular degeneration, retinopathy and arthritis in a mammal in need of such treatment comprising administering an effective $\alpha_V\beta_3$ inhibiting amount of a compound or salt of claim 6.

13. A pharmaceutical composition comprising a therapeutically effective amount of a compound or salt of claim 3 and a pharmaceutically acceptable carrier and a cytotoxic agent.

14. A pharmaceutical composition comprising a therapeutically effective amount of at least one compound or salt of claim 3 and a pharmaceutically acceptable carrier and a cytotoxic agent.

15. A method for treating a condition mediated by $\alpha_v\beta_3$ integrin selected from the group consisting of tumor metastasis, solid tumor growth, angiogenesis, osteoporosis, humoral hypercalcemia of malignancy, smooth muscle cell migration, restenosis, atheroscelorosis, macular degeneration, retinopathy and arthritis in a mammal in need of such treatment comprising administering an effective $\alpha_v\beta_3$ inhibiting amount of a compound or salt of claim 3.

16. A pharmaceutical composition comprising a therapeutically effective amount of a compound or salt of claim 4 and a pharmaceutically acceptable carrier.

17. A pharmaceutical composition comprising a therapeutically effective amount of at least one compound or salt of claim 4 and a pharmaceutically acceptable carrier and a cytotoxic agent.

18. A method for treating a condition mediated by $\alpha_v\beta_3$ integrin selected from the group consisting of tumor metastasis, solid tumor growth, angiogenesis, osteoporosis, humoral hypercalcemia of malignancy, smooth muscle cell migration, restenosis, atheroscelorosis, macular degeneration, retinopathy and arthritis in a mammal in need of such treatment comprising administering an effective $\alpha_v\beta_3$ inhibiting amount of a compound or salt of claim 4.

19. A compound or a pharmaceutically acceptable salt thereof, wherein:

the compound corresponds in structure to Formula I:

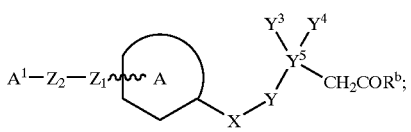

I the structure:

is a thiazole or isoxazole, wherein:

the thiazole or isoxazole is optionally substituted with one or more substituents independently selected from the group consisting of alkyl, haloalkyl, aryl, heteroaryl, halogen, alkoxyalkyl, aminoalkyl, hydroxy, nitro, alkoxy, hydroxyalkyl, alkylthio, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —(CH$_2$)$_m$COR;

each m is independently zero, 1, or 2;

each R is independently selected from the group consisting of hydroxy, alkoxy, alkyl, amino, and sulfone;

$A^1$ is selected from the group consisting of:

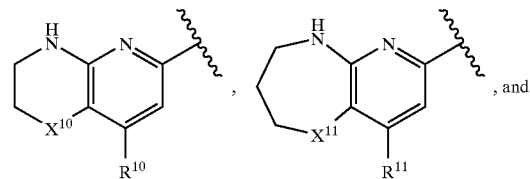

, and

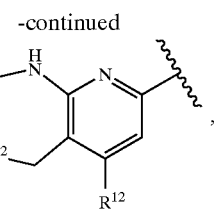

, wherein any such substituent is optionally substituted by one or more substituents independently selected from the group consisting of hydroxy, alkyl, alkoxy, alkoxyalkyl, alkylthio, haloalkyl, cyano, amino, alkylamino, halogen, acylamino, sulfonamide, and —COR$^4$;

$X^{10}$ is CH$_2$, O, S, SO$_2$, CO, CF$_2$, or C(CH$_3$)$_2$;
$X^{11}$ is CH$_2$, O, S, SO$_2$, CO, CF$_2$, or C(CH$_3$)$_2$;
$X^{12}$ is CH$_2$, O, S, SO$_2$, CO, or C(CH$_3$)$_2$;
$R^{10}$ is H, CH$_3$, OCH$_3$, or OH;
$R^{11}$ is H, CH$_3$, OCH$_3$, or OH;
$R^{12}$ is H, CH$_3$, OCH$_3$, or OH;

each $R^4$ is independently hydroxy, alkoxy, alkyl, or amino;

$Z_1$ is selected from the group consisting of CH$_2$, O, CH$_2$O, NH, CO, S, SO, CH(OH), and SO$_2$; and $Z_2$ is a 1–5 carbon linker optionally containing one or more heteroatoms independently selected from the group consisting of O, S, and N;

each $R^c$ is independently selected from the group consisting of alkyl, haloalkyl, aryl, heteroaryl, halogen, alkoxyalkyl, aminoalkyl, hydroxy, alkoxy, carboxamide, and cyano;

any carbon and nitrogen atoms of $Z_1$ and $Z_2$ are optionally substituted by a moiety selected from the group consisting of alkyl, alkoxy, alkylthio, alkylsulfone, aryl, alkoxyalkyl, hydroxy, alkylamino, heteroaryl, alkenyl, alkynyl, carboxyalkyl, halogen, haloalkyl, and acylamino;

Y is selected from the group consisting of —(CH$_2$)$_p$—, —CHR$^g$—, NR$^g$—, —CO—, and —SO$_2$—;

each R$^g$ is independently selected from the group consisting of H, alkyl, haloalkyl, alkoxyalkyl, alkynyl, aryl, heteroaryl, aralkyl, hydroxy, alkoxy, and carboxyalkyl;

p is zero or 1;

X and $Y^3$, together with the atom(s) to which they are both bonded, form a 3–7 membered monocyclic ring, wherein the ring:

optionally contains one or more moieties independently selected from the group consisting of O, NR$^g$, S, CO, and SO$_2$, and optionally is substituted with one or more substituents independently selected from the group consisting of alkyl, halogen, alkoxy, haloalkyl, hydroxyalkyl, and alkoxyalkyl;

as to $Y^4$ and $Y^5$:

$Y^5$ is nitrogen, and $Y^4$ is absent; or $Y^5$ is carbon, and $Y^4$ is selected from the group consisting of H, alkyl, haloalkyl, halogen, aryl, arakyl, heteroaralkyl, heteroaryl, alkenes, hydroxyalkyl, and alkyne, wherein:

the alkyl optionally contains one or more moieties independently selected from the group consisting of N, O, S, sulfone, sulfonamide sulfonamide, nitrile, carboxamide, carboalkoxy, and carboxyl, and the aryl and heteroaryl rings:
> are monocyclic or bicylic optionally containing 1–5 heteroatoms, and
> > may optionally be substituted by one or more $R^c$ substituents; or $R^b$ is $X_2$—$R^h$;

$X^2$ is selected from the group consisting of O, S, and $NR^j$; and $R^h$ and $R^j$ are independently selected from the group consisting of H, alkyl, aryl, aralkyl, acyl, and alkoxyalkyl.

20. A pharmaceutical composition comprising a therapeutically effective amount of a compound or salt of claim 19 and a pharmaceutically acceptable carrier.

21. A pharmaceutical composition comprising a therapeutically effective amount of at least one compound or salt of claim 19 and a pharmaceutically acceptable carrier and a cytotoxic agent.

22. A method for treating a condition mediated by $\alpha_v\beta_3$ integrin selected from the group consisting of tumor metastasis, solid tumor growth, angiogenesis, osteoporosis, humoral hypercalcemia of malignancy, smooth muscle cell migration, restenosis, atheroscelorosis, macular degeneration, retinopathy and arthritis in a mammal in need of such treatment comprising administering an effective $\alpha_v\beta_3$ inhibiting amount of a compound or salt of claim 19.

* * * * *